US012595469B2

(12) United States Patent
Bartsevich et al.

(10) Patent No.: US 12,595,469 B2
(45) Date of Patent: Apr. 7, 2026

(54) TREATMENT OF RETINITIS PIGMENTOSA USING IMPROVED ENGINEERED MEGANUCLEASES

(71) Applicant: Precision BioSciences, Inc., Durham, NC (US)

(72) Inventors: Victor Bartsevich, Durham, NC (US); Derek Jantz, Durham, NC (US); James Jefferson Smith, Morrisville, NC (US); Michael G. Nicholson, Chapel Hill, NC (US)

(73) Assignee: Precision BioSciences, Inc., Durham, NC (US)

( * ) Notice: Subject to any disclaimer, the term of this patent is extended or adjusted under 35 U.S.C. 154(b) by 701 days.

(21) Appl. No.: 17/924,352

(22) PCT Filed: May 11, 2021

(86) PCT No.: PCT/US2021/031867
§ 371 (c)(1),
(2) Date: Nov. 9, 2022

(87) PCT Pub. No.: WO2021/231495
PCT Pub. Date: Nov. 18, 2021

(65) Prior Publication Data
US 2023/0193230 A1      Jun. 22, 2023

Related U.S. Application Data

(60) Provisional application No. 63/068,971, filed on Aug. 21, 2020, provisional application No. 63/023,665, filed on May 12, 2020.

(51) Int. Cl.
| | |
|---|---|
| *C12N 9/22* | (2006.01) |
| *A61K 31/7105* | (2006.01) |
| *A61K 38/46* | (2006.01) |
| *A61K 48/00* | (2006.01) |
| *A61P 27/02* | (2006.01) |
| *C12N 15/11* | (2006.01) |
| *C12N 15/86* | (2006.01) |
| *C12N 15/90* | (2006.01) |

(52) U.S. Cl.
CPC ........... *C12N 9/22* (2013.01); *A61K 31/7105* (2013.01); *A61K 38/465* (2013.01); *A61K 48/005* (2013.01); *A61P 27/02* (2018.01); *C12N 15/11* (2013.01); *C12N 15/86* (2013.01); *C12N 15/907* (2013.01); *C12N 2310/20* (2017.05); *C12N 2750/14143* (2013.01); *C12N 2750/14145* (2013.01); *C12N 2800/80* (2013.01)

(58) Field of Classification Search
None
See application file for complete search history.

(56) References Cited

FOREIGN PATENT DOCUMENTS

WO      WO 2017/044649 A1      3/2017

*Primary Examiner* — Jehanne S Sitton
(74) *Attorney, Agent, or Firm* — Womble Bond Dickinson (US) LLP

(57) ABSTRACT

Disclosed are recombinant meganucleases engineered to bind and cleave a recognition sequence present in a mutant RHO P23H allele. The invention further relates to the use of such recombinant meganucleases in a method for treating retinitis pigmentosa, wherein the mutant RHO P23H allele is preferentially targeted, cleaved, and inactivated.

14 Claims, 20 Drawing Sheets

Specification includes a Sequence Listing.

```
RHO 1-2L.609(SEQ ID NO: 11)    MNTKYNKEFLLYLAGFVDGDGSIFARIFKGQHWKFKHYIRLTFSVRQKTQRRWFLDKLVD    60
RHO 1-2L.664(SEQ ID NO: 12)    MNTKYNKEFLLYLAGFVDGDGSIFARIFKGQHWKFKHYIRLTFSVRQKTQRRWFLDKLVD    60
RHO 1-2L.692(SEQ ID NO: 14)    MNTKYNKEFLLYLAGFVDGDGSIFAKIFKGQHWKFKHYIRLTFSVRQKTQRRWFLDKLVD    60
RHO 1-2L.687(SEQ ID NO: 13)    MNTKYNKEFLLYLAGFVDGDGSIYARIFKGQHWKFKHYIRLTFSVRQKTQRRWFLDKLVD    60
                               ********************** ************************************

RHO 1-2L.609(SEQ ID NO: 11)    EIGVGYVVDSGSVSEYYLSEIKPLHNFLTQLQPFLKLKQKQANLVLKIIEQLPSAKESPD    120
RHO 1-2L.664(SEQ ID NO: 12)    EIGVGYVCDSGSVSEYYLSEIKPLHNFLTQLQPFLKLKQKQANLVLKIIEQLPSAKESPD    120
RHO 1-2L.692(SEQ ID NO: 14)    EIGVGYVVDSGSVSEYYLSEIKPLHNFLTQLQPFLKLKQKQANLVLKIIEQLPSAKESPD    120
RHO 1-2L.687(SEQ ID NO: 13)    EIGVGYVQDSGSVSEYYLSEIKPLHNFLTQLQPFLKLKQKQANLVLKIIEQLPSAKESPD    120
                               ******* ****************************************************

RHO 1-2L.609(SEQ ID NO: 11)    KFLEVCTWVDQIAALNDSKTRKTTSETVRAVLDSLPGSVGGLSPSQASSAASSASSSPGS    180
RHO 1-2L.664(SEQ ID NO: 12)    KFLEVCTWVDQIAALNDSKTRKTTSETVRAVLDSLPGSVGGLSPSQASSAASSASSSPGS    180
RHO 1-2L.692(SEQ ID NO: 14)    KFLEVCTWVDQIAALNDSKTRKTTSETVRAVLDSLPGSVGGLSPSQASSAASSASSSPGS    180
RHO 1-2L.687(SEQ ID NO: 13)    KFLEVCTWVDQIAALNDSKTRKTTSETVRAVLDSLPGSVGGLSPSQASSAASSASSSPGS    180
                               ************************************************************

RHO 1-2L.609(SEQ ID NO: 11)    GISEALRAGAGSGTGYNKEFLLYLAGFVDGDGSIWASIIPEQRLKFKHRLRLSFTVAQKT    240
RHO 1-2L.664(SEQ ID NO: 12)    GISEALRAGAGSGTGYNKEFLLYLAGFVDGDGSIWASIIPEQNGKFKHRLRLSFTVAQKT    240
RHO 1-2L.692(SEQ ID NO: 14)    GISEALRAGAGSGTGYNKEFLLYLAGFVDGDGSIWASIIPEQKSKFKHRLRLSFTVAQKT    240
RHO 1-2L.687(SEQ ID NO: 13)    GISEALRAGAGSGTGYNKEFLLYLAGFVDGDGSIWASIIPEQAYKFKHRLRLSFTVAQKT    240
                               ****************************************** ****************

RHO 1-2L.609(SEQ ID NO: 11)    QRRWFLDKLVDEIGVGYVVDQGSVSEYRLSEIKPLHNFLTQLQPFLKLKQKQANLVLKII    300
RHO 1-2L.664(SEQ ID NO: 12)    QRRWFLDKLVDEIGVGYVVDQGSVSEYRLSEIKPLHNFLTQLQPFLKLKQKQANLVLKII    300
RHO 1-2L.692(SEQ ID NO: 14)    QRRWFLDKLVDEIGVGYVVDQGSVSEYRLSEIKPLHNFLTQLQPFLKLKQKQANLVLKII    300
RHO 1-2L.687(SEQ ID NO: 13)    QRRWFLDKLVDEIGVGYVVDQGSVSEYRLSEIKPLHNFLTQLQPFLKLKQKQANLVLKII    300
                               ************************************************************

RHO 1-2L.609(SEQ ID NO: 11)    EQLPSAKESPDKFLEVCTWVDQIAALNDSKTRKTTSETVRAVLDSLSEKKKSSP    354
RHO 1-2L.664(SEQ ID NO: 12)    EQLPSAKESPDKFLEVCTWVDQIAALNDSKTRKTTSETVRAVLDSLSEKKKSSP    354
RHO 1-2L.692(SEQ ID NO: 14)    EQLPSAKESPDKFLEVCTWVDQIAALNDSKTRKTTSETVRAVLDSLSEKKKSSP    354
RHO 1-2L.687(SEQ ID NO: 13)    EQLPSAKESPDKFLEVCTWVDQIAALNDSKTRKTTSETVRAVLDSLSEKKKSSP    354
                               *****************************************************
```

FIGURE 4

A.
6 WPI
B.
9 WPI
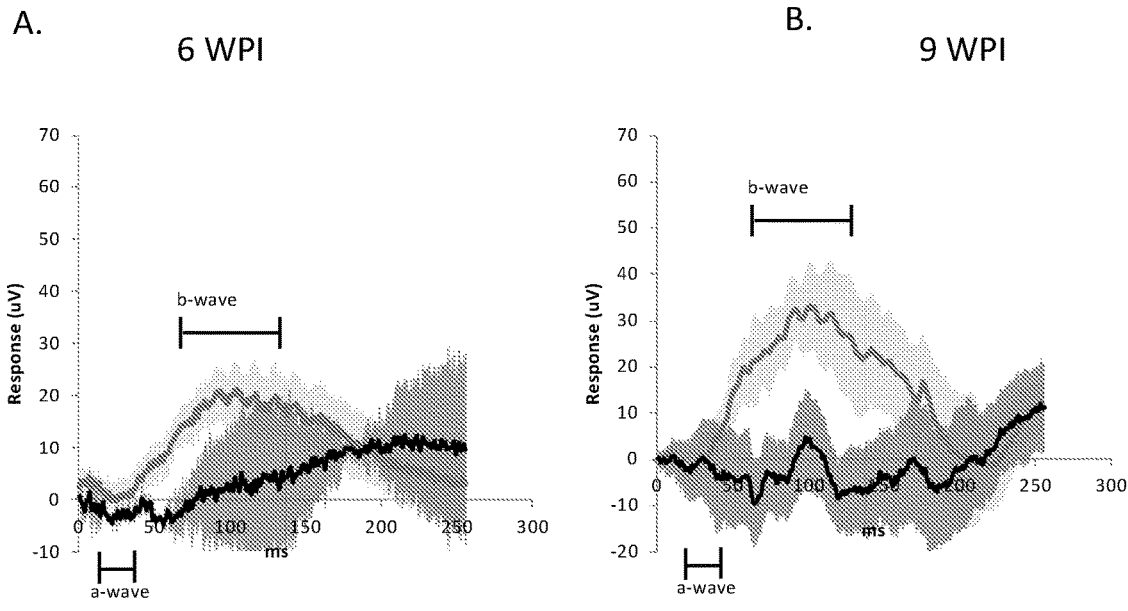
C.
15 WPI
D.
26 WPI
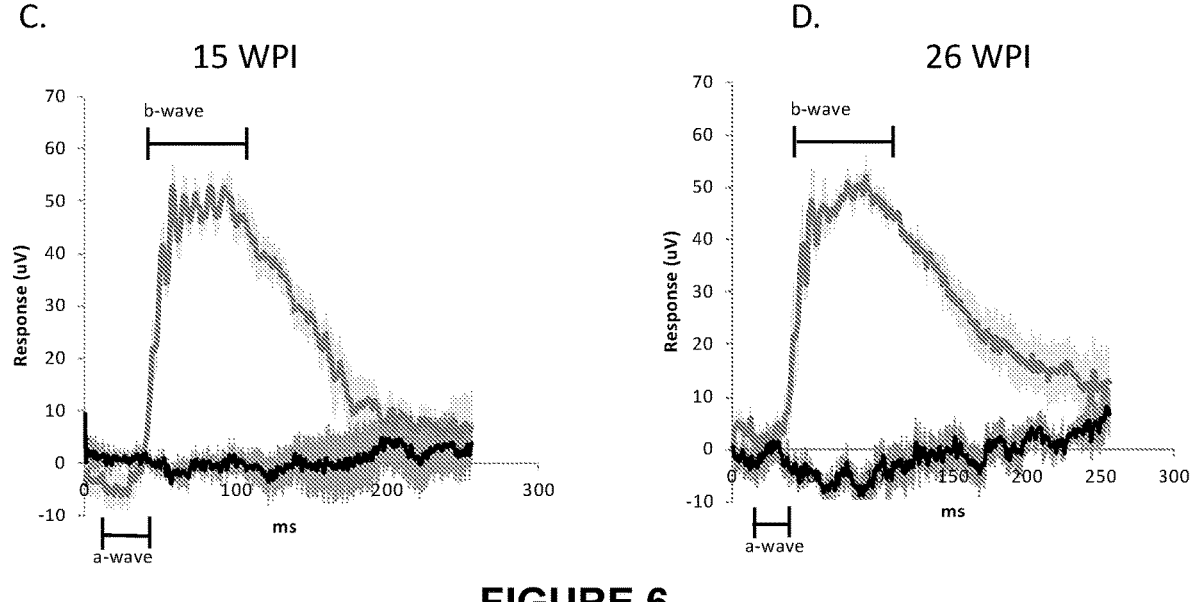
FIGURE 6

26WPI

12 WPI

OD: RHO1-2L609                      OS: no injection

OD: RHO1-2L609

OS: PBS

TREATMENT OF RETINITIS PIGMENTOSA USING IMPROVED ENGINEERED MEGANUCLEASES

CROSS-REFERENCE TO RELATED APPLICATIONS

This Application is a national stage filing under 35 U.S.C. 371 of International Patent Application Serial No. PCT/US2021/031867, filed May 11, 2021, which claims priority to U.S. Provisional Application Ser. No. 63/023,665, filed May 12, 2020, and U.S. Application Ser. No. 63/068,971, filed Aug. 21, 2020. The contents of each of these applications are incorporated herein by reference in their entireties.

FIELD OF THE INVENTION

The invention relates to the field of molecular biology and recombinant nucleic acid technology. In particular, the invention relates to recombinant meganucleases engineered to bind and cleave a recognition sequence found in a human rhodopsin gene allele. The invention further relates to the use of such recombinant meganucleases in methods for treating retinitis pigmentosa.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Nov. 8, 2022, is named P109070035US04-SEQ-EPG and is 74,582 bytes in size.

BACKGROUND OF THE INVENTION

Retinitis pigmentosa (RP) is an inherited degenerative eye disease that causes severe vision impairment due to the progressive degeneration of photoreceptor cells in the retina. RP is characterized by an initial decline in rod photoreceptor cells, resulting in compromised peripheral and dim light vision. Progressive rod degeneration is followed by abnormalities in the retinal pigment epithelium and deterioration of cone photoreceptor cells. As the disease advances, patients experience nyctalopia, progressive tunnel vision, and eventual blindness. RP affects approximately 1 in 3000 people and can occur alone or together with other systemic disorders. Currently, RP has no effective treatment.

The genetic causes of RP have been identified as autosomal dominant, autosomal recessive, X-linked, or maternally acquired. The autosomal dominant form of RP represents 30-40% of cases (Ma et al. (2105), *Scientific Reports*. 18(5:9236):1-6) and has been associated with mutations in genes expressed in rod photoreceptor cells and the retinal pigment epithelium. The human rhodopsin gene (RHO) was the first gene shown to contribute to the pathogenesis of autosomal dominant RP and remains the most common gene associated with this form of the disease (McWilliam et al. (1989) *Genomics*. 5:619-622; Dryja et al. (1990) *Nature*. 343:364-366; Farrar et al. (1990) EMBO *Journal*. 21:857-864). Indeed, RHO mutations are associated with 30-40% of autosomal dominant RP cases worldwide and are observed in approximately 26.5% of cases in the United States (Illing et al. (2002) *Journal of Bio. Chem.* 277(37):34150-34160).

Rhodopsin is an essential photopigment expressed in retinal rod photoreceptor cells that is responsible for conversion of light stimuli into electrical signals in the first step of phototransduction. Rhodopsin is expressed as a light-sensitive G-protein-coupled receptor that consists of an opsin protein moiety bound to an 11-cis-retinal chromophore and represents the main component of the disk membranes of rod photoreceptor cell outer segments.

The first RHO mutation shown to contribute to autosomal dominant RP was a C to A mutation at position 68 of the RHO gene coding sequence, which confers a proline to histidine substitution at position 23 (P23H) of the encoded protein. This mutation is referred to herein as the "RHO P23H mutation," and a RHO allele comprising the mutation is referred to herein as a "mutant RHO P23H allele." The RHO P23H mutation is the most frequently reported RHO mutation in autosomal dominant RP cases in North America (Mao et al. (2011) *Human Gene Therapy*. 22:567-575), and patients having a single mutant RHO P23H allele can develop RP despite the presence of a functional wild-type RHO allele.

Rhodopsin proteins that contain the P23H substitution fold improperly, accumulate in the endoplasmic reticulum of rod photoreceptor cells, and do not reconstitute with the 11-cis-retinal chromophore. In many cases of autosomal dominant RP, misfolded P23H rhodopsin contributes to rod photoreceptor cell degeneration and death. Accumulated P23H rhodopsin undergoes proteasomal and lysosomal degradation and has been shown to stimulate the ER-associated unfolded protein response, which can induce ER stress and cellular apoptosis (Lin et al. (2007), *Science*. 318:944-949; Gorbatyuk et al. (2010) *PNAS U.S.A.* 107(13):5961-5966). Misfolding of P23H rhodopsin may also contribute to cell death by interfering with the transport or function of wild-type rhodopsin (Illing et al., 2002, Lin et al., 2007). Furthermore, P23H rhodopsin has been shown to exhibit delayed dephosphorylation, and cell death may result from abnormal cytosolic $Ca^{2+}$ levels (Saito et al. (2008) *Clin. Opthamol.* 2:821-828).

Multiple strategies have been pursued to treat autosomal dominant RP, including nutritional therapies, pharmaceuticals, and gene therapy. Gene therapy approaches have adopted either an indirect or a direct strategy for treating autosomal dominant RP. Indirect approaches have aimed to promote the survival of rod photoreceptor cells without directly affecting the expression of pathogenic mutant proteins. For example, gene therapy has been used to introduce neurotrophic factors, such as GDNF, and anti-apoptotic proteins, such as XIAP, in retinal cells in order to inhibit apoptosis in rod photoreceptor cells.

By contrast, direct approaches in gene therapy have sought to modulate the levels of proteins that directly contribute to the pathogenesis of autosomal dominant RP. In the context of RHO-associated autosomal dominant RP, one strategy has been to enhance the proteasomal degradation of P23H rhodopsin, though no significant success has been made in animal models. Another strategy has utilized targeted RNA-based therapy to silence a mutant RHO allele while maintaining expression of the functional wild-type allele. Such approaches have used ribozymes and RNA interference (RNAi) to target specific mRNA transcripts produced by a mutant RHO P23H transgene in rats.

Further strategies have pursued a "suppression and replacement" approach by non-specifically silencing both the wild-type RHO allele and the mutant RHO allele, while concurrently delivering a replacement copy of wild-type RHO to express the wild-type protein. For example, O'Reilly et al. utilized adeno-associated virus (AAV) vectors to deliver and express short hairpin RNAs designed to target and suppress both the wild-type and mutant RHO alleles in heterozygous Pro23His$^{+/-}$ mice, while also delivering and expressing a RHO replacement gene (O'Reilly et al. (2007) *Amer. J. of Human Genetics.* 81:127-135). Palfi et al. similarly demonstrated the use of AAV vectors to deliver a RHO replacement gene to Rho$^{-/-}$ knockout mice (Palfi et al. (2010) *Human Gene Therapy.* 21:311-323). However, in such approaches, toxicity and off-target effects may be induced if RHO replacement levels are too high. Furthermore, off-target effects of RNAi approaches are a known complication, and it has been shown that siRNAs greater than 21 base pairs in length can induce retinal degeneration in animal models (Kleinman et al. (2012) *Mol. Ther.* 20(1): 101-108).

The present invention provides a recombinant meganuclease that is engineered to bind and cleave the P23H recognition sequence (SEQ ID NO:7), which is present in the mutant RHO P23H allele but not in the wild-type RHO allele. The present invention further provides the use of such a recombinant meganuclease in a method for treating RP, preferably autosomal dominant RP, wherein the mutant RHO P23H allele is preferentially targeted and cleaved. In this manner, expression of P23H rhodopsin is suppressed due to NHEJ at the meganuclease cleavage site, while the functional wild-type RHO allele remains intact to express wild-type rhodopsin in rod photoreceptor cells of the retina.

Thus, the invention requires the use of site-specific, rare-cutting, homing endonucleases (also called "meganucleases") that are engineered to recognize specific DNA sequences in a locus of interest. Homing endonucleases are a group of naturally-occurring nucleases which recognize 15-40 base pair cleavage sites commonly found in the genomes of plants and fungi. They are frequently associated with parasitic DNA elements, such as group 1 self-splicing introns and inteins. They naturally promote homologous recombination or gene insertion at specific locations in the host genome by producing a double-stranded break in the chromosome, which recruits the cellular DNA-repair machinery (Stoddard (2006), *Q. Rev. Biophys.* 38:49-95). Homing endonucleases are commonly grouped into four families: the LAGLIDADG (SEQ ID NO:2) family, the GIY-YIG family, the His-Cys box family and the HNH family. These families are characterized by structural motifs, which affect catalytic activity and recognition sequence. For instance, members of the LAGLIDADG (SEQ ID NO:2) family are characterized by having either one or two copies of the conserved LAGLIDADG (SEQ ID NO:2) motif (Chevalier et al. (2001), *Nucleic Acids Res.* 29(18): 3757-3774). The LAGLIDADG (SEQ ID NO:2) homing endonucleases with a single copy of the LAGLIDADG (SEQ ID NO:2) motif form homodimers, whereas members with two copies of the LAGLIDADG (SEQ ID NO:2) motif are found as monomers.

Methods for producing engineered, site-specific recombinant meganucleases are known in the art. I-CreI (SEQ ID NO:1) is a member of the LAGLIDADG (SEQ ID NO:2) family of homing endonucleases which recognizes and cuts a 22 base pair recognition sequence in the chloroplast chromosome of the algae *Chlamydomonas reinhardtii.* Genetic selection techniques have been used to modify the wild-type I-CreI cleavage site preference (Sussman et al. (2004), *J. Mol. Biol.* 342: 31-41; Chames et al. (2005), *Nucleic Acids Res.* 33: e178; Seligman et al. (2002), *Nucleic Acids Res.* 30: 3870-9, Arnould et al. (2006), *J. Mol. Biol.* 355: 443-58). More recently, a method of rationally-designing mono-LAGLIDADG (SEQ ID NO:93) homing endonucleases was described which is capable of comprehensively redesigning I-CreI and other homing endonucleases to target widely-divergent DNA sites, including sites in mammalian, yeast, plant, bacterial, and viral genomes (WO 2007/047859).

As first described in WO 2009/059195, I-CreI and its engineered derivatives are normally dimeric but can be fused into a single polypeptide using a short peptide linker that joins the C-terminus of a first subunit to the N-terminus of a second subunit (Li, et al. (2009) *Nucleic Acids Res.* 37:1650-62; Grizot, et al. (2009) *Nucleic Acids Res.* 37:5405-19.) Thus, a functional "single-chain" meganuclease can be expressed from a single transcript. Such engineered meganucleases exhibit an extremely low frequency of off-target cutting. By delivering a gene encoding a single-chain meganuclease to retinal cells, and preferably to rod photoreceptor cells, it is possible to specifically and preferentially target, cleave, and inactivate the mutant RHO P23H allele, thus suppressing expression of P23H rhodopsin.

The use of engineered nucleases for cleaving DNA targets in the human RHO gene was previously disclosed in U.S. application Ser. No. 13/367,216 (the '216 application). The authors of the '216 application disclosed several approaches for targeting and modulating the expression of mutant RHO alleles. The authors discussed the use of engineered DNA binding domains, such as zinc finger proteins (ZFP) and TAL effector (TALE) proteins, as repressors of RHO gene expression. The authors also described fusion proteins comprising a ZFP or TALE binding domain operably linked to a regulatory or functional domain. The functional domain could be a transcriptional repressor domain that downregulates RHO gene expression. Alternatively, the functional domain could be a transcriptional activation domain. Further, the functional domain could comprise a nuclease domain. When linked to a nuclease domain, the resulting fusion proteins include zinc finger nucleases (ZFNs) and TALE-nucleases (TALENs).

In addition to ZFNs and TALENs, the '216 application discusses the use of meganucleases for targeting and inhibiting the expression of wild-type and/or mutant RHO alleles. The '216 application describes the use of such meganucleases for disrupting RHO gene expression via non-homologous end joining (NHEJ) at the recognition sequence, and for introducing a replacement wild-type RHO gene sequence to express the wild-type rhodopsin protein. However, the recognition sequences in the RHO gene that are identified by the '216 application are limited to three pairs of ZFN target sites found in the wild-type RHO gene (see, '216 application at Table 2).

The use of engineered meganucleases for cleaving DNA targets in the RHO gene was also disclosed in U.S. application Ser. No. 13/697,614 (the '614 application). The authors of the '614 application disclosed meganucleases designed to target various regions of the RHO gene for use in one of three gene therapy strategies. The first strategy is gene correction, wherein the engineered meganucleases are specific for a recognition sequence in the vicinity of a specified mutation, induce a double-strand break at that site, and rely on homologous recombination of a corresponding non-mutant allelic sequence into the genome. The second strategy disclosed in the '614 application is exon knock-in, wherein a functional protein is reconstituted by using a meganuclease to introduce a synthetic wild-type coding sequence into the genome while preventing the expression of the pathologic mutation. The third strategy disclosed in the '614 application is gene inactivation by mutagenesis, which relies a meganuclease to induce a double-strand break at a target recognition sequence in the genome, and NHEJ at the cleavage site to induce a mutation.

The present invention improves upon the methods disclosed in the '216 application and the '614 application. The present inventors identified a 22 base pair meganuclease recognition sequence (SEQ ID NO:7), referred to herein as the "P23H recognition sequence," that is present in the mutant RHO P23H allele. The P23H recognition sequence spans nucleotides 49-70 of the mutant RHO P23H coding sequence (SEQ ID NO:4), and includes the C68A mutation (see, FIG. 1A). As such, the P23H recognition sequence is not present in the wild-type RHO allele, which comprises C at position 68.

Although naturally-occurring meganucleases do not target the P23H recognition sequence, the present invention provides recombinant meganucleases engineered to bind and cleave this recognition sequence. Thus, in some aspects, the recombinant meganucleases of the invention bind and cleave the P23H recognition sequence, leading to mutagenesis at the cut site and inactivation of the mutant RHO P23H allele. In further aspects, recombinant meganucleases of the invention preferentially bind and cleave the P23H recognition sequence relative to the corresponding recognition sequence present in the wild-type RHO allele (SEQ ID NO: 9). As a result, only the functional wild-type RHO allele remains intact to express wild-type rhodopsin in rod photoreceptor cells of the retina.

By contrast, neither the '216 application nor the '614 application identified the P23H recognition sequence, nor did they disclose recombinant meganucleases capable of cleaving the P23H recognition sequence. Moreover, neither the '216 application nor the '614 application disclose any recognition sequences that, when cleaved, could specifically inactivate the mutant RHO P23H allele but not the wild-type RHO allele. Although one pair of ZFN recognition sequences described by the '216 application overlap nucleotides 49-70 of the RHO coding sequence (see, SEQ ID NO:24 of the '216 application), the ZFN recognition sequences include the C68 nucleotide of the wild-type RHO allele. Therefore, the ZFNs of the '216 application could not target the mutant RHO P23H allele, which comprises the C68A mutation. The RHO gene recognition sequences taught by the '614 application (e.g., Rho34, Rho_7, Rho36, Rho31, and their derived targets) are positioned at regions of the RHO gene which could be found on either the wild-type RHO allele or the mutant RHO P23H allele. Thus, the '614 application also does not describe any recombinant meganucleases that can specifically target the RHO P23H allele.

Applicants previously disclosed in PCT International Patent Application No. PCT/US2016/050809 ('809 application) a number of first-generation engineered meganucleases having specificity for a recognition sequence present in the RHO gene, including the RHO P23H recognition sequence (SEQ ID NO: 7).

The present invention improves upon the engineered meganucleases previously described in the '809 application in a number of aspects. When generating an endonuclease for therapeutic administration to a patient, it is critical that on-target specificity is enhanced while reducing or eliminating off-target cutting within the target cell genome. Here, Applicants have developed second-generation engineered meganucleases that target the RHO 1-2 recognition sequence (SED ID NO: 7). The meganucleases of the present invention have novel and unique sequences, which were generated through extensive experimentation. Additionally, these second-generation meganucleases have a significant reduction in off-target cutting in the host cell genome. Thus, the meganucleases of the invention advance the art that is necessary for development of a clinical product that preferentially targets and inactivates the RHO P23H allele for treatment of RP.

SUMMARY OF THE INVENTION

The present invention provides second-generation engineered meganucleases engineered to bind and cleave the P23H recognition sequence set forth in SEQ ID NO: 7. The present invention further provides a method comprising the delivery of an engineered meganuclease, or a polynucleotide comprising a nucleic acid sequence encoding an engineered meganuclease, to the cells of a patient having RP, such that the engineered meganuclease preferentially targets and cleaves the RHO P23H recognition sequence (SEQ ID NO: 7) present on the mutant RHO P23H allele. Cleavage at the recognition sequence by an engineered meganuclease disclosed herein can modify expression of a RHO P23H allele due to non-homologous end joining (NHEJ) at the cleavage site. NHEJ can result in insertions, deletions, or result in a frameshift mutation that can interfere with gene expression. Alternatively, a sequence of interest can be introduced into a RHO P23H gene allele via homologous recombination. In some aspects described herein, NHEJ occurs at the cleavage site, resulting in mutagenesis and disruption of the mutant RHO P23H allele, while the functional wild-type RHO allele remains intact to express wild-type rhodopsin in rod photoreceptor cells of the retina. Preferential inactivation of the mutant RHO P23H allele, and disruption of P23H rhodopsin expression, is expected to delay, prevent, or reverse the progression of RP in patients.

Thus, in one aspect, the invention provides an engineered meganuclease that binds and cleaves a recognition sequence comprising SEQ ID NO: 7 in a rhodopsin (RHO) gene, wherein the engineered meganuclease comprises a first subunit and a second subunit, wherein the first subunit binds to a first recognition half-site of the recognition sequence and comprises a first hypervariable (HVR1) region, and wherein the second subunit binds to a second recognition half-site of the recognition sequence and comprises a second hypervariable (HVR2) region.

In another aspect, the invention provides an engineered meganuclease that binds and cleaves a recognition sequence comprising SEQ ID NO: 7 in a rhodopsin (RHO) gene, wherein the engineered meganuclease comprises a first subunit and a second subunit, wherein the first subunit binds to a first recognition half-site of the recognition sequence and comprises a first hypervariable (HVR1) region, and wherein the second subunit binds to a second recognition half-site of the recognition sequence and comprises a second hypervariable (HVR2) region, wherein the HVR2 has at least 93% sequence identity to an amino acid sequence corresponding to residues 24-79 of any one of SEQ ID NOs: 11-14. In some embodiments, the HVR1 region comprises an amino acid sequence having at least 80%, at least 85%, at least 90%, at least 91%, at least 92%, at least 93%, at least 94%, at least 95%, at least 96%, at least 97%, at least 98%, at least 99%, or more or more sequence identity to an amino acid sequence corresponding to residues 215-270 of any one of SEQ ID NOs: 11-14. In certain embodiments, the HVR1 region comprises an amino acid sequence corresponding to residues 215-270 of any one of SEQ ID NOs: 11-14 with up to 1, 2, 3, 4, 5, 6, 7, 8, 9, 10, or 11 amino acid substitutions. In some embodiments, the HVR1 region comprises one or more residues corresponding to residues 215, 217, 219, 221, 223, 224, 229, 231, 233, 235, 237, 259, 261, 266, and 268 of any one of SEQ ID NOs: 11-14. In some embodiments, the HVR1 region comprises residues corresponding to residues 215, 217, 219, 221, 223, 224, 229, 231, 233, 235, 237, 259, 261, 266, and 268 of any one of SEQ ID NOs: 11-14.

In some embodiments, the HVR1 region comprises Y, R, K, or D at a residue corresponding to residue 257 of any one of SEQ ID NOs: 11-14.

In some embodiments, the HVR1 region comprises residues 215-270 of any one of SEQ ID NOs: 11-14.

In some embodiments, the first subunit comprises an amino acid sequence having at least 80%, at least 85%, at least 90%, at least 91%, at least 92%, at least 93%, at least 94%, at least 95%, at least 96%, at least 97%, at least 98%, at least 99%, or more sequence identity to residues 198-344 of any one of SEQ ID NOs: 11-14. In particular embodiments, the first subunit comprises an amino acid sequence corresponding to residues 198-344 of any one of SEQ ID NOs: 11-14 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions.

In some embodiments, the first subunit comprises G, S, or A at a residue corresponding to residue 210 of any one of SEQ ID NOs: 11-14.

In some embodiments, the first subunit comprises E, Q, or K at a residue corresponding to residue 271 of any one of SEQ ID NOs: 11-14.

In particular embodiments, the first subunit comprises residues 198-344 of any one of SEQ ID NOs: 11-14.

In some embodiments, the HVR2 region comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to an amino acid sequence corresponding to residues sequence identity to an amino acid sequence corresponding to residues 24-79 of any one of SEQ ID NOs: 11-14. In certain embodiments, the HVR2 region comprises an amino acid sequence corresponding to residues 24-79 of any one of SEQ ID NOs: 11-14 with up to 1, 2, 3, 4, 5, 6, 7, 8, 9, 10, or 11 amino acid substitutions In some embodiments, the HVR2 region comprises one or more residues corresponding to residues 24, 26, 28, 30, 32, 33, 38, 40, 42, 44, 46, 68, 70, 75, and 77 of any one of SEQ ID NOs: 11-14. In some embodiments, the HVR2 region comprises residues corresponding to residues 24, 26, 28, 30, 32, 33, 38, 40, 42, 44, 46, 68, 70, 75, and 77 of any one of SEQ ID NOs: 11-14. In some embodiments, the HVR2 region comprises residues corresponding to residues 29 and 39 of any one of SEQ ID NOs: 11-14.

In some embodiments, the HVR2 region comprises Y, R, K, or D at a residue corresponding to residue 66 of any one of SEQ ID NOs: 11-14.

In some embodiments, the HVR2 region comprises residues 24-79 of any one of SEQ ID NOs: 11-14.

In some embodiments, the second subunit comprises an amino acid sequence having at least at least 80%, at least 85%, at least 90%, at least 91%, at least 92%, at least 93%, at least 94%, at least 95%, at least 96%, at least 97%, at least 98%, at least 99%, or more sequence identity to residues 7-153 of any one of SEQ ID NOs: 11-14. In particular embodiments, the second subunit comprises an amino acid sequence corresponding to residues 7-153 of any one of SEQ ID NOs: 11-14 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions.

In some embodiments, the second subunit comprises G, S, or A at a residue corresponding to residue 19 of any one of SEQ ID NOs: 11-14.

In some embodiments, the second subunit comprises E, Q, or K at a residue corresponding to residue 80 of any one of SEQ ID NOs: 11-14.

In particular embodiments, the second subunit comprises residues 7-153 of any one of SEQ ID NOs: 11-14.

In some embodiments, the engineered meganuclease is a single-chain meganuclease comprising a linker, wherein the linker covalently joins the first subunit and the second subunit.

In some embodiments, the engineered meganuclease comprises an amino acid sequence having at least 80%, at least 85%, at least 90%, at least 91%, at least 92%, at least 93%, at least 94%, at least 95%, at least 96%, at least 97%, at least 98%, or at least 99% or more sequence identity to any one of SEQ ID NOs: 11-14.

In some embodiments, the engineered meganuclease comprises the amino acid sequence of any one of SEQ ID NOs: 11-14.

Another aspect described herein is an engineered meganuclease that binds and cleaves a recognition sequence comprising SEQ ID NO: 7 in a RHO gene, wherein the engineered meganuclease comprises a first subunit and a second subunit, wherein the first subunit binds to a first recognition half-site of the recognition sequence and comprises: (a) an amino acid sequence having at least 90%, 91%, 92%, 93%, 94%, 95%, 96%, 97%, 98%, 99% or more sequence identity to residues 198-344 of any one of SEQ ID NOs: 11-14; and (b) a first hypervariable (HVR1) region, wherein the HVR1 region has at least 90%, 91%, 92%, 93%, 94%, 95%, 96%, 97%, 98%, 99% or more sequence identity to an amino acid sequence corresponding to residues 215-270 of any one of SEQ ID NOs: 11-14;

and wherein the second subunit binds to a second recognition half-site of the recognition sequence and comprises: (i) an amino acid sequence having at least 90%, 91%, 92%, 93%, 94%, 95%, 96%, 97%, 98%, 99% or more sequence identity to residues 7-153 of any one of SEQ ID NOs: 11-14; and (ii) a second hypervariable (HVR2) region, wherein the HVR2 region has at least 90%, 91%, 92%, 93%, 94%, 95%, 96%, 97%, 98%, 99% or more sequence identity to an amino acid sequence corresponding to residues 24-79 of any one of SEQ ID NOs: 11-14.

In some embodiments, the engineered meganuclease is encoded by a nucleic acid sequence having at least 80%, at least 85%, at least 90%, at least 91%, at least 92%, at least 93%, at least 94%, at least 95%, at least 96%, at least 97%, at least 98%, at least 99%, or more, sequence identity to a nucleic acid sequence of any one of SEQ ID NOs: 25-28. In some embodiments, the engineered meganuclease is encoded by a nucleic acid sequence of any one of SEQ ID NOs: 25-28.

In some embodiments, the engineered meganuclease comprises a nuclear localization signal (NLS). In certain embodiments, the NLS is positioned at the N-terminus of the engineered meganuclease. In certain embodiments, the NLS is positioned at the C-terminus of the engineered meganuclease. In certain embodiments, the engineered meganuclease comprises a first NLS at the N-terminus and a second NLS at the C-terminus. In some such embodiments, the first NLS and the second NLS are identical. In other such embodiments, the first NLS and the second NLS are not identical. In some embodiments, the NLS comprises an amino acid sequence having at least 90%, at least 91%, at least 92%, at least 93%, at least 94%, at least 95%, at least 96%, at least 97%, at least 98%, at least 99%, or more, sequence identity to SEQ ID NO: 29. In particular embodiments, the NLS comprises an amino acid sequence of SEQ ID NO: 29.

In another aspect, the invention provides a polynucleotide comprising a nucleic acid sequence encoding an engineered meganuclease described herein. In some embodiments, the polynucleotide is an mRNA.

In another aspect, the invention provides a recombinant DNA construct comprising a polynucleotide comprising a nucleic acid sequence encoding an engineered meganuclease described herein. In some embodiments, the recombinant DNA construct encodes a recombinant virus comprising the polynucleotide comprising the nucleic acid sequence encoding the engineered meganuclease. In some embodiments, the recombinant virus is a recombinant adenovirus, a recombinant lentivirus, a recombinant retrovirus, or a recombinant adeno-associated virus (AAV). In certain embodiments, the recombinant virus is a recombinant AAV.

In some embodiments of the recombinant DNA construct, the recombinant AAV has an AAV5 serotype. In some embodiments, the recombinant AAV has an AAV2 serotype. In some embodiments, the nucleic acid sequence comprises a promoter sequence operably linked to the nucleic acid sequence encoding the engineered meganuclease. In some embodiments, the promoter is an eye specific promoter. In some embodiments, the promoter is a retina cell-specific promoter. In some embodiments, the promoter is a rod photoreceptor cell-specific promoter. In some embodiments, the promoter is a human G-protein-coupled receptor protein kinase 1 (GRK1) promoter.

In another aspect, the invention provides a recombinant virus comprising a nucleic acid sequence encoding an engineered meganuclease described herein. In some embodiments, the recombinant virus is a recombinant adenovirus, a recombinant lentivirus, a recombinant retrovirus, or a recombinant AAV. In particular embodiments, the recombinant virus is a recombinant AAV.

In another aspect, the invention provides a lipid nanoparticle composition comprising lipid nanoparticles comprising a polynucleotide, wherein the polynucleotide comprises a nucleic acid sequence encoding an engineered meganuclease described herein. In some embodiments, the polynucleotide is an mRNA described herein.

In another aspect, the invention provides a genetically-modified eukaryotic cell comprising a polynucleotide described herein. In some embodiments, the genetically-modified eukaryotic cell is a genetically-modified mammalian cell. In some embodiments, the genetically-modified eukaryotic cell is a genetically-modified human cell.

In some embodiments of the recombinant virus, the recombinant AAV has an AAV5 serotype. In some embodiments, the recombinant AAV has an AAV2 serotype. In some embodiments, the nucleic acid sequence comprises a promoter sequence operably linked to the nucleic acid sequence encoding the engineered meganuclease. In some embodiments, the promoter is an eye specific promoter. In some embodiments, the promoter is a retina cell-specific promoter. In some embodiments, the promoter is a rod photoreceptor cell-specific promoter. In some embodiments, the promoter is a human G-protein-coupled receptor protein kinase 1 (GRK1) promoter.

In another aspect, the invention provides a method for producing a genetically-modified eukaryotic cell having a disrupted target sequence in a chromosome of the genetically-modified eukaryotic cell, the method comprising: introducing into a eukaryotic cell a polynucleotide comprising a nucleic acid sequence encoding an engineered meganuclease described herein wherein the engineered meganuclease is expressed in the eukaryotic cell; wherein the engineered meganuclease produces a cleavage site in the chromosome at a recognition sequence comprising SEQ ID NO: 7 and generates a modified RHO gene. In some embodiments, the cleavage site is repaired by non-homologous end joining, and wherein the modified RHO gene comprises an insertion or deletion that disrupts expression of the encoded RHO protein.

In another aspect, the invention provides a method for producing a genetically-modified eukaryotic cell having a disrupted target sequence in a chromosome of the genetically-modified eukaryotic cell, the method comprising introducing into a eukaryotic cell a polynucleotide comprising a nucleic acid sequence encoding any engineered meganuclease of the invention, wherein the engineered meganuclease is expressed in the eukaryotic cell; wherein the engineered meganuclease produces a cleavage site in the chromosome at a recognition sequence comprising SEQ ID NO: 7; and wherein the target sequence is modified by non-homologous end-joining at the cleavage site.

In some embodiments, the method produces a modified RHO gene that does not encode a full-length endogenous RHO polypeptide. In some embodiments, the genetically-modified eukaryotic cell comprises the recognition sequence in a RHO P23H gene allele. In some embodiments, the RHO P23H gene allele comprises SEQ ID NO: 4. In some embodiments, the engineered meganuclease does not produce a cleavage site within SEQ ID NO: 9. In some embodiments, the method is effective to reduce levels of an endogenous RHO P23H polypeptide in the cell by at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80% relative to a reference level. In some embodiments, the RHO P23H polypeptide levels are reduced by about 1-5%, 5%-10%, 10%-20%, 20%-30%, 30%-40%, 40%-50%, 50%-60%, 60%-70%, or 70%-80%, relative to a reference level.

In some embodiments, the eukaryotic cell is a mammalian cell. In some embodiments, the mammalian cell is selected from a human cell, a non-human primate cell, a mouse cell, or a pig cell. In some embodiments, the mammalian cell is a cell within the eye. In some embodiments, the mammalian cell is a rod photoreceptor cell.

In some embodiments, the polynucleotide is introduced into the eukaryotic cell by an mRNA or a recombinant virus. In one such embodiment, the mRNA is packaged within a lipid nanoparticle. In another such an embodiment, the recombinant virus is a recombinant adenovirus, a recombinant lentivirus, a recombinant retrovirus, or a recombinant AAV. In a particular embodiment, the recombinant virus is a recombinant AAV.

In another aspect, the invention provides a method for producing a genetically-modified eukaryotic cell having a disrupted target sequence in a chromosome of the eukaryotic cell, the method comprising: introducing into a eukaryotic cell an engineered meganuclease described herein; wherein the engineered meganuclease produces a cleavage site in the chromosome at a recognition sequence comprising SEQ ID NO: 7. In some embodiments, the cleavage site is repaired by non-homologous end joining, and wherein the modified RHO gene comprises an insertion or deletion that disrupts expression of the encoded RHO protein.

In another aspect, the invention provides a method for producing a genetically-modified eukaryotic cell having a disrupted target sequence in a chromosome of the eukaryotic cell, the method comprising: introducing into a eukaryotic cell an engineered meganuclease described herein; wherein the engineered meganuclease produces a cleavage site in the chromosome at a recognition sequence comprising SEQ ID NO: 7, and wherein the target sequence is disrupted by non-homologous end-joining at the cleavage site.

In some embodiments, the method produces a modified RHO gene that does not encode a full-length endogenous RHO polypeptide. In some embodiments, the genetically-modified eukaryotic cell comprises the recognition sequence in a RHO P23H gene allele. In some embodiments, the RHO P23H gene allele comprises SEQ ID NO: 4. In some embodiments, the engineered meganuclease does not produce a cleavage site within SEQ ID NO: 9. In some embodiments, the method is effective to reduce levels of an endogenous RHO P23H polypeptide in the cell by at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80% relative to a reference level. In some embodiments, the RHO P23H polypeptide levels are reduced by about 1-5%, 5%-10%, 10%-20%, 20%-30%, 30%-40%, 40%-50%, 50%-60%, 60%-70%, or 70%-80%, relative to a reference level.

In some embodiments, the eukaryotic cell is a mammalian cell. In some embodiments, the mammalian cell is selected from a human cell, a non-human primate cell, a mouse cell, or a pig cell. In some embodiments, the mammalian cell is a cell within the eye. In some embodiments, the mammalian cell is a rod photoreceptor cell.

In another aspect, the invention provides a method for producing a genetically-modified eukaryotic cell comprising an exogenous sequence of interest inserted into a chromosome of the genetically-modified eukaryotic cell, the method comprising introducing into a eukaryotic cell one or more polynucleotides including: a first nucleic acid sequence encoding an engineered meganuclease described herein, wherein the engineered meganuclease is expressed in the eukaryotic cell; and a second nucleic acid sequence including the sequence of interest; wherein the engineered meganuclease produces a cleavage site in the chromosome at a recognition sequence comprising SEQ ID NO: 7; and wherein the sequence of interest is inserted into the chromosome at the cleavage site.

In some embodiments, the second nucleic acid sequence further comprises nucleic acid sequences homologous to nucleic acid sequences flanking the cleavage site and the sequence of interest is inserted at the cleavage site by homologous recombination.

In some embodiments, the method produces a modified RHO gene that does not encode a full-length endogenous RHO polypeptide. In some embodiments, the genetically-modified eukaryotic cell comprises the recognition sequence in a RHO P23H gene allele. In some embodiments, the RHO P23H gene allele comprises SEQ ID NO: 4. In some embodiments, the engineered meganuclease does not produce a cleavage site within SEQ ID NO: 9. In some embodiments, the method is effective to reduce levels of an endogenous RHO P23H polypeptide in the cell by at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80% relative to a reference level. In some embodiments, the RHO P23H polypeptide levels are reduced by about 1-5%, 5%-10%, 10%-20%, 20%-30%, 30%-40%, 40%-50%, 50%-60%, 60%-70%, or 70%-80%, relative to a reference level.

In some embodiments, the eukaryotic cell is a mammalian cell. In some embodiments, the mammalian cell is selected from a human cell, a non-human primate cell, a mouse cell, or a pig cell. In some embodiments, the mammalian cell is a cell within the eye. In some embodiments, the mammalian cell is a rod photoreceptor cell.

In some embodiments, the polynucleotide is introduced into the eukaryotic cell by an mRNA or a recombinant virus. In one such embodiment, the mRNA is packaged within a lipid nanoparticle. In another such an embodiment, the recombinant virus is a recombinant adenovirus, a recombinant lentivirus, a recombinant retrovirus, or a recombinant AAV. In a particular embodiment, the recombinant virus is a recombinant AAV.

In another aspect, the invention provides a method for producing a genetically-modified eukaryotic cell comprising an exogenous sequence of interest inserted into a chromosome of the eukaryotic cell, the method comprising: introducing an engineered meganuclease described herein into a eukaryotic cell; and introducing a polynucleotide comprising a nucleic acid sequence including the sequence of interest into the eukaryotic cell; wherein the engineered meganuclease produces a cleavage site in the chromosome at a recognition sequence comprising SEQ ID NO: 7; and wherein the sequence of interest is inserted into the chromosome at the cleavage site.

In some embodiments, the polynucleotide further comprises nucleic acid sequences homologous to nucleic acid sequences flanking the cleavage site and the sequence of interest is inserted at the cleavage site by homologous recombination.

In some embodiments, the method produces a modified RHO gene that does not encode a full-length endogenous RHO polypeptide. In some embodiments, the genetically-modified eukaryotic cell comprises the recognition sequence in a RHO P23H gene allele. In some embodiments, the RHO P23H gene allele comprises SEQ ID NO: 4. In some embodiments, the engineered meganuclease does not produce a cleavage site within SEQ ID NO: 9. In some embodiments, the method is effective to reduce levels of an endogenous RHO P23H polypeptide in the cell by at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80% relative to a reference level. In some embodiments, the RHO P23H polypeptide levels are reduced by about 1-5%, 5%-10%, 10%-20%, 20%-30%, 30%-40%, 40%-50%, 50%-60%, 60%-70%, or 70%-80%, relative to a reference level.

In some embodiments, the eukaryotic cell is a mammalian cell. In some embodiments, the mammalian cell is selected from a human cell, a non-human primate cell, a mouse cell, or a pig cell. In some embodiments, the mammalian cell is a cell within the eye. In some embodiments, the mammalian cell is a rod photoreceptor cell.

In some embodiments, the nucleic acid polynucleotide is introduced into the eukaryotic cell by an mRNA or a recombinant virus. In one such embodiment, the mRNA is packaged within a lipid nanoparticle. In another such an embodiment, the recombinant virus is a recombinant adenovirus, a recombinant lentivirus, a recombinant retrovirus, or a recombinant AAV. In a particular embodiment, the recombinant virus is a recombinant AAV.

In another aspect, the invention provides a genetically-modified eukaryotic cell prepared by any method of the invention.

In another aspect, the invention provides, a genetically-modified eukaryotic cell comprising a modified RHO gene, wherein the modified RHO gene comprises an insertion or deletion at an engineered meganuclease cleavage site within SEQ ID NO: 7, but not in SEQ ID NO: 9, and wherein the modified RHO gene does not encode a full-length endogenous RHO P23H polypeptide.

In some embodiments, the genetically-modified eukaryotic cell has reduced levels of an endogenous RHO P23H polypeptide in the cell of at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80% relative to a reference level. In some embodiments, the RHO P23H polypeptide levels are reduced by about 1-5%, 5%-10%, 10%-20%, 20%-30%, 30%-40%, 40%-50%, 50%-60%, 60%-70%, or 70%-80%, relative to a reference level.

In some embodiments, the eukaryotic cell is a mammalian cell. In some embodiments, the mammalian cell is selected from a human cell, a non-human primate cell, a mouse cell, or a pig cell. In some embodiments, the mammalian cell is a cell within the eye. In some embodiments, the mammalian cell is a rod photoreceptor cell.

In another aspect, the invention provides a pharmaceutical composition comprising a pharmaceutically-acceptable carrier and an engineered meganuclease described herein, or a polynucleotide comprising a nucleic acid sequence encoding an engineered meganuclease described herein.

In some embodiments, the polynucleotide is an mRNA. In one such embodiment, the mRNA is packaged within a lipid nanoparticle.

In some embodiments of the pharmaceutical composition, the pharmaceutical composition comprises a recombinant DNA construct comprising the polynucleotide.

In some embodiments, the pharmaceutical composition comprises a recombinant virus comprising the polynucleotide. In some such embodiments, the recombinant virus is a recombinant adenovirus, a recombinant lentivirus, a recombinant retrovirus, or a recombinant AAV. In a particular embodiment, the recombinant virus recombinant AAV.

In some embodiments, the pharmaceutical composition is for the treatment of a subject having retinitis pigmentosa (RP).

In another aspect, the invention provides a method for treating retinitis pigmentosa in a subject, the method comprising delivering to a target cell in the subject the engineered meganuclease, or a polynucleotide comprising a nucleic acid sequence encoding the engineered meganuclease described herein.

In another aspect, the invention provides a method for treating RP in a subject, the method comprising administering to the subject: (a) a therapeutically-effective amount of a polynucleotide comprising a nucleic acid sequence encoding an engineered meganuclease described herein, wherein the polynucleotide is delivered to a target cell in the subject, wherein the engineered meganuclease is expressed in the target cell; or (b) a therapeutically-effective amount of an engineered meganuclease described herein, wherein the engineered meganuclease is delivered to a target cell in the subject; wherein the engineered meganuclease produces a cleavage site at a recognition sequence comprising SEQ ID NO: 7, wherein the method produces a modified RHO gene in the target cell. In some embodiments, the cleavage site is repaired by non-homologous end joining, such that the modified RHO gene comprises an insertion or deletion.

In some embodiments, the method is for treating autosomal dominant retinitis pigmentosa. In some embodiments, the eukaryotic cell is a mammalian cell. In some embodiments, the mammalian cell is selected from a human cell, a non-human primate cell, a mouse cell, or a pig cell. In some embodiments, the mammalian cell is a cell within the eye. In some embodiments, the mammalian cell is a rod photoreceptor cell.

In some embodiments, the polynucleotide is an mRNA. In some embodiments, the polynucleotide is DNA.

In some embodiments, the polynucleotide is encapsulated in a lipid nanoparticle and the lipid nanoparticle is delivered to the target cell in the subject.

In some embodiments, the polynucleotide is delivered to the target cell using a recombinant virus comprising the polynucleotide. In some such embodiments, the recombinant virus is a recombinant adenovirus, a recombinant lentivirus, a recombinant retrovirus, or a recombinant AAV. In a particular embodiment, the recombinant virus is a recombinant AAV.

In some embodiments, levels of a RHO P23H gene are reduced in one or more tissues of an eye of the subject relative to a reference level. In some embodiments, the levels of RHO P23H gene are reduced by about 10% to about 80% relative to a reference level. In some embodiments, the level of RHO P23H is reduced by about 10%-20%, 20%-30%, 30%-40%, 40%-50%, 50%-60%, 60%-70%, 70%-80%, or more, relative to a reference level. In some such embodiments, the level of RHO P23H is reduced by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, or more, relative to a reference level.

In another aspect, the invention provides a method for treating retinitis pigmentosa in a subject in need thereof, the method comprising administering to the subject an effective amount of the pharmaceutical composition described herein.

In some embodiments, the method is effective to reduce levels of a RHO P23H gene in the subject relative to a reference level. In some embodiments, the RHO P23H gene levels are reduced in one or more tissues of an eye of the subject relative to a reference level. In some embodiments, the RHO P23H levels are reduced by about 10% to about 80% relative to a reference level. In some embodiments, the level of RHO P23H is reduced by about 10%-20%, 20%-30%, 30%-40%, 40%-50%, 50%-60%, 60%-70%, 70%-80%, or more, relative to a reference level. In some such embodiments, the level of RHO P23H is reduced by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, or more, relative to a reference level. In some embodiments, the subject is a human subject.

In another aspect, the invention provides an engineered meganuclease described herein for use as a medicament. In some embodiments, the medicament is useful for treating a disease in a subject in need thereof, such as a subject having retinitis pigmentosa.

In another aspect, the invention provides an engineered meganuclease described herein for use in manufacturing a medicament for reducing levels of RHO P23H in a subject.

In another aspect, the invention provides a method for modifying a RHO P23H gene in a target cell in a subject, the method comprising delivering to the target cell: (a) a polynucleotide comprising a nucleic acid sequence encoding an engineered meganuclease described herein, wherein the engineered meganuclease is expressed in the target cell; or (b) an engineered meganuclease described herein; wherein the engineered meganuclease produces a cleavage site in the RHO P23H gene at a recognition sequence comprising SEQ ID NO: 7 and generates a modified RHO P23H gene in the target cell.

In some embodiments, the cleavage site is repaired by non-homologous end joining, and wherein the modified RHO P23H gene comprises an insertion or deletion that disrupts expression of the encoded RHO P23H protein. In some embodiments, the modified RHO P23H gene does not encode a full-length endogenous RHO P23H protein. In some embodiments, the expression of a full-length endogenous RHO P23H protein by the target cell is reduced compared to a control cell. In some embodiments, the expression of full-length endogenous RHO P23H protein are reduced in the subject relative to a control subject.

In some embodiments, the subject is a mammal. In some embodiments, the subject is a human. In some embodiments, the target cell is a mammalian cell. In some embodiments, the mammalian cell is selected from a human cell, a non-human primate cell, a mouse cell, or a pig cell. In some embodiments, the mammalian cell is a cell within an eye of the subject. In some embodiments, the mammalian cell is a rod photoreceptor cell.

In some embodiments, the polynucleotide is an mRNA. In some embodiments, the polynucleotide is an mRNA described herein. In some embodiments, the polynucleotide is a recombinant DNA construct described herein. In some embodiments, the polynucleotide is a recombinant DNA construct described herein. In some embodiments, the polynucleotide is delivered to the target cell by a lipid nanoparticle. In some embodiments, the polynucleotide is delivered to the target cell by a recombinant virus. In some embodiments, the recombinant virus is a recombinant described herein.

In some embodiments, the levels of a RHO P23H gene are reduced in one or more tissues of an eye of the subject relative to a reference level. In some embodiments, the levels of RHO P23H gene are reduced by about 10% to about 80% relative to a reference level. In some embodiments, the level of RHO P23H is reduced by about 10%-20%, 20%-30%, 30%-40%, 40%-50%, 50%-60%, 60%-70%, 70%-80%, or more, relative to a reference level. In some such embodiments, the level of RHO P23H is reduced by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, or more, relative to a reference level.

In some of the embodiments and aspects described herein, the eukaryotic cell can be a pluripotent cell. In such an embodiment, the pluripotent cell can be an induced pluripotent stem (iPS) cell. In a particular embodiment, the iPS cell can be a human iPS cell.

In another aspect, the invention provides a genetically-modified cell, wherein the genetically-modified cell comprises a wild-type RHO allele and a disrupted P23H allele, wherein the genetically-modified cell expresses a wild-type RHO protein and does not express a RHO P23H protein, and wherein the genetically-modified cell is produced according to the methods of the invention described herein. In particular embodiments, the genetically-modified cell is a pluripotent cell, an iPS cell, or a human iPS cell.

Further, in embodiments of the method, the genetically-modified cell is a genetically-modified iPS cell. In such an embodiment, the genetically-modified iPS cell differentiates into a cell that expresses wild-type RHO protein when it is delivered to the target tissue. In a particular embodiment, the genetically-modified iPS cell differentiates into a retinal cell, and particularly into a rod photoreceptor cell, which expresses the wild-type rhodopsin protein but not the RHO P23H protein.

BRIEF DESCRIPTION OF THE FIGURES

FIG. 1A is an alignment of the 22 base pair RHO P23H recognition sequence (SEQ ID NO: 7) with the corresponding 22 base pair recognition sequence present in the wild-type human RHO gene allele (SEQ ID NO: 9). These sequences span nucleotides 49 to 70 of the P23H mutant or wild-type RHO gene coding sequences (SEQ ID NOs: 4 and 3, respectively). The C68A mutation within the P23H recognition sequence is underlined. In FIG. 1B the P23H recognition sequence comprises two recognition half-sites, referred to as RHO1 and RHO2. Each recognition half-site comprises 9 base pairs as shown. Half-sites in the recognition sequence are separated by a 4 base pair central region.

FIG. 4. Is a multi-sequence alignment between the RHO 1-2L.609, RHO 1-2L.664, RHO 1-2L.687, and RHO 1-2L.692 meganucleases. Asterisks indicate conserved residues amongst all aligned nucleases, and a space indicates that at least one amino acid differed amongst the meganucleases.

FIGS. 6A-6D. Time-dependent effects of the RHO 1-2L.609 meganuclease vs. DPBS control on rod-driven scotopic visual function by electroretinography (ERG) 0.001 cd/m² in a mini swine model of RP that carries transgenic (Tg) P23H human rhodopsin (hRho). FIGS. 6A-6D are the average of the first five ERG readings from a dim (0.001 cd/m2) flash after dark adapting the animals. FIG. 6A-FIG. 6D shows the Scotopic ERG 0.001 cd/m² at the following weeks post injection (WPI): 6 WPI (FIG. 6A), 9 WPI (FIG. 6B), 15 WPI (FIG. 6C), and 26 WPI (FIG. 6D). The gray trace shows the right (OD) injected with the RHO 1-2L.609 meganuclease and the black trace shows the left (OS) control injected with DPBS.

In FIG. 7A the baseline ERG was evaluated at postnatal day 2 (PND2) in untreated right (OD) and left (OS) eyes; grey and black traces, respectively. FIG. 7B-FIG. 7F shows the Scotopic ERG 0.001 cd/m² at the following WPI: 6 WPI (FIG. 7B), 9 WPI (FIG. 7C), 15 WPI (FIG. 7D), 26 WPI (FIG. 7E), and 40 WPI (FIG. 7F), respectively. The gray trace shows the right (OD) injected with the RHO 1-2L.609 meganuclease and the black trace shows the left (OS) control injected with DPBS.

In FIG. 8A the ERG was evaluated at 40 WPI in meganuclease injected right (OD) and control PBS injected left (OS) eyes; grey and black traces, respectively. FIG. 8B shows the cone cell response to a photopic 30 Hz flicker at 40 WPI in meganuclease injected right (OD) and control PBS injected left (OS) eyes; grey and black traces, respectively.

FIG. 9A is a fundus image from a Tg P23H hRHO pig injected with the RHO 1-2L.609 meganuclease. FIG. 9B provides OCT imaging of the fundus with dotted line showing the site of retinotomy and a horizontal line indicating the position of optical cross-sectioning. The dark line bisects the retinotomy to provide an OCT cross-section of the sub retinal injection site for the RHO 1-2L.609 meganuclease. FIG. 9C shows an OCT optical cross-section of the RHO 1-2L.609 meganuclease injected pig retina.

FIG. 10A depicts 11-12 WPI averaged data of dark adapted, scotopic ERG responses, to a low-intensity (0.001 cd/m²) flash for pig eyes injected with varying titers of the RHO 1-2L.609 meganuclease, as well as untreated eyes. The b-wave and a-wave is indicated by the labelled brackets. FIG. 10B depicts data from FIG. 10A but extended to the study terminal timepoint of approximately 140 days post injection.

FIG. 11A shows data similar to FIG. 8 but is 11-12 WPI averaged data of light adapted, photopic ERG responses, to a high intensity (3 cd/m²) flash for pig eyes injected with varying titers of RHO 1-2L.609 meganuclease, as well as untreated eyes. FIG. 11B shows data from FIG. 11A but extended to the study terminal timepoint of approximately 140 days post injection.

In FIG. 13 the meganuclease is represented by GFP expression (AAV5.GFP co-injected with meganuclease), rhodopsin staining is indicated by the top white arrow, and nuclei are stained with DAPI. The white arrow on the left side of FIG. 13A depicts areas of little to no meganuclease expression and areas of little to no rhodopsin expression. Conversely, the white arrow on the right side of FIG. 13A depicts areas of meganuclease expression and concomitant rhodopsin expression. The large white arrow at the bottom of FIG. 13A provides the transition zone of meganuclease and rhodopsin expression. FIG. 13B provides a zoomed in image of the retina showing localization of the rhodopsin protein in a meganuclease injected (OD) eye (indicated by the black arrow on the right side of the figure). FIG. 13C shows residual mis-localized rhodopsin expression indicated by white arrows in PBS treated eyes.

BRIEF DESCRIPTION OF THE SEQUENCES

Figure 1A:
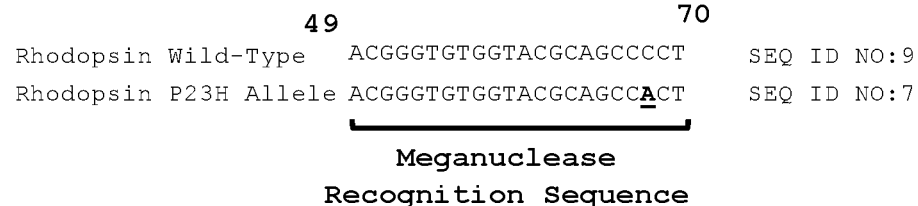
FIGS. 1A and 1B. RHO P23H recognition sequence.

SEQ ID NO: 1 sets forth the amino acid sequence of the wild-type I-CreI meganuclease from *Chlamydomonas reinhardtii*.

SEQ ID NO: 2 sets forth the amino acid sequence of the LAGLIDADG motif.

SEQ ID NO: 3 sets forth the nucleic acid sequence of the human rhodopsin gene sequence (NCBI GENE ID: 6010).

SEQ ID NO: 4 sets forth sets forth the nucleic acid sequence of the human rhodopsin gene comprising a C68A mutation that encodes a P23H substitution in rhodopsin.

SEQ ID NO: 5 sets forth the amino acid sequence of the wild type human rhodopsin protein sequence.

SEQ ID NO: 6 sets forth the amino acid sequence of the human rhodopsin gene comprising a C68A mutation that encodes a P23H substitution in rhodopsin.

SEQ ID NO: 7 sets forth the nucleic acid sequence of the sense strand of the RHO 1-2 recognition sequence, which has the C68A mutation that results in a P23H mutation in the human rhodopsin gene.

SEQ ID NO: 8 sets forth the nucleic acid sequence of the antisense strand of the RHO 1-2 recognition sequence, which has the C68A mutation that results in a P23H mutation in the human rhodopsin gene.

SEQ ID NO: 9 sets forth the nucleic acid sequence of the sense strand of a 22 base pair region of the wild type human rhodopsin gene, which corresponds positionally to the RHO 1-2 recognition sequence, which does not have the C68A mutation that results in a P23H mutation in the human rhodopsin gene.

SEQ ID NO: 10 sets forth the nucleic acid sequence of the antisense strand of a 22 base pair region of the wild type human rhodopsin gene, which corresponds positionally to the RHO 1-2 recognition sequence, which does not have the C68A mutation that results in a P23H mutation in the human rhodopsin gene.

SEQ ID NO: 11 sets forth the amino acid sequence of the RHO 1-2L.609 meganuclease.

SEQ ID NO: 12 sets forth the amino acid sequence of the RHO 1-2L.664 meganuclease.

SEQ ID NO: 13 sets forth the amino acid sequence of the RHO 1-2L.687 meganuclease.

SEQ ID NO: 14 sets forth the amino acid sequence of the RHO 1-2L.692 meganuclease. SEQ ID NO: 15 sets forth the amino acid sequence of the RHO 1-2L.609 meganuclease RHO1-binding subunit.

SEQ ID NO: 16 sets forth the amino acid sequence of the RHO 1-2L.664 meganuclease RHO1-binding subunit.

SEQ ID NO: 17 sets forth the amino acid sequence of the RHO 1-2L.687 meganuclease RHO1-binding subunit.

SEQ ID NO: 18 sets forth the amino acid sequence of the RHO 1-2L.692 meganuclease RHO1-binding subunit.

SEQ ID NO: 19 sets forth the amino acid sequence of the RHO 1-2L.609 meganuclease RHO2-binding subunit.

SEQ ID NO: 20 sets forth the amino acid sequence of the RHO 1-2L.664 meganuclease RHO2-binding subunit.

SEQ ID NO: 21 sets forth the amino acid sequence of the RHO 1-2L.687 meganuclease RHO2-binding subunit.

SEQ ID NO: 22 sets forth the amino acid sequence of the RHO 1-2L.692 meganuclease RHO2-binding subunit.

SEQ ID NO: 23 sets for the nucleic acid sequence of the sense strand an identified off-target recognition sequence for the RHO 2-L5-14 meganuclease of PCT/US2016/050809.

SEQ ID NO: 24 sets for the nucleic acid sequence of the antisense strand an identified off-target recognition sequence for the RHO 2-L5-14 meganuclease of PCT/US2016/050809.

SEQ ID NO: 25 sets forth the nucleic acid sequence encoding an RHO 1-2L.609 meganuclease.

SEQ ID NO: 26 sets forth the nucleic acid sequence encoding an RHO 1-2L.664 meganuclease.

SEQ ID NO: 27 sets forth the nucleic acid sequence encoding an RHO 1-2L.687 meganuclease.

SEQ ID NO: 28 sets forth the nucleic acid sequence encoding an RHO 1-2L.692 meganuclease.

SEQ ID NO: 29 sets forth the amino acid sequence of an SV40 nuclear localization sequence.

DETAILED DESCRIPTION OF THE INVENTION

1.1 References and Definitions

The patent and scientific literature referred to herein establishes knowledge that is available to those of skill in the art. The issued US patents, allowed applications, published foreign applications, and references, including GenBank database sequences, which are cited herein are hereby incorporated by reference to the same extent as if each was specifically and individually indicated to be incorporated by reference.

The present invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the instant disclosure, which do not depart from the instant invention.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, and other references mentioned herein are incorporated by reference herein in their entirety.

As used herein, "a," "an," or "the" can mean one or more than one. For example, "a" cell can mean a single cell or a multiplicity of cells.

As used herein, unless specifically indicated otherwise, the word "or" is used in the inclusive sense of "and/or" and not the exclusive sense of "either/or."

As used herein, the terms "nuclease" and "endonuclease" are used interchangeably to refer to naturally-occurring or engineered enzymes, which cleave a phosphodiester bond within a polynucleotide chain. Engineered nucleases can include, without limitation, engineered meganucleases such as those described herein.

As used herein, the terms "cleave" or "cleavage" refer to the hydrolysis of phosphodiester bonds within the backbone of a recognition sequence within a target sequence that results in a double-stranded break within the target sequence, referred to herein as a "cleavage site".

As used herein, the term "meganuclease" refers to an endonuclease that binds double-stranded DNA at a recognition sequence that is greater than 12 base pairs. In some embodiments, the recognition sequence for a meganuclease of the present disclosure is 22 base pairs. A meganuclease can be an endonuclease that is derived from I-CreI (SEQ ID NO: 1), and can refer to an engineered variant of I-CreI that has been modified relative to natural I-CreI with respect to, for example, DNA-binding specificity, DNA cleavage activity, DNA-binding affinity, or dimerization properties. Methods for producing such modified variants of I-CreI are known in the art (e.g., WO 2007/047859, incorporated by reference in its entirety). A meganuclease as used herein binds to double-stranded DNA as a heterodimer. A meganuclease may also be a "single-chain meganuclease" in which a pair of DNA-binding domains is joined into a single polypeptide using a peptide linker. The term "homing endonuclease" is synonymous with the term "meganuclease." Meganucleases of the present disclosure are substantially non-toxic when expressed in the targeted cells as described herein such that cells can be transfected and maintained at 37° C. without observing deleterious effects on cell viability or significant reductions in meganuclease cleavage activity when measured using the methods described herein.

As used herein, the term "single-chain meganuclease" refers to a polypeptide comprising a pair of nuclease sub-units joined by a linker. A single-chain meganuclease has the organization: N-terminal subunit-Linker-C-terminal subunit. The two meganuclease subunits will generally be non-identical in amino acid sequence and will bind non-identical DNA sequences. Thus, single-chain meganucleases typically cleave pseudo-palindromic or non-palindromic recognition sequences. A single-chain meganuclease may be referred to as a "single-chain heterodimer" or "single-chain heterodimeric meganuclease" although it is not, in fact, dimeric. For clarity, unless otherwise specified, the term "meganuclease" can refer to a dimeric or single-chain meganuclease.

As used herein, the term "linker" refers to an exogenous peptide sequence used to join two nuclease subunits into a single polypeptide. A linker may have a sequence that is found in natural proteins or may be an artificial sequence that is not found in any natural protein. A linker may be flexible and lacking in secondary structure or may have a propensity to form a specific three-dimensional structure under physiological conditions. A linker can include, without limitation, those encompassed by U.S. Pat. Nos. 8,445, 251, 9,340,777, 9,434,931, and 10,041,053, each of which is incorporated by reference in its entirety. In some embodiments, a linker may have at least 80%, at least 85%, at least 90%, at least 91%, at least 92%, at least 93%, at least 94%, at least 95%, at least 96%, at least 97%, at least 98%, at least 99%, or 100 sequence identity to residues 154-195 of any one of SEQ ID NOs: 11-14. In some embodiments, a linker may have an amino acid sequence comprising residues 154-195 of any one of SEQ ID NOs: 11-14.

As used herein, the terms "recombinant" or "engineered," with respect to a protein, means having an altered amino acid sequence as a result of the application of genetic engineering techniques to nucleic acids that encode the protein and cells or organisms that express the protein. With respect to a nucleic acid, the term "recombinant" or "engineered" means having an altered nucleic acid sequence as a result of the application of genetic engineering techniques. Genetic engineering techniques include, but are not limited to, PCR and DNA cloning technologies; transfection, transformation, and other gene transfer technologies; homologous recombination; site-directed mutagenesis; and gene fusion. In accordance with this definition, a protein having an amino acid sequence identical to a naturally-occurring protein but produced by cloning and expression in a heterologous host, is not considered recombinant or engineered. Exemplary transfection techniques of the disclosure include, but are not limited to, electroporation and lipofection using Lipofectamine (e.g., Lipofectamine® MessengerMax (ThermoFisher)).

As used herein, the term "wild-type" refers to the most common naturally occurring allele (i.e., polynucleotide sequence) in the allele population of the same type of gene, wherein a polypeptide encoded by the wild-type allele has its original functions. The term "wild-type" also refers to a polypeptide encoded by a wild-type allele. Wild-type alleles (i.e., polynucleotides) and polypeptides are distinguishable from mutant or variant alleles and polypeptides, which comprise one or more mutations and/or substitutions relative to the wild-type sequence(s). Whereas a wild-type allele or polypeptide can confer a normal phenotype in an organism, a mutant or variant allele or polypeptide can, in some instances, confer an altered phenotype. Wild-type nucleases are distinguishable from recombinant or non-naturally-occurring nucleases. The term "wild-type" can also refer to a cell, an organism, and/or a subject which possesses a wild-type allele of a particular gene, or a cell, an organism, and/or a subject used for comparative purposes.

As used herein, the term "genetically-modified" refers to a cell or organism in which, or in an ancestor of which, a genomic DNA sequence has been deliberately modified by recombinant technology. As used herein, the term "genetically-modified" encompasses the term "transgenic."

As used herein, the term with respect to recombinant proteins, the term "modification" means any insertion, deletion, or substitution of an amino acid residue in the recombinant sequence relative to a reference sequence (e.g., a wild-type or a native sequence).

As used herein, the terms "recognition sequence" or "recognition site" refers to a DNA sequence that is bound and cleaved by a nuclease. In the case of a meganuclease, a recognition sequence comprises a pair of inverted, 9 basepair "half sites" which are separated by four basepairs. In the case of a single-chain meganuclease, the N-terminal domain of the protein contacts a first half-site and the C-terminal domain of the protein contacts a second half-site. Cleavage by a meganuclease produces four basepair 3' overhangs. "Overhangs," or "sticky ends" are short, single-stranded DNA segments that can be produced by endonuclease cleavage of a double-stranded DNA sequence. In the case of meganucleases and single-chain meganucleases derived from I-CreI, the overhang comprises bases 10-13 of the 22 basepair recognition sequence.

As used herein, the term "disrupted" or "disrupts" or "disrupts expression" or "disrupting a target sequence" refers to the introduction of a mutation (e.g., frameshift mutation) that interferes with the gene function and prevents expression and/or function of the polypeptide/expression product encoded thereby. For example, nuclease-mediated disruption of a gene can result in the expression of a truncated protein and/or expression of a protein that does not retain its wild-type function. Additionally, introduction of a donor template into a gene can result in no expression of an encoded protein, expression of a truncated protein, and/or expression of a protein that does not retain its wild-type function.

As used herein, the terms "target site" or "target sequence" refers to a region of the chromosomal DNA of a cell comprising a recognition sequence for a nuclease. This term embraces chromosomal DNA duplexes as well as single-stranded chromosomal DNA.

As used herein, the terms "DNA-binding affinity" or "binding affinity" means the tendency of a nuclease to non-covalently associate with a reference DNA molecule (e.g., a recognition sequence or an arbitrary sequence). Binding affinity is measured by a dissociation constant, Kd. As used herein, a nuclease has "altered" binding affinity if the Kd of the nuclease for a reference recognition sequence is increased or decreased by a statistically significant percent change relative to a reference nuclease.

As used herein, the term "specificity" refers to the ability of a nuclease to bind and cleave double-stranded DNA molecules only at a particular sequence of base pairs referred to as the recognition sequence, or only at a particular set of recognition sequences. The set of recognition sequences will share certain conserved positions or sequence motifs, but may be degenerate at one or more positions. A highly-specific nuclease is capable of cleaving only one or a very few recognition sequences. Specificity can be determined by any method known in the art, such as unbiased identification of DSBs enabled by sequencing (GUIDE-seq), oligonucleotide (oligo) capture assay, whole genome sequencing, and long-range next generation sequencing of the recognition sequence. In some embodiments, specificity is measured using GUIDE-seq. As used herein, "specificity" is synonymous with a low incidence of cleavage of sequences different from the target sequences (non-target sequences), i.e., off-target cutting. A low incidence of off-target cutting may comprise an incidence of cleavage of non-target sequences of less than 25%, less than 20%, less than 18%, less than 15%, less than 12.5%, less than 10%, less than 9%, less than 8%, less than 7%, less than 6%, less than 5%, less than 4%, less than 3%, less than 2.5%, less than 2%, less than 1.5%, less than 1%, less than 0.75%, less than 0.5%, or less than 0.25%.

As used herein, the term "altered specificity," when referencing to a nuclease, means that a nuclease binds to and cleaves a recognition sequence, which is not bound to and cleaved by a reference nuclease (e.g., a wild-type) under physiological conditions, or that the rate of cleavage of a recognition sequence is increased or decreased by a biologically significant amount (e.g., at least 2×, or 2×-10×) relative to a reference nuclease. In some embodiments, the presently disclosed engineered meganucleases have improved (i.e., increased) specificity for the recognition sequence that comprises SEQ ID NO: 7 (i.e., RHO 1-2) as compared to the RHO 2-L5-14 meganuclease of PCT/US2016/050809. Thus, in certain embodiments, the presently disclosed engineered meganucleases exhibit reduced off-target cleavage as compared to the RHO 2-L5-14 meganuclease. Off-target cleavage by a meganuclease can be measured using any method known in the art, including for example, oligo capture analysis, a T7 endonuclease (T7E) assay, digital PCR, targeted sequencing of particular off-target sites, exome sequencing, whole genome sequencing, direct in situ breaks labeling enrichment on streptavidin and next-generation sequencing (BLESS), genome-wide, unbiased identification of DSBs enabled by sequencing (GUIDE-seq), and linear amplification-mediated high-throughput genome-wide translocation sequencing (LAM-HTGTS) (see, e.g., Zischewski et al. (2017), Biotechnology Advances 35(1):95-104, which is incorporated by reference in its entirety).

As used herein, the term "efficiency of cleavage" refers to the incidence by which a meganuclease cleaves a recognition sequence in a double-stranded DNA molecule relative to the incidence of all cleavage events by the meganuclease on the DNA molecule. "Efficiency of cleavage" is synonymous with DNA editing efficiency or on-target editing. Efficiency of cleavage and/or indel formation by a meganuclease can be measured using any method known in the art, including T7E assay, digital PCR (ddPCR), mismatch detection assays, mismatch cleavage assay, high-resolution melting analysis (HRMA), heteroduplex mobility assay, sequencing, and fluorescent PCR capillary gel electrophoresis (see, e.g., Zischewski et al. (2017) Biotechnology Advances 35(1):95-104, which is incorporated by reference in its entirety). In some embodiments, efficiency of cleavage is measured by ddPCR. In some embodiments, the disclosed meganucleases generate efficiencies of cleavage of at least about 35%, 40%, 50%, 60%, 70%, 80%, 85%, 90%, 95%, 98%, or 99% at the recognition sequence.

An "indel", as used herein, refers to the insertion or deletion of a nucleobase within a nucleic acid, such as DNA. In some embodiments, it is desirable to generate one or more insertions or deletions (i.e., indels) in the nucleic acid, e.g., in a foreign nucleic acid such as viral DNA. Accordingly, as used herein, "efficiency of indel formation" refers to the incidence by which a meganuclease generates one or more indels through cleavage of a recognition sequence relative to the incidence of all cleavage events by the meganuclease on the DNA molecule. In some embodiments, efficiency of indel formation is measured by ddPCR. In some embodiments, the disclosed meganucleases generate efficiencies of indel formation of at least about 35%, 40%, 50%, 60%, 70%, 80%, 85%, 90%, 95%, 98%, or 99% at the recognition sequence. The disclosed meganucleases may generate efficiencies of cleavage and/or efficiencies of indel formation of at least about 60%, 61%, 62%, 63%, 64%, 65%, 66%, 67%, 68%, 69%, 70%, 71%, 72%, 73%, 74%, or 75% at the recognition sequence.

As used herein, the term "homologous recombination" or "HR" refers to the natural, cellular process in which a double-stranded DNA-break is repaired using a homologous DNA sequence as the repair template (see, e.g. Cahill et al. (2006), Front. Biosci. 11:1958-1976). The homologous DNA sequence may be an endogenous chromosomal sequence or an exogenous nucleic acid that was delivered to the cell.

As used herein, a "template nucleic acid" or "donor template" refers to a nucleic acid sequence that is desired to be inserted into a cleavage site within a cell's genome. Such template nucleic acids or donor templates can comprise, for example, a transgene, such as an exogenous transgene, which encodes a protein of interest. The template nucleic acid or donor template can comprise 5' and 3' homology arms having homology to 5' and 3' sequences, respectively, that flank a cleavage site in the genome where insertion of the template is desired. Insertion can be accomplished, for example, by homology-directed repair (HDR).

As used herein, the term "non-homologous end-joining" or "NHEJ" refers to the natural, cellular process in which a double-stranded DNA-break is repaired by the direct joining of two non-homologous DNA segments (see, e.g. Cahill et al. (2006), Front. Biosci. 11:1958-1976). DNA repair by non-homologous end-joining is error-prone and frequently results in the untemplated addition or deletion of DNA sequences at the site of repair. In some instances, cleavage at a target recognition sequence results in NHEJ at a target recognition site. Nuclease-induced cleavage of a target site in the coding sequence of a gene followed by DNA repair by NHEJ can introduce mutations into the coding sequence, such as frameshift mutations, that disrupt gene function. Thus, engineered nucleases can be used to effectively knock-out a gene in a population of cells.

As used herein, the term "homology arms" or "sequences homologous to sequences flanking a nuclease cleavage site" refer to sequences flanking the 5' and 3' ends of a nucleic acid molecule, which promote insertion of the nucleic acid molecule into a cleavage site generated by a nuclease. In general, homology arms can have a length of at least 50 base pairs, preferably at least 100 base pairs, and up to 2000 base pairs or more, and can have at least 90%, preferably at least 95%, or more, sequence homology to their corresponding sequences in the genome. In some embodiments, the homology arms are about 500 base pairs.

As used herein, the term with respect to both amino acid sequences and nucleic acid sequences, the terms "percent identity," "sequence identity," "percentage similarity," "sequence similarity" and the like refer to a measure of the degree of similarity of two sequences based upon an alignment of the sequences that maximizes similarity between aligned amino acid residues or nucleotides, and which is a function of the number of identical or similar residues or nucleotides, the number of total residues or nucleotides, and the presence and length of gaps in the sequence alignment. A variety of algorithms and computer programs are available for determining sequence similarity using standard parameters. As used herein, sequence similarity is measured using the BLASTp program for amino acid sequences and the BLASTn program for nucleic acid sequences, both of which are available through the National Center for Biotechnology Information (www.ncbi.nlm.nih.gov/), and are described in, for example, Altschul et al. (1990), J. Mol. Biol. 215:403-410; Gish and States (1993), Nature Genet. 3:266-272; Madden et al. (1996), Meth. Enzymol. 266:131-141; Altschul et al. (1997), Nucleic Acids Res. 25:33 89-3402); Zhang et al. (2000), J. Comput. Biol. 7(1-2):203-14. As used herein, percent similarity of two amino acid sequences is the score based upon the following parameters for the BLASTp algorithm: word size=3; gap opening penalty=-11; gap extension penalty=-1; and scoring matrix=BLOSUM62. As used herein, percent similarity of two nucleic acid sequences is the score based upon the following parameters for the BLASTn algorithm: word size=11; gap opening penalty=-5; gap extension penalty=-2; match reward=1; and mismatch penalty=-3.

As used herein, the term "corresponding to" with respect to modifications of two proteins or amino acid sequences is used to indicate that a specified modification in the first protein is a substitution of the same amino acid residue as in the modification in the second protein, and that the amino acid position of the modification in the first protein corresponds to or aligns with the amino acid position of the modification in the second protein when the two proteins are subjected to standard sequence alignments (e.g., using the BLASTp program). Thus, the modification of residue "X" to amino acid "A" in the first protein will correspond to the modification of residue "Y" to amino acid "A" in the second protein if residues X and Y correspond to each other in a sequence alignment and despite the fact that X and Y may be different numbers.

As used herein, the term "recognition half-site," "recognition sequence half-site," or simply "half-site" means a nucleic acid sequence in a double-stranded DNA molecule that is recognized and bound by a monomer of a homodimeric or heterodimeric meganuclease or by one subunit of a single-chain meganuclease.

As used herein, the term "preferentially" refers to the specificity of a recombinant meganuclease for recognizing and cleaving a particular target recognition sequence in the genome relative to a second, reference recognition sequence. By way of example, a recombinant meganuclease of the invention may preferentially bind and cleave the P23H recognition sequence (SEQ ID NO:7) with greater efficiency than it binds and cleaves the corresponding wild-type recognition sequence (SEQ ID NO:9), as determined by methods known in the art, including those methods provided in the examples herein. In some embodiments, a recombinant meganuclease of the invention may bind and cleave the P23H recognition sequence with greater than about 5%, 10%, 15%, 20%, 25%, 30%, 40%, 50%, 60%, 70%, 80%, 90%, or 100% more efficiency than it binds and cleaves the corresponding wild-type recognition sequence. In other embodiments, a recombinant meganuclease of the invention may bind and cleave the P23H recognition sequence with greater than about 1-fold, 2-fold, 5-fold, 10-fold, 50-fold, 100-fold, or 1000-fold more efficiency than it binds and cleaves the corresponding wild-type recognition sequence.

As used herein, the term "hypervariable region" refers to a localized sequence within a meganuclease monomer or subunit that comprises amino acids with relatively high variability. A hypervariable region can comprise about 50-60 contiguous residues, about 53-57 contiguous residues, or preferably about 56 residues. In some embodiments, the residues of a hypervariable region may correspond to positions 24-79 or positions 215-270 of any one of SEQ ID NOs: 11-14. A hypervariable region can comprise one or more residues that contact DNA bases in a recognition sequence and can be modified to alter base preference of the monomer or subunit. A hypervariable region can also comprise one or more residues that bind to the DNA backbone when the meganuclease associates with a double-stranded DNA recognition sequence. Such residues can be modified to alter the binding affinity of the meganuclease for the DNA backbone and the target recognition sequence. In different embodiments of the invention, a hypervariable region may comprise between 1-20 residues that exhibit variability and can be modified to influence base preference and/or DNA-binding affinity. In particular embodiments, a hypervariable region comprises between about 15-20 residues that exhibit variability and can be modified to influence base preference and/or DNA-binding affinity. In some embodiments, variable residues within a hypervariable region correspond to one or more of positions 24, 26, 28, 30, 32, 33, 38, 40, 42, 44, 46, 68, 70, 75, and 77 of any one of SEQ ID NOs: 11-14. In other embodiments, variable residues within a hypervariable region correspond to one or more of positions 215, 217, 219, 221, 223, 224, 229, 231, 233, 235, 237, 259, 261, 266, and 268 of SEQ ID NOs:11-14.

As used herein, the terms "RHO," "RHO gene," "rhodopsin gene," and "wild-type RHO allele" are used interchangeably and refer to the human rhodopsin gene, preferably the gene identified by NCBI Reference Sequence NG 009115.1 or Gene ID No. 6010 (SEQ ID NO:3). The terms "mutant RHO allele" and "mutant RHO P23H allele" are used interchangeably and refer to a RHO allele sequence comprising a C68A mutation (SEQ ID NO:4), which results in a P23H substitution in the encoded protein. The terms "rhodopsin" and "wild-type rhodopsin" are used interchangeably and refer to the protein encoded by the wild-type rhodopsin gene, particularly the protein identified by NCBI Reference Sequence NP_000530.1 (SEQ ID NO:5). The term "P23H rhodopsin" refers to the mutant rhodopsin protein comprising a P23H substitution, particularly the protein set forth in SEQ ID NO:6.

The terms a "decrease" or "reduction" in RHO P23H levels refers to any decrease in the levels of RHO P23H expression relative to a reference level including a reduction of RHO P23H expression of at least 1%, 2%, 3%, 4%, 5%, 10%, 15%, 20%, 25%, 30%, 40%, 50%, 60%, 70%, 80%, 90%, 95%, or 100% when compared to a reference level or control. In some embodiments, a decrease in RHO P23H levels refers to a decrease in full-length RHO P23H polypeptide expression relative to a reference level including a reduction of full-length RHO P23H polypeptide expression of at least 1%, 2%, 3%, 4%, 5%, 10%, 15%, 20%, 25%, 30%, 40%, 50%, 60%, 70%, 80%, 90%, 95%, or 100% when compared to a reference level or control.

As used herein, the term "modified RHO gene" refers to any modification to a RHO gene, such as an insertion, deletion, or substitution within the RHO gene. As used herein, the term "modified RHO gene" refers to any modification to a RHO gene, such as an insertion, deletion, or substitution within the RHO gene. In some embodiments, the modification to a RHO gene alters (e.g., decreases) RHO levels. In some further embodiments, a RHO P23H gene allele is modified and the wild type RHO allele is not modified. In some embodiments, the modification to a RHO gene alters (e.g., decreases) RHO levels. In some further embodiments, a RHO P23H gene allele is modified and the wild type RHO allele is not modified.

As used herein, the term "reference level" refers to a level of RHO or RHO P23H as measured in, for example, a control cell, control cell population or a control subject, at a previous time point in the control cell, the control cell population or the subject undergoing treatment (e.g., a pre-dose baseline level obtained from the control cell, control cell population or subject), or a pre-defined threshold level of RHO or RHO P23H (e.g., a threshold level identified through previous experimentation).

As used herein, the term "gc/kg" or "gene copies/kilogram" refers to the number of copies of a nucleic acid encoding an engineered nuclease or the number of copies of a template nucleic acid described herein per weight in kilograms of a subject that is administered the nucleic acid encoding the engineered nuclease and/or the template nucleic acid.

As used herein, a "control cell," "control cell population," or "a control subject" refers to a cell, cell population, or a control subject that provides a reference point for measuring changes in genotype or phenotype of a genetically-modified cell, genetically-modified cell population, or genetically-modified subject. A control cell or cell population may comprise, for example: (a) a wild-type cell or cell population, i.e., of the same genotype as the starting material for the genetic alteration which resulted in the genetically-modified cell; (b) a cell or cell population of the same genotype as the genetically-modified cell or cell population but which has been transformed with a null construct (i.e., with a construct which has no known effect on the trait of interest); or, (c) a cell or cell population genetically identical to the genetically-modified cell but which is not exposed to conditions or stimuli or further genetic modifications that would induce expression of altered genotype or phenotype. A control subject may comprise, for example: a wild-type subject, i.e., of the same genotype as the starting subject for the genetic alteration which resulted in the genetically-modified subject (e.g., a subject having the same mutation in a RHO gene), which is not exposed to conditions or stimuli or further genetic modifications that would induce expression of altered genotype or phenotype in the subject.

As used herein, the term "recombinant DNA construct," "recombinant construct," "expression cassette," "expression construct," "chimeric construct," "construct," and "recombinant DNA fragment" are used interchangeably herein and are single or double-stranded polynucleotides. A recombinant construct comprises an artificial combination of nucleic acid fragments, including, without limitation, regulatory and coding sequences that are not found together in nature. For example, a recombinant DNA construct may comprise regulatory sequences and coding sequences that are derived from different sources, or regulatory sequences and coding sequences derived from the same source and arranged in a manner different than that found in nature. Such a construct may be used by itself or may be used in conjunction with a vector.

As used herein, the term "vector" or "recombinant DNA vector" may be a construct that includes a replication system and sequences that are capable of transcription and translation of a polypeptide-encoding sequence in a given host cell. If a vector is used, then the choice of vector is dependent upon the method that will be used to transform host cells as is well known to those skilled in the art. Vectors can include, without limitation, plasmid vectors and recombinant AAV vectors, or any other vector known in the art suitable for delivering a gene to a target cell. The skilled artisan is well aware of the genetic elements that must be present on the vector in order to successfully transform, select and propagate host cells comprising any of the isolated nucleotides or nucleic acid sequences of the invention. In some embodiments, a "vector" also refers to a viral vector. Viral vectors can include, without limitation, retroviral vectors, lentiviral vectors, adenoviral vectors, and adeno-associated viral vectors (AAV).

As used herein, a "self-cleaving" recombinant DNA construct refers to a DNA construct that comprises at least one coding sequence for a nuclease and at least one recognition sequence.

As used herein, a "target cell" refers to a cell that comprises at least one RHO allele comprising the RHO P23H recognition sequence (SEQ ID NO:7). As used herein, a "target cell" refers to a cell that comprises at least one RHO allele comprising the RHO P23H recognition sequence (SEQ ID NO:7). Such target cells can express mutant RHO P23H protein. Target cells can include, without limitation, cells of the eye, preferably cells in the posterior segment of the eye, and even more preferably cells of the retina, including rod photoreceptor cells comprising the RHO P23H recognition sequence in at least one RHO gene allele.

As used herein, the term "operably linked" is intended to mean a functional linkage between two or more elements. For example, an operable linkage between a nucleic acid sequence encoding a nuclease as disclosed herein and a regulatory sequence (e.g., a promoter) is a functional link that allows for expression of the nucleic acid sequence encoding the nuclease. Operably linked elements may be contiguous or non-contiguous. When used to refer to the joining of two protein coding regions, by operably linked is intended that the coding regions are in the same reading frame.

As used herein, the terms "treatment" or "treating a subject" refers to the administration of an engineered nuclease of the invention, or a nucleic acid encoding engineered nuclease of the invention, to a subject having RP for the purpose of providing partial or complete relief of one or more symptoms of RP. In some aspects, engineered nuclease of the invention, or a nucleic acid encoding the same, is administered during treatment in the form of a pharmaceutical composition of the invention.

As used herein, the term "effective amount" or "therapeutically effective amount" refers to an amount sufficient to effect beneficial or desirable biological and/or clinical results. The therapeutically effective amount will vary depending on the formulation or composition used, the disease and its severity and the age, weight, physical condition and responsiveness of the subject to be treated. In some specific embodiments, an effective amount of a nucleic acid encoding an engineered meganuclease comprises about $1\times10^{10}$ gc/kg to about $1\times10^{14}$ gc/kg (e.g., $1\times10^{10}$ gc/kg, $1\times10^{11}$ gc/kg, $1\times10^{12}$ gc/kg, $1\times10^{13}$ gc/kg, or $1\times10^{14}$ gc/kg)

of a polynucleotide comprising a nucleic acid encoding the engineered nuclease or of a template polynucleotide. In specific embodiments, an effective amount of a polynucleotide comprising a nucleic acid sequence encoding an engineered nuclease and/or a template polynucleotide, or a pharmaceutical composition comprising a polynucleotide comprising a nucleic acid sequence encoding an engineered nuclease and/or a template polynucleotide disclosed herein, reduces at least one symptom of a disease in a subject. In specific embodiments, an effective amount of the engineered meganuclease or pharmaceutical compositions disclosed herein reduces the level of rhodopsin P23H in a subject (e.g., in the eyes of a subject).

As used herein, the term "lipid nanoparticle" refers to a lipid composition having a typically spherical structure with an average diameter between 10 and 1000 nanometers. In some formulations, lipid nanoparticles can comprise at least one cationic lipid, at least one non-cationic lipid, and at least one conjugated lipid. Lipid nanoparticles known in the art that are suitable for encapsulating nucleic acids, such as mRNA, are contemplated for use in the invention.

As used herein, the recitation of a numerical range for a variable is intended to convey that the present disclosure may be practiced with the variable equal to any of the values within that range. Thus, for a variable which is inherently discrete, the variable can be equal to any integer value within the numerical range, including the end-points of the range. Similarly, for a variable which is inherently continuous, the variable can be equal to any real value within the numerical range, including the end-points of the range. As an example, and without limitation, a variable which is described as having values between 0 and 2 can take the values 0, 1 or 2 if the variable is inherently discrete, and can take the values 0.0, 0.1, 0.01, 0.001, or any other real values 0 and 2 if the variable is inherently continuous.

2.1 Principle of Targeting and Inactivating the Mutant RHO P23H Allele

The present invention is based, in part, on the hypothesis that autosomal dominant RP can be corrected or prevented by targeting, cleaving, and inactivating a mutant RHO P23H allele, which encodes the pathogenic P23H rhodopsin protein. Surprisingly, second generation recombinant meganucleases have been engineered to bind and cleave the P23H recognition sequence (SEQ ID NO:7) present in the mutant RHO P23H allele with reduced off-targeting. Such recombinant meganucleases can preferentially target and cleave the mutant RHO P23H allele relative to the corresponding sequence present in the wild-type allele (SEQ ID NO:9). NHEJ at the cleavage site results in mutagenesis and disruption of the mutant RHO P23H allele, while the functional wild-type RHO allele remains intact to express wild-type rhodopsin in rod photoreceptor cells of the retina. Preferential inactivation of the mutant RHO P23H allele, and disruption of P23H rhodopsin expression, is expected to prevent, delay, or reverse the progression of RP in patients. Indeed, as described further herein, this reversal of RP symptoms was demonstrated in a swine model of RP.

2.2 Meganucleases for Recognizing and Cleaving the P23H Recognition Sequence

It is known in the art that it is possible to use a site-specific nuclease to make a DNA break in the genome of a living cell, and that such a DNA break can result in permanent modification of the genome via homologous recombination with a transgenic DNA sequence. The use of nucleases to induce a double-strand break in a target locus is known to stimulate homologous recombination, particularly of transgenic DNA sequences flanked by sequences that are homologous to the genomic target. In this manner, exogenous nucleic acid sequences can be inserted into a target locus.

It is known in the art that it is possible to use a site-specific nuclease to make a DNA break in the genome of a living cell, and that such a DNA break can result in permanent modification of the genome via mutagenic NHEJ repair or via homologous recombination with a transgenic DNA sequence. NHEJ can produce mutagenesis at the cleavage site, resulting in inactivation of the allele. NHEJ-associated mutagenesis may inactivate an allele via generation of early stop codons, frameshift mutations producing aberrant non-functional proteins, or could trigger mechanisms such as nonsense-mediated mRNA decay. The use of nucleases to induce mutagenesis via NHEJ can be used to target a specific mutation or a sequence present in a wild-type allele. Further, the use of nucleases to induce a double-strand break in a target locus is known to stimulate homologous recombination, particularly of transgenic DNA sequences flanked by sequences that are homologous to the genomic target. In this manner, exogenous nucleic acid sequences can be inserted into a target locus. Such exogenous nucleic acids can encode any sequence or polypeptide of interest.

In some embodiments, the nucleases used to practice the invention are meganucleases. In particular embodiments, the nucleases used to practice the invention are single-chain meganucleases. A single-chain meganuclease comprises an N-terminal subunit and a C-terminal subunit joined by a linker peptide. Each of the two domains recognizes and binds to half of the recognition sequence (i.e., a recognition half-site) and the site of DNA cleavage is at the middle of the recognition sequence near the interface of the two subunits. DNA strand breaks are offset by four base pairs such that DNA cleavage by a meganuclease generates a pair of four base pair, 3' single-strand overhangs.

In some embodiments, engineered meganucleases of the invention have been engineered to bind and cleave the P23H recognition sequence (SEQ ID NO:7). Such meganucleases preferentially cleave the P23H recognition sequence on the mutant RHO P23H allele relative to the corresponding wild-type RHO recognition sequence (SEQ ID NO:9). Such engineered meganucleases are collectively referred to herein as "RHO 1-2 meganucleases."

Engineered meganucleases of the invention comprise a first subunit, comprising a first hypervariable (HVR1) region, and a second subunit, comprising a second hypervariable (HVR2) region. Further, the first subunit binds to a first recognition half-site in the P23H recognition sequence (i.e., the RHO1 half-site), and the second subunit binds to a second recognition half-site in the P23H recognition sequence (i.e., the RHO2 half-site). In embodiments where the engineered meganuclease is a single-chain meganuclease, the first and second subunits can be oriented such that the first subunit, which comprises the HVR1 region and binds the first half-site, is positioned as the N-terminal subunit, and the second subunit, which comprises the HVR2 region and binds the second half-site, is positioned as the C-terminal subunit. In alternative embodiments, the first and second subunits can be oriented such that the first subunit, which comprises the HVR1 region and binds the first half-site, is positioned as the C-terminal subunit, and the second subunit, which comprises the HVR2 region and binds the second half-site, is positioned as the N-terminal subunit. Exemplary RHO 1-2 meganucleases of the invention are provided in SEQ ID NOs: 11-14 and summarized in Table 1.

TABLE 1

Exemplary engineered meganucleases engineered to bind and cleave
the RHO P23H recognition sequence (SEQ ID NOs: 11-14).

| Meganuclease | AA SEQ ID | RHO1 Subunit Residues | RHO1 Subunit SEQ ID | RHO1 Subunit % | RHO2 Subunit Residues | RHO2 Subunit SEQ ID | RHO2 Subunit % |
|---|---|---|---|---|---|---|---|
| RHO 1-2L.609 | 11 | 198-344 | 15 | 100 | 7-153 | 19 | 100 |
| RHO 1-2L.664 | 12 | 198-344 | 16 | 96.43 | 7-153 | 20 | 98.21 |
| RHO 1-2L.687 | 13 | 198-344 | 17 | 96.43 | 7-153 | 21 | 98.21 |
| RHO 1-2L.692 | 14 | 198-344 | 18 | 96.43 | 7-153 | 22 | 96.43 |

"RHO1 Subunit %" and "RHO2 Subunit %" represent the amino acid sequence identity between the RHO1-binding and RHO2-binding subunit regions of each meganuclease and the RHO1-binding and RHO2-binding subunit regions, respectively, of the RHO 1-2L.609 meganuclease.

In certain embodiments of the invention, the engineered meganuclease binds and cleaves a recognition sequence comprising SEQ ID NO: 7 within a RHO gene, wherein the engineered meganuclease comprises a first subunit and a second subunit, wherein the first subunit binds to a first recognition half-site of the recognition sequence and comprises a first hypervariable (HVR1) region, and wherein the second subunit binds to a second recognition half-site of the recognition sequence and comprises a second hypervariable (HVR2) region.

In some embodiments, the HVR1 region comprises an amino acid sequence having at least 80%, 85%, 90%, 91%, 92%, 93%, 94%, 95%, 96%, 97%, 98%, 99% or more sequence identity to an amino acid sequence corresponding to residues 215-270 of SEQ ID NO: 11. In some embodiments, the HVR1 region comprises one or more residues corresponding to residues 215, 217, 219, 221, 223, 224, 229, 231, 233, 235, 237, 259, 261, 266, and 268 of SEQ ID NO: 11. In some embodiments, the HVR1 region comprises residues corresponding to residues 215, 217, 219, 221, 223, 224, 229, 231, 233, 235, 237, 259, 261, 266, and 268 of SEQ ID NO: 11. In some embodiments, the HVR1 region comprises Y, R, K, or D at a residue corresponding to residue 257 of SEQ ID NO: 11. In some embodiments, the HVR1 region comprises residues 215-270 of SEQ ID NO: 11 with up to 1, 2, 3, 4, 5, 6, 7, 8, 9, 10, or 11 amino acid substitutions. In some embodiments, the HVR1 region comprises residues 215-270 of SEQ ID NO: 11.

In some embodiments, the HVR2 region comprises an amino acid sequence having at least 80%, 85%, 90%, 91%, 92%, 93%, 94%, 95%, 96%, 97%, 98%, 99% or more sequence identity to an amino acid sequence corresponding to residues 24-79 of SEQ ID NO: 11. In some embodiments, the HVR2 region comprises one or more residues corresponding to residues 24, 26, 28, 30, 32, 33, 38, 40, 42, 44, 46, 68, 70, 75, and 77 of SEQ ID NO: 11. In some such embodiments, the HVR2 region comprises residues corresponding to residues 29 and 39 of SEQ ID NO: 11. In some embodiments, the HVR2 region comprises residues corresponding to residues 24, 26, 28, 30, 32, 33, 38, 40, 42, 44, 46, 68, 70, 75, and 77 of SEQ ID NO: 11. In some embodiments, the HVR2 region comprises Y, R, K, or D at a residue corresponding to residue 66 of SEQ ID NO: 11. In some embodiments, the HVR2 region comprises residues 24-79 of SEQ ID NO: 11 with up to 1, 2, 3, 4, 5, 6, 7, 8, 9, 10, or 11 amino acid substitutions. In some embodiments, the HVR2 region comprises residues 24-79 of SEQ ID NO: 11.

In some embodiments, the first subunit comprises an amino acid sequence having at least 80%, 85%, 90%, 91%, 92%, 93%, 94%, 95%, 96%, 97%, 98%, 99% or more sequence identity to residues 198-344 of SEQ ID NO: 11. In some embodiments, the first subunit comprises G, S, or A at a residue corresponding to residue 210 of SEQ ID NO: 11. In some embodiments, the first subunit comprises E, Q, or K at a residue corresponding to residue 271 of SEQ ID NO: 11. In some embodiments, the first subunit comprises residues 198-344 of SEQ ID NO: 11 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the first subunit comprises residues 198-344 of SEQ ID NO: 11.

In some embodiments, the second subunit comprises an amino acid sequence having at least 80%, 85%, 90%, 91%, 92%, 93%, 94%, 95%, 96%, 97%, 98%, 99% or more sequence identity to residues 7-153 of SEQ ID NO: 11. In some embodiments, the second subunit comprises G, S, or A at a residue corresponding to residue 19 of SEQ ID NO: 11. In some embodiments, the second subunit comprises E, Q, or K at a residue corresponding to residue 80 of SEQ ID NO: 11. In some embodiments, the second subunit comprises residues 198-344 of SEQ ID NO: 11 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the second subunit comprises residues 198-344 of SEQ ID NO: 11.

In some embodiments, the engineered meganuclease is a single-chain meganuclease comprising a linker, wherein the linker covalently joins said first subunit and said second subunit. In some embodiments, the engineered meganuclease comprises an amino acid sequence having at least 80%, 85%, 90%, 91%, 92%, 93%, 94%, 95%, 96%, 97%, 98%, 99% or more sequence identity SEQ ID NO: 11. In some embodiments, the engineered meganuclease comprises an amino acid sequence of SEQ ID NO: 11. In some embodiments, the engineered meganuclease is encoded by a nucleic sequence having at least 80%, 85%, 90%, 91%, 92%, 93%, 94%, 95%, 96%, 97%, 98%, 99% or more sequence identity to a nucleic acid sequence set forth in SEQ ID NO: 25. In some embodiments, the engineered meganuclease is encoded by a nucleic acid sequence set forth in SEQ ID NO: 25.

In some embodiments, the HVR1 region comprises an amino acid sequence having at least 80%, 85%, 90%, 91%, 92%, 93%, 94%, 95%, 96%, 97%, 98%, 99% or more sequence identity to an amino acid sequence corresponding to residues 215-270 of SEQ ID NO: 12. In some embodiments, the HVR1 region comprises one or more residues corresponding to residues 215, 217, 219, 221, 223, 224, 229, 231, 233, 235, 237, 259, 261, 266, and 268 of SEQ ID NO: 12. In some embodiments, the HVR1 region comprises residues corresponding to residues 215, 217, 219, 221, 223, 224, 229, 231, 233, 235, 237, 259, 261, 266, and 268 of SEQ ID NO: 12. In some embodiments, the HVR1 region comprises Y, R, K, or D at a residue corresponding to residue 257 of SEQ ID NO: 12. In some embodiments, the HVR1 region comprises residues 215-270 of SEQ ID NO: 12 with up to 1, 2, 3, 4, 5, 6, 7, 8, 9, 10, or 11 amino acid substitutions. In some embodiments, the HVR1 region comprises residues 215-270 of SEQ ID NO: 12.

In some embodiments, the HVR2 region comprises an amino acid sequence having at least 80%, 85%, 90%, 91%, 92%, 93%, 94%, 95%, 96%, 97%, 98%, 99% or more sequence identity to an amino acid sequence corresponding to residues 24-79 of SEQ ID NO: 12. In some embodiments, the HVR2 region comprises one or more residues corresponding to residues 24, 26, 28, 30, 32, 33, 38, 40, 42, 44, 46, 68, 70, 75, and 77 of SEQ ID NO: 12. In some such embodiments, the HVR2 region comprises residues corresponding to residues 29 and 39 of SEQ ID NO: 12. In some embodiments, the HVR2 region comprises residues corresponding to residues 24, 26, 28, 30, 32, 33, 38, 40, 42, 44, 46, 68, 70, 75, and 77 of SEQ ID NO: 12. In some embodiments, the HVR2 region comprises Y, R, K, or D at a residue corresponding to residue 66 of SEQ ID NO: 12. In some embodiments, the HVR2 region comprises residues 24-79 of SEQ ID NO: 12 with up to 1, 2, 3, 4, 5, 6, 7, 8, 9, 10, or 11 amino acid substitutions. In some embodiments, the HVR2 region comprises residues 24-79 of SEQ ID NO: 12.

In some embodiments, the first subunit comprises an amino acid sequence having at least 80%, 85%, 90%, 91%, 92%, 93%, 94%, 95%, 96%, 97%, 98%, 99% or more sequence identity to residues 198-344 of SEQ ID NO: 12. In some embodiments, the first subunit comprises G, S, or A at a residue corresponding to residue 210 of SEQ ID NO: 12. In some embodiments, the first subunit comprises E, Q, or K at a residue corresponding to residue 271 of SEQ ID NO: 12. In some embodiments, the first subunit comprises residues 198-344 of SEQ ID NO: 12 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the first subunit comprises residues 198-344 of SEQ ID NO: 12.

In some embodiments, the second subunit comprises an amino acid sequence having at least 80%, 85%, 90%, 91%, 92%, 93%, 94%, 95%, 96%, 97%, 98%, 99% or more sequence identity to residues 7-153 of SEQ ID NO: 12. In some embodiments, the second subunit comprises G, S, or A at a residue corresponding to residue 19 of SEQ ID NO: 12. In some embodiments, the second subunit comprises E, Q, or K at a residue corresponding to residue 80 of SEQ ID NO: 12. In some embodiments, the second subunit comprises residues 198-344 of SEQ ID NO: 12 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the second subunit comprises residues 198-344 of SEQ ID NO: 12.

In some embodiments, the engineered meganuclease is a single-chain meganuclease comprising a linker, wherein the linker covalently joins said first subunit and said second subunit. In some embodiments, the engineered meganuclease comprises an amino acid sequence having at least 80%, 85%, 90%, 91%, 92%, 93%, 94%, 95%, 96%, 97%, 98%, 99% or more sequence identity SEQ ID NO: 12. In some embodiments, the engineered meganuclease comprises an amino acid sequence of SEQ ID NO: 12. In some embodiments, the engineered meganuclease is encoded by a nucleic sequence having at least 80%, 85%, 90%, 91%, 92%, 93%, 94%, 95%, 96%, 97%, 98%, 99% or more sequence identity to a nucleic acid sequence set forth in SEQ ID NO: 26. In some embodiments, the engineered meganuclease is encoded by a nucleic acid sequence set forth in SEQ ID NO: 26.

In some embodiments, the HVR1 region comprises an amino acid sequence having at least 80%, 85%, 90%, 91%, 92%, 93%, 94%, 95%, 96%, 97%, 98%, 99% or more sequence identity to an amino acid sequence corresponding to residues 215-270 of SEQ ID NO: 13. In some embodiments, the HVR1 region comprises one or more residues corresponding to residues 215, 217, 219, 221, 223, 224, 229, 231, 233, 235, 237, 259, 261, 266, and 268 of SEQ ID NO: 13. In some embodiments, the HVR1 region comprises residues corresponding to residues 215, 217, 219, 221, 223, 224, 229, 231, 233, 235, 237, 259, 261, 266, and 268 of SEQ ID NO: 13. In some embodiments, the HVR1 region comprises Y, R, K, or D at a residue corresponding to residue 257 of SEQ ID NO: 13. In some embodiments, the HVR1 region comprises residues 215-270 of SEQ ID NO: 13 with up to 1, 2, 3, 4, 5, 6, 7, 8, 9, 10, or 11 amino acid substitutions. In some embodiments, the HVR1 region comprises residues 215-270 of SEQ ID NO: 13.

In some embodiments, the HVR2 region comprises an amino acid sequence having at least 80%, 85%, 90%, 91%, 92%, 93%, 94%, 95%, 96%, 97%, 98%, 99% or more sequence identity to an amino acid sequence corresponding to residues 24-79 of SEQ ID NO: 13. In some embodiments, the HVR2 region comprises one or more residues corresponding to residues 24, 26, 28, 30, 32, 33, 38, 40, 42, 44, 46, 68, 70, 75, and 77 of SEQ ID NO: 13. In some such embodiments, the HVR2 region comprises residues corresponding to residues 29 and 39 of SEQ ID NO: 13. In some embodiments, the HVR2 region comprises residues corresponding to residues 24, 26, 28, 30, 32, 33, 38, 40, 42, 44, 46, 68, 70, 75, and 77 of SEQ ID NO: 13. In some embodiments, the HVR2 region comprises Y, R, K, or D at a residue corresponding to residue 66 of SEQ ID NO: 13. In some embodiments, the HVR2 region comprises residues 24-79 of SEQ ID NO: 13 with up to 1, 2, 3, 4, 5, 6, 7, 8, 9, 10, or 11 amino acid substitutions. In some embodiments, the HVR2 region comprises residues 24-79 of SEQ ID NO: 13.

In some embodiments, the first subunit comprises an amino acid sequence having at least 80%, 85%, 90%, 91%, 92%, 93%, 94%, 95%, 96%, 97%, 98%, 99% or more sequence identity to residues 198-344 of SEQ ID NO: 13. In some embodiments, the first subunit comprises G, S, or A at a residue corresponding to residue 210 of SEQ ID NO: 13. In some embodiments, the first subunit comprises E, Q, or K at a residue corresponding to residue 271 of SEQ ID NO: 13. In some embodiments, the first subunit comprises residues 198-344 of SEQ ID NO: 13 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the first subunit comprises residues 198-344 of SEQ ID NO: 13.

In some embodiments, the second subunit comprises an amino acid sequence having at least 80%, 85%, 90%, 91%, 92%, 93%, 94%, 95%, 96%, 97%, 98%, 99% or more sequence identity to residues 7-153 of SEQ ID NO: 13. In some embodiments, the second subunit comprises G, S, or A at a residue corresponding to residue 19 of SEQ ID NO: 13. In some embodiments, the second subunit comprises E, Q, or K at a residue corresponding to residue 80 of SEQ ID NO: 13. In some embodiments, the second subunit comprises residues 198-344 of SEQ ID NO: 13 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the second subunit comprises residues 198-344 of SEQ ID NO: 13.

In some embodiments, the engineered meganuclease is a single-chain meganuclease comprising a linker, wherein the linker covalently joins said first subunit and said second subunit. In some embodiments, the engineered meganuclease comprises an amino acid sequence having at least 80%, 85%, 90%, 91%, 92%, 93%, 94%, 95%, 96%, 97%, 98%, 99% or more sequence identity SEQ ID NO: 13. In some embodiments, the engineered meganuclease comprises an amino acid sequence of SEQ ID NO: 13. In some embodiments, the engineered meganuclease is encoded by a nucleic sequence having at least 80%, 85%, 90%, 91%, 92%, 93%, 94%, 95%, 96%, 97%, 98%, 99% or more sequence identity to a nucleic acid sequence set forth in SEQ ID NO: 27. In some embodiments, the engineered meganuclease is encoded by a nucleic acid sequence set forth in SEQ ID NO: 27.

In some embodiments, the HVR1 region comprises an amino acid sequence having at least 80%, 85%, 90%, 91%, 92%, 93%, 94%, 95%, 96%, 97%, 98%, 99% or more sequence identity to an amino acid sequence corresponding to residues 215-270 of SEQ ID NO: 14. In some embodiments, the HVR1 region comprises one or more residues corresponding to residues 215, 217, 219, 221, 223, 224, 229, 231, 233, 235, 237, 259, 261, 266, and 268 of SEQ ID NO: 14. In some embodiments, the HVR1 region comprises residues corresponding to residues 215, 217, 219, 221, 223, 224, 229, 231, 233, 235, 237, 259, 261, 266, and 268 of SEQ ID NO: 14. In some embodiments, the HVR1 region comprises Y, R, K, or D at a residue corresponding to residue 257 of SEQ ID NO: 14. In some embodiments, the HVR1 region comprises residues 215-270 of SEQ ID NO: 14 with up to 1, 2, 3, 4, 5, 6, 7, 8, 9, 10, or 11 amino acid substitutions. In some embodiments, the HVR1 region comprises residues 215-270 of SEQ ID NO: 14.

In some embodiments, the HVR2 region comprises an amino acid sequence having at least 80%, 85%, 90%, 91%, 92%, 93%, 94%, 95%, 96%, 97%, 98%, 99% or more sequence identity to an amino acid sequence corresponding to residues 24-79 of SEQ ID NO: 14. In some embodiments, the HVR2 region comprises one or more residues corresponding to residues 24, 26, 28, 30, 32, 33, 38, 40, 42, 44, 46, 68, 70, 75, and 77 of SEQ ID NO: 14. In some such embodiments, the HVR2 region comprises residues corresponding to residues 29 and 39 of SEQ ID NO: 14. In some embodiments, the HVR2 region comprises residues corresponding to residues 24, 26, 28, 30, 32, 33, 38, 40, 42, 44, 46, 68, 70, 75, and 77 of SEQ ID NO: 14. In some embodiments, the HVR2 region comprises Y, R, K, or D at a residue corresponding to residue 66 of SEQ ID NO: 14. In some embodiments, the HVR2 region comprises residues 24-79 of SEQ ID NO: 14 with up to 1, 2, 3, 4, 5, 6, 7, 8, 9, 10, or 11 amino acid substitutions. In some embodiments, the HVR2 region comprises residues 24-79 of SEQ ID NO: 14.

In some embodiments, the first subunit comprises an amino acid sequence having at least 80%, 85%, 90%, 91%, 92%, 93%, 94%, 95%, 96%, 97%, 98%, 99% or more sequence identity to residues 198-344 of SEQ ID NO: 14. In some embodiments, the first subunit comprises G, S, or A at a residue corresponding to residue 210 of SEQ ID NO: 14. In some embodiments, the first subunit comprises E, Q, or K at a residue corresponding to residue 271 of SEQ ID NO: 14. In some embodiments, the first subunit comprises residues 198-344 of SEQ ID NO: 14 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the first subunit comprises residues 198-344 of SEQ ID NO: 14.

In some embodiments, the second subunit comprises an amino acid sequence having at least 80%, 85%, 90%, 91%, 92%, 93%, 94%, 95%, 96%, 97%, 98%, 99% or more sequence identity to residues 7-153 of SEQ ID NO: 14. In some embodiments, the second subunit comprises G, S, or A at a residue corresponding to residue 19 of SEQ ID NO: 14. In some embodiments, the second subunit comprises E, Q, or K at a residue corresponding to residue 80 of SEQ ID NO: 14. In some embodiments, the second subunit comprises residues 198-344 of SEQ ID NO: 14 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the second subunit comprises residues 198-344 of SEQ ID NO: 14.

In some embodiments, the engineered meganuclease is a single-chain meganuclease comprising a linker, wherein the linker covalently joins said first subunit and said second subunit. In some embodiments, the engineered meganuclease comprises an amino acid sequence having at least 80%, 85%, 90%, 91%, 92%, 93%, 94%, 95%, 96%, 97%, 98%, 99% or more sequence identity SEQ ID NO: 14. In some embodiments, the engineered meganuclease comprises an amino acid sequence of SEQ ID NO: 14. In some embodiments, the engineered meganuclease is encoded by a nucleic sequence having at least 80%, 85%, 90%, 91%, 92%, 93%, 94%, 95%, 96%, 97%, 98%, 99% or more sequence identity to a nucleic acid sequence set forth in SEQ ID NO: 28. In some embodiments, the engineered meganuclease is encoded by a nucleic acid sequence set forth in SEQ ID NO: 28.

2.3 Methods for Delivering and Expressing Recombinant Meganucleases

The invention provides methods for producing genetically-modified cells, both in vitro and in vivo, using engineered nucleases that bind and cleave recognition sequences found within a RHO gene and specifically within a mutant RHO P23H allele (e.g., SEQ ID NO:7). Cleavage at such recognition sequences can allow for NHEJ at the cleavage site and/or insertion of an exogenous sequence via homologous recombination, thereby disrupting expression of the endogenous RHO P23H polypeptide in the genetically-modified cell. The invention further provides methods for treating retinitis pigmentosa in a subject by administering a pharmaceutical composition comprising a pharmaceutically acceptable carrier and a nucleic acid encoding an engineered nuclease or the engineered nuclease polypeptide.

A subject having RP or a subject who may be particularly receptive to treatment with the engineered meganucleases described herein may be identified by ascertaining the presence or absence of one or more risk factors, diagnostic, or prognostic indicators including for example, performing a dilated eye exam, optical coherence tomography, fluorescein angiography, a visual field test, or an electroretinogram as is known in the art.

Expression of RHO and RHO P23H in a genetically-modified cell or subject can be detected using standard methods in the art. For example, levels of RHO and RHO P23H may be assessed based on the level of any variable associated with RHO and RHO P23H gene expression, e.g., mRNA level or protein level, retina sensitivity and functionality (e.g., rod cell function), fundus autofluorescence levels, structural abnormalities of the retina (e.g., as assessed through optical coherence tomography). A reduction in the levels of RHO or RHO P23H or expression may be assessed by a change in an absolute or relative level of one or more of these variables compared with a reference level. RHO or RHO P23H levels may be measured in a biological sample isolated from a subject, such as a tissue biopsy from an eye, or a bodily fluid that contains RHO or RHO P23H, such the peripheral blood. Optionally, RHO or RHO P23H levels are normalized to a standard protein or substance in the sample. Further, RHO or RHO P23H levels can be assessed any time before, during, or after treatment in accordance with the methods herein.

The methods include administration of any of the engineered meganucleases described herein, or nucleic acids encoding the meganucleases, to reduce RHO P23H levels in a genetically-modified cell or a subject (e.g., as measured in a cell, a tissue, an organ, or a biological sample obtained from the subject), e.g., by at least 1%, 2%, 3%, 4%, 5%, 10%, 15%, 20%, 25%, 30%, 40%, 50%, 60%, 70%, 80%, 90%, 95%, or 100% relative to a reference level. In some embodiments, the methods herein are effective to reduce the level of RHO P23H by about 10% to about 80% (e.g., 10%-20%, 20%-30%, 30%-40%, 40%-50%, 50%-60%, 60%-70%, 70%-80%, or more) relative to a reference level. In some embodiments, a decrease in RHO P23H levels refers to a decrease in full-length RHO P23H polypeptide expression relative to a reference level including a reduction of full-length RHO P23H polypeptide expression of at least 1%, 2%, 3%, 4%, 5%, 10%, 15%, 20%, 25%, 30%, 40%, 50%, 60%, 70%, 80%, 90%, 95%, or 100% when compared to a reference level or control. In certain embodiments, a RHO P23H polypeptide that is not the full-length polypeptide has reduced activity of at least 1%, 2%, 3%, 4%, 5%, 10%, 15%, 20%, 25%, 30%, 40%, 50%, 60%, 70%, 80%, 90%, 95%, or 100% when compared to the activity of the full-length RHO P23H polypeptide.

In each case, the invention includes that an engineered nuclease of the invention, or a nucleic acid encoding the engineered nuclease, can be delivered (i.e., introduced) into cells that would typically be involved in the transduction of signal from the eye to the brain for vision. Such cells include without limitation rod cells and/or cone cells of the eye.

Engineered nucleases of the invention can be delivered into a cell in the form of protein or, preferably, as a nucleic acid encoding the engineered nuclease. Such nucleic acid can be DNA (e.g., circular or linearized plasmid DNA or PCR products) or RNA (e.g., mRNA).

For embodiments in which the engineered nuclease coding sequence is delivered in DNA form, it should be operably linked to a promoter to facilitate transcription of the nuclease gene. Mammalian promoters suitable for the invention include constitutive promoters such as the cytomegalovirus early (CMV) promoter (Thomsen et al. (1984), Proc Natl Acad Sci USA. 81(3):659-63) or the SV40 early promoter (Benoist and Chambon (1981), Nature. 290(5804): 304-10) as well as inducible promoters such as the tetracycline-inducible promoter (Dingermann et al. (1992), Mol Cell Biol. 12(9):4038-45). An engineered nuclease of the invention can also be operably linked to a synthetic promoter. Synthetic promoters can include, without limitation, the JeT promoter (WO 2002/012514). In specific embodiments, a polynucleotide comprising a nucleic acid sequence encoding an engineered nuclease of the invention is operably linked to a tissue-specific promoter, such as an eye specific promoter. Examples of eye specific promoters include, without limitation, the human rhodopsin kinase promoter, the proximal mouse opsin promoter (mOP), the human G-protein-coupled receptor protein kinase 1 promoter (hGRK1), and the human interphotoreceptor retinoid-binding protein (IRBP) promoter.

In specific embodiments, a nucleic acid sequence encoding at least one engineered nuclease is delivered on a recombinant DNA construct or expression cassette. For example, the recombinant DNA construct can comprise an expression cassette (i.e., "cassette") comprising a promoter and a nucleic acid sequence encoding an engineered nuclease described herein.

In some embodiments, mRNA encoding the engineered nuclease is delivered to a cell because this reduces the likelihood that the gene encoding the engineered nuclease will integrate into the genome of the cell.

Such mRNA encoding an engineered nuclease can be produced using methods known in the art such as in vitro transcription. In some embodiments, the mRNA is 5' capped using 7-methyl-guanosine, anti-reverse cap analogs (ARCA) (U.S. Pat. No. 7,074,596), CleanCap® analogs such as Cap 1 analogs (Trilink, San Diego, CA), or enzymatically capped using vaccinia capping enzyme or similar. In some embodiments, the mRNA may be polyadenylated. The mRNA may contain various 5' and 3' untranslated sequence elements to enhance expression the encoded engineered nuclease and/or stability of the mRNA itself. Such elements can include, for example, posttranslational regulatory elements such as a woodchuck hepatitis virus posttranslational regulatory element. The mRNA may contain nucleoside analogs or naturally-occurring nucleosides, such as pseudouridine, 5-methylcytidine, N6-methyladenosine, 5-methyluridine, or 2-thiouridine. Additional nucleoside analogs include, for example, those described in U.S. Pat. No. 8,278,036.

Purified nuclease proteins can be delivered into cells to cleave genomic DNA, which allows for homologous recombination or non-homologous end-joining at the cleavage site with an exogenous nucleic acid molecule encoding a polypeptide of interest as described herein, by a variety of different mechanisms known in the art, including those further detailed herein.

In another particular embodiment, a nucleic acid encoding a nuclease of the invention is introduced into the cell using a single-stranded DNA template. The single-stranded DNA can further comprise a 5' and/or a 3' AAV inverted terminal repeat (ITR) upstream and/or downstream of the sequence encoding the engineered nuclease. The single-stranded DNA can further comprise a 5' and/or a 3' homology arm upstream and/or downstream of the sequence encoding the engineered nuclease.

In another particular embodiment, genes encoding a nuclease of the invention is introduced into a cell using a linearized DNA template. Such linearized DNA templates can be produced by methods known in the art. For example, a plasmid DNA encoding a nuclease can be digested by one or more restriction enzymes such that the circular plasmid DNA is linearized prior to being introduced into a cell.

Treating RP using the invention requires that a recombinant meganuclease be expressed in cells in the appropriate tissues. The target tissue(s) for delivery of recombinant meganucleases of the invention are cells of the eye, preferably cells in the posterior segment of the eye, and even more preferably cells of the retina, including rod photoreceptor cells. Recombinant meganucleases can be delivered as purified protein or as RNA or DNA encoding the meganucleases. In one embodiment, recombinant meganuclease proteins, or mRNA or vector encoding recombinant meganucleases, are supplied to target cells (e.g., cells in the retina) via injection directly to the target tissue. For example, delivery of RNA, DNA, or recombinant AAVs to the eye via subretinal or intravitreal injection is described in the art (see for example, Martin et al. (2002) *Methods*. 28:267-275; Hauswirth et al. (2008) *Human Gene Therapy*. 19(10):979-990; Johnson et al. (2008) *Molecular Vision*. 14:2211-2226). Alternatively, a meganuclease protein, mRNA, DNA or cells expressing meganucleases can be delivered systemically via the circulatory system.

Purified engineered nuclease proteins, or nucleic acids encoding engineered nucleases, can be delivered into cells to cleave genomic DNA by a variety of different mechanisms known in the art, including those further detailed herein below.

In some embodiments, nuclease proteins, DNA/mRNA encoding nucleases, or cells expressing nuclease proteins are formulated for systemic administration, or administration to target tissues, in a pharmaceutically acceptable carrier in accordance with known techniques. See, e.g., Remington, The Science And Practice of Pharmacy (21st ed., Philadelphia, Lippincott, Williams & Wilkins, 2005). In the manufacture of a pharmaceutical formulation according to the invention, proteins/RNA/mRNA/cells are typically admixed with a pharmaceutically acceptable carrier. The carrier must be acceptable in the sense of being compatible with any other ingredients in the formulation and must not be deleterious to the patient. The carrier can be a solid or a liquid, or both, and can be formulated with the compound as a unit-dose formulation.

In some embodiments, the nuclease proteins, or DNA/mRNA encoding the nuclease, are coupled to a cell penetrating peptide or targeting ligand to facilitate cellular uptake. Examples of cell penetrating peptides known in the art include poly-arginine (Jearawiriyapaisarn, et al. (2008) *Mol Ther.* 16:1624-9), TAT peptide from the HIV virus (Hudecz et al. (2005), *Med. Res. Rev.* 25: 679-736), MPG (Simeoni, et al. (2003) *Nucleic Acids Res.* 31:2717-2724), Pep-1 (Deshayes et al. (2004) *Biochemistry* 43: 7698-7706, and HSV-1 VP-22 (Deshayes et al. (2005) *Cell Mol Life Sci.* 62:1839-49. In an alternative embodiment, engineered nucleases, or DNA/mRNA encoding nucleases, are coupled covalently or non-covalently to an antibody that recognizes a specific cell-surface receptor expressed on target cells such that the nuclease protein/DNA/mRNA binds to and is internalized by the target cells. Alternatively, engineered nuclease protein/DNA/mRNA can be coupled covalently or non-covalently to the natural ligand (or a portion of the natural ligand) for such a cell-surface receptor. (McCall, et al. (2014) *Tissue Barriers*. 2(4):e944449; Dinda, et al. (2013) *Curr Pharm Biotechnol*. 14:1264-74; Kang, et al. (2014) *Curr Pharm Biotechnol*. 15(3):220-30; Qian et al. (2014) *Expert Opin Drug Metab Toxicol*. 10(11):1491-508). Examples of targeting ligands to direct delivery to cells in the eye include RGD (Pollinger et al. (2013) PNAS. 110 (15): 6115-6120), transferrin (Lajunen et al. (2014) *Eur J Pharm Sci*. 62: 23-32), and hyaluronic acid (Martens et al. (2015) *J Control Release*. 202: 83-92).

In some embodiments, nuclease proteins, or DNA/mRNA encoding nucleases, are encapsulated within biodegradable hydrogels for injection or implantation within the desired region of the eye (e.g., intravitreal or subconjunctival injection). Hydrogels can provide sustained and tunable release of the therapeutic payload to the desired region of the eye without the need for frequent injections, and stimuli-responsive materials (e.g., temperature- and pH-responsive hydrogels) can be designed to release the payload in response to environmental or externally applied cues (Kang Derwent et al. (2008) Trans Am Ophthalmol Soc. 106:206-214).

In some embodiments, nuclease proteins, or DNA/mRNA encoding nucleases, are coupled covalently or, preferably, non-covalently to a nanoparticle or encapsulated within such a nanoparticle using methods known in the art (Sharma, et al. (2014) *Biomed Res Int.* 2014). A nanoparticle is a nanoscale delivery system whose length scale is <1 μm, preferably <100 nm. Such nanoparticles may be designed using a core composed of metal, lipid, polymer, or biological macromolecule, and multiple copies of the nuclease proteins, mRNA, or DNA can be attached to or encapsulated with the nanoparticle core. This increases the copy number of the protein/mRNA/DNA that is delivered to each cell and, so, increases the intracellular expression of each nuclease to maximize the likelihood that the target recognition sequences will be cut. The surface of such nanoparticles may be further modified with polymers or lipids (e.g., chitosan, cationic polymers, or cationic lipids) to form a core-shell nanoparticle whose surface confers additional functionalities to enhance cellular delivery and uptake of the payload (Jian et al. (2012) *Biomaterials*. 33(30): 7621-30). Nanoparticles may additionally be advantageously coupled to targeting molecules to direct the nanoparticle to the appropriate cell type and/or increase the likelihood of cellular uptake. Examples of such targeting molecules include antibodies specific for cell-surface receptors and the natural ligands (or portions of the natural ligands) for cell surface receptors.

In some embodiments, the nuclease proteins or DNA/mRNA encoding the nucleases are encapsulated within liposomes or complexed using cationic lipids (see, e.g., LIPOFECTAMINE™, Life Technologies Corp., Carlsbad, CA; Zuris et al. (2015) Nat Biotechnol. 33: 73-80; Mishra et al. (2011) J Drug Deliv. 2011:863734). The liposome and lipoplex formulations can protect the payload from degradation, enhance accumulation and retention at the target site, and facilitate cellular uptake and delivery efficiency through fusion with and/or disruption of the cellular membranes of the target cells.

In some embodiments, nuclease proteins, or DNA/mRNA encoding nucleases, are encapsulated within polymeric scaffolds (e.g., PLGA) or complexed using cationic polymers (e.g., PEI, PLL) (Tamboli et al. (2011) *Ther Deliv.* 2(4): 523-536). Polymeric carriers can be designed to provide tunable drug release rates through control of polymer erosion and drug diffusion, and high drug encapsulation efficiencies can offer protection of the therapeutic payload until intracellular delivery to the desired target cell population.

In some embodiments, nuclease proteins, or DNA/mRNA encoding nucleases, are combined with amphiphilic molecules that self-assemble into micelles (Tong et al. (2007) *J Gene Med.* 9(11): 956-66). Polymeric micelles may include a micellar shell formed with a hydrophilic polymer (e.g., polyethyleneglycol) that can prevent aggregation, mask charge interactions, and reduce nonspecific interactions.

In some embodiments, nuclease proteins, or DNA/mRNA encoding nucleases, are formulated into an emulsion or a nanoemulsion (i.e., having an average particle diameter of <1 nm) for administration and/or delivery to the target cell. The term "emulsion" refers to, without limitation, any oil-in-water, water-in-oil, water-in-oil-in-water, or oil-in-water-in-oil dispersions or droplets, including lipid structures that can form as a result of hydrophobic forces that drive apolar residues (e.g., long hydrocarbon chains) away from water and polar head groups toward water, when a water immiscible phase is mixed with an aqueous phase. These other lipid structures include, but are not limited to, unilamellar, paucilamellar, and multilamellar lipid vesicles, micelles, and lamellar phases. Emulsions are composed of an aqueous phase and a lipophilic phase (typically containing an oil and an organic solvent). Emulsions also frequently contain one or more surfactants. Nanoemulsion formulations are well known, e.g., as described in U.S. Pat. Nos. 6,015,832, 6,506,803, 6,635,676, 6,559,189, and 7,767,216, each of which is incorporated herein by reference in its entirety.

In some embodiments, nuclease proteins, or DNA/mRNA encoding nucleases, are covalently attached to, or non-covalently associated with, multifunctional polymer conjugates, DNA dendrimers, and polymeric dendrimers (Mastorakos et al. (2015) *Nanoscale.* 7(9): 3845-56; Cheng et al. (2008) *J Pharm Sci.* 97(1): 123-43). The dendrimer generation can control the payload capacity and size, and can provide a high payload capacity. Moreover, display of multiple surface groups can be leveraged to improve stability, reduce nonspecific interactions, and enhance cell-specific targeting and drug release.

In some embodiments, genes encoding a nuclease are introduced into a cell using a recombinant virus (e.g., a recombinant viral vector). Such recombinant viruses are known in the art and include retroviruses, lentiviruses, adenoviruses, and adeno-associated viruses (AAVs) (reviewed in Vannucci, et al. (2013 *New Microbiol.* 36:1-22). Recombinant AAVs useful in the invention can have any serotype that allows for transduction of the recombinant virus into a target cell type and expression of the nuclease gene in the target cell. For example, in some embodiments, recombinant AAVs have a serotype of AAV2, AAV5, AAV8, or AAV9. In some embodiments, the recombinant viruses are injected directly into target tissues (e.g., the eye). In alternative embodiments, the recombinant viruses are delivered systemically via the circulatory system. It is known in the art that different AAVs tend to localize to different tissues. In retinal target tissues, effective transduction of retinal photoreceptor cells has been shown, for example, with AAV serotypes 1, 2, 5, 8, and 9 (Petrs-Silva et al. (2014) *Clinical Ophthalmology.* 8:127-136). Sands (2011) Methods Mol. Biol. 807:141-157). Accordingly, in some embodiments, the AAV serotype is AAV1. In some embodiments, the AAV serotype is AAV2. In alternative embodiments, the AAV serotype is AAV5. In other embodiments, the AAV serotype is AAV8. In still other embodiments, the AAV serotype is AAV9. AAVs can also be self-complementary such that they do not require second-strand DNA synthesis in the host cell (McCarty, et al. (2001) Gene Ther. 8:1248-54). Nucleic acid molecules delivered by recombinant AAVs can include left (5') and right (3') inverted terminal repeats.

In one embodiment, a recombinant virus used for meganuclease gene delivery is a self-limiting recombinant virus. A self-limiting recombinant virus can have limited persistence time in a cell or organism due to the presence of a recognition sequence for an engineered meganuclease within the vector. Thus, a self-limiting recombinant virus can be engineered to provide coding for a promoter, a meganuclease described herein, and a meganuclease recognition site within the ITRs. The self-limiting recombinant virus delivers the meganuclease gene to a cell, tissue, or organism, such that the meganuclease is expressed and able to cut the genome of the cell at an endogenous recognition sequence within the genome. The delivered meganuclease will also find its target site within the self-limiting viral genome, and cut the viral genome at this target site. Once cut, the 5' and 3' ends of the viral genome will be exposed and degraded by exonucleases, thus killing the virus and ceasing production of the meganuclease.

If the nuclease genes are delivered in DNA form (e.g. plasmid) and/or via a recombinant virus (e.g., an AAV) they can be operably linked to a promoter. In some embodiments, this can be a viral promoter such as endogenous promoters from the viral vector (e.g. the LTR of a lentivirus) or the well-known cytomegalovirus- or SV40 virus-early promoters. In a particular embodiment, nuclease genes are operably linked to a promoter that drives gene expression preferentially in the target cells. Examples of retina and/or rod photoreceptor cell-specific promoters include, without limitation, the human rhodopsin kinase promoter, the proximal mouse opsin promoter (mOP), the human G-protein-coupled receptor protein kinase 1 promoter (hGRK1), and the human interphotoreceptor retinoid-binding protein (IRBP) promoter (Khani et al. (2007) *Invest. Ophthamol. Vis. Sci.* 48(9):3954-3961); Beltran et al. (2010) *Gene Therapy.* 17(9):1162-1174); Yokoyama et al. (1992) *Exp. Eye Res.* 55(2):225-233), as well as rod photoreceptor cell-specific promoters disclosed in US 2014/0287510.

In some embodiments, a subject is administered a pharmaceutical composition at a dose of about $1\times10^{10}$ gc/kg to about $1\times10^{14}$ gc/kg (e.g., $1\times10^{10}$ gc/kg, $1\times10^{11}$ gc/kg, $1\times10^{12}$ gc/kg, $1\times10^{13}$ gc/kg, or $1\times10^{14}$ gc/kg) of a polynucleotide comprising a nucleic sequence encoding an engineered nuclease. In some embodiments, a subject is administered a pharmaceutical composition at a dose of at least about $1\times10^{10}$ gc/kg, at least about $1\times10^{11}$ gc/kg, at least about $1\times10^{12}$ gc/kg, at least about $1\times10^{13}$ gc/kg, or at least about $1\times10^{14}$ gc/kg of a polynucleotide comprising a nucleic sequence encoding an engineered nuclease. In some embodiments, a subject is administered a pharmaceutical composition at a dose of about $1\times10^{10}$ gc/kg to about $1\times10^{11}$ gc/kg, about $1\times10^{11}$ gc/kg to about $1\times10^{12}$ gc/kg, about $1\times10^{12}$ gc/kg to about $1\times10^{13}$ gc/kg, or about $1\times10^{13}$ gc/kg to about $1\times10^{14}$ gc/kg of a polynucleotide comprising a nucleic sequence encoding an engineered nuclease. In certain embodiments, a subject is administered a pharmaceutical composition at a dose of about $1\times10^{12}$ gc/kg to about $9\times10^{13}$ gc/kg (e.g., about $1\times10^{12}$ gc/kg, about $2\times10^{12}$ gc/kg, about $3\times10^{12}$ gc/kg, about $4\times10^{12}$ gc/kg, about $5\times10^{12}$ gc/kg, about $6\times10^{12}$ gc/kg, about $7\times10^{12}$ gc/kg, about $8\times10^{12}$ gc/kg, about $9\times10^{12}$ gc/kg, about $1\times10^{13}$ gc/kg, about $2\times10^{13}$ gc/kg, about $3\times10^{13}$ gc/kg, about $4\times10^{13}$ gc/kg, about $5\times10^{13}$ gc/kg, about $6\times10^{13}$ gc/kg, about $7\times10^{13}$ gc/kg, about $8\times10^{13}$ gc/kg, or about $9\times10^{13}$ gc/kg) of a polynucleotide comprising a nucleic sequence encoding an engineered nuclease.

In some embodiments, a subject is administered a lipid nanoparticle formulation at a dose of about 0.1 mg/kg to about 3 mg/kg of mRNA encoding an engineered nuclease. In some embodiments, the subject is administered a lipid nanoparticle formulation at a dose of at least about 0.1 mg/kg, at least about 0.25 mg/kg, at least about 0.5 mg/kg, at least about 0.75 mg/kg, at least about 1.0 mg/kg, at least about 1.5 mg/kg, at least about 2.0 mg/kg, at least about 2.5 mg/kg, or at least about 3.0 mg/kg of mRNA encoding an engineered nuclease. In some embodiments, the subject is administered a lipid nanoparticle formulation at a dose of within about 0.1 mg/kg to about 0.25 mg/kg, about 0.25 mg/kg to about 0.5 mg/kg, about 0.5 mg/kg to about 0.75 mg/kg, about 0.75 mg/kg to about 1.0 mg/kg, about 1.0 mg/kg to about 1.5 mg/kg, about 1.5 mg/kg to about 2.0 mg/kg, about 2.0 mg/kg to about 2.5 mg/kg, or about 2.5 mg/kg to about 3.0 mg/kg of mRNA encoding an engineered nuclease.

The target tissue(s) for delivery of engineered nucleases of the invention, or nucleic acids encoding engineered nucleases of the invention, include without limitation, tissues of the eye including, without limitation, rod photoreceptor cells and cone photoreceptor cells.

In an in vivo aspect of the methods of the invention, a retrovirus, pseudotype, or recombinant AAV is constructed, which encodes the engineered nuclease and is administered to the subject. Administration of a recombinant virus encoding the engineered nuclease can occur, for example, with administration of a recombinant AAV that encodes a secretion-impaired hepatotoxin, or encodes tPA, which stimulates hepatocyte regeneration without acting as a hepatotoxin.

In various embodiments of the methods described herein, the one or more engineered nucleases, polynucleotides encoding such engineered nucleases, or viruses comprising one or more polynucleotides encoding such engineered nucleases, as described herein, can be administered via any suitable route of administration known in the art. Accordingly, the one or more engineered nucleases, polynucleotides comprising nucleic acid sequences encoding such engineered nucleases, or recombinant virus comprising one or more polynucleotides comprising a nucleic acid sequence encoding such engineered nucleases, as described herein may be administered by an administration route comprising intravenous, intramuscular, intraperitoneal, subcutaneous, intrahepatic, transmucosal, transdermal, intraarterial, intravitreal, and sublingual. In some embodiments, nuclease proteins, or mRNA, or DNA vectors encoding nucleases, are supplied to target cells (e.g., cells in the eye) via injection directly to the target tissue. Other suitable routes of administration of the engineered nucleases, polynucleotides encoding such engineered nucleases, or recombinant viruses comprising one or more polynucleotides encoding such engineered nucleases may be readily determined by the treating physician as necessary.

In some embodiments, a therapeutically effective amount of an engineered nuclease described herein is administered to a subject in need thereof. As appropriate, the dosage or dosing frequency of the engineered nuclease may be adjusted over the course of the treatment, based on the judgment of the administering physician. Appropriate doses will depend, among other factors, on the specifics of any AAV chosen (e.g., serotype, etc.), on the route of administration, on the subject being treated (i.e., age, weight, sex, and general condition of the subject), and the mode of administration. Thus, the appropriate dosage may vary from patient to patient. An appropriate effective amount can be readily determined by one of skill in the art. Dosage treatment may be a single dose schedule or a multiple dose schedule. Moreover, the subject may be administered as many doses as appropriate. One of skill in the art can readily determine an appropriate number of doses. The dosage may need to be adjusted to take into consideration an alternative route of administration or balance the therapeutic benefit against any side effects.

In some embodiments, the methods comprise delivering an engineered meganuclease described herein (or a nucleic acid encoding the same) and a polynucleotide comprising a nucleic acid sequence encoding a sequence of interest and sequences homologous to sequences flanking the meganuclease cleavage site, wherein the engineered meganuclease binds and cleaves a recognition sequence comprising SEQ ID NO: 7 within a RHO P23H gene, thus cleaving the RHO P23H gene, wherein the sequence of interest is inserted at the cleavage site by homologous recombination. Exogenous nucleic acid molecules of the invention may be introduced into a cell and/or delivered to a subject by any of the means previously discussed. In a particular embodiment, exogenous nucleic acid molecules are introduced by way of a recombinant virus, such as a recombinant lentivirus, recombinant retrovirus, recombinant adenovirus, or a recombinant AAV. Recombinant AAVs useful for introducing an exogenous nucleic acid molecule can have any serotype that allows for transduction of the virus into the cell and insertion of the exogenous nucleic acid molecule sequence into the cell genome. In some embodiments, recombinant AAVs have a serotype of AAV2, AAV5, AAV8, or AAV9. The recombinant AAVs can also be self-complementary such that they do not require second-strand DNA synthesis in the host cell. Exogenous nucleic acid molecules introduced using a recombinant AAV can be flanked by a 5' (left) and 3' (right) inverted terminal repeat.

In another particular embodiment, an exogenous nucleic acid molecule can be introduced into a cell using a single-stranded DNA template. The single-stranded DNA can comprise the exogenous nucleic acid molecule and, in particular embodiments, can comprise 5' and 3' homology arms to promote insertion of the nucleic acid sequence into the nuclease cleavage site by homologous recombination. The single-stranded DNA can further comprise a 5' AAV inverted terminal repeat (ITR) sequence 5' upstream of the 5' homology arm, and a 3' AAV ITR sequence 3' downstream of the 3' homology arm.

In another particular embodiment, genes encoding a nuclease of the invention and/or an exogenous nucleic acid molecule of the invention can be introduced into a cell by transfection with a linearized DNA template. A plasmid DNA encoding an engineered nuclease and/or an exogenous nucleic acid molecule can, for example, be digested by one or more restriction enzymes such that the circular plasmid DNA is linearized prior to transfection into the cell.

When delivered to a cell, an exogenous nucleic acid of the invention can be operably linked to any promoter suitable for expression of the encoded polypeptide in the cell, including those mammalian promoters and inducible promoters previously discussed. An exogenous nucleic acid of the invention can also be operably linked to a synthetic promoter. Synthetic promoters can include, without limitation, the JeT promoter (WO 2002/012514).

It is envisioned that a single treatment will permanently inactivate the mutant P23H RHO allele in a percentage of patient target cells. If the frequency of P23H allele inactivation is low, however, or if a large percentage of target cells need to be corrected, it may be necessary to perform multiple treatments on each patient.

2.4 Pharmaceutical Compositions

In some embodiments, the invention provides a pharmaceutical composition comprising a pharmaceutically acceptable carrier and engineered nuclease of the invention, or a pharmaceutically acceptable carrier and an isolated polynucleotide comprising a nucleic acid encoding an engineered nuclease of the invention. In particular, pharmaceutical compositions are provided that comprise a pharmaceutically acceptable carrier and a therapeutically effective amount of a nucleic acid encoding an engineered nuclease or an engineered nuclease, wherein the engineered nuclease has specificity for a recognition sequence within a RHO gene and in particular a RHO P23H gene such as RHO 1-2 (SEQ ID NO: 7).

Accordingly, pharmaceutical compositions of the invention can be useful for treating retinitis pigmentosa and reducing the level of RHO P23H, or reducing the symptoms associated with retinitis pigmentosa in a subject. A subject having retinitis pigmentosa or a subject who may be particularly receptive to treatment with the engineered meganucleases herein may be identified by ascertaining the presence or absence of one or more risk factors, diagnostic, or prognostic indicators, such as indicators including for example, performing a dilated eye exam, optical coherence tomography, fluorescein angiography, a visual field test, or an electroretinogram as is known in the art.

RHO P23H levels can be assessed any time before, during, or after treatment in accordance with the methods herein using any methods known in the art. RHO P23H levels may be assessed based on the level of any variable associated with RHO P23H gene expression, e.g., mRNA level or protein level, retina sensitivity and functionality (e.g., rod cell function), fundus autofluorescence levels, structural abnormalities of the retina (e.g., as assessed through optical coherence tomography). A reduction in the levels of RHO or RHO P23H or expression may be assessed by a change in an absolute or relative level of one or more of these variables compared with a reference level. RHO or RHO P23H levels may be measured in a biological sample isolated from a subject, such as a tissue biopsy from an eye, or a bodily fluid that contains RHO or RHO P23H, such the peripheral blood. Optionally, RHO or RHO P23H levels are normalized to a standard protein or substance in the sample. Further, RHO or RHO P23H levels can be assessed any time before, during, or after treatment in accordance with the methods herein.

In some embodiments, the claimed methods include administration of any of the engineered meganucleases described herein, or nucleic acids encoding the meganucleases, to reduce RHO P23H levels in a subject, by at least 1%, 2%, 3%, 4%, 5%, 10%, 15%, 20%, 25%, 30%, 40%, 50%, 60%, 70%, 80%, 90%, 95%, or 100% relative to a reference level.

Pharmaceutical compositions of the invention can be useful for treating a subject having retinitis pigmentosa by modifying a mutant RHO P23H allele in accordance with the present invention. Such pharmaceutical compositions can be prepared in accordance with known techniques. See, e.g., Remington, The Science And Practice of Pharmacy (21st ed., Philadelphia, Lippincott, Williams & Wilkins, 2005). In the manufacture of a pharmaceutical formulation according to the invention, nuclease polypeptides (or DNA/RNA encoding the same or cells expressing the same) are typically admixed with a pharmaceutically acceptable carrier, and the resulting composition is administered to a subject. The carrier must, of course, be acceptable in the sense of being compatible with any other ingredients in the formulation and must not be deleterious to the subject. In some embodiments, pharmaceutical compositions of the invention can further comprise one or more additional agents or biological molecules useful in the treatment of a disease in the subject. Likewise, the additional agent(s) and/or biological molecule(s) can be co-administered as a separate composition.

In particular embodiments of the invention, the pharmaceutical composition comprises a recombinant virus comprising a polynucleotide comprising a nucleic acid sequence encoding an engineered nuclease described herein. Such recombinant viruses are known in the art and include recombinant retroviruses, recombinant lentiviruses, recombinant adenoviruses, and recombinant adeno-associated virus (AAVs) (reviewed in Vannucci, et al. (2013 *New Microbiol.* 36:1-22). Recombinant AAVs useful in the invention can have any serotype that allows for transduction of the virus into a target cell type and expression of the nuclease gene by the target cell. For example, in some embodiments, recombinant AAVs have a serotype of AAV2, AAV5, AAV8, or AAV9. In some embodiments, the recombinant viruses are injected directly into target tissues. In alternative embodiments, the recombinant viruses are delivered systemically via the circulatory system. It is known in the art that different AAVs tend to localize to different tissues. In liver target tissues, effective transduction of hepatocytes has been shown, for example, with AAV serotypes 2, 8, and 9 (Sands (2011) Methods Mol. Biol. 807: 141-157). Accordingly, in some embodiments, the AAV serotype is AAV2. In alternative embodiments, the AAV serotype is AAV5. In other embodiments, the AAV serotype is AAV8. In still other embodiments, the AAV serotype is AAV9. AAVs can also be self-complementary such that they do not require second-strand DNA synthesis in the host cell (McCarty, et al. (2001) Gene Ther. 8:1248-54). Nucleic acid molecules delivered by recombinant AAVs can include left (5') and right (3') inverted terminal repeats.

In particular embodiments of the invention, the pharmaceutical composition comprises one or more mRNAs described herein (e.g., mRNAs encoding engineered nucleases) formulated within lipid nanoparticles.

The selection of cationic lipids, non-cationic lipids and/or lipid conjugates which comprise the lipid nanoparticle, as well as the relative molar ratio of such lipids to each other, is based upon the characteristics of the selected lipid(s), the nature of the intended target cells, and the characteristics of the mRNA to be delivered. Additional considerations include, for example, the saturation of the alkyl chain, as well as the size, charge, pH, pKa, fusogenicity and toxicity of the selected lipid(s). Thus, the molar ratios of each individual component may be adjusted accordingly.

The lipid nanoparticles for use in the method of the invention can be prepared by various techniques which are presently known in the art. Nucleic acid-lipid particles and their method of preparation are disclosed in, for example, U.S. Patent Publication Nos. 20040142025 and 20070042031, the disclosures of which are herein incorporated by reference in their entirety for all purposes.

Selection of the appropriate size of lipid nanoparticles must take into consideration the site of the target cell and the application for which the lipid nanoparticles is being made. Generally, the lipid nanoparticles will have a size within the range of about 25 to about 500 nm. In some embodiments, the lipid nanoparticles have a size from about 50 nm to about 300 nm, or from about 60 nm to about 120 nm. The size of the lipid nanoparticles may be determined by quasi-electric light scattering (QELS) as described in Bloomfield, Ann. Rev. Biophys. Bioeng., 10:421^150 (1981), incorporated herein by reference. A variety of methods are known in the art for producing a population of lipid nanoparticles of particular size ranges, for example, sonication or homogenization. One such method is described in U.S. Pat. No. 4,737,323, incorporated herein by reference.

Some lipid nanoparticles contemplated for use in the invention comprise at least one cationic lipid, at least one non-cationic lipid, and at least one conjugated lipid. In more particular examples, lipid nanoparticles can comprise from about 50 mol % to about 85 mol % of a cationic lipid, from about 13 mol % to about 49.5 mol % of a non-cationic lipid, and from about 0.5 mol % to about 10 mol % of a lipid conjugate, and are produced in such a manner as to have a non-lamellar (i.e., non-bilayer) morphology. In other particular examples, lipid nanoparticles can comprise from about 40 mol % to about 85 mol % of a cationic lipid, from about 13 mol % to about 49.5 mol % of a non-cationic lipid, and from about 0.5 mol % to about 10 mol % of a lipid conjugate, and are produced in such a manner as to have a non-lamellar (i.e., non-bilayer) morphology.

Cationic lipids can include, for example, one or more of the following: palmitoyi-oleoyl-nor-arginine (PONA), MPDACA, GUADACA, ((6Z,9Z,28Z,31Z)-heptatriaconta-6,9,28,31-tetraen-19-yl4-(dimethylamino)butanoate) (MC3), LenMC3, CP-LenMC3, γ-LenMC3, CP-γ-LenMC3, MC3MC, MC2MC, MC3 Ether, MC4 Ether, MC3 Amide, Pan-MC3, Pan-MC4 and Pan MC5, 1,2-dilinoleyloxy-N,N-dimethylaminopropane (DLinDMA), 1,2-dilinolenyloxy-N,N-dimethylaminopropane (DLenDMA), 2,2-dilinoleyl-4-(2-dimethylaminoethyl)-[1,3]-dioxolane (DLin-K-C2-DMA; "XTC2"), 2,2-dilinoleyl-4-(3-dimethylaminopropyl)-[1,3]-dioxolane (DLin-K-C3-DMA), 2,2-dilinoleyl-4-(4-dimethylaminobutyl)-[1,3]-dioxolane (DLin-K-C4-DMA), 2,2-dilinoleyl-5-dimethylaminomethyl-[1,3]-dioxane (DLin-K6-DMA), 2,2-dilinoleyl-4-N-methylpepiazino-[1,3]-dioxolane (DLin-K-MPZ), 2,2-dilinoleyl-4-dimethylaminomethyl-[1,3]-dioxolane (DLin-K-DMA), 1,2-dilinoleylcarbamoyloxy-3-dimethylaminopropane (DLin-C-DAP), 1,2-dilinoleyoxy-3-(dimethylamino)acetoxypropane (DLin-DAC), 1,2-dilinoleyoxy-3-morpholinopropane (DLin-MA), 1,2-dilinoleoyl-3-dimethylaminopropane (DLinDAP), 1,2-dilinoleylthio-3-dimethylaminopropane (DLin-S-DMA), 1-linoleoyl-2-linoleyloxy-3-dimethylaminopropane (DLin-2-DMAP), 1,2-dilinoleyloxy-3-trimethylaminopropane chloride salt (DLin-TMA.Cl), 1,2-dilinoleoyl-3-trimethylaminopropane chloride salt (DLin-TAP.Cl), 1,2-dilinoleyloxy-3-(N-methylpiperazino)propane (DLin-MPZ), 3-(N,N-dilinoleylamino)-1,2-propanediol (DLinAP), 3-(N,N-dioleylamino)-1,2-propanedio (DOAP), 1,2-dilinoleyloxo-3-(2-N,N-dimethylamino)ethoxypropane (DLin-EG-DMA), N,N-dioleyl-N,N-dimethylammonium chloride (DODAC), 1,2-dioleyloxy-N,N-dimethylaminopropane (DODMA), 1,2-distearyloxy-N,N-dimethylaminopropane (DSDMA), N-(1-(2,3-dioleyloxy)propyl)-N,N,N-trimethylammonium chloride (DOTMA), N,N-distearyl-N,N-dimethylammonium bromide (DDAB), N-(1-(2,3-dioleoyloxy)propyl)-N,N,N-trimethylammonium chloride (DOTAP), 3-(N—(N',N'-dimethylaminoethane)-carbamoyl)cholesterol (DC-Chol), N-(1,2-dimyristyloxyprop-3-yl)-N,N-dimethyl-N-hydroxyethyl ammonium bromide (DMRIE), 2,3-dioleyloxy-N-[2 (spermine-carboxamido)ethyl]-N,N-dimethyl-1-propan-aminiumtrifluoroacetate (DOSPA), dioctadecylamidoglycyl spermine (DOGS), 3-dimethylamino-2-(cholest-5-en-3-beta-oxybutan-4-oxy)-1-(cis,cis-9,12-octadecadienoxy)propane (CLinDMA), 2-[5'-(cholest-5-en-3-beta-oxy)-3'-oxapentoxy)-3-dimethy-1-(cis,cis-9',1-2'-octadecadienoxy)propane (CpLinDMA), N,N-dimethyl-3,4-dioleyloxybenzylamine (DMOB A), 1,2-N,N'-dioleylcarbamyl-3-dimethylaminopropane (DOcarbDAP), 1,2-N,N'-dilinoleylcarbamyl-3-dimethylaminopropane (DLincarbDAP), or mixtures thereof. The cationic lipid can also be DLinDMA, DLin-K-C2-DMA ("XTC2"), MC3, LenMC3, CP-LenMC3, γ-LenMC3, CP-γ-LenMC3, MC3MC, MC2MC, MC3 Ether, MC4 Ether, MC3 Amide, Pan-MC3, Pan-MC4, Pan MC5, or mixtures thereof.

In various embodiments, the cationic lipid comprises from about 50 mol % to about 90 mol %, from about 50 mol % to about 85 mol %, from about 50 mol % to about 80 mol %, from about 50 mol % to about 75 mol %, from about 50 mol % to about 70 mol %, from about 50 mol % to about 65 mol %, or from about 50 mol % to about 60 mol % of the total lipid present in the particle.

In other embodiments, the cationic lipid comprises from about 40 mol % to about 90 mol %, from about 40 mol % to about 85 mol %, from about 40 mol % to about 80 mol %, from about 40 mol % to about 75 mol %, from about 40 mol % to about 70 mol %, from about 40 mol % to about 65 mol %, or from about 40 mol % to about 60 mol % of the total lipid present in the particle.

The non-cationic lipid may comprise, e.g., one or more anionic lipids and/or neutral lipids. In particular embodiments, the non-cationic lipid comprises one of the following neutral lipid components: (1) cholesterol or a derivative thereof; (2) a phospholipid; or (3) a mixture of a phospholipid and cholesterol or a derivative thereof. Examples of cholesterol derivatives include, but are not limited to, cholestanol, cholestanone, cholestenone, coprostanol, cholesteryl-2'-hydroxyethyl ether, cholesteryl-4'-hydroxybutyl ether, and mixtures thereof. The phospholipid may be a neutral lipid including, but not limited to, dipalmitoylphosphatidylcholine (DPPC), distearoylphosphatidylcholine (DSPC), dioleoylphosphatidylethanolamine (DOPE), palmitoyloleoyl-phosphatidylcholine (POPC), palmitoyloleoyl-phosphatidylethanolamine (POPE), palmitoyloleyol-phosphatidylglycerol (POPG), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), stearoyloleoyl-phosphatidylethanolamine (SOPE), egg phosphatidylcholine (EPC), and mixtures thereof. In certain particular embodiments, the phospholipid is DPPC, DSPC, or mixtures thereof.

In some embodiments, the non-cationic lipid (e.g., one or more phospholipids and/or cholesterol) comprises from about 10 mol % to about 60 mol %, from about 15 mol % to about 60 mol %, from about 20 mol % to about 60 mol %, from about 25 mol % to about 60 mol %, from about 30 mol % to about 60 mol %, from about 10 mol % to about 55 mol %, from about 15 mol % to about 55 mol %, from about 20 mol % to about 55 mol %, from about 25 mol % to about 55 mol %, from about 30 mol % to about 55 mol %, from about 13 mol % to about 50 mol %, from about 15 mol % to about 50 mol % or from about 20 mol % to about 50 mol % of the total lipid present in the particle. When the non-cationic lipid is a mixture of a phospholipid and cholesterol or a cholesterol derivative, the mixture may comprise up to about 40, 50, or 60 mol % of the total lipid present in the particle.

The conjugated lipid that inhibits aggregation of particles may comprise, e.g., one or more of the following: a polyethyleneglycol (PEG)-lipid conjugate, a polyamide (ATTA)-lipid conjugate, a cationic-polymer-lipid conjugates (CPLs), or mixtures thereof. In one particular embodiment, the nucleic acid-lipid particles comprise either a PEG-lipid conjugate or an ATTA-lipid conjugate. In certain embodiments, the PEG-lipid conjugate or ATTA-lipid conjugate is used together with a CPL. The conjugated lipid that inhibits aggregation of particles may comprise a PEG-lipid including, e.g., a PEG-diacylglycerol (DAG), a PEG dialkyloxypropyl (DAA), a PEG-phospholipid, a PEG-ceramide (Cer), or mixtures thereof. The PEG-DAA conjugate may be PEG-dilauryloxypropyl (C12), a PEG-dimyristyloxypropyl (C14), a PEG-dipalmityloxypropyl (C16), a PEG-distearyloxypropyl (C18), or mixtures thereof.

Additional PEG-lipid conjugates suitable for use in the invention include, but are not limited to, mPEG2000-1,2-di-O-alkyl-sn3-carbomoylglyceride (PEG-C-DOMG). The synthesis of PEG-C-DOMG is described in PCT Application No. PCT/US08/88676. Yet additional PEG-lipid conjugates suitable for use in the invention include, without limitation, 1-[8'-(1,2-dimyristoyl-3-propanoxy)-carboxamido-3',6'-di-oxaoctanyl]carbamoyl-ω-methyl-poly(ethylene glycol) (2KPEG-DMG). The synthesis of 2KPEG-DMG is described in U.S. Pat. No. 7,404,969.

In some cases, the conjugated lipid that inhibits aggregation of particles (e.g., PEG-lipid conjugate) may comprise from about 0.1 mol % to about 2 mol %, from about 0.5 mol % to about 2 mol %, from about 1 mol % to about 2 mol %, from about 0.6 mol % to about 1.9 mol %, from about 0.7 mol % to about 1.8 mol %, from about 0.8 mol % to about 1.7 mol %, from about 1 mol % to about 1.8 mol %, from about 1.2 mol % to about 1.8 mol %, from about 1.2 mol % to about 1.7 mol %, from about 1.3 mol % to about 1.6 mol %, from about 1.4 mol % to about 1.5 mol %, or about 1, 1.1, 1.2, 1.3, 1.4, 1.5, 1.6, 1.7, 1.8, 1.9, or 2 mol % (or any fraction thereof or range therein) of the total lipid present in the particle. Typically, in such instances, the PEG moiety has an average molecular weight of about 2,000 Daltons. In other cases, the conjugated lipid that inhibits aggregation of particles (e.g., PEG-lipid conjugate) may comprise from about 5.0 mol % to about 10 mol %, from about 5 mol % to about 9 mol %, from about 5 mol % to about 8 mol %, from about 6 mol % to about 9 mol %, from about 6 mol % to about 8 mol %, or about 5 mol %, 6 mol %, 7 mol %, 8 mol %, 9 mol %, or 10 mol % (or any fraction thereof or range therein) of the total lipid present in the particle. Typically, in such instances, the PEG moiety has an average molecular weight of about 750 Daltons.

In other embodiments, the composition comprises amphoteric liposomes, which contain at least one positive and at least one negative charge carrier, which differs from the positive one, the isoelectric point of the liposomes being between 4 and 8. This objective is accomplished owing to the fact that liposomes are prepared with a pH-dependent, changing charge.

Liposomal structures with the desired properties are formed, for example, when the amount of membrane-forming or membrane-based cationic charge carriers exceeds that of the anionic charge carriers at a low pH and the ratio is reversed at a higher pH. This is always the case when the ionizable components have a pKa value between 4 and 9. As the pH of the medium drops, all cationic charge carriers are charged more and all anionic charge carriers lose their charge.

Cationic compounds useful for amphoteric liposomes include those cationic compounds previously described herein above. Without limitation, strongly cationic compounds can include, for example: DC-Chol 3-β-[N—(N',N'-dimethylmethane) carbamoyl] cholesterol, TC-Chol 3-β-[N—(N',N',N'-trimethylaminoethane) carbamoyl cholesterol, BGSC bisguanidinium-spermidine-cholesterol, BGTC bis-guadinium-tren-cholesterol, DOTAP (1,2-dioleoyloxypropyl)-N,N,N-trimethylammonium chloride, DOSPER (1,3-dioleoyloxy (6-carboxy-spermyl)-propylarnide, DOTMA (1,2-dioleoyloxypropyl)-N,N,N-trimethylamronium chloride) (Lipofectin®), DORIE 1,2-dioleoyloxypropyl) dimethylhydroxyethylammonium bromide, DOSC (1,2-dioleoyl-3-succinyl-sn-glyceryl choline ester), DOGSDSO (1,2-dioleoyl-sn-glycero-3-succinyl-2-hydroxyethyl disulfide omithine), DDAB dimethyldioctadecylammonium bromide, DOGS ((C18)2GlySper3+) N,N-dioctadecylamido-glycol-spermin (Transfectam®) (C18)2Gly+N, N-dioctadecylamido-glycine, CTAB cetyltrimethylammonium bromide, CpyC cetylpyridinium chloride, DOEPC 1,2-dioleoly-sn-glycero-3-ethylphosphocholine or other O-alkyl-phosphatidylcholine or ethanolamines, amides from lysine, arginine or ornithine and phosphatidyl ethanolamine.

Examples of weakly cationic compounds include, without limitation: His-Chol (histaminyl-cholesterol hemisuccinate), Mo-Chol (morpholine-N-ethylamino-cholesterol hemisuccinate), or histidinyl-PE.

Examples of neutral compounds include, without limitation: cholesterol, ceramides, phosphatidyl cholines, phosphatidyl ethanolamines, tetraether lipids, or diacyl glycerols.

Anionic compounds useful for amphoteric liposomes include those non-cationic compounds previously described herein. Without limitation, examples of weakly anionic compounds can include: CHEMS (cholesterol hemisuccinate), alkyl carboxylic acids with 8 to 25 carbon atoms, or diacyl glycerol hemisuccinate. Additional weakly anionic compounds can include the amides of aspartic acid, or glutamic acid and PE as well as PS and its amides with glycine, alanine, glutamine, asparagine, serine, cysteine, threonine, tyrosine, glutamic acid, aspartic acid or other amino acids or aminodicarboxylic acids. According to the same principle, the esters of hydroxycarboxylic acids or hydroxydicarboxylic acids and PS are also weakly anionic compounds.

In some embodiments, amphoteric liposomes contain a conjugated lipid, such as those described herein above. Particular examples of useful conjugated lipids include, without limitation, PEG-modified phosphatidylethanolamine and phosphatidic acid, PEG-ceramide conjugates (e.g., PEG-CerC14 or PEG-CerC20), PEG-modified dialkylamines and PEG-modified 1,2-diacyloxypropan-3-amines. Some particular examples are PEG-modified diacylglycerols and dialkylglycerols.

In some embodiments, the neutral lipids comprise from about 10 mol % to about 60 mol %, from about 15 mol % to about 60 mol %, from about 20 mol % to about 60 mol %, from about 25 mol % to about 60 mol %, from about 30 mol % to about 60 mol %, from about 10 mol % to about 55 mol %, from about 15 mol % to about 55 mol %, from about 20 mol % to about 55 mol %, from about 25 mol % to about 55 mol %, from about 30 mol % to about 55 mol %, from about 13 mol % to about 50 mol %, from about 15 mol % to about 50 mol % or from about 20 mol % to about 50 mol % of the total lipid present in the particle.

In some cases, the conjugated lipid that inhibits aggregation of particles (e.g., PEG-lipid conjugate) comprises from about 0.1 mol % to about 2 mol %, from about 0.5 mol % to about 2 mol %, from about 1 mol % to about 2 mol %, from about 0.6 mol % to about 1.9 mol %, from about 0.7 mol % to about 1.8 mol %, from about 0.8 mol % to about 1.7 mol %, from about 1 mol % to about 1.8 mol %, from about 1.2 mol % to about 1.8 mol %, from about 1.2 mol % to about 1.7 mol %, from about 1.3 mol % to about 1.6 mol %, from about 1.4 mol % to about 1.5 mol %, or about 1, 1.1, 1.2, 1.3, 1.4, 1.5, 1.6, 1.7, 1.8, 1.9, or 2 mol % (or any fraction thereof or range therein) of the total lipid present in the particle. Typically, in such instances, the PEG moiety has an average molecular weight of about 2,000 Daltons. In other cases, the conjugated lipid that inhibits aggregation of particles (e.g., PEG-lipid conjugate) may comprise from about 5.0 mol % to about 10 mol %, from about 5 mol % to about 9 mol %, from about 5 mol % to about 8 mol %, from about 6 mol % to about 9 mol %, from about 6 mol % to about 8 mol %, or about 5 mol %, 6 mol %, 7 mol %, 8 mol %, 9 mol %, or 10 mol % (or any fraction thereof or range therein) of the total lipid present in the particle. Typically, in such instances, the PEG moiety has an average molecular weight of about 750 Daltons.

Considering the total amount of neutral and conjugated lipids, the remaining balance of the amphoteric liposome can comprise a mixture of cationic compounds and anionic compounds formulated at various ratios. The ratio of cationic to anionic lipid may selected in order to achieve the desired properties of nucleic acid encapsulation, zeta potential, pKa, or other physicochemical property that is at least in part dependent on the presence of charged lipid components.

In some embodiments, the lipid nanoparticles have a composition that specifically enhances delivery and uptake in the eye or a particular cell type of the eye (e.g., a rod photoreceptor cell or a cone photoreceptor cell).

In some embodiments, pharmaceutical compositions of the invention can further comprise one or more additional agents useful in the treatment of retinitis pigmentosa in the subject.

The present disclosure also provides engineered meganucleases described herein (or nucleic acids encoding the same or cells expressing the engineered meganucleases) for use as a medicament. The present disclosure further provides the use of an engineered meganuclease described herein (or a nucleic acid encoding the same or cells expressing an engineered meganuclease) in the manufacture of a medicament for treating retinitis pigmentosa or reducing the symptoms associated with retinitis pigmentosa.

2.5 Methods for Producing Recombinant Viruses

In some embodiments, the invention provides recombinant viruses (i.e., recombinant viral vectors; e.g., recombinant AAVs) for use in the methods of the invention. Recombinant AAVs are typically produced in mammalian cell lines such as HEK-293. Because the viral cap and rep genes are removed from the recombinant virus to prevent its self-replication to make room for the therapeutic gene(s) to be delivered (e.g. the nuclease gene), it is necessary to provide these in trans in the packaging cell line. In addition, it is necessary to provide the "helper" (e.g. adenoviral) components necessary to support replication (Cots et al. (2013), Curr. Gene Ther. 13(5): 370-81). Frequently, recombinant AAVs are produced using a triple-transfection in which a cell line is transfected with a first plasmid encoding the "helper" components, a second plasmid comprising the cap and rep genes, and a third plasmid comprising the viral ITRs containing the intervening DNA sequence to be packaged into the virus. Viral particles comprising a genome (ITRs and intervening gene(s) of interest) encased in a capsid are then isolated from cells by freeze-thaw cycles, sonication, detergent, or other means known in the art. Particles are then purified using cesium-chloride density gradient centrifugation or affinity chromatography and subsequently delivered to the gene(s) of interest to cells, tissues, or an organism such as a human patient.

Because recombinant AAV particles are typically produced (manufactured) in cells, precautions must be taken in practicing the current invention to ensure that the engineered nuclease is not expressed in the packaging cells. Because the viral genomes of the invention may comprise a recognition sequence for the nuclease, any nuclease expressed in the packaging cell line may be capable of cleaving the viral genome before it can be packaged into viral particles. This will result in reduced packaging efficiency and/or the packaging of fragmented genomes. Several approaches can be used to prevent nuclease expression in the packaging cells.

The nuclease can be placed under the control of a tissue-specific promoter that is not active in the packaging cells. For example, if a viral vector is developed for delivery of a nuclease gene(s) to muscle tissue, a muscle-specific promoter can be used. Examples of muscle-specific promoters include C5-12 (Liu, et al. (2004) Hum Gene Ther. 15:783-92), the muscle-specific creatine kinase (MCK) promoter (Yuasa, et al. (2002) Gene Ther. 9:1576-88), or the smooth muscle 22 (SM22) promoter (Haase, et al. (2013) BMC Biotechnol. 13:49-54). Examples of CNS (neuron)-specific promoters include the NSE, Synapsin, and MeCP2 promoters (Lentz, et al. (2012) Neurobiol Dis. 48:179-88). Examples of liver-specific promoters include, for example, albumin promoters (such as Palb), human al-antitrypsin (such as Pa1AT), and hemopexin (such as Phpx) (Kramer et al., (2003) Mol. Therapy 7:375-85), hybrid liver-specific promoter (hepatic locus control region from ApoE gene (ApoE-HCR) and a liver-specific alpha1-antitrypsin promoter), human thyroxine binding globulin (TBG) promoter, and apolipoprotein A-II promoter. Examples of eye-specific promoters include opsin, and corneal epithelium-specific K12 promoters (Martin et al. (2002) Methods (28): 267-75) (Tong et al., (2007) J Gene Med, 9:956-66). These promoters, or other tissue-specific promoters known in the art, are not highly-active in HEK-293 cells and, thus, will not be expected to yield significant levels of nuclease gene expression in packaging cells when incorporated into viral vectors of the present invention. Similarly, the recombinant viruses of the present invention contemplate the use of other cell lines with the use of incompatible tissue specific promoters (i.e., the well-known HeLa cell line (human epithelial cell) and using the liver-specific hemopexin promoter). Other examples of tissue specific promoters include: synovial sarcomas PDZD4 (cerebellum), C6 (liver), ASBS (muscle), PPP1R12B (heart), SLC5A12 (kidney), cholesterol regulation APOM (liver), ADPRHL1 (heart), and monogenic malformation syndromes TP73L (muscle). (Jacox et al., (2010), PLoS One v.5(8):e12274).

Alternatively, the recombinant virus can be packaged in cells from a different species in which the nuclease is not likely to be expressed. For example, viral particles can be produced in microbial, insect, or plant cells using mammalian promoters, such as the well-known cytomegalovirus- or SV40 virus-early promoters, which are not active in the non-mammalian packaging cells. In a particular embodiment, viral particles are produced in insect cells using the baculovirus system as described by Gao, et al. (Gao et al. (2007), J. Biotechnol. 131(2):138-43). A nuclease under the control of a mammalian promoter is unlikely to be expressed in these cells (Airenne et al. (2013), Mol. Ther. 21(4):739-49). Moreover, insect cells utilize different mRNA splicing motifs than mammalian cells. Thus, it is possible to incorporate a mammalian intron, such as the human growth hormone (HGH) intron or the SV40 large T antigen intron, into the coding sequence of a nuclease. Because these introns are not spliced efficiently from pre-mRNA transcripts in insect cells, insect cells will not express a functional nuclease and will package the full-length genome. In contrast, mammalian cells to which the resulting recombinant AAV particles are delivered will properly splice the pre-mRNA and will express functional nuclease protein. Haifeng Chen has reported the use of the HGH and SV40 large T antigen introns to attenuate expression of the toxic proteins barnase and diphtheria toxin fragment A in insect packaging cells, enabling the production of recombinant AAV vectors carrying these toxin genes (Chen, H (2012) Mol Ther Nucleic Acids. 1(11): e57).

The nuclease gene can be operably linked to an inducible promoter such that a small-molecule inducer is required for nuclease expression. Examples of inducible promoters include the Tet-On system (Clontech; Chen et al. (2015), BMC Biotechnol. 15(1):4)) and the RheoSwitch system (Intrexon; Sowa et al. (2011), Spine, 36(10): E623-8). Both systems, as well as similar systems known in the art, rely on ligand-inducible transcription factors (variants of the Tet Repressor and Ecdysone receptor, respectively) that activate transcription in response to a small-molecule activator (Doxycycline or Ecdysone, respectively). Practicing the current invention using such ligand-inducible transcription activators includes: 1) placing the nuclease gene under the control of a promoter that responds to the corresponding transcription factor, the nuclease gene having (a) binding site(s) for the transcription factor; and 2) including the gene encoding the transcription factor in the packaged viral genome. The latter step is necessary because the nuclease will not be expressed in the target cells or tissues following recombinant AAV delivery if the transcription activator is not also provided to the same cells. The transcription activator then induces nuclease gene expression only in cells or tissues that are treated with the cognate small-molecule activator. This approach is advantageous because it enables nuclease gene expression to be regulated in a spatio-temporal manner by selecting when and to which tissues the small-molecule inducer is delivered. However, the requirement to include the inducer in the viral genome, which has significantly limited carrying capacity, creates a drawback to this approach.

In another particular embodiment, recombinant AAV particles are produced in a mammalian cell line that expresses a transcription repressor that prevents expression of the nuclease. Transcription repressors are known in the art and include the Tet-Repressor, the Lac-Repressor, the Cro repressor, and the Lambda-repressor. Many nuclear hormone receptors such as the ecdysone receptor also act as transcription repressors in the absence of their cognate hormone ligand. To practice the current invention, packaging cells are transfected/transduced with a vector encoding a transcription repressor and the nuclease gene in the viral genome (packaging vector) is operably linked to a promoter that is modified to comprise binding sites for the repressor such that the repressor silences the promoter. The gene encoding the transcription repressor can be placed in a variety of positions. It can be encoded on a separate vector; it can be incorporated into the packaging vector outside of the ITR sequences; it can be incorporated into the cap/rep vector or the adenoviral helper vector; or it can be stably integrated into the genome of the packaging cell such that it is expressed constitutively. Methods to modify common mammalian promoters to incorporate transcription repressor sites are known in the art. For example, Chang and Roninson modified the strong, constitutive CMV and RSV promoters to comprise operators for the Lac repressor and showed that gene expression from the modified promoters was greatly attenuated in cells expressing the repressor (Chang and Roninson (1996), Gene 183:137-42). The use of a non-human transcription repressor ensures that transcription of the nuclease gene will be repressed only in the packaging cells expressing the repressor and not in target cells or tissues transduced with the resulting recombinant AAV.

2.6 Engineered Meganuclease Variants

Embodiments of the invention encompass the engineered meganucleases described herein, and variants thereof. Further embodiments of the invention encompass polynucleotides comprising a nucleic acid sequence encoding the meganucleases described herein, template nucleic acids described herein, the exogenous nucleic acid molecules described herein, and variants thereof.

As used herein, "variants" is intended to mean substantially similar sequences. A "variant" polypeptide is intended to mean a polypeptide derived from the "native" polypeptide by deletion or addition of one or more amino acids at one or more internal sites in the native protein and/or substitution of one or more amino acids at one or more sites in the native polypeptide. As used herein, a "native" polynucleotide or polypeptide comprises a parental sequence from which variants are derived. Variant polypeptides encompassed by the embodiments are biologically active. That is, they continue to possess the desired biological activity of the native protein; for example, the ability to bind and cleave the RHO 1-2 recognition sequence (SEQ ID NO: 7) within the RHO P23H gene. Such variants may result, for example, from human manipulation. In some embodiments, biologically active variants of a native polypeptide of the embodiments (e.g., SEQ ID NO: 11), or biologically active variants of the recognition half-site binding subunits described herein, will have at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, or about 99%, sequence identity to the amino acid sequence of the native polypeptide, native subunit, native HVR1, or native HVR2 as determined by sequence alignment programs and parameters described elsewhere herein. A biologically active variant of a polypeptide or subunit of the embodiments may differ from that polypeptide or subunit by as few as about 1-40 amino acid residues, as few as about 1-20, as few as about 1-10, as few as about 5, as few as 4, 3, 2, or even 1 amino acid residue.

The polypeptides of the embodiments may be altered in various ways including amino acid substitutions, deletions, truncations, and insertions. Methods for such manipulations are generally known in the art. For example, amino acid sequence variants can be prepared by mutations in the DNA. Methods for mutagenesis and polynucleotide alterations are well known in the art. See, for example, Kunkel (1985) Proc. Natl. Acad. Sci. USA 82:488-492; Kunkel et al. (1987) Methods in Enzymol. 154:367-382; U.S. Pat. No. 4,873,192; Walker and Gaastra, eds. (1983) Techniques in Molecular Biology (MacMillan Publishing Company, New York) and the references cited therein. Guidance as to appropriate amino acid substitutions that do not affect biological activity of the protein of interest may be found in the model of Dayhoff et al. (1978) Atlas of Protein Sequence and Structure (Natl. Biomed. Res. Found., Washington, D.C.), herein incorporated by reference. Conservative substitutions, such as exchanging one amino acid with another having similar properties, may be optimal.

In some embodiments, engineered meganucleases of the invention can comprise variants of the HVR1 and HVR2 regions disclosed herein. Parental HVR regions can comprise, for example, residues 24-79 or residues 215-270 of the exemplified engineered meganucleases. Thus, variant HVRs can comprise an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to an amino acid sequence corresponding to residues 24-79 or residues 215-270 of the engineered meganucleases exemplified herein, such that the variant HVR regions maintain the biological activity of the engineered meganuclease (i.e., binding to and cleaving the recognition sequence). Further, in some embodiments of the invention, a variant HVR1 region or variant HVR2 region can comprise residues corresponding to the amino acid residues found at specific positions within the parental HVR. In this context, "corresponding to" means that an amino acid residue in the variant HVR is the same amino acid residue (i.e., a separate identical residue) present in the parental HVR sequence in the same relative position (i.e., in relation to the remaining amino acids in the parent sequence). By way of example, if a parental HVR sequence comprises a serine residue at position 26, a variant HVR that "comprises a residue corresponding to" residue 26 will also comprise a serine at a position that is relative (i.e., corresponding) to parental position 26.

In particular embodiments, engineered meganucleases of the invention comprise an HVR1 that has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more sequence identity to an amino acid sequence corresponding to residues 215-270 of any one of SEQ ID NO: 11-14.

In certain embodiments, engineered meganucleases of the invention comprise an HVR2 that has 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more sequence identity to an amino acid sequence corresponding to residues 24-79 of any one of SEQ ID NO: 11-14.

A substantial number of amino acid modifications to the DNA recognition domain of the wild-type I-CreI meganuclease have previously been identified (e.g., U.S. Pat. No. 8,021,867) which, singly or in combination, result in engineered meganucleases with specificities altered at individual bases within the DNA recognition sequence half-site, such that the resulting rationally-designed meganucleases have half-site specificities different from the wild-type enzyme. Table 3 provides potential substitutions that can be made in an engineered meganuclease monomer or subunit to enhance specificity based on the base present at each half-site position (−1 through −9) of a recognition half-site.

TABLE 3

| Posn. | \multicolumn{11}{c}{Favored Sense-Strand Base} |
|---|---|---|---|---|---|---|---|---|---|---|---|
|  | A | C | G | T | A/T | A/C | A/G | C/T | G/T | A/G/T | A/C/G/T |
| -1 | Y75 | R70* | K70 | Q70* |  |  |  | T46* |  |  | G70 |
|  | L75* | H75* | E70* | C70 |  |  |  |  |  |  | A70 |
|  | C75* | R75* | E75* | L70 |  |  |  |  |  |  | S70 |
|  | Y139* | H46* | E46* | Y75* |  |  |  |  |  |  | G46* |
|  | C46* | K46* | D46* | Q75* |  |  |  |  |  |  |  |
|  | A46* | R46* |  | H75* |  |  |  |  |  |  |  |
|  |  |  |  | H139 |  |  |  |  |  |  |  |
|  |  |  |  | Q46* |  |  |  |  |  |  |  |
|  |  |  |  | H46* |  |  |  |  |  |  |  |
| -2 | Q70 | E70 | H70 | Q44* | C44* |  |  |  |  |  |  |
|  | 744* | D70 | D44* |  |  |  |  |  |  |  |  |
|  | A44* | K44* | E44* |  |  |  |  |  |  |  |  |
|  | V44* | R44* |  |  |  |  |  |  |  |  |  |
|  | I44* |  |  |  |  |  |  |  |  |  |  |
|  | L44* |  |  |  |  |  |  |  |  |  |  |
|  | N44* |  |  |  |  |  |  |  |  |  |  |
| -3 | Q68 | E68 | R68 | M68 |  | H68 |  | Y68 | K68 |  |  |
|  | C24* | F68 |  | C68 |  |  |  |  |  |  |  |
|  | I24* | K24* |  | L68 |  |  |  |  |  |  |  |
|  |  | R24* |  | F68 |  |  |  |  |  |  |  |
| -4 | A26* | E77 | R77 |  |  |  |  | S77 |  |  | S26* |
|  | Q77 | K26* | E26* |  |  |  |  | Q26* |  |  |  |
| -5 |  | E42 | R42 |  |  | K28* | C28* |  |  |  | M66 |
|  |  |  |  |  |  |  | Q42 |  |  |  | K66 |
| -6 | Q40 | E40 | R40 | C40 | A40 |  |  |  |  |  | S40 |
|  | C28* | R28* |  | I40 | A79 |  |  |  |  |  | S28* |
|  |  |  |  | V40 | A28* |  |  |  |  |  |  |
|  |  |  |  | C79 | H28* |  |  |  |  |  |  |
|  |  |  |  | I79 |  |  |  |  |  |  |  |
|  |  |  |  | V79 |  |  |  |  |  |  |  |
|  |  |  |  | Q28* |  |  |  |  |  |  |  |
| -7 | N30* | E38 | K38 | I38 |  |  | C38 |  |  |  | H38 |
|  | Q38 | K30* | R38 | L38 |  |  |  |  |  |  | N38 |
|  |  | R30* | E30* |  |  |  |  |  |  |  | Q30* |
| -8 | F33 | E33 | F33 | L33 |  | R32* | R33 |  |  |  |  |
|  | Y33 | D33 | H33 | V33 |  |  |  |  |  |  |  |
|  |  |  |  | I33 |  |  |  |  |  |  |  |
|  |  |  |  | F33 |  |  |  |  |  |  |  |
|  |  |  |  | C33 |  |  |  |  |  |  |  |
| -9 |  | E32 | R32 | L32 |  |  |  |  | D32 |  | S32 |
|  |  |  | K32 | V32 |  |  |  |  | I32 |  | N32 |
|  |  |  |  | A32 |  |  |  |  |  |  | H32 |
|  |  |  |  | C32 |  |  |  |  |  |  | Q32 |
|  |  |  |  |  |  |  |  |  |  |  | T32 |

Bold entries are wild-type contact residues and do not constitute "modifications" as used herein.
An asterisk indicates that the residue contacts the base on the antisense strand.

Certain modifications can be made in an engineered meganuclease monomer or subunit to modulate DNA-binding affinity and/or activity. For example, an engineered meganuclease monomer or subunit described herein can comprise a G, S, or A at a residue corresponding to position 19 of I-CreI or any one of SEQ ID NOs: 11-14 (WO 2009001159), a Y, R, K, or D at a residue corresponding to position 66 of I-CreI or any one of SEQ ID NOs: 11-14, and/or an E, Q, or K at a residue corresponding to position 80 of I-CreI or any one of SEQ ID NOs: 11-14. (U.S. Pat. No. 8,021,867).

For polynucleotides, a "variant" comprises a deletion and/or addition of one or more nucleotides at one or more sites within the native polynucleotide. One of skill in the art will recognize that variants of the nucleic acids of the embodiments will be constructed such that the open reading frame is maintained. For polynucleotides, conservative variants include those sequences that, because of the degeneracy of the genetic code, encode the amino acid sequence of one of the polypeptides of the embodiments. Variant polynucleotides include synthetically derived polynucleotides, such as those generated, for example, by using site-directed mutagenesis but which still encode an engineered meganuclease, or an exogenous nucleic acid molecule, or template nucleic acid of the embodiments. Generally, variants of a particular polynucleotide of the embodiments will have at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more sequence identity to that particular polynucleotide as determined by sequence alignment programs and parameters described elsewhere herein. Variants of a particular polynucleotide of the embodiments (i.e., the reference polynucleotide) can also be evaluated by comparison of the percent sequence identity between the polypeptide encoded by a variant polynucleotide and the polypeptide encoded by the reference polynucleotide.

The deletions, insertions, and substitutions of the protein sequences encompassed herein are not expected to produce radical changes in the characteristics of the polypeptide. However, when it is difficult to predict the exact effect of the substitution, deletion, or insertion in advance of doing so, one skilled in the art will appreciate that the effect will be evaluated by screening the polypeptide for its ability to preferentially bind and cleave recognition sequences found within a RHO gene (e.g., RHO P23H).

EXAMPLES

This invention is further illustrated by the following examples, which should not be construed as limiting. Those skilled in the art will recognize, or be able to ascertain, using no more than routine experimentation, numerous equivalents to the specific substances and procedures described herein. Such equivalents are intended to be encompassed in the scope of the claims that follow the examples below.

Example 1

Evaluation of Meganucleases that Bind and Cleave the RHO P23H Recognition Sequence
1. Meganucleases that Bind and Cleave the RHO P23H Recognition Sequence Second generation recombinant meganucleases, collectively referred to herein as "RHO 1-2 meganucleases," were engineered to bind and cleave the P23H recognition sequence (e.g., meganucleases according to SEQ ID NOs: 11-14), which is present in the mutant RHO P23H allele (see, FIG. 1A). Each RHO 1-2 recombinant meganuclease comprises an N-terminal nuclease-localization signal derived from SV40, a first meganuclease subunit, a linker sequence, and a second meganuclease subunit. A first subunit in each RHO 1-2 meganuclease binds to the RHO1 recognition half-site of SEQ ID NO:1, while a second subunit binds to the RHO2 recognition half-site (see, FIG. 1B).

Figure 2:
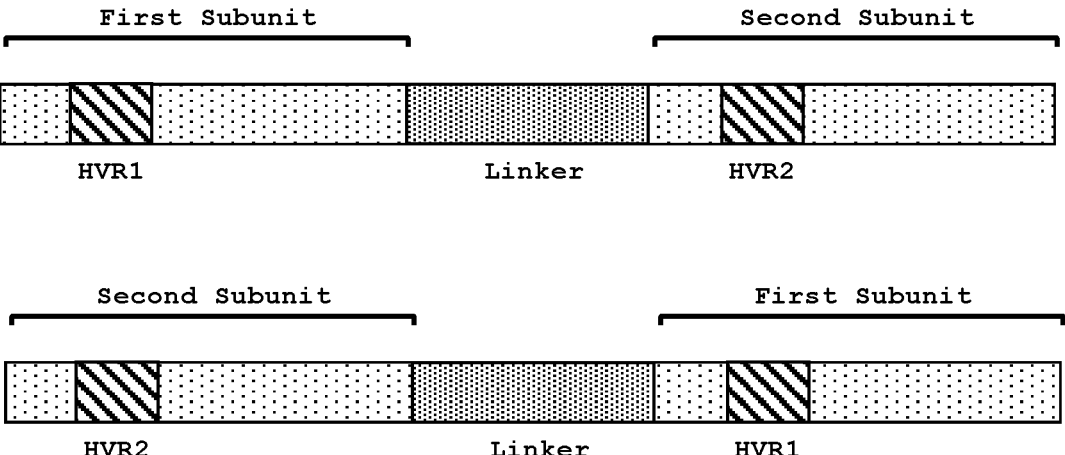
FIG. 2. The recombinant meganucleases described herein comprise two subunits, wherein the first subunit comprising the HVR1 region binds to a first recognition half-site (e.g., RHO1-2 (1)) and the second subunit comprising the HVR2 region binds to a second recognition half-site (e.g., RHO1-2 (2)). In embodiments where the recombinant meganuclease is a single-chain meganuclease, the first subunit comprising the HVR1 region can be positioned as either the N-terminal or C-terminal subunit. Likewise, the second subunit comprising the HVR2 region can be positioned as either the N-terminal or C-terminal subunit.
Figure 3:
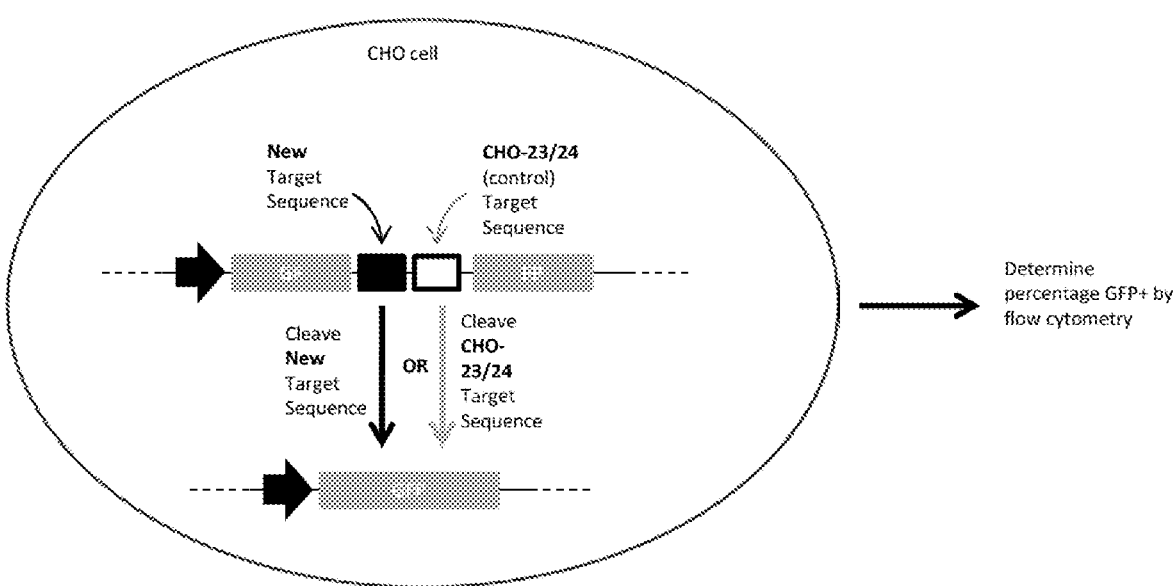
FIG. 3. Schematic of reporter assay in CHO cells for evaluating recombinant meganucleases targeting the mutant recognition sequence found in the RHO P23H gene (SEQ ID NO: 4), the wild type gene (SEQ ID NO: 3), or an off-target recognition sequence (SEQ ID NO: 23). For the recombinant meganucleases described herein, a CHO cell line was produced in which a reporter cassette was integrated stably into the genome of the cell. The reporter cassette comprised, in 5' to 3' order: an SV40 Early Promoter; the 5' 2/3 of the GFP gene; the recognition sequence for an engineered meganuclease described herein (e.g., the RHO 1-2 recognition sequence); the recognition sequence for the CHO-23/24 meganuclease (WO/2012/167192); and the 3' 2/3 of the GFP gene. Cells stably transfected with this cassette did not express GFP in the absence of a DNA break-inducing agent. Meganucleases were introduced by transduction of an mRNA encoding each meganuclease. When a DNA break was induced at either of the meganuclease recognition sequences, the duplicated regions of the GFP gene recombined with one another to produce a functional GFP gene. The percentage of GFP-expressing cells could then be determined by flow cytometry as an indirect measure of the frequency of genome cleavage by the meganucleases.

As illustrated in FIG. 2, the RHO1-2 binding subunits each comprise a 56 base pair hypervariable region, referred to as HVR1 and HVR2, respectively. As an example, the HVR1 region of the RHO 1-2L.609 meganuclease consists of residues 215-270 of SEQ ID NO: 11. The HVR2 region of the RHO 1-2L.609 meganuclease consists of residues 24-79 of SEQ ID NO: 11. The RHO 1-2 binding regions of SEQ ID NO: 11 are provided as SEQ ID NOs: 15 and 19.
2. Generation of Second-Generation Rho 1-2 Meganucleases A first-generation RHO 1-2 targeting meganuclease RHO 2-L5-14 disclosed in PCT/US2016/050809 was evaluated for sequence specificity using a method very similar to GUIDE-seq (Tsai et al. (2015), Nat Biotechnology 33:187-197) but adjusted to find potential off-target sites for meganucleases. In general, potential off-target sites were identified by capturing a probe oligonucleotide in the double strand DNA break. The RHO meganucleases described herein generate a four base pair 3' overhang so the probe oligo also contains randomized four base pair overhangs to improve ligation efficiency at sites more likely created by the nuclease cleavage. A principle off-target sequence was identified in the following sequence: 5'-CCGGGCGAAGGGTGTGGTGAGTGGCCACTTG-3' (SEQ ID NO: 23). Specificity analysis of RHO 2-L5-14 in HEK 293 cells highlighted a number of positions within the protein-DNA interface that were not discriminating the correct sequence adequately. A group of second-generation nucleases were prepared to potentially minimize off target binding. These second generation RHO 1-2 meganucleases were evaluated using an integrated iGFFP assay (as described below) to determine on versus off target cleavage.
3. Cleavage of RHO 1-2 Recognition Sequences in a CHO Cell Reporter Assay To determine whether a library of RHO 1-2 meganucleases could bind and cleave the RHO 1-2 recognition sequence present in the RHO P23H gene allele having a nucleotide mutation c68a (SEQ ID NO: 7), each recombinant meganuclease was evaluated using the CHO cell reporter assay previously described (see, WO/2012/167192 and FIG. 3). The second generation RHO meganucleases were also tested to determine if reduced off-targeting of the identified off target sequence (SEQ ID NO: 23) was achieved and if selectivity of the RHO P23H gene allele over wild type allele was maintained. To perform the assays, CHO cell reporter lines were produced, which carried a non-functional Green Fluorescent Protein (GFP) gene expression cassette integrated into the genome of the cells. The GFP gene in each cell line was interrupted by a pair of recognition sequences such that intracellular cleavage of either recognition sequence by a meganuclease would stimulate a homologous recombination event resulting in a functional GFP gene (see FIG. 3).

Figure 1B:
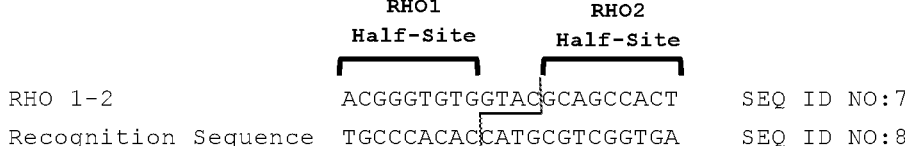

In CHO reporter cell lines developed for this study, one recognition sequence inserted into the GFP gene was the RHO P23H gene allele recognition sequence (SEQ ID NO: 7), the identified off target sequence (SEQ ID NO: 23), or the WT RHO sequence (SEQ ID NO: 9), which corresponds positionally to the RHO P23H gene allele recognition sequence (SEQ ID NO: 7; see schematic in FIGS. 1A and 1B). The second recognition sequence inserted into the GFP gene was a CHO-23/24 recognition sequence, which is recognized and cleaved by a control meganuclease called "CHO-23/24."

CHO reporter cells were transfected with mRNA encoding the test RHO 1-2 meganucleases. CHO reporter cells were also transfected with mRNA encoding the CHO-23/24 meganuclease. In each assay, 5e4 CHO reporter cells were transfected with 90 ng of mRNA in a 96-well plate using Lipofectamine® MessengerMax (ThermoFisher) according to the manufacturer's instructions. The CHO reporter cells were evaluated by flow cytometry at 2 days, 5 days, and 7 days post transfection to determine the percentage of GFP-positive cells compared to an untransfected negative control. Data obtained at each time point was normalized to the % GFP positive cells observed using the CHO-23/24 meganuclease to determine an "activity score," and the normalized data from the earliest time point was subtracted from that of the latest time point to determine a "toxicity score." The activity and toxicity scores were then added together to determine an "activity index," which was then normalized to the activity index of the CHO-23/24 meganuclease to compare data between cell lines.

3. Results

Figure 5:
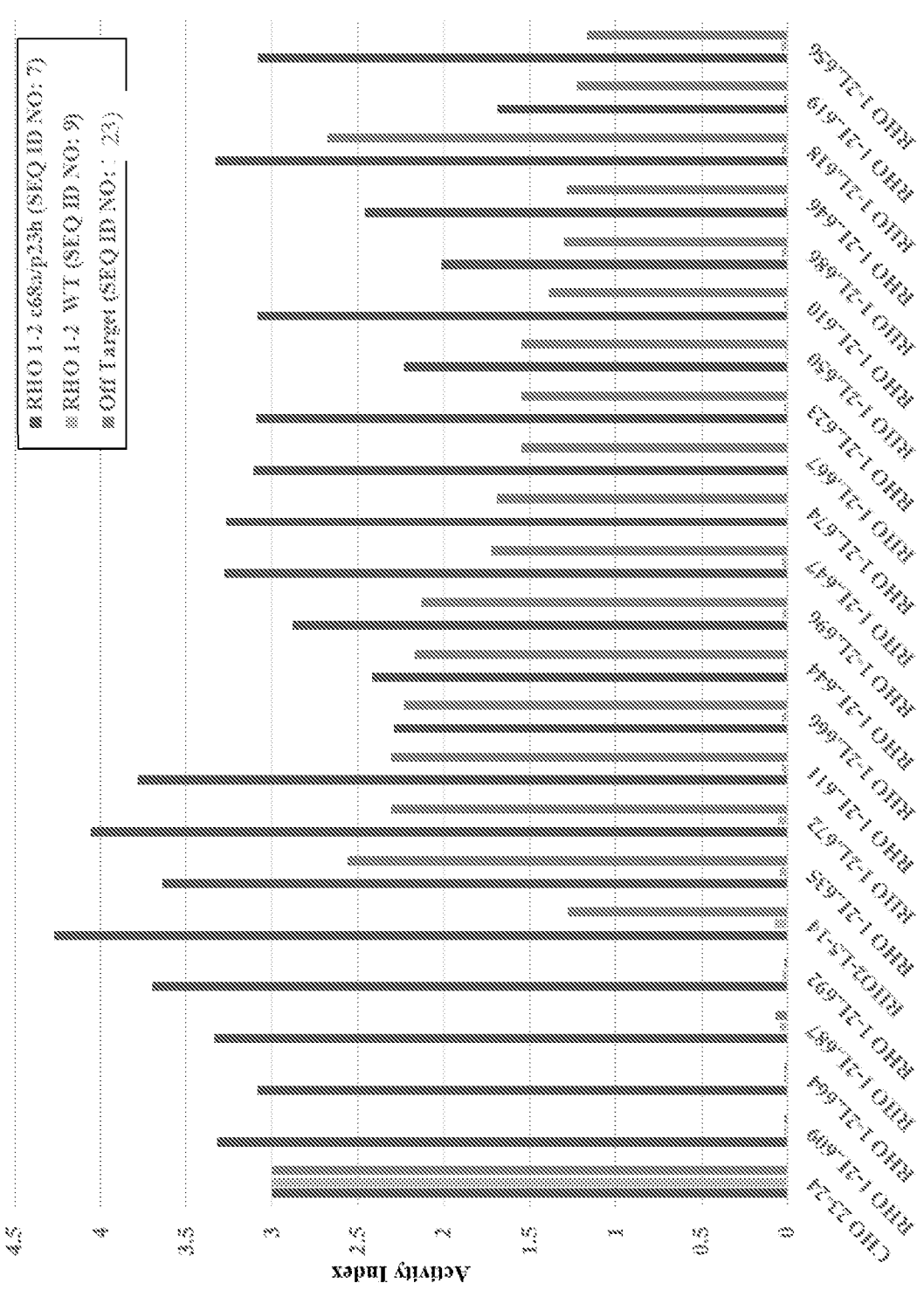
FIG. 5. Efficiency of engineered RHO 1-2 meganucleases described herein for binding and cleaving the recognition sequence (SEQ ID NO: 7) in the RHO P23H gene (SEQ ID NO: 4), or the corresponding recognition sequence (SEQ ID NO: 9) in the RHO WT gene (SEQ ID NO: 3), and an identified off target sequence (SEQ ID NO: 23) in a CHO cell reporter assay. The activity index represents % GFP positive cells for each cell line expressing the test meganuclease normalized to the cell line expressing the CHO-23/24 meganuclease accounting for the toxicity of the meganuclease.

As shown in FIG. 5, a group of second generation engineered RHO 1-2 meganucleases were tested for on target cutting of the RHO 1-2 c68a/P23H gene allele (SEQ ID NO: 7) compared to off target cutting at the identified off target site (SEQ ID NO: 23) or at the RHO 1-2 WT site (SEQ ID NO: 9). Each of the meganucleases retained the one nucleotide specificity for the RHO1-2 c68a/p23h site over the corresponding wild type site. Four of the meganucleases in the tested set, RHO1-2L.609, RHO1-2L.664, RHO1-2L.687, and RHO1-2L.692 showed significantly reduced off-target cutting while maintaining high levels of on target cutting of the RHO 1-2 c68a/P23H recognition sequence. The RHO1-2L.609 meganuclease demonstrated the best cutting specificity out of this group.

4. Conclusions

These studies show that the RHO1-2L.609, RHO1-2L.664, RHO1-2L.687, and RHO1-2L.692 RHO meganucleases, which was prepared from a library of second generation meganucleases, had significantly reduced off target binding and cutting compared to a previously described meganuclease RHO 2-L5-14. In addition, these meganucleases had unexpectedly better off targeting than many other prepared second generation meganucleases.

Example 2

In Vivo Evaluation of Rod and Cone Function Following Treatment with a RHO 1-2 Meganuclease in a Retinitis Pigmentosa Pig Model 1. Experimental Design and Methods The RHO 1-2L.609 meganuclease (SEQ ID NO: 11) was analyzed in vivo in an inbred miniature pig model of retinitis pigmentosa as previously described (Ross et al., *Invest. Opthalmol. Vis. Sci.* 53(1), pp. 501-507 (2012)). The pigs were injected in the eyes with either DPBS or 2e10 VG (viral genomes) of an AAV5 vector encoding the RHO 1-2L.609 meganuclease and GFP. The analysis of rod and cone function (data provided in FIGS. 6A-6D and FIG. 7A-7F) was determined according to methods known in the art (see e.g., Ross et al., *Invest. Opthalmol. Vis. Sci.* 53(1), pp.

501-507 (2012) and Scott et al., *Invest. Opthalmol. Vis. Sci.* 55(4), pp. 2452-2459 (2014)).

2. Results

FIG. 6A-6D provides the dark adapted, scotopic ERG response, to a low-intensity ($0.001$ cd/m$^2$) flash, directly after dark adaptation, for OS and OD at various days post-RHO1-2L.609 treatment. These represent the average of five ERG responses to the low-intensity flash after dark adapting the animals. Any amount of light exposure has the potential to stimulate the cone response to some degree, therefore the ERG separation and measurement of rod responses recorded in FIG. 6A-6D are even more sensitive than those of FIG. 7, but the average of the readings may be more variable. These data indicate that rod-driven visual function is absent without treatment of RHO 1-2L.609 meganuclease. By 6 weeks post injection (WPI) there is a small but clear and distinct a-wave and b-wave induced in OD (gray line), injected with 2e10 viral genomes of the RHO 1-2L.609 meganuclease, while OS (black line), DPBS injected vehicle control, has no discreet a-wave or b-wave (FIG. 6A). The presence of a-/b-waves for OD suggest that treatment with RHO 1-2L.609 meganuclease begins to induce and rescue rod-driven visual function as early as 6WPI. At 9WPI, the RHO 1-2L.609 meganuclease injected OD shows a more pronounced b-wave, while DPBS injected OS does not show this large positive amplitude (FIG. 6B). The largest recovery in rod-driven visual function was observed first at 15WPI (FIG. 6C) as the scotopic visual response to $0.001$ cd/m$^2$ for the RHO 1-2L.609 treated OD yielded a clear a-wave and a robust b-wave with pronounced oscillatory potentials, while DPBS treated OS does not have an ERG response suggesting no rod-driven visual function in OS at this timepoint. FIG. 6D shows the persistence of the rod-driven visual function through 26 WPI in the eye treated with RHO 1-2L.609.

Figure 7A:
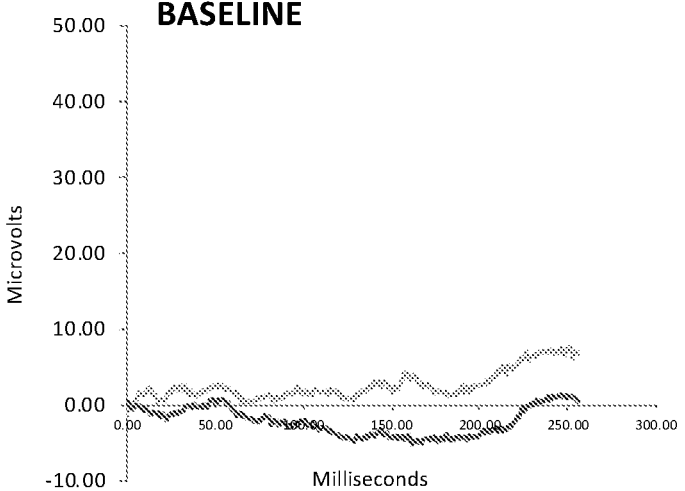
FIGS. 7A-7F. Time dependent effects of the RHO 1-2L.609 meganuclease vs. DPBS control on rod-driven scotopic visual function by electroretinography (ERG) 0.001 cd/m² in a mini swine model of RP that carries transgenic (Tg) P23H human rhodopsin (hRho). Panels 7A-7F are the average of 15 ERG readings from a dim (0.001 cd/m2) flash, with these 15 readings taken after an initial 5 ERG readings from the same intensity flash.
Figure 7B:
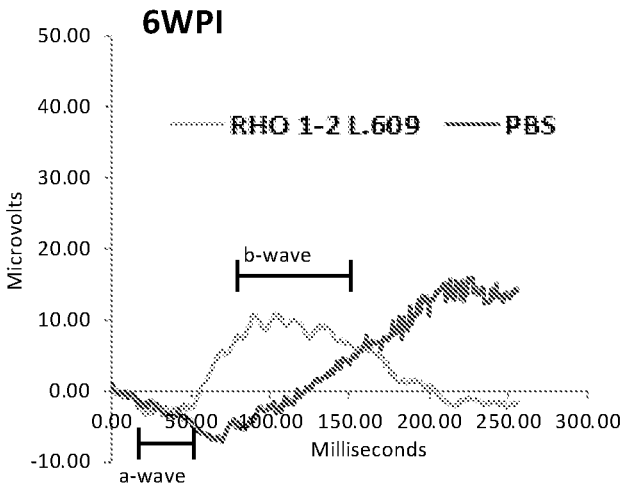
Figure 7C:
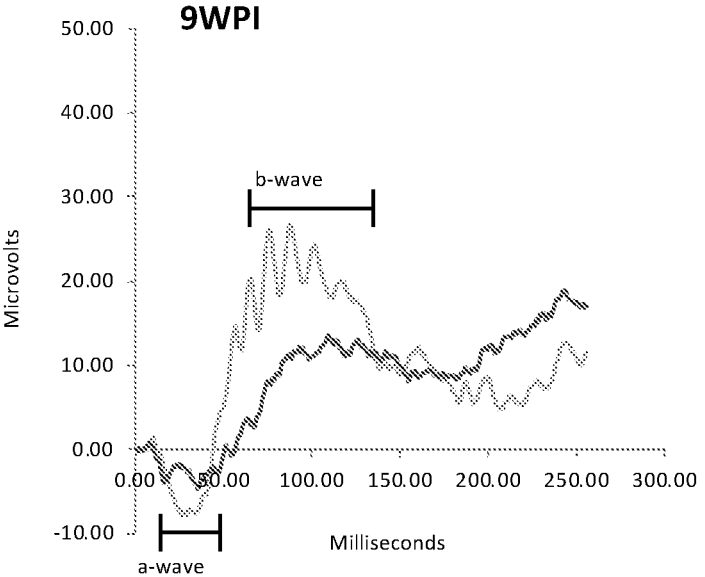
Figure 7D:
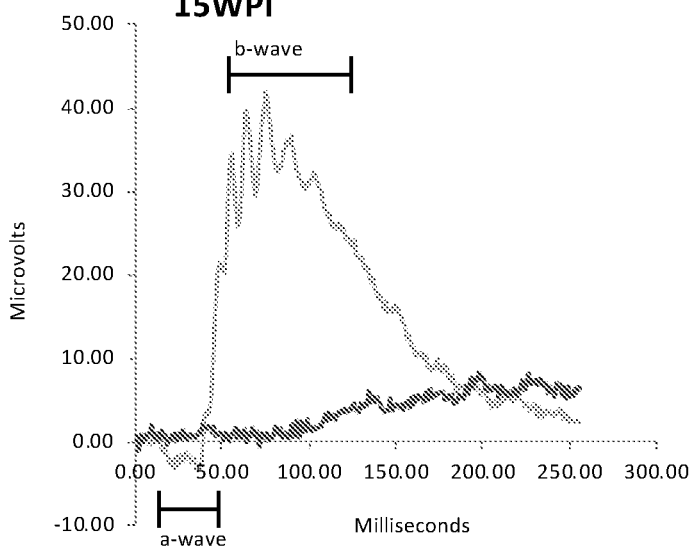
Figure 7E:
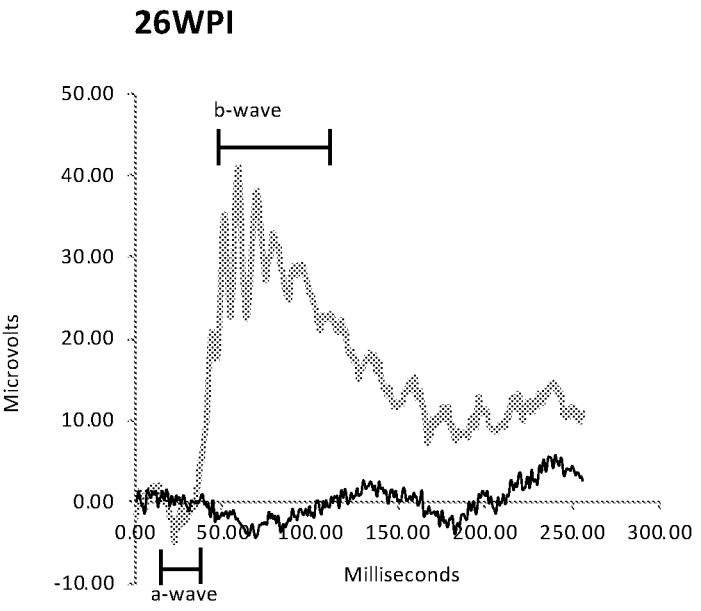
Figure 7F:
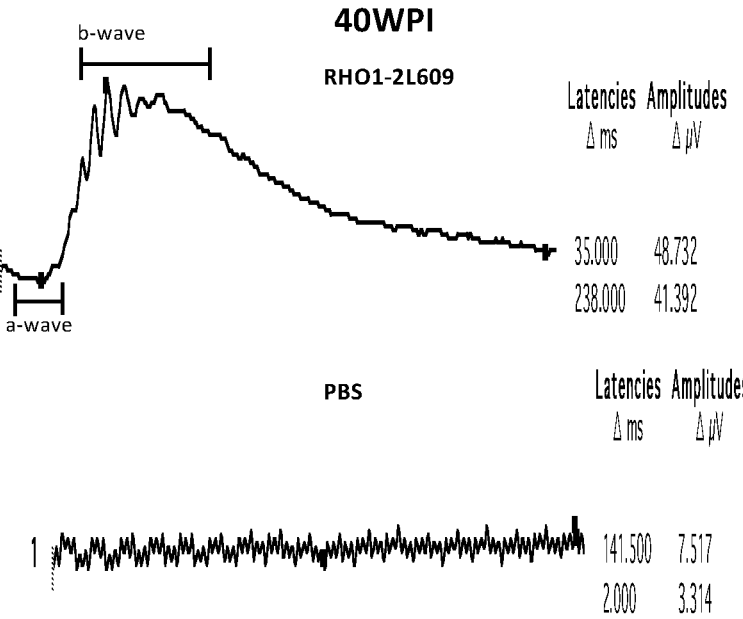

FIG. 7A provides the dark adapted, scotopic ERG response, to a low-intensity ($0.001$ cd/m$^2$) flash for OS and OD at post-natal day 2 (PND2). There is an absence of a-wave or b-wave responses. These data indicate that rod-driven visual function is absent in both eyes prior to treatment. All responses are the average of 15 ERG recordings taken after the recordings shown in FIG. 6. By 6 weeks post injection (WPI) there is a small but clear and distinct a-wave and b-wave for OD, injected with 2e10 viral genomes of the RHO 1-2L.609 meganuclease, while OS, DPBS injected vehicle control, has no discernable a-wave or b-wave (FIG. 7B). The presence of a-/b-waves for OD suggest that treatment with RHO 1-2L.609 meganuclease begins to rescue rod-driven visual function as early as 6WPI. At 9WPI, the RHO 1-2L.609 meganuclease injected OD shows a pronounced a-wave and b-wave along with oscillatory potentials while DPBS injected OS does not show this large positive amplitude. The anomalous waveform in OS is likely attributed to improper electrode placement on the eye (FIG. 7C). The largest recovery in rod-driven visual function was observed first at 15WPI (FIG. 7D) as the scotopic visual response to $0.001$ cd/m$^2$ for the RHO 1-2L.609 treated OD yielded a clear a-wave and a robust b-wave with pronounced oscillatory potentials, while DPBS treated OS does not have an ERG response suggesting no rod-driven visual function in OS at this timepoint. FIGS. 7E and 7F show persistence of the rod-driven visual function through 26 and 40WPI in the eye treated with RHO 1-2L.609.

Figures 8A, 8B:
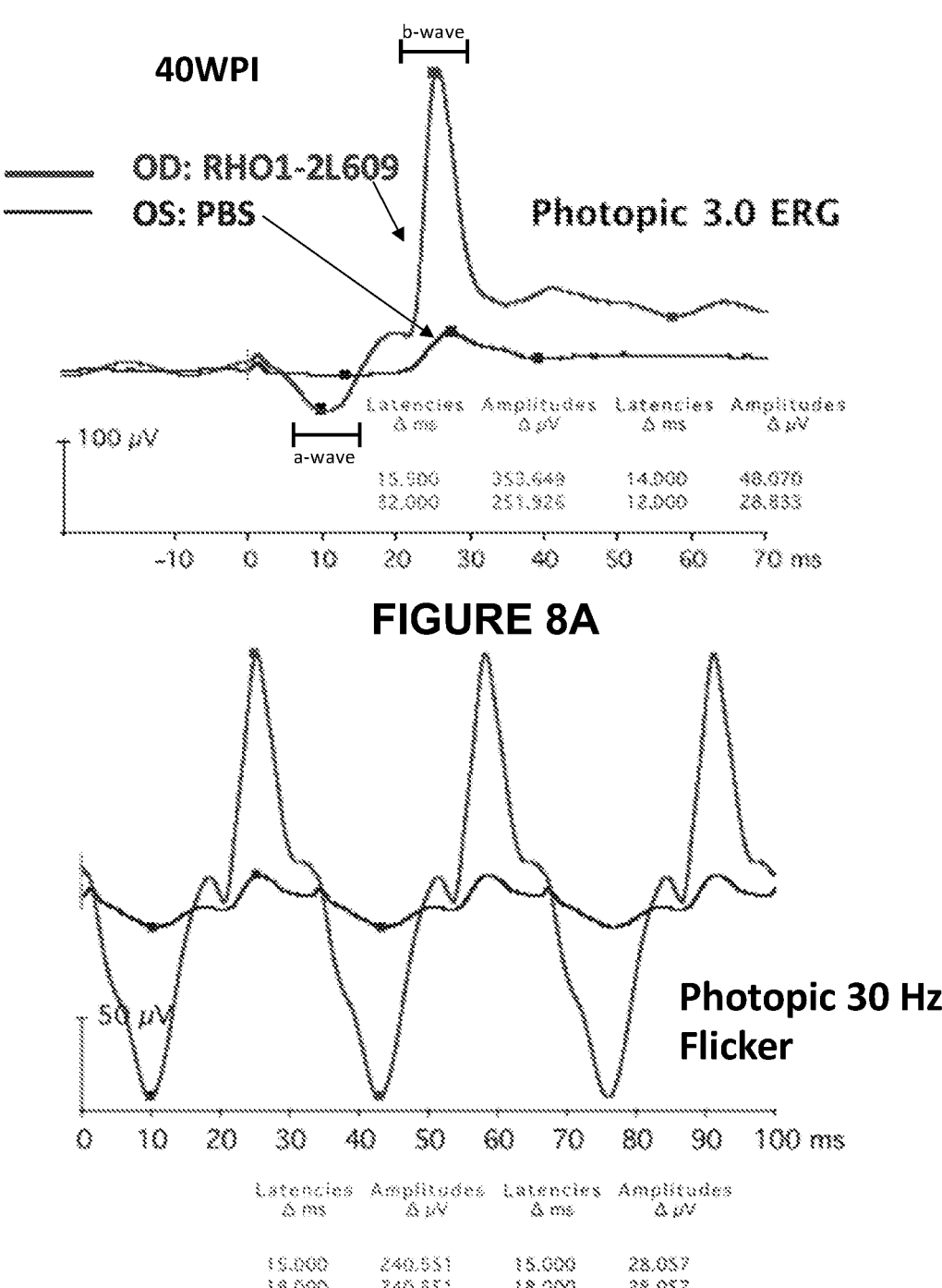
FIGS. 8A and 8B. Time-dependent effects of the RHO 1-2L.609 meganuclease vs. DPBS control on rod-driven scotopic visual function by electroretinography (ERG) 0.001 cd/m² in a mini swine model of RP that carries transgenic (Tg) P23H human rhodopsin (hRho).
Figure 9A:
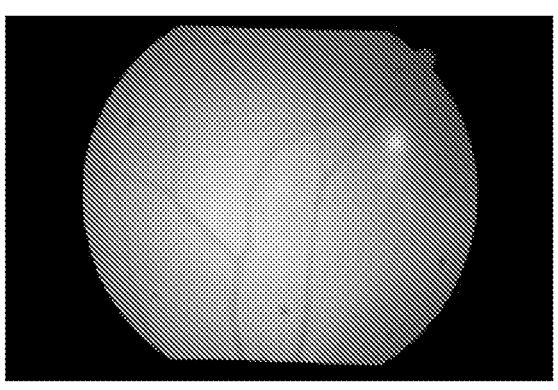
FIGS. 9A-9C. In-vivo imaging by fundoscopy and optical coherence tomography (OCT) from eyes injected with 2e10 viral genomes (vg) of the RHO 1-2L.609 meganuclease.
Figure 9B:
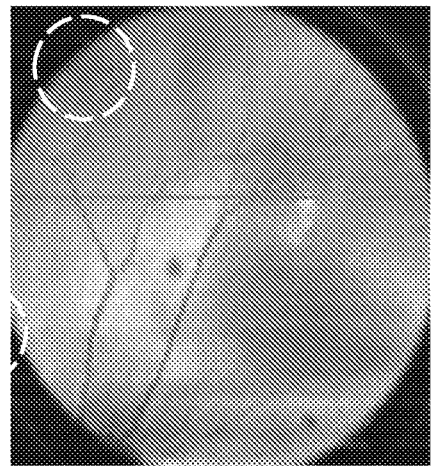
Figure 9C:
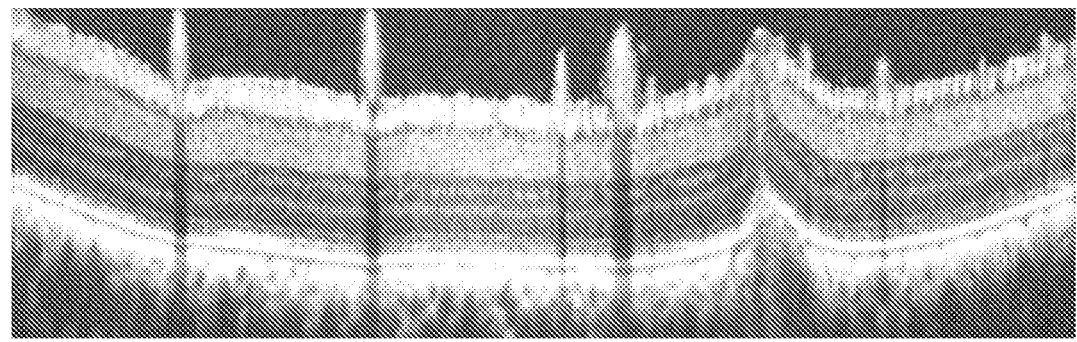

FIG. 8 extends the findings of FIG. 7. At 40 WPI, the RHO 1-2L.609 meganuclease injected OD shows a pronounced a-wave and b-wave under photopic (light-adapted) conditions (FIG. 8A). Under these conditions the photoreceptor response is driven primarily from cone cells. In the retinitis pigmentosa pig model, cones progressively die off over time. As seen in FIG. 8A, the eye treated with the RHO 1-2L.609 meganuclease has a large cone response, while the PBS-treated eye has a greatly diminished cone cell response. FIG. 8B supports these results. Response to a photopic 30 Hz Flicker is driven by cone activity as rods cannot recover quickly enough to respond to this light cycling. FIG. 8B shows robust cone activity in the RHO 1-2L.609 treated eye, while the PBS-treated eye has little cone function and no rod function (FIG. 8B) at this timepoint. A fundus image from a pig injected with the RHO 1-2L.609 meganuclease shows that no inflammation is observed aside from the site of retinotomy, which is an incision into the retina (dotted line; FIG. 9A). The OCT imaging of the fundus is shown in FIG. 9B. The OCT optical cross-section of the RHO 1-2L.609 meganuclease injected pig retina showed retinal damage at the retinotomy site (dotted line) while the adjacent retinal architecture appeared normal (FIG. 9C).

3. Conclusions

Taken together, data provided in FIGS. 6 and 7 demonstrates a time dependent rescue of rod-driven visual function in the RHO 1-2L.609 injected OD as evaluated by scotopic ERG 0.001 cd/m². At all timepoints evaluated the vehicle treated OS did not develop an ERG signal to indicate rod-driven visual function. Furthermore, FIG. 8 shows preservation of cone-driven visual function in the pig model at an age where cone death progresses following rod death. In addition, data provided in FIG. 9 shows no detectable atrophy, inflammation, or loss of retinal architecture aside from the mechanical damage caused by the retinotomy. These data indicate that an engineered meganuclease according to the invention is capable of rescuing rod-driven visual function.

Example 3

Additional In Vivo Evaluation of Rod Function Following Treatment with a RHO 1-2 Meganuclease in a Retinitis Pigmentosa Pig Model 1. Experimental Design and Methods The RHO 1-2L.609 meganuclease (SEQ ID NO: 11) was analyzed in vivo in an inbred miniature pig model of retinitis pigmentosa as previously described (Ross et al., *Invest. Opthalmol. Vis. Sci.* 53(1), pp. 501-507 (2012)). Pig eyes were left uninjected or were injected with varying titers of an AAV5 vector encoding the RHO 1-2L.609 meganuclease. Titers of the meganuclease ranged from 2e9 vg to 6e10 vg. The analysis of rod function was determined according to methods known in the art (see e.g., Ross et al., *Invest. Opthalmol. Vis. Sci.* 53(1), pp. 501-507 (2012) and Scott et al., *Invest. Opthalmol. Vis. Sci.* 55(4), pp. 2452-2459 (2014)).

2. Results

Figure 10A:
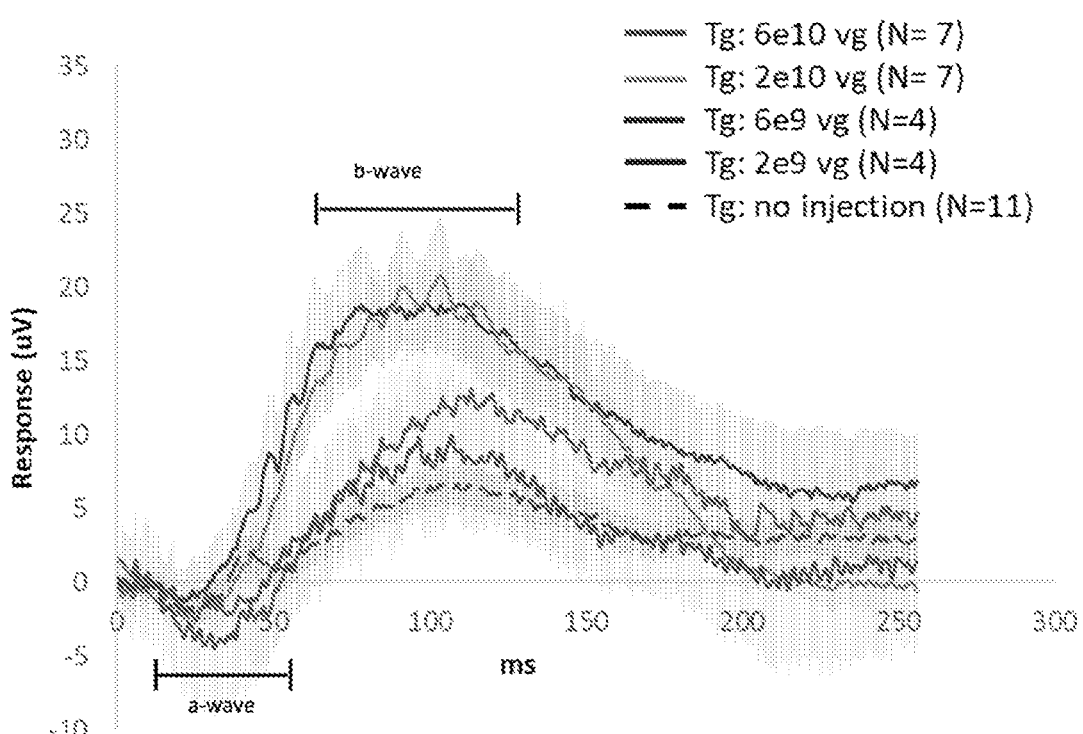
FIGS. 10A and 10B.
Figure 10B:
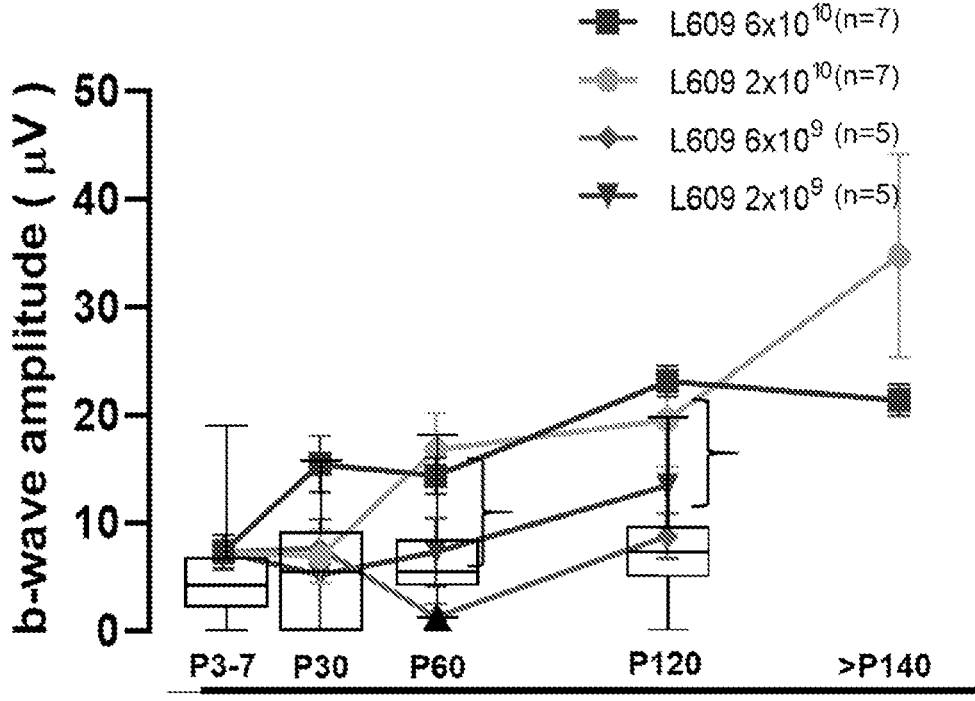

FIG. 10A provides 11-12 WPI averaged data of dark adapted, scotopic ERG responses, to a low-intensity (0.001 cd/m²) flash for pig eyes injected with varying titers of RHO 1-2L.609 meganuclease, as well as untreated eyes. FIG. 10 shows a dose-dependent rod-driven ERG response. As the injected dose of RHO 1-2 L.609 increases, there is an increased b-wave response compared to uninjected eyes. The recovery in rod-driven visual function was observed to varying degrees at 11-12 WPI as the scotopic visual response to 0.001 cd/m² for the RHO 1-2L.609 treatment yielded clear a-waves and b-waves at higher viral dose compared to uninjected and low-dose treated eyes. The data observed in FIG. 10A is also presented in FIG. 10B and extended to the terminal study endpoint of P140. The P140 data is comprised of 2 animals at the doses depicted. At these higher doses of RHO1-2L.609, an increased visual response is indicated by a b-wave amplitude higher than untreated eyes and this was maintained out to P140.

Figure 11A:
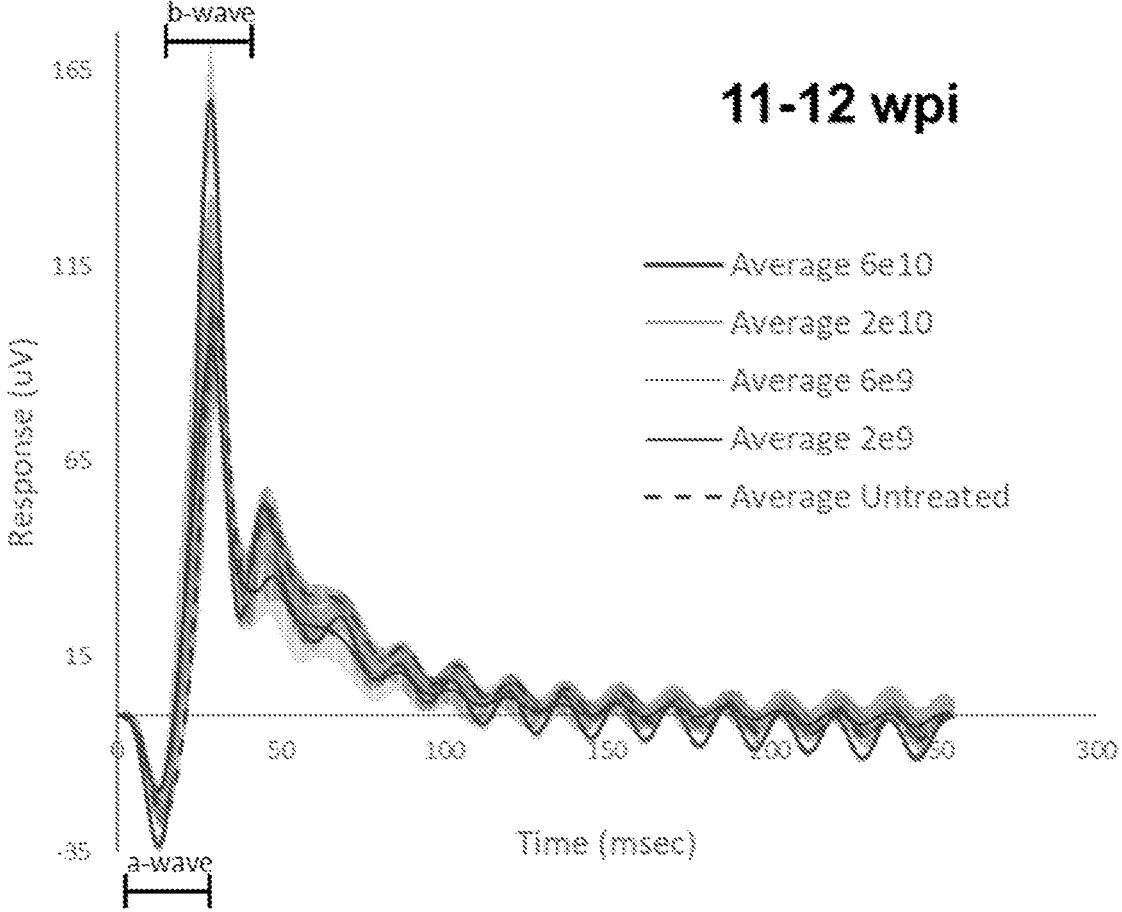
FIGS. 11A and 11B.
Figure 11B:
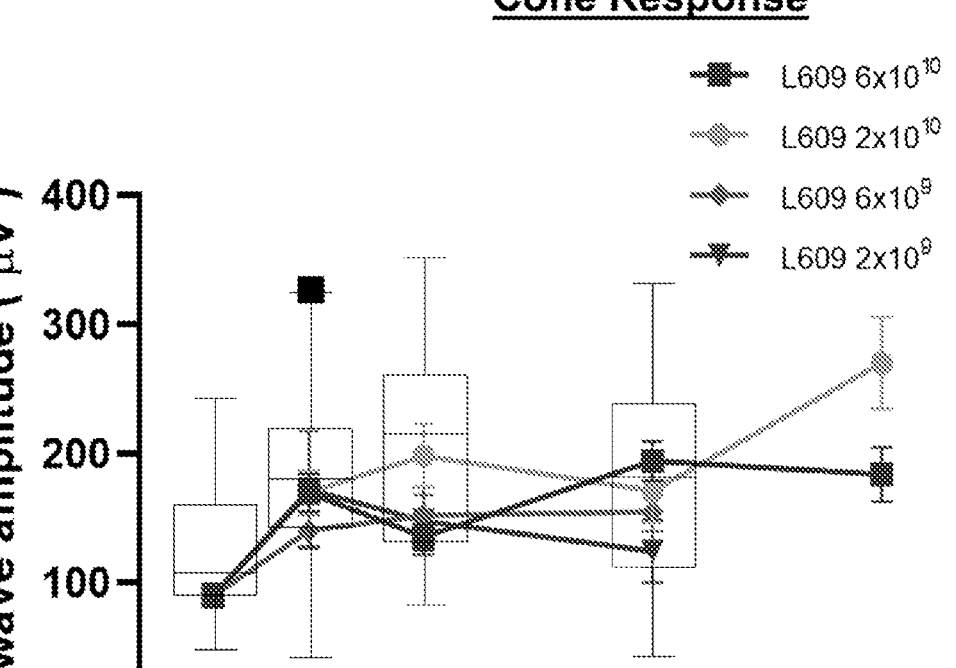

FIG. 11 shows the maintenance of a cone-driven ERG response in a dose-dependent manner. FIG. 11A provides 11-12 WPI averaged data of light adapted, photopic ERG responses to a high-intensity (3 cd/m2) flash for pig eyes injected with varying titers of RHO 1-2L.609 meganuclease, as well as untreated eyes. In untreated Tg animals, the cone response decreases over time. In eyes treated with higher doses of RHO1-2L.609, the cone-driven ERG response is increased over the untreated eyes. The maintenance of cone-driven visual function was observed to varying degrees at 11-12WPI as the photopic response to 3 cd/m2 for the RHO1-2L.609 treatment shows clear a-wave and b-waves, and the b-wave amplitude of high-dose treated eyes is elevated over untreated eyes. FIG. 11B provides additional data regarding the cone response of treated and untreated eyes. The data in this figure extends that of FIG. 11A out to the study's terminal time point of 140 days, showing the cone-driven ERG response is maintained through the length of the study.

Figure 12:
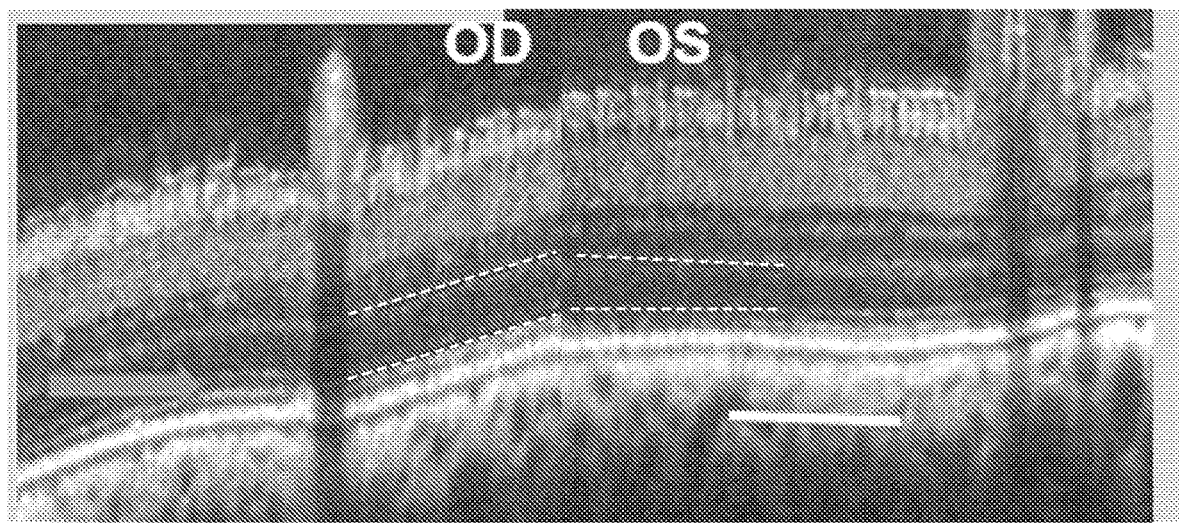
FIG. 12. Provides a 11-12 WPI OCT optical cross-section of two retinas—one eye injected with 6e10 vg RHO 1-2L.609 (OD) and the other uninjected (OS). The outer nuclear layer (ONL) is shown as dashed lines and the breakdown of the outer segment (OS) and inner segment (IS) is shown with the arrow.

FIG. 12 is a 11-12 WPI OCT optical cross-section of two retinas; one eye injected with 6e10 vg RHO 1-2L.609 and the other uninjected. The OCT shows retinal degeneration differences between the two eyes. The uninjected eye has a thinner outer nuclear layer (ONL, dashed white lines) and shows breakdown of the outer segment (OS)/inner segment (IS) doublet (arrow). Photoreceptor cell bodies make up the ONL and the OS/IS contains rhodopsin. As photoreceptors die, these retinal layers would be expected to degenerate. The OCT of the RHO 1-2L.609 injected eye shows preservation of these layers.

3. Conclusions

FIGS. 10A and 10B demonstrate a dose-dependent rescue of rod-driven visual function in the RHO 1-2L.609 injected eyes as evaluated at 11-12 WPI by scotopic ERG 0.001 cd/m². At all doses evaluated, there is some degree of activity detected in the ERG signal to indicate rod-driven visual function compared to an uninjected eye; this rod-driven response increased with increasing dose. In addition to rescue of rod-driven visual function, FIGS. 11A and 11B show that treated eyes also exhibit clear maintenance of cone-driven visual response at this same and later time points. In addition, data provided in FIG. 12 shows an eye treated with RHO 1-2L.609 maintains ONL, OS/IS thickness compared to an untreated eye. The thinning of the ONL and degeneration of the OS/IS indicates photoreceptor death. These data indicate that an engineered meganuclease according to the invention is capable of rescuing rod-driven visual function and retina structure. The data additionally gives an indication of dosing that may be required.

Example 4

In Vivo Evaluation of Eye Histology Following Treatment with a RHO 1-2 Meganuclease in a Retinitis Pigmentosa Pig Model 1. Experimental Design and Methods The RHO 1-2L.609 meganuclease (SEQ ID NO: 11) was analyzed in vivo in an inbred miniature pig model of retinitis pigmentosa as previously described (Ross et al., *Invest. Opthalmol. Vis. Sci.* 53(1), pp. 501-507 (2012)). The pigs were injected in the eyes with either DPBS or 2e10 VG (viral genomes) of an AAV5 vector encoding the RHO 1-2L.609 meganuclease and an AAV5 encoding GFP. Histological analysis of retina structure was determined according to methods known in the art.

2. Results

Figure 13A:
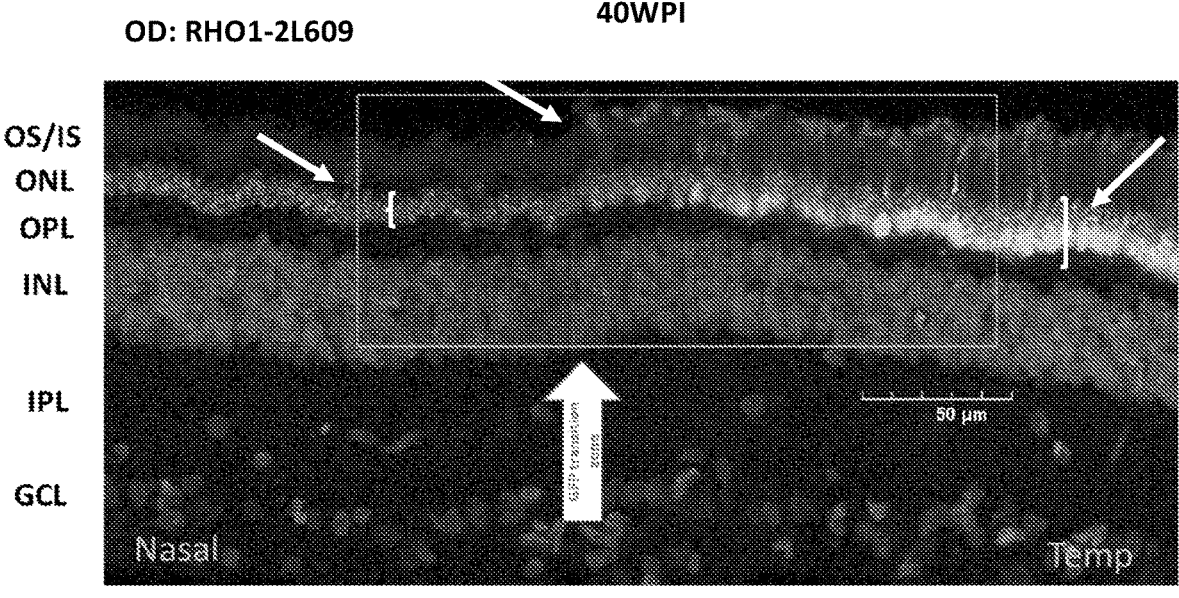
FIGS. 13A-13C provides 40 WPI histological data for a pig eye injected with RHO 1-2 L.609 meganuclease compared to PBS injected eye.
Figure 13B:
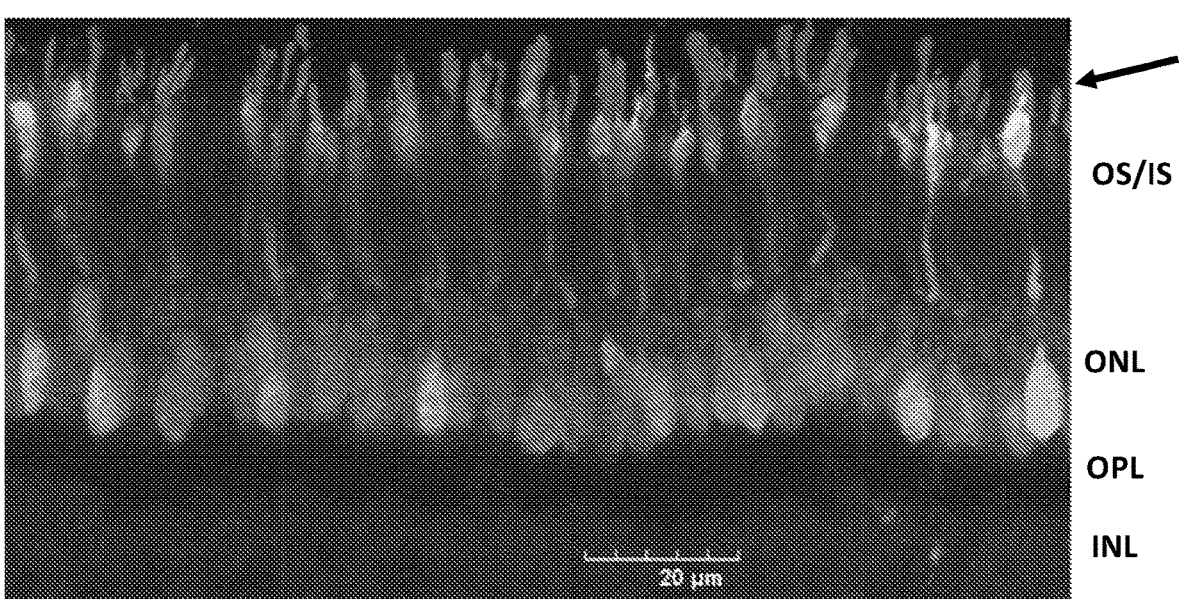
Figure 13C:
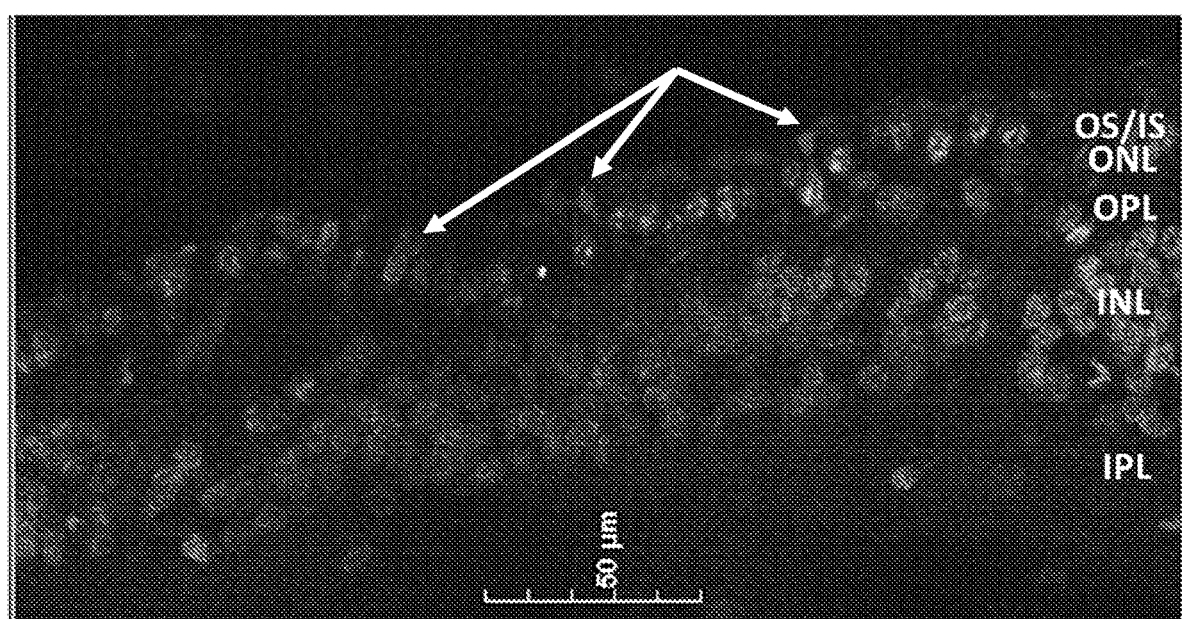

FIGS. 13A-13C provides 40 WPI histological data for a pig eye injected with RHO 1-2L.609 meganuclease, compared to PBS injected eye. In FIGS. 13A-13C, the meganuclease is represented by GFP expression (AAV5.GFP co-injected with meganuclease), rhodopsin is stained red and cell nuclei are blue (DAPI). FIG. 13A shows a clear transition where upon injection, part of the retina received meganuclease and another part did not. There is a strong correlation between the presence of the RHO 1-2L.609 meganuclease (indicated by the white arrow showing cells expressing GFP on the right hand side of the FIG. 13A past the arrow indicating the GFP transition zone where the meganuclease is expressed) and rhodopsin (top white arrow indicating cells expressing rhodopsin). Where there is no meganuclease expression (indicated by GFP expression), there is very little detectable rhodopsin as shown by cells with the white arrow on the left hand side of FIG. 13A. FIG. 13C shows some residual rhodopsin in a PBS-treated eye, but this is disorganized and not localized to the correct OS/IS layer as seen in the meganuclease-treated eye (FIG. 13A). FIG. 13B is a higher magnification of a RHO 1-2L.609 treated area of the retina; organized and properly localized rhodopsin is clearly evident (black arrows). Furthermore, the photoreceptor, ONL layer thickness has been preserved within the meganuclease (green) area, as indicated by white arrows and brackets. The ONL is clearly thinner where no nuclease present (areas lacking a GFP signal).

3. Conclusions

FIG. 13 shows a correlation between presence of RHO1-2 L.609 meganuclease and presence of organized, properly localized rhodopsin. Additionally, where there is meganuclease, the ONL layer remains thicker and the retina architecture has been preserved. These data indicate that an engineered meganuclease according to the invention is capable of preserving retina structure and rescuing rods, and those rods are able to produce the rhodopsin needed for rod visual function.

Example 5

Phenotypic Correction of Loss of Visual Acuity Following Treatment with a RHO 1-2 Meganuclease in a Retinitis Pigmentosa Pig Model 1. Experimental Design and Methods The RHO 1-2L.609 meganuclease (SEQ ID NO: 11) was analyzed in vivo in an inbred miniature pig model of retinitis pigmentosa as previously described (Ross et al., *Invest. Opthalmol. Vis. Sci.* 53(1), pp. 501-507 (2012)). Two wild type and two Tg hP23H littermate pigs were injected in one eye with either 2e10vg or 6e10vg of an AAV5 vector encoding the RHO 1-2L.609 meganuclease, while the other eye was left uninjected. The analysis of visual acuity was determined by time to navigate a maze with one eye covered with a method similar to that previously described (see Barone et al., *J Am Assoc Lab Anim Sci.* 2018 Jul. 1; 57(4):350-356. Briefly, a 10-obstacle maze was set up in a very dimly lit room. The pig is dark-adapted and is video-recorded and timed as they navigate the maze with a covering over one eye. The pattern of the obstacles is then altered, and the pig must navigate the maze with the other eye covered.

2. Results

Figure 14:
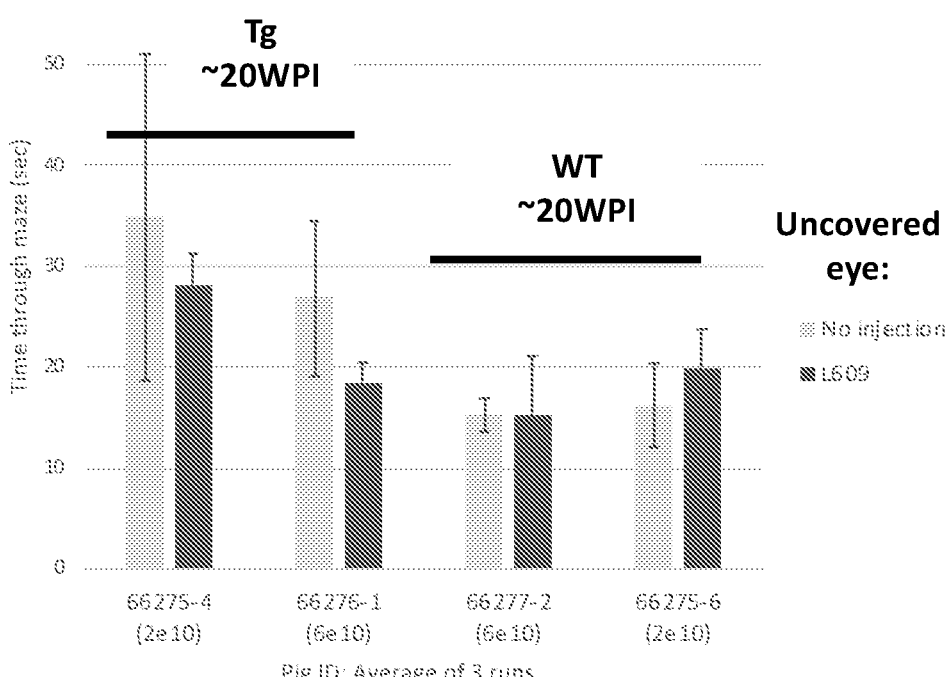
FIG. 14 provides visual acuity data for a mini swine model of RP that carries transgenic (Tg) P23H human rhodopsin (hRho)Tg (animal IDs: 66275-4 and 66276-1) and wild type pigs (66277-2 and 66275-6) that were treated with the RHO 1-2L.609 meganuclease at either 2e10 or 6e10 viral genomes (vg) in one eye. The other eye of each animal was not injected and served as a control. The Y axis indicates the time for each animal to navigate through a maze and the X axis indicates each individual pig with an average of three runs through the maze.

FIG. 14 provides averaged data of time for a dark-adapted pig to navigate a maze in dim light with the RHO1-2 L.609 treated eye uncovered and covered. Both the pig treated with 2e10vg and 6e10vg show shorter navigation times when the treated eye is left uncovered. As expected, the navigation times of wild type animals is not improved with RHO1-2L.609 treatment.

3. Conclusions

FIG. 14 shows a correlation between treating an eye with the RHO 1-2 L.609 meganuclease in Tg hP23H pigs and improved ability to navigate through an obstacle maze under dim conditions. Under these conditions, rod photoreceptors are expected to be active if they are present and functional. The data shown here indicates an improvement in visual acuity, as determined by shortened maze navigation times, when Tg hP23H pigs are treated with the RHO1-2 L.609 meganuclease.

---

Sequence Listing

SEQ ID NO: 1
MNTKYNKEFLLYLAGFVDGDGSIIAQIKPNQSYKFKHQLSLAFQVTQKTQRRWFLD
KLVDEIGVGYVRDRGSVSDYILSEIKPLHNFLTQLQPFLKLKQKQANLVLKIIWRLPS
AKESPDKFLEVCTWVDQIAALNDSKTRKTTSETVRAVLDSLSEKKKSSP

SEQ ID NO: 2
LAGLIDADG

SEQ ID NO: 3
GTGGGGGACCAGGAGAAAGAAAGCCAAGGAAGAGGAGGAGGAGGAGGAGAAG
GAGGAGAAGGATGCTGACCTAGCAGCTCCTCTCACAGCAGCTCCTCTCTTGCAGA
GGCTGAAGAGCGATTTGTGCCCTGCAAGCTAAGCCCCTAATCCACCGAGGCAAA
GGCAAAGCCCCTAGCCGGGCTCCCGAGGGCTGGGACTCGGGTGCCCCAAGATGG
CTGCATCCAGCCATCTTGGCTTAGAAAGCCCCCCACATGCCAGCTTGGCCAACAC
CCACACCATGGGTTTCTCTGGACTGCCCGACACAAGGTGTGGGTGCTGGCCAGGC
CTGTGTTCAAATCCCAGCTCTGCAGAGGAACTTTGACCCTGCATACCCCAGATTC
CTCAGTGGTCAGTGGGGAGTTAGACCCTCTTCATAGGGGGCAGGAGGAGTTGTTC
ATTCATTCAACAAATGTTTATTGAACACCTCCTATGGGTTGTGAGCTCAGAGGCA
GCGATGAACAGGCCAGGCTGGTCCTGCATTCTAGAAATAGATGGGAAGTCAGTC
AATAAGTAGACAAATGAGGCCAGGTGTGGTGGCATGCCTGTAGACCCAGTTACT
CGGGATGCTGAGGTAGGAGGATCACTTGAGCCTAGGACAGGAATTCAAGGCTGC
AGTAAGCTATGATTGCGCCACTGCACTCCAGCCTGGGCAACAGAGCAAGACTCA
TCTCTAAAAAACATTTAAAAATTGTTTTAAGAAGACAAATGAGATAGTCGCTGAT
GGTAATGACTGTGTAAAAACTGAACATGGCTGGGTGTGGTTGCTCACACCTATAA
TCTCAGCACTTTGGGAGGCTGAGATTACAGCCTCCCAAGTGGCTCCCAAGGCAGG
AGGATCACTTGAGCCTGGGAGTTAGAGAACAGCTTGGACAATATAGGGAGAGCC
CAACTCTACAAAAATGAAAATAAATTAGCCAGGCATGGTGGCACACACCAATGG

Sequence Listing

```
TCCCAGCTACTCAGGGGTTGAGGTGGTGGACCGCTTGAGCCCAGGAGGTTGAGG
CTGCAGTGAGCCATGATCATGCCGCTGCACTCCAACCTGAGTCACAGAGTGATAC
CCTGTCTCAAAAAACAATAGGCCAGGTGTGGTGGCTCACGCCTGTAACCCCAGC
ACTTTGGGAGGCCGAGGCGGATGGATCACTTGAGATCAGGAGTTAGAGACCAGC
CTGGCTAACATGGCAAAATCCTGTCTGTACTAAAAATATAAAAATTAGCCAGGC
ATGGCAGTACATGCCTGTAGTCCTGGTTACTTGGGAGGCTAAGGCAGGAGAATC
GCTTGAACCCAGGAAGAGGAGGTTGCAGTGAGCCAAGATCACACCACTGCACTC
CAGCTTGGGTGACAGAGTGAGACCCTGTCTCAAAACAGCTAAACCTGGTGGGGG
TGCCTGGTGTGTAGGATGGTCAGGGGTGGTCTCTCCAAGGACATGAGTGTGAGC
GGAGACCTGAAGGAGACTCAGGAAGAGATTAATACTGTCAGCAACAAATATATT
GATCACTTACAAGCACTCCCAATAATCCTATTAGGTAGGCACTATTATCATTCCC
ATTTTACAGAGTGGAGAACCGAAGCACACTCTCGGGAGGGCGGGGTAGCTGGCT
GCACCCAGGCTGTGTAGCCTCAGTCCAGATGTAAGGGTGGGTGGAAAAGAGCCT
TGCCCAATGAGGGAGAACAGTGAAACCAAGGCCATAGGGTCTAAAGATTCACGA
ACCAGGCTCTCATGGAGAAAGCAGGTGAGGTTTACTGTATAGATGGGTGTGCCC
CTACCCCACACTGAGGCTTCCTCGTCTGAGCAAACTGAGGCCCAGAGAGGGGAA
GGAAGCAGGACTACCATGGTGACTCAAAGACCAGCTAGAATCCAGCCTCCTCTC
CTCGAGGCTTCCACTGCCCCACGCCAGGCCTGTGTGACTCAGTCTAGGGCCTTTC
CATTACCCCAGCTAAACCTTTCTTTAGTCATTTATACCATGGTGTGAATGGCTGGC
TGGTCTTTCCTGAGAGCTATCTTTGATGAGGGGAGGGAGGCATGACTCAGGTTTGG
GAAGCTGATACCCCAGGAAGCCCAGTTGACTGTGTGGGTTATAGCCCAGGCTGTC
ACTGATTTGTAACGGGACCTGAGCAACTCTGCAGAGCTAGGCCTCAGTCTTTTCA
TCTGCAAAATGGATATAGCAGAGATGGTCAGAGTAGGTGACTTCGAATGACCCT
TCCAGCTCACTATGAGTCTGTTTTCCTGAACAAAGAGCATTTTTTGTTTAAAAAA
AAATTTCTTGGGCCGGACACGGTGGTTCACTCCTATAATCCTGGCACTTTGGGAG
GCCGAGGAGGGTGGATCGCTTGAGCCAGGAGTTCAGGACCAGCCTGGGCAACAT
AGCGAGACTCCACCCCTACAAAAAATACAAAAACTAGTGGTGTGCACTTGTGGT
CCCAGCTACTCAGGAGGCTGAGGTGAGGATCGCTTGAGCCCAGGAGGCAGAG
GCTACAGTGAGCTATGATTGTGGCACTGCACTCCAGCCTGGGCGACAGAGACCTT
GTCTCAAAACTTTTTTTTTCTTCGTCAAGCTTTACAGAATAAAGAGCACTGTCACC
TCAGTGATGGCTGTTAGTTCCCCATCACCAGGGCTCCATGAGGTTGCAATTGTGA
AACTCACAAAGGAGGAACCTGAGACAGAGAGGGGAAGTACTGAGATCATCTAG
GTCCATTCCCCCACTCACTCGTTCATTCAACAAATATTCAGGAGCACCTTCTAGGT
GCCAGGCCCTGGAGACACATCAGTGAACAAAACAGACATCATCCCACCTCTTTC
CACTACAGGCCAAGCACCATGCTGGTCTCTGGGAACCCTGTTGTGAGCAAGACA
GACCCAGGCTTACCCTTGTGGACTCATGTTACAGGCAGGGAGACGGGCACAAAA
CACAAATAAAAAGCTTCCATGCTGTCAGAAGCACTATGCAAAAAGCAAGATGCT
GAGGTACTGCTAAGCTGTGTGGGATGGGGGCTCAGCCCGGCCAGGGAGGGGCCA
GTTGTGGGTCAGTCTTGACCCAAGGCATCCAGGACACCCTCCTTCTGGCCATGAG
GGTCCACGTCAGAATCAAACCCTCACCTTAACCTCATTAGCGTTGGGCATAATCA
CCAGGCCAAGCGCCTTAAACTACGAGAGGCCCCATCCCACCCGCCCTGCCTTAGC
CCTGCCACGTGTGCCAAACGCTGTTAGACCCAACACCACCCAGGCCAGGTAGGG
GGCTGGAGCCCAGGTGGGCTGCAGGGAAGGGGGCACTCTTCTGAGCAGACAGAT
CTGGGAATCCTGGGTGGGAAGAGAGACAGTGAGAGAGAGATTAAGGGATATTTC
CCAGGCATCAGGGCTTTGCACTCTCAGGGGTCCTTCCGCCTGGATGTCCTTCCCC
TGAAGCTTCCTCCTGTTGTTCCGTTCTCAGCTCAAGCTCCAGCTTCTCAGAGAAGC
CTCCTGTGTTGGGAGTGGCTGCGACTGAACTGTCCCTACTGTTATTCGCTCTTCTA
TTTGTTTGTGGTCCCTGTGCCCCCTCACCCCACAAAAACACTGGCTTCTTGTGAGC
AGGAGCTTGCTCTTTCGTGTACCCTGTGTGTCCCCAAGGACCAAGCACCTTGTCT
GGGCCACAGTAGGTGCTCAATACACATGTTGGCTGGACAGTGGTCACTGAGCGG
CCGCACGTCGGGCACTCTCAGCACTTGCACAGGCCGCCCCAGACACCCCACTTCA
TTCCTGGGAGGTGTCATCATGTTGCTTGGACGACGGGGAGAGGGGGACCTGCCA
GTGTTGGCCTCCATTTTCCCCCAGTCATCTGCCCCCAAGGCTCTGACTACTTTCTT
TCTCACGGTACATCCTGCTATTCTGGAATCGGCCCTCGTGGGGCCACCTGGTACA
TGGCATTTGAGGCCCTCGTGGCTGATTAGGCCTCCCCCAACAGTGCCCTGTCTGC
TGCCTCCAGGGCCAGCCTCCCCTTCAGACTGGAGTCCCCTGAAGGGTTCTGCCCC
TCCCCTGCTCTGGTAGCCCCCTCCATCCTCCCTCCCTCCACTCCATCTTTGGGGGC
ATTTGAGTCACCTTTCTACACCAGTGATCTGCCCAAGCCACTGCTCACTTTCCTCT
GGATAAAGCCAGGTTCCCCGGCCTAGCGTTCAAGACCCATTACAACTGCCCCCA
GCCCAGATCTTCCCCACCTAGCCACCTGGCAAACTGCTCCTTCTCTCAAAGGCCC
AAACATGGCCTCCCAGACTGCAACCCCCAGGCAGTCAGGCCCTGTCTCCACAAC
CTCACAGCCACCCTGGACGGAATCTGCTTCTTCCCACATTTGAGTCCTCCTCAGC
CCCTGAGCTCCTCTGGGCAGGGCTGTTTCTTTCCATCTTTGTATTCCCAGGGGCCT
GCAAATAAATGTTTAATGAACGAACAAGAGAGTGAATTCCAATTCCATGCAACA
AGGATTGGGCTCCTGGGCCCTAGGCTATGTGTCTGGCACCAGAAACGGAAGCTG
CAGGTTGCAGCCCCTGCCCTCATGGAGCTCCTCCTGTCAGAGGAGTGTGGGGACT
GGATGACTCCAGAGGTAACTTGTGGGGGAACGAACAGGTAAGGGGCTGTGTGAC
GAGATGAGAGACTGGGAGAATAAACCAGAAAGTCTCTAGCTGTCCGAGGACAT
AGCACAGAGGCCCATGGTCCCTATTTCAAACCCAGGCCACCAGACTGAGCTGGG
ACCTTGGGACAGACAAGTCATGCAGAAGTTAGGGGACCTTCTCCTCCCTTTTCCT
GGATCCTGAGTACCTCTCCTCCCTGACCTCAGGCTTCCTCCTAGTGTCACCTTGGC
CCCTCTTAGAAGCCAATTAGGCCCTCAGTTTCTGCAGCGGGGATTAATATGATTA
TGAACACCCCCAATCTCCCAGATGCTGATTCAGCCAGGAGCTTAGGAGGGGGAG
GTCACTTTATAAGGGTCTGGGGGGGTCAGAACCCAGAGTCATCCAGCTGGAGCC
CTGAGTGGCTGAGCTCAGGCCTTCGCAGCATTCTTGGGTGGGAGCAGCCACGGGT
CAGCCACAAGGGCCACAGCCATGAATGGCACAGAAGGCCCTAACTTCTACGTGC
CCTTCTCCAATGCGACGGGTGTGGTACGCAGCCCCTTCGAGTACCCACAGTACTA
```

-continued

Sequence Listing

```
CCTGGCTGAGCCATGGCAGTTCTCCATGCTGGCCGCCTACATGTTTCTGCTGATC
GTGCTGGGCTTCCCCATCAACTTCCTCACGCTCTACGTCACCGTCCAGCACAAGA
AGCTGCGCACGCCTCTCAACTACATCCTGCTCAACCTAGCCGTGGCTGACCTCTT
CATGGTCCTAGGTGGCTTCACCAGCACCCTCTACACCTCTCTGCATGGATACTTC
GTCTTCGGGCCCACAGGATGCAATTTGGAGGGCTTCTTTGCCACCCTGGGCGGTA
TGAGCCGGGTGTGGGTGGGGTGTGCAGGAGCCCGGGAGCATGGAGGGGTCTGGG
AGAGTCCCGGGCTTGGCGGTGGTGGCTGAGAGGCCTTCTCCCTTCTCCTGTCCTG
TCAATGTTATCCAAAGCCCTCATATATTCAGTCAACAAACACCATTCATGGTGAT
AGCCGGGCTGCTGTTTGTGCAGGGCTGGCACTGAACACTGCCTTGATCTTATTTG
GAGCAATATGCGCTTGTCTAATTTCACAGCAAGAAAACTGAGCTGAGGCTCAAA
GAAGTCAAGCGCCCTGCTGGGGCGTCACACAGGGACGGGTGCAGAGTTGAGTTG
GAAGCCCGCATCTATCTCGGGCCATGTTTGCAGCACCAAGCCTCTGTTTCCCTTG
GAGCAGCTGTGCTGAGTCAGACCCAGGCTGGGCACTGAGGGAGAGCTGGGCAAG
CCAGACCCCTCCTCTCTGGGGGCCCAAGCTCAGGGTGGGAAGTGGATTTTCCATT
CTCCAGTCATTGGGTCTTCCCTGTGCTGGGCAATGGGCTCGGTCCCCTCTGGCATC
CTCTGCCTCCCCTCTCAGCCCCTGTCCTCAGGTGCCCCTCCAGCCTCCCTGCCGCG
TTCCAAGTCTCCTGGTGTTGAGAACCGCAAGCAGCCGCTCTGAAGCAGTTCCTTT
TTGCTTTAGAATAATGTCTTGCATTTAACAGGAAAACAGATGGGGTGCTGCAGGG
ATAACAGATCCCACTTAACAGAGAGGAAAACTGAGGCAGGGAGAGGGGAAGAG
ACTCATTTAGGGATGTGGCCAGGCAGCAACAAGAGCCTAGGTCTCCTGGCTGTG
ATCCAGGAATATCTCTGCTGAGATGCAGGAGGAGACGCTAGAAGCAGCCATTGC
AAAGCTGGGTGACGGGGAGAGCTTACCGCCAGCCACAAGCGTCTCTCTGCCAGC
CTTGCCCTGTCTCCCCCATGTCCAGGCTGCTGCCTCGGTCCCATTCTCAGGGAATC
TCTGGCCATTGTTGGGTGTTTGTTGCATTCAATAATCACAGATCACTCAGTTCTGG
CCAGAAGGTGGGTGTGCCACTTACGGGTGGTTGTTCTCTGCAGGGTCAGTCCCAG
TTTACAAATATTGTCCCTTTCACTGTTAGGAATGTCCCAGTTTGGTTGATTAACTA
TATGGCCACTCTCCCTATGGAACTTCATGGGGTGGTGAGCAGGACAGATGTCTGA
ATTCCATCATTTCCTTCTTCTTCCTCTGGGCAAAACATTGCACATTGCTTCATGGC
TCCTAGGAGAGGCCCCCACATGTCCGGGTTATTTCATTTCCCGAGAAGGGAGAGG
GAGGAAGGACTGCCAATTCTGGGTTTCCACCACCTCTGCATTCCTTCCCAACAAG
GAACTCTGCCCCACATTAGGATGCATTCTTCTGCTAAACACACACACACACACAC
ACACACACAACACACACACACACACACACACACACACACACACACAAAACTCCCTA
CCGGGTTCCCAGTTCAATCCTGACCCCCTGATCTGATTCGTGTCCCTTATGGGCCC
AGAGCGCTAAGCAAATAACTTCCCCCATTCCCTGGAATTTCTTTGCCCAGCTCTC
CTCAGCGTGTGGTCCCTCTGCCCCTTCCCCCTCCTCCCAGCACCAAGCTCTCTCCT
TCCCCAAGGCCTCCTCAAATCCCTCTCCCACTCCTGGTTGCCTTCCTAGCTACCCT
CTCCCTGTCTAGGGGGGAGTGCACCCTCCTTAGGCAGTGGGGTCTGTGCTGACCG
CCTGCTGACTGCCTTGCAGGTGAAATTGCCCTGTGGTCCTTGGTGGTCCTGGCCA
TCGAGCGGTACGTGGTGGTGTGTAAGCCCATGAGCAACTTCCGCTTCGGGGAGA
ACCATGCCATCATGGGCGTTGCCTTCACCTGGGTCATGGCGCTGGCCTGCGCCGC
ACCCCCACTCGCCGGCTGGTCCAGGTAATGGCACTGAGCAGAAGGGAAGAAGCT
CCGGGGGCTCTTTGTAGGGTCCTCCAGTCAGGACTCAAACCCAGTAGTGTCTGGT
TCCAGGCACTGACCTTGTATGTCTCCTGGCCCAAATGCCCACTCAGGGTAGGGGT
GTAGGGCAGAAGAAGAAACAGACTCTAATGTTGCTACAAGGGCTGGTCCCATCT
CCTGAGCCCCATGTCAAACAGAATCCAAGACATCCCAACCCTTCACCTTGGCTGT
GCCCCTAATCCTCAACTAAGCTAGGCGCAAATTCCAATCCTCTTTGGTCTAGTAC
CCCGGGGGCAGCCCCCTCTAACCTTGGGCCTCAGCAGCAGGGGAGGCCACACCT
TCCTAGTGCAGGTGGCCATATTGTGGCCCCCTTGGAACTGGGTCCCACTCAGCCTC
TAGGCGATTGTCTCCTAATGGGGCTGAGATGAGACACAGTGGGGACAGTGGTTT
GGACAATAGGACTGGTGACTCTGGTCCCCAGAGGCCTCATGTCCCTCTGTCTCCA
GAAAATTCCCACTCTCACTTCCCTTTCCTCCTCAGTCTTGCTAGGGTCCATTTCTT
ACCCCTTGCTGAATTTGAGCCCACCCCCTGGACTTTTTCCCCATCTTCTCCAATCT
GGCCTAGTTCTATCCTCTGGAAGCAGAGCCGCTGGACGCTCTGGGTTTCCTGAGG
CCCGTCCACTGTCACCAATATCAGGAACCATTGCCACGTCCTAATGACGTGCGCT
GGAAGCCTCTAGTTTCCAGAAGCTGCACAAAGATCCCTTAGATACTCTGTGTGTC
CATCTTTGGCCTGGAAAATACTCTCACCCTGGGGCTAGGAAGACCTCGGTTTGTA
CAAACTTCCTCAAATGCAGAGCCTGAGGGCTCTCCCCACCTCCTCACCAACCCTC
TGCGTGGCATAGCCCTAGCCTCAGCGGGCAGTGGATGCTGGGGCTGGGCATGCA
GGGAGAGGCTGGGTGGTGTCATCTGGTAACGCAGCCACCAAACAATGAAGCGAC
ACTGATTCCACAAGGTGCATCTGCATCCCCATCTGATCCATTCCATCCTGTCACCC
AGCCATGCAGACGTTTATGATCCCCTTTTCCAGGGAGGGAATGTGAAGCCCCAGA
AAGGGCCAGCGCTCGGCAGCCACCTTGGCTGTTCCCAAGTCCCTCACAGGCAGG
GTCTCCCTACCTGCCTGTCCTCAGGTACATCCCCGAGGGCCTGCAGTGCTCGTGT
GGAATCGACTACTACACGCTCAAGCCGGAGGTCAACAACGAGTCTTTTGTCATCT
ACATGTTCGTGGTCCACTTCACCATCCCCATGATTATCATCTTTTTCTGCTATGGG
CAGCTCGTCTTCACCGTCAAGGAGGTACGGGCCGGGGGGTGGGCGGCCTCACGG
CTCTGAGGGTCCAGCCCCCAGCATGCATCTGCGGCTCCTGCTCCCTGGAGGAGCC
ATGGTCTGGACCCGGGTCCCGTGTCCTGCAGGCCGCTGCCCAGCAGCAGGAGTC
AGCCACCACACAGAAGGCAGAGAAGGAGGTCACCCGCATGGTCATCATCATGGT
CATCGCTTTCCTGATCTGCTGGGTGCCCTACGCCAGCGTGGCATTCTACATCTTCA
CCCACCAGGGCTCCAACTTCGGTCCCATCTTCATGACCATCCCAGCGTTCTTTGCC
AAGAGCGCCGCCATCTACAACCCTGTCATCTATATCATGATGAACAAGCAGGTGC
CTACTGCGGGTGGGAGGGCCCCAGTGCCCCAGGCCACAGGCGCTGCCTGCCAAG
GACAAGCTACTTCCCAGGGCAGGGGAGGGGGCTCCATCAGGGTTACTGGCAGCA
GTCTTGGGTCAGCAGTCCCAATGGGGAGTGTGTGAGAAATGCAGATTCCTGGCCC
CACTCAGAACTGCTGAATCTCAGGGTGGGCCCAGGAACCTGCATTTCCAGCAAG
CCCTCCACAGGTGGCTCAGATGCTCACTCAGGTGGGAGAAGCTCCAGTCAGCTA
```

-continued

Sequence Listing

```
GTTCTGGAAGCCCAATGTCAAAGTCAGAAGGACCCAAGTCGGGAATGGGATGGG
CCAGTCTCCATAAAGCTGAATAAGGAGCTAAAAAGTCTTATTCTGAGGGGTAAA
GGGGTAAAGGGTTCCTCGGAGAGGTACCTCCGAGGGGTAAACAGTTGGGTAAAC
AGTCTCTGAAGTCAGCTCTGCCATTTTCTAGCTGTATGGCCCTGGGCAAGTCAAT
TTCCTTCTCTGTGCTTTGGTTTCCTCATCCATAGAAAGGTAGAAAGGGCAAAACA
CCAAACTCTTGGATTACAAGAGATAATTTACAGAACACCCTTGGCACACAGAGG
GCACCATGAAATGTCACGGGTGACACAGCCCCCTTGTGCTCAGTCCCTGGCATCT
CTAGGGGTGAGGAGCGTCTGCCTAGCAGGTTCCCTCCAGGAAGCTGGATTTGAGT
GGATGGGGCGCTGGAATCGTGAGGGGCAGAAGCAGGCAAAGGGTCGGGGCGAA
CCTCACTAACGTGCCAGTTCCAAGCACACTGTGGGCAGCCCTGGCCCTGACTCAA
GCCTCTTGCCTTCCAGTTCCGGAACTGCATGCTCACCACCATCTGCTGCGGCAAG
AACCCACTGGGTGACGATGAGGCCTCTGCTACCGTGTCCAAGACGGAGACGAGC
CAGGTGGCCCCGGCCTAAGACCTGCCTAGGACTCTGTGGCCGACTATAGGCGTCT
CCCATCCCCTACACCTTCCCCCAGCCACAGCCATCCCACCAGGAGCAGCGCCTGT
GCAGAATGAACGAAGTCACATAGGCTCCTTAATTTTTTTTTTTTTTTTAAGAAATA
ATTAATGAGGCTCCTCACTCACCTGGGACAGCCTGAGAAGGGACATCCACCAAG
ACCTACTGATCTGGAGTCCCACGTTCCCCAAGGCCAGCGGGATGTGTGCCCCTCC
TCCTCCCAACTCATCTTTCAGGAACACGAGGATTCTTGCTTTCTGGAAAAGTGTC
CCAGCTTAGGGATAAGTGTCTAGCACAGAATGGGGCACACAGTAGGTGCTTAAT
AAATGCTGGATGGATGCAGGAAGGAATGGAGGAATGAATGGGAAGGGAGAACA
TATCTATCCTCTCAGACCCTCGCAGCAGCAGCAACTCATACTTGGCTAATGATAT
GGAGCAGTTGTTTTTCCCTCCCTGGGCCTCACTTTCTTCTCCTATAAAATGGAAAT
CCCAGATCCCTGGTCCTGCCGACACGCAGCTACTGAGAAGACCAAAAGAGGTGT
GTGTGTGTCTATGTGTGTGTTTCAGCACTTTGTAAATAGCAAGAAGCTGTACAGA
TTCTAGTTAATGTTGTGAATAACATCAATTAATGTAACTAGTTAATTACTATGATT
ATCACCTCCTGATAGTGAACATTTTGAGATTGGGCATTCAGATGATGGGGTTTCA
CCCAACCTTGGGGCAGGTTTTTAAAAATTAGCTAGGCATCAAGGCCAGACCAGG
GCTGGGGGTTGGGCTGTAGGCAGGGACAGTCACAGGAATGCAGAATGCAGTCAT
CAGACCTGAAAAAACAACACTGGGGGAGGGGGACGGTGAAGGCCAAGTTCCCA
ATGAGGGTGAGATTGGGCCTGGGGTCTCACCCCTAGTGTGGGGCCCCAGGTCCC
GTGCCTCCCCTTCCCAATGTGGCCTATGGAGAGACAGGCCTTTCTCTCAGCCTCT
GGAAGCCACCTGCTCTTTTGCTCTAGCACCTGGGTCCCAGCATCTAGAGCATGGA
GCCTCTAGAAGCCATGCTCACCCGCCCACATTTAATTAACAGCTGAGTCCCTGAT
GTCATCCTTATCTCGAAGAGCTTAGAAACAAAGAGTGGGAAATTCCACTGGGCCT
ACCTTCCTTGGGGATGTTCATGGGCCCCAGTTTCCAGTTTCCCTTGCCAGACAAG
CCCATCTTCAGCAGTTGCTAGTCCATTCTCCATTCTGGAGAATCTGCTCCAAAAA
GCTGGCCACATCTCTGAGGTGTCAGAATTAAGCTGCCTCAGTAACTGCTCCCCCT
TCTCCATATAAGCAAAGCCAGAAGCTCTAGCTTTACCCAGCTCTGCCTGGAGACT
AAGGCAAATTGGGCCATTAAAAGCTCAGCTCCTATGTTGGTATTAACGGTGGTGG
GTTTTGTTGCTTTCACACTCTATCCACAGGATAGATTGAAACTGCCAGCTTCCACC
TGATCCCTGACCCTGGGATGGCTGGATTGAGCAATGAGCAGAGCCAAGCAGCAC
AGAGTCCCCTGGGGCTAGAGGTGGAGGAGGCAGTCCTGGGAATGGGAAAAACCC
CAACTTTGGGGTCATAGAGGCACAGGTAACCCATAAAACTGCAAACAAGCTTTG
TCACCTCTCAGAGCTTCCTTATCTGCAAAAAAGAATCTTAAAACTGACCTTGGCT
GGGCACAGTGGCTCACACCTCTAATCCCAGCACTTTGGGAGGCCAAGGTGGGCA
GATCACGAGGTCAGGAGTTTGAGACCAGCCTGACCAACACGGTGAAACCCTGTC
TCTACTAAAAATACAAAAATCAGCTGGGCATGGTGGCGCGTGCCTGTAATCCCA
GCTATTCAGTGGGCTGAGGCAGGAGAATCGCTTGAACCTGGGAGGTGGAGGTTG
CAGTGAGCCGAGATTGCGCCACTGCACTCCAGCCTGAGCAACAGAGGGACAGTC
TGTCTCCAAACAAAACAAAACAAACAAACAAACAAACAAACAAACAAAAAACA
ACAACAAAAAAACCACTTGATCCTAAGGGGATTAGATGCGACTGTGGACTTTAA
GTGGCCAGCCTACTGCCTGGCATGCAGCAGATGAGACTATGGCAATACTGGGCTT
CAGCTCAGAGCTGGCCTTACTAGAGACCCTGTCCCAAAGGGGAAAAGGATGGAG
CTAAAGCTCCCGAGAGTCACCCCCTCCTCCGAGGTGAGAAAGGAGGGCAGGAGC
ATGAGATAGCCGATCCTCGGTGCCTTGGTGAGGCTGGGGCAAATCATGCTGGGA
TCTCTATCATTGTCCCTCTTTACTGTGACTCACTAGATAATATCAGTCAGGATACT
TTTGGTCACAAGTGATAGGAAATCCAACTCATTTGGGCTGAAGCAAAAGGGACA
CATTGTTGGCTCACATGAACAAAAAGCCCGGGGCTTCAGGCACAGGGTATCACC
ATGACTGAGATGGGGATTAATTCTGTGATTGGCCAAGTCTAGGTCACCTGATCAT
ACGTAACTCATTTATGCCTGAGGTTGCAATTTTTTGGATTTTTGCAATCAGACCTT
GGCGATGACCTTGAGCAGTAGGATATAAATAACTCCCACATGCTTAGCGTTCCAA
TAATGGAATACTAGGCATACGCAGGTCTAACTGCATCACCATGGCTGGAATGGG
GATTCATCCTCTGATTGGTCAGACCTAGGTCACATGCTCACCCTGCAGCCCAAGC
AGGCTGAATGGGGAGAGGTAGGTTTCACAAAGGAAAGCCCAGGTGCTGTTACCT
GAAGTAGGAGGGCAGGAGGCAGGGTGAGCAGAGCCAACATCAACCCAGAGGGA
ATGGAATCTAAGTTGGTGTTTTCTGGGCACGTGGCTGGACCAGGCCTCCCTCCCT
CATCATCTCAGGGACATGAGGGAGAAGATTCCTATGGGTGGTCCCGAAGGTCTC
ACCCTTTGTTTTGGATGCTGTGTTGGGCCAGGGTGGCAGTGGGTGGGACAGTGGC
ATCTTAGCTGCCCTGACTTGCAGGCAGCCCATTCCAGCTCCCCGCCCCAACCCCA
ACCCAGCCCACTTTTTCTGAGAAATGGTACATTTGCCCCAGCCTCATGTCCAGAG
GAAAATTTTACTCTAACACCAGAACATTCTCTGGTTTGTCCTGATAGACAAGAAA
GCCTCCACCTCCTTAATTTACAAATGACTTGACAGCTGCTTCGTGGGCACTTGCAT
ACATAAAGAGAAGGAGCTGCTGCCTTAAGTTGCAGCAAGTTTGGCCCCACCTCAT
CTCCAGGCAGCCAGCAGATGTACAGAGTGCCTCTTGGGTACAATGGCAGCTCCAT
TCAACCAAACCTGAGCAAGCTGACCCCATGCCAGAATGCACTGGGGACTCGGAG
ATGAATTGGAGCCTAGAGACCAAGTCTCTAGGCTATGACCTGGGCTGCCTCACGG
CCACAGAGCTCTGTCACGCCAAGGGAGAGATGCACCCCTGAAAGCCTGAGGTGC
```

-continued

Sequence Listing
_____

CCCATAAGGAGAGAGTGGGTGCCCTTCCCAACTATGTAGCTTCAGGGCAAGTTCT
CTTTCTTTCTTTTTCTTTCTTTCTCTTTCTTTCTTTCTTT

SEQ ID NO: 4
GTGGGGGACCAGGAGAAAGAAAGCCAAGGAAGAGGAGGAGGAGGAGGAGAAG
GAGGAGAAGGATGCTGACCTAGCAGCTCCTCTCACAGCAGCTCCTCTCTTGCAGA
GGCTGAAGAGCGATTTGTGCCCTGCAAGCTAAGCCCCTAATCCACCGAGGCAAA
GGCAAAGCCCCTAGCCGGGCTCCCGAGGGCTGGGACTCGGGTGCCCCAAGATGG
CTGCATCCAGCCATCTTGGCTTAGAAAGCCCCCCACATGCCAGCTTGGCCAACAC
CCACACCATGGGTTTCTCTGGACTGCCCGACACAAGGTGTGGGTGCTGGCCAGGC
CTGTGTTCAAATCCCAGCTCTGCAGAGGAACTTTGACCCTGCATACCCCAGATTC
CTCAGTGGTCAGTGGGGAGTTAGACCCTCTTCATAGGGGGCAGGAGGAGTTGTTC
ATTCATTCAACAAATGTTTATTGAACACCTCCTATGGGTTGTGAGCTCAGAGGCA
GCGATGAACAGGCCAGGCTGGTCCTGCATTCTAGAAATAGATGGGAAGTCAGTC
AATAAGTAGACAAATGAGGCCAGGTGTGGTGGCATGCCTGTAGACCCAGTTACT
CGGGATGCTGAGGTAGGAGGATCACTTGAGCCTAGGACAGGAATTCAAGGCTGC
AGTAAGCTATGATTGCGCCACTGCACTCCAGCCTGGGCAACAGAGCAAGACTCA
TCTCTAAAAAACATTTAAAAATTGTTTTAAGAAGACAAATGAGATAGTCGCTGAT
GGTAATGACTGTGTAAAAACTGAACATGGCTGGGTGTGGTTGCTCACACCTATAA
TCTCAGCACTTTGGGAGGCTGAGATTACAGCCTCCCAAGTGGCTCCCAAGGCAGG
AGGATCACTTGAGCCTGGGAGTTAGAGAACAGCTTGGACAATATAGGGAGAGCC
CAACTCTACAAAAATGAAAATAAATTAGCCAGGCATGGTGGCACACACCAATGG
TCCCAGCTACTCAGGGGTTGAGGTGGTGGACCGCTTGAGCCCAGGAGGTTGAGG
CTGCAGTGAGCCATGATCATGCCGCTGCACTCCAACCTGAGTCACAGAGTGATAC
CCTGTCTCAAAAAACAATAGGCCAGGTGTGGTGGCTCACGCCTGTAACCCCAGC
ACTTTGGGAGGCCGAGGCGGATGGATCACTTGAGATCAGGAGTTAGAGACCAGC
CTGGCTAACATGGCAAAATCCTGTCTGTACTAAAAATATAAAAATTAGCCAGGC
ATGGCAGTACATGCCTGTAGTCCTGGTTACTTGGGAGGCTAAGGCAGGAGAATC
GCTTGAACCCAGGAAGAGGAGGTTGCAGTGAGCCAAGATCACACCACTGCACTC
CAGCTTGGGTGACAGAGTGAGACCCTGTCTCAAAACAGCTAAACCTGGTGGGGG
TGCCTGGTGTGTAGGATGGTCAGGGGTGGTCTCTCCAAGGACATGAGTGTGAGC
GGAGACCTGAAGGAGACTCAGGAAGAGATTAATACTGTCAGCAACAAATATATT
GATCACTTACAAGCACTCCCAATAATCCTATTAGGTAGGCACTATTATCATTCCC
ATTTTACAGAGTGGAGAACCGAAGCACACTCTCGGGAGGGCGGGGTAGCTGGCT
GCACCCAGGCTGTGTAGCCTCAGTCCAGATGTAAGGGTGGGTGGAAAAGAGCCT
TGCCCAATGAGGGAGAACAGTGAAACCAAGGCCATAGGGTCTAAAGATTCACGA
ACCAGGCTCTCATGGAGAAAGCAGGTGAGGTTTACTGTATAGATGGGTGTGCCC
CTACCCCACACTGAGGCTTCCTCGTCTGAGCAAACTGAGGCCCAGAGAGGGGAA
GGAAGCAGGACTACCATGGTGACTCAAAGACCAGCTAGAATCCAGCCTCCTCTC
CTCGAGGCTTCCACTGCCCCACGCCAGGCCTGTGTGACTCAGTCTAGGGCCTTTC
CATTACCCCAGCTAAACCTTTCTTTAGTCATTTATACCATGGTGTGAATGGCTGGC
TGGTCTTTCCTGAGAGCTATCTTTGATGAGGGGAGGGAGGCATAGCCAGGTTTGG
GAAGCTGATACCCCAGGAAGCCCAGTTGACTGTGTGGGTTATAGCCCAGGCTGTC
ACTGATTTGTAACGGGACCTGAGCAACTCTGCAGAGCTAGGCCTCAGTCTTTTCA
TCTGCAAAATGGATATAGCAGAGATGGTCAGAGTAGGTGACTTCGAAATGACCCT
TCCAGCTCACTATGAGTCTGTTTTCCTGAACAAAGAGCATTTTTTGTTTAAAAAA
AAATTTCTTGGGCCGGACACGGTGGTTCACTCCTATAATCCTGGCACTTTGGGAG
GCCGAGGAGGGTGGATCGCTTGAGCCAGGAGTTCAGGACCAGCCTGGGCAACAT
AGCGAGACTCCACCCCTACAAAAAATACAAAAACTAGTGGTGTGCACTTGTGGT
CCCAGCTACTCAGGAGGCTGAGGTGAGAGGATCGCTTGAGCCCAGGAGGCAGAG
GCTACAGTGAGCTATGATTGTGGCACTGCACTCCAGCCTGGGCGACAGAGACCTT
GTCTCAAAACTTTTTTTTTCTTCGTCAAGCTTTACAGAATAAAGAGCACTGTCACC
TCAGTGATGGCTGTTAGTTCCCCATCACCAGGGCTCCATGAGGTTGCAATTGTGA
AACTCACAAAGGAGGAACCTGAGACAGAGAGGGGAAGTACTGAGATCATCTAG
GTCCATTCCCCCACTCACTCGTTCATTCAACAAATATTCAGGAGCACCTTCTAGGT
GCCAGGCCCTGGAGACACATCAGTGAACAAAACAGACATCATCCCACCTCTTTC
CACTACAGGCCAAGCACCATGCTGGTCTCTGGGAACCCTGTTGTGAGCAAGACA
GACCCAGGCTTACCCTTGTGGACTCATGTTACAGGCAGGGAGACGGGCACAAAA
CACAAATAAAAAGCTTCCATGCTGTCAGAAGCACTATGCAAAAAGCAAGATGCT
GAGGTACTGCTAAGCTGTGTGGGATGGGGGCTCAGCCCGGCCAGGGAGGGGCCA
GTTGTGGGTCAGTCTTGACCCAAGGCATCCAGGACACCCTCCTTCTGGCCATGAG
GGTCCACGTCAGAATCAAACCCTCACCTTAACCTCATTAGCGTTGGGCATAATCA
CCAGGCCAAGCGCCTTAAACTACGAGAGGCCCCATCCCACCCGCCCTGCCTTAGC
CCTGCCACGTGTGCCAAACGCTGTTAGACCCAACACCACCCAGGCCAGGTAGGG
GGCTGGAGCCCAGGTGGGCTGCAGGGAAGGGGGCACTCTTCTGAGCAGACAGAT
CTGGGAATCCTGGGTGGGAAGAGAGACAGTGAGAGAGAGATTAAGGGATATTTC
CCAGGCATCAGGGCTTTGCACTCTCAGGGGTCCTTCCGCCTGGATGTCCTTCCCC
TGAAGCTTCCTCCTGTTGTTCCGTTCTCAGCTCAAGCTCCAGCTTCTCAGAGAAGC
CTCCTGTGTTGGGAGTGGCTGCGACTGAACTGTCCCTACTGTTATTCGCTCTTCTA
TTTGTTTGTGGTCCCTGTGCCCCCTCACCCCACAAAAACACTGGCTTCTTGTGAGC
AGGAGCTTGCTCTTTCGTGTACCCTGTGTGTCCCCAAGGACCAAGCACCTTGTCT
GGGCCACAGTAGGTGCTCAATACACATGTTGGCTGGACAGTGGTCACTGAGCGG
CCGCACGTCGGGCACTCTCAGCACTTGCACAGGCCGCCCCAGACACCCCACTTCA
TTCCTGGGAGGTGTCATCATGTTGCTTGGACGACGGGGAGAGGGGGGACCTGCCA
GTGTTGGCCTCCATTTTCCCCCAGTCATCTGCCCCCAAGGCTCTGACTACTTTCTT
TCTCACGGTACATCCTGCTATTCTGGAATCGGCCCTCGTGGGGCCACCTGGTACA
TGGCATTTGAGGCCCTCGTGGCTGATTAGGCCTCCCCCAACAGTGCCCTGTCTGC

-continued

---

Sequence Listing

---

```
TGCCTCCAGGGCCAGCCTCCCCTTCAGACTGGAGTCCCCTGAAGGGTTCTGCCCC
TCCCCTGCTCTGGTAGCCCCCTCCATCCTCCCTCCCTCCACTCCATCTTTGGGGGC
ATTTGAGTCACCTTTCTACACCAGTGATCTGCCCAAGCCACTGCTCACTTTCCTCT
GGATAAAGCCAGGTTCCCCGGCCTAGCGTTCAAGACCCATTACAACTGCCCCCA
GCCCAGATCTTCCCCACCTAGCCACCTGGCAAACTGCTCCTTCTCTCAAAGGCCC
AAACATGGCCTCCCAGACTGCAACCCCCAGGCAGTCAGGCCCTGTCTCCACAAC
CTCACAGCCACCCTGGACGGAATCTGCTTCTTCCCACATTTGAGTCCTCCTCAGC
CCCTGAGCTCCTCTGGGCAGGGCTGTTTCTTTCCATCTTTGTATTCCCAGGGGCCT
GCAAATAAATGTTTAATGAACGAACAAGAGAGTGAATTCCAATTCCATGCAACA
AGGATTGGGCTCCTGGGCCCTAGGCTATGTGTCTGGCACCAGAAACGGAAGCTG
CAGGTTGCAGCCCCTGCCCTCATGGAGCTCCTCCTGTCAGAGGAGTGTGGGGACT
GGATGACTCCAGAGGTAACTTGTGGGGGAACGAACAGGTAAGGGGCTGTGTGAC
GAGATGAGAGACTGGGAGAATAAACCAGAAAGTCTCTAGCTGTCCAGAGGACAT
AGCACAGAGGCCCATGGTCCCTATTTCAAACCCAGGCCACCAGACTGAGCTGGG
ACCTTGGGACAGACAAGTCATGCAGAAGTTAGGGGACCTTCTCCTCCCTTTTCCT
GGATCCTGAGTACCTCTCCTCCCTGACCTCAGGCTTCCTCCTAGTAGTGTCACCTTGGC
CCCTCTTAGAAGCCAATTAGGCCCTCAGTTTCTGCAGCGGGGATTAATATGATTA
TGAACACCCCCAATCTCCCAGATGCTGATTCAGCCAGGAGCTTAGGAGGGGGAG
GTCACTTTATAAGGGTCTGGGGGGGTCAGAACCCAGAGTCATCCAGCTGGAGCC
CTGAGTGGCTGAGCTCAGGCCTTCGCAGCATTCTTGGGTGGGAGCAGCCACGGGT
CAGCCACAAGGGCCACAGCCATGAATGGCACAGAAGGCCCTAACTTCTACGTGC
CCTTCTCCAATGCGACGGGTGTGGTACGCAGCCACTTCGAGTACCCACAGTACTA
CCTGGCTGAGCCATGGCAGTTCTCCATGCTGGCCGCCTACATGTTTCTGCTGATC
GTGCTGGGCTTCCCCATCAACTTCCTCACGCTCTACGTCACCGTCCAGCACAAGA
AGCTGCGCACGCCTCTCAACTACATCCTGCTCAACCTAGCCGTGGCTGACCTCTT
CATGGTCCTAGGTGGCTTCACCAGCACCCTCTACACCTCTCTGCATGGATACTTC
GTCTTCGGGCCCACAGGATGCAATTTGGAGGGCTTCTTTGCCACCCTGGGCGGTA
TGAGCCGGGTGTGGGTGGGGTGTGCAGGAGCCCGGGAGCATGGAGGGGTCTGGG
AGAGTCCCGGGCTTGGCGGTGGTGGCTGAGAGGCCTTCTCCCTTCTCCTGTCCTG
TCAATGTTATCCAAAGCCCTCATATATTCAGTCAACAAACACCATTCATGGTGAT
AGCCGGGCTGCTGTTTGTGCAGGGCTGGCACTGAACACTGCCTTGATCTTATTTG
GAGCAATATGCGCTTGTCTAATTTCACAGCAAGAAAACTGAGCTGAGGCTCAAA
GAAGTCAAGCGCCCTGCTGGGGCGTCACACAGGGACGGGTGCAGAGTTGAGTTG
GAAGCCCGCATCTATCTCGGGCCATGTTTGCAGCACCAAGCCTCTGTTTCCCTTG
GAGCAGCTGTGCTGAGTCAGACCCAGGCTGGGCACTGAGGGAGAGCTGGGCAAG
CCAGACCCCTCCTCTCTGGGGGCCCAAGCTCAGGGTGGGAAGTGGATTTTCCATT
CTCCAGTCATTGGGTCTTCCCTGTGCTGGGCAATGGGCTCGGTCCCCTCTGGCATC
CTCTGCCTCCCCTCTCAGCCCCTGTCCTCAGGTGCCCCTCCAGCCTCCCTGCCGCG
TTCCAAGTCTCCTGGTGTTGAGAACCGCAAGCAGCCGCTCTGAAGCAGTTCCTTT
TTGCTTTAGAATAATGTCTTGCATTTAACAGGAAAACAGATGGGGTGCTGCAGGG
ATAACAGATCCCACTTAACAGAGAGGAAAACTGAGGCAGGGAGAGGGGAAGAG
ACTCATTTAGGGATGTGGCCAGGCAGCAACAAGAGCCTAGGTCTCCTGGCTGTG
ATCCAGGAATATCTCTGCTGAGATGCAGGAGGAGACGCTAGAAGCAGCCATTGC
AAAGCTGGGTGACGGGGAGAGCTTACCGCCAGCCACAAGCGTCTCTCTGCCAGC
CTTGCCCTGTCTCCCCCATGTCCAGGCTGCTGCCTCGGTCCCATTCTCAGGGAATC
TCTGGCCATTGTTGGGTGTTTGTTGCATTCAATAATCACAGATCACTCAGTTCTGG
CCAGAAGGTGGGTGTGCCACTTACGGGTGGTTGTTCTCTGCAGGGTCAGTCCCAG
TTTACAAATATTGTCCCTTTCACTGTTAGGAATGTCCCAGTTTGGTTGATTAACTA
TATGGCCACTCTCCCTATGGAACTTCATGGGGTGGTGAGCAGGACAGATGTCTGA
ATTCCATCATTTCCTTCTTCTTCCTCTGGGCAAAACATTGCACATTGCTTCATGGC
TCCTAGGAGAGGCCCCCACATGTCCGGGTTATTTCATTTCCCGAGAAGGGAGAGG
GAGGAAGGACTGCCAATTCTGGGTTTCCACCACCTCTGCATTCCTTCCCAACAAG
GAACTCTGCCCCACATTAGGATGCATTCTTCTGCTAAACACACACACACACACAC
ACACACACAACACACACACACACACACACACACACACACACACAAAACTCCCTA
CCGGGTTCCCAGTTCAATCCTGACCCCCTGATCTGATTCGTGTCCCTTATGGGCCC
AGAGCGCTAAGCAAATAACTTCCCCCATTCCCTGGAATTTCTTTGCCCAGCTCTC
CTCAGCGTGTGGTCCCTCTGCCCCTTCCCCCTCCTCCCAGCACCAAGCTCTCTCCT
TCCCCAAGGCCTCCTCAAATCCCTCTCCCACTCCTGGTTGCCTTCCTAGCTACCCT
CTCCCTGTCTAGGGGGGAGTGCACCCTCCTTAGGCAGTGGGGTCTGTGCTGACCG
CCTGCTGACTGCCTTGCAGGTGAAATTGCCCTGTGGTCCTTGGTGGTCCTGGCCA
TCGAGCGGTACGTGGTGGTGTGTAAGCCCATGAGCAACTTCCGCTTCGGGGAGA
ACCATGCCATCATGGGCGTTGCCTTCACCTGGGTCATGGCGCTGGCCTGCGCCGC
ACCCCCACTCGCCGGCTGGTCCAGGTAATGGCACTGAGCAGAAGGGAAGAAGCT
CCGGGGGGCTCTTTGTAGGGTCCTCCAGTCAGGACTCAAACCCAGTAGTGTCTGGT
TCCAGGCACTGACCTTGTATGTCTCCTGGCCCAAATGCCCACTCAGGGTAGGGGT
GTAGGGCAGAAGAAGAAACAGACTCTAATGTTGCTACAAGGGCTGGTCCCATCT
CCTGAGCCCCATGTCAAACAGAATCCAAGACATCCCAACCCTTCACCTTGGCTGT
GCCCCTAATCCTCAACTAAGCTAGGCGCAAATTCCAATCCTCTTTGGTCTAGTAC
CCCGGGGGCAGCCCCCTCTAACCTTGGGCCTCAGCAGCAGGGGAGGCCACACCT
TCCTAGTGCAGGTGGCCATATTGTGGCCCCTTGGAACTGGGTCCCACTCAGCCTC
TAGGCGATTGTCTCCTAATGGGGCTGAGATGAGACAGTGGGGACAGTGGTTT
GGACAATAGGACTGGTGACTCTGGTCCCCAGAGGCCTCATGTCCCTCTGTCTCCA
GAAAATTCCCACTCTCACTTCCCTTTCCTCCTCAGTCTTGCTAGGGTCCATTTCTT
ACCCCTTGCTGAATTTGAGCCCACCCCCTGGACTTTTTCCCCATCTTCTCCAATCT
GGCCTAGTTCTATCCTCTGGAAGCAGAGCCGCTGGACGCTCTGGGTTTCCTGAGG
CCCGTCCACTGTCACCAATATCAGGAACCATTGCCACGTCCTAATGACGTGCGCT
GGAAGCCTCTAGTTTCCAGAAGCTGCACAAAGATCCCTTAGATACTCTGTGTGTC
```

-continued

Sequence Listing

```
CATCTTTGGCCTGGAAAATACTCTCACCCTGGGGCTAGGAAGACCTCGGTTTGTA
CAAACTTCCTCAAATGCAGAGCCTGAGGGCTCTCCCCACCTCCTCACCAACCCTC
TGCGTGGCATAGCCCTAGCCTCAGCGGGCAGTGGATGCTGGGGCTGGGCATGCA
GGGAGAGGCTGGGTGGTGTCATCTGGTAACGCAGCCACCAAACAATGAAGCGAC
ACTGATTCCACAAGGTGCATCTGCATCCCCATCTGATCCATTCCATCCTGTCACCC
AGCCATGCAGACGTTTATGATCCCCTTTTCCAGGGAGGGAATGTGAAGCCCCAGA
AAGGGCCAGCGCTCGGCAGCCACCTTGGCTGTTCCCAAGTCCCTCACAGGCAGG
GTCTCCCTACCTGCCTGTCCTCAGGTACATCCCCGAGGGCCTGCAGTGCTCGTGT
GGAATCGACTACTACACGCTCAAGCCGGAGGTCAACAACGAGTCTTTTGTCATCT
ACATGTTCGTGGTCCACTTCACCATCCCCATGATTATCATCTTTTTCTGCTATGGG
CAGCTCGTCTTCACCGTCAAGGAGGTACGGGCCGGGGGGTGGGCGGCCTCACGG
CTCTGAGGGTCCAGCCCCCAGCATGCATCTGCGGCTCCTGCTCCCTGGAGGAGCC
ATGGTCTGGACCCGGGTCCCGTGTCCTGCAGGCCGCTGCCCAGCAGCAGGAGTC
AGCCACCACACAGAAGGCAGAGAAGGAGGTCACCCGCATGGTCATCATCATGGT
CATCGCTTTCCTGATCTGCTGGGTGCCCTACGCCAGCGTGGCATTCTACATCTTCA
CCCACCAGGGCTCCAACTTCGGTCCCATCTTCATGACCATCCCAGCGTTCTTTGCC
AAGAGCGCCGCCATCTACAACCCTGTCATCTATATCATGATGAACAAGCAGGTGC
CTACTGCGGGTGGGAGGGCCCCAGTGCCCCAGGCCACAGGCGCTGCCTGCCAAG
GACAAGCTACTTCCCAGGGCAGGGGAGGGGGCTCCATCAGGGTTACTGGCAGCA
GTCTTGGGTCAGCAGTCCCAATGGGGAGTGTGTGAGAAATGCAGATTCCTGGCCC
CACTCAGAACTGCTGAATCTCAGGGTGGGCCCAGGAACCTGCATTTCCAGCAAG
CCCTCCACAGGTGGCTCAGATGCTCACTCAGGTGGGAGAAGCTCCAGTCAGCTA
GTTCTGGAAGCCCAATGTCAAAGTCAGAAGGACCCAAGTCGGGAATGGGATGGG
CCAGTCTCCATAAAGCTGAATAAGGAGCTAAAAAGTCTTATTCTGAGGGGTAAA
GGGGTAAAGGGTTCCTCGGAGAGGTACCTCCGAGGGGTAAACAGTTGGGTAAAC
AGTCTCTGAAGTCAGCTCTGCCATTTTCTAGCTGTATGGCCCTGGGCAAGTCAAT
TTCCTTCTCTGTGCTTTGGTTTCCTCATCCATAGAAAGGTAGAAAGGGCAAAACA
CCAAACTCTTGGATTACAAGAGATAATTTACAGAACACCCTTGGCACACAGAGG
GCACCATGAAATGTCACGGGTGACACAGCCCCCTTGTGCTCAGTCCCTGGCATCT
CTAGGGGTGAGGAGCGTCTGCCTAGCAGGTTCCCTCCAGGAAGCTGGATTTGAGT
GGATGGGGCGCTGGAATCGTGAGGGGCAGAAGCAGGCAAAGGGTCGGGGCGAA
CCTCACTAACGTGCCAGTTCCAAGCACACTGTGGGCAGCCCTGGCCCTGACTCAA
GCCTCTTGCCTTCCAGTTCCGGAACTGCATGCTCACCACCATCTGCTGCGGCAAG
AACCCACTGGGTGACGATGAGGCCTCTGCTACCGTGTCCAAGACGGAGACGAGC
CAGGTGGCCCCGGCCTAAGACCTGCCTAGGACTCTGTGGCCGACTATAGGCGTCT
CCCATCCCCTACACCTTCCCCCAGCCACAGCCATCCCACCAGGAGCAGCGCCTGT
GCAGAATGAACGAAGTCACATAGGCTCCTTAATTTTTTTTTTTTTTTTTAAGAAATA
ATTAATGAGGCTCCTCACTCACCTGGGACAGCCTGAGAAGGGACATCCACCAAG
ACCTACTGATCTGGAGTCCCACGTTCCCCAAGGCCAGCGGGATGTGTGCCCCTCC
TCCTCCCAACTCATCTTTCAGGAACACGAGGATTCTTGCTTTCTGGAAAAGTGTC
CCAGCTTAGGGATAAGTGTCTAGCACAGAATGGGGCACACAGTAGGTGCTTAAT
AAATGCTGGATGGATGCAGGAAGGAATGGAGGAATGAATGGGAAGGGAGAACA
TATCTATCCTCTCAGACCCTCGCAGCAGCAGCAACTCATACTTGGCTAATGATAT
GGAGCAGTTGTTTTTCCCTCCCTGGGCCTCACTTTCTTCTCCTATAAAATGGAAAT
CCCAGATCCCTGGTCCTGCCGACACGCAGCTACTGAGAAGACCAAAAGAGGTGT
GTGTGTGTCTATGTGTGTGTTTCAGCACTTTGTAAATAGCAAGAAGCTGTACAGA
TTCTAGTTAATGTTGTGAATAACATCAATTAATGTAACTAGTTAATTACTATGATT
ATCACCTCCTGATAGTGAACATTTTGAGATTGGGCATTCAGATGATGGGGTTTCA
CCCAACCTTGGGGCAGGTTTTTAAAAATTAGCTAGGCATCAAGGCCAGACCAGG
GCTGGGGGTTGGGCTGTAGGCAGGGACAGTCACAGGAATGCAGAATGCAGTCAT
CAGACCTGAAAAAACAACACTGGGGGAGGGGGACGGTGAAGGCCAAGTTCCCA
ATGAGGGTGAGATTGGGCCTGGGGTCTCACCCCTAGTGTGGGGCCCCAGGTCCC
GTGCCTCCCCTTCCCAATGTGGCCTATGGAGAGACAGGCCTTTCTCTCAGCCTCT
GGAAGCCACCTGCTCTTTTGCTCTAGCACCTGGGTCCCAGCATCTAGAGCATGGA
GCCTCTAGAAGCCATGCTCACCCGCCCACATTTAATTAACAGCTGAGTCCCTGAT
GTCATCCTTATCTCGAAGAGCTTAGAAACAAAGAGTGGGAAATTCCACTGGGCCT
ACCTTCCTTGGGGATGTTCATGGGCCCCAGTTTCCAGTTTCCCTTGCCAGACAAG
CCCATCTTCAGCAGTTGCTAGTCCATTCTCCATTCTGGAGAATCTGCTCCAAAAA
GCTGGCCACATCTCTGAGGTGTCAGAATTAAGCTGCCTCAGTAACTGCTCCCCCT
TCTCCATATAAGCAAAGCCAGAAGCTCTAGCTTTACCCAGCTCTGCCTGGAGACT
AAGGCAAATTGGGCCATTAAAAGCTCAGCTCCTATGTTGGTATTAACGGTGGTGG
GTTTTGTTGCTTTCACACTCTATCCACAGGATAGATTGAAACTGCCAGCTTCCACC
TGATCCCTGACCCTGGGATGGCTGGATTGAGCAATGAGCAGAGCCAAGCAGCAC
AGAGTCCCCTGGGGCTAGAGGTGGAGGAGGCAGTCCTGGGAATGGGAAAAACCC
CAACTTTGGGGTCATAGAGGCACAGGTAACCCATAAAACTGCAAACAAGCTTTG
TCACCTCTCAGAGCTTCCTTATCTGCAAAAAAGAATCTTAAAACTGACCTTGGCT
GGGCACAGTGGCTCACACCTCTAATCCCAGCACTTTGGGAGGCCAAGGTGGGCA
GATCACGAGGTCAGGAGTTTGAGACCAGCCTGACCAACACGGTGAAACCCTGTC
TCTACTAAAAATACAAAAATCAGCTGGGCATGGTGGCGCGTGCCTGTAATCCCA
GCTATTCAGTGGGCTGAGGCAGGAGAATCGCTTGAACCTGGGAGGTGGAGGTTG
CAGTGAGCCGAGATTGCGCCACTGCACTCCAGCCTGAGCAACAGAGGGCAGATC
TGTCTCCAAACAAAACAAAACAAACAAACAAACAAACAAACAAACAAAAACA
ACAACAAAAAAACCACTTGATCCTAAGGGGATTAGATGCGACTGTGGACTTTAA
GTGGCCAGCCTACTGCCTGGCATGCAGCAGATGAGACTATGGCAATACTGGGCTT
CAGCTCAGAGCTGGCCTTACTAGAGACCCTGTCCCAAAGGGGAAAAGGATGGAG
CTAAAGCTCCCGAGAGTCACCCCCTCCTCCGAGGTGAGAAAGGAGGGCAGGAGC
ATGAGATAGCCGATCCTCGGTGCCTTGGTGAGGCTGGGGCAAATCATGCTGGGA
```

Sequence Listing

```
TCTCTATCATTGTCCCTCTTTACTGTGACTCACTAGATAATATCAGTCAGGATACT
TTTGGTCACAAGTGATAGGAAATCCAACTCATTTGGGCTGAAGCAAAAGGGACA
CATTGTTGGCTCACATGAACAAAAAGCCCGGGGCTTCAGGCACAGGGTATCACC
ATGACTGAGATGGGGATTAATTCTGTGATTGGCCAAGTCTAGGTCACCTGATCAT
ACGTAACTCATTTATGCCTGAGGTTGCAATTTTTTGGATTTTTGCAATCAGACCTT
GGCGATGACCTTGAGCAGTAGGATATAAATAACTCCCACATGCTTAGCGTTCCAA
TAATGGAATACTAGGCATACGCAGGTCTAACTGCATCACCATGGCTGGAATGGG
GATTCATCCTCTGATTGGTCAGACCTAGGTCACATGCTCACCCTGCAGCCCAAGC
AGGCTGAATGGGGAGAGGTAGGTTTCACAAAGGAAAGCCCAGGTGCTGTTACCT
GAAGTAGGAGGGCAGGAGGCAGGGTGAGCAGAGCCAACATCAACCCAGAGGGA
ATGGAATCTAAGTTGGTGTTTTCTGGGCACGTGGCTGGACCAGGCCTCCCTCCCT
CATCATCTCAGGGACATGAGGGAGAAGATTCCTATGGGTGGTCCCGAAGGTCTC
ACCCTTTGTTTTGGATGCTGTGTTGGGCCAGGGTGGCAGTGGGTGGGACAGTGGC
ATCTTAGCTGCCCTGACTTGCAGGCAGCCCATTCCAGCTCCCCGCCCCAACCCCA
ACCCAGCCCACTTTTTCTGAGAAATGGTACATTTGCCCCAGCCTCATGTCCAGAG
GAAAATTTTACTCTAACACCAGAACATTCTCTGGTTTGTCCTGATAGACAAGAAA
GCCTCCACCTCCTTAATTTACAAATGACTTGACAGCTGCTTCGTGGGCACTTGCAT
ACATAAAGAGAAGGAGCTGCTGCCTTAAGTTGCAGCAAGTTTGGCCCCACCTCAT
CTCCAGGCAGCCAGCAGATGTACAGAGTGCCTCTTGGGTACAATGGCAGCTCCAT
TCAACCAAACCTGAGCAAGCTGACCCCATGCCAGAATGCACTGGGGACTCGGAG
ATGAATTGGAGCCTAGAGACCAAGTCTCTAGGCTATGACCTGGGCTGCCTCACGG
CCACAGAGCTCTGTCACGCCAAGGGAGAGATGCACCCCTGAAAGCCTGAGGTGC
CCCATAAGGAGAGAGTGGGTGCCCTTCCCAACTATGTAGCTTCAGGGCAAGTTCT
CTTTCTTTCTTTTTCTTTCTTTCTCTTTCTTTCTTTCTTT
```

SEQ ID NO: 5
```
MNGTEGPNFYVPFSNATGVVRSPFEYPQYYLAEPWQFSMLAAYMFLLIVLGFPINFL
TLYVTVQHKKLRTPLNYILLNLAVADLFMVLGGFTSTLYTSLHGYFVFGPTGCNLEG
FFATLGGEIALWSLVVLAIERYVVVCKPMSNFRFGENHAIMGVAFTWVMALACAAP
PLAGWSRYIPEGLQCSCGIDYYTLKPEVNNESFVIYMFVVHFTIPMIIIFFCYGQLVFT
VKEAAAQQQESATTQKAEKEVTRMVIIMVIAFLICWVPYASVAFYIFTHQGSNFGPIF
MTIPAFFAKSAAIYNPVIYIMMNKQFRNCMLTTICCGKNPLGDDEASATVSKTETSQ
VAPA
```

SEQ ID NO: 6
```
MNGTEGPNFYVPFSNATGVVRSHFEYPQYYLAEPWQFSMLAAYMFLLIVLGFPINFL
TLYVTVQHKKLRTPLNYILLNLAVADLFMVLGGFTSTLYTSLHGYFVFGPTGCNLEG
FFATLGGEIALWSLVVLAIERYVVVCKPMSNFRFGENHAIMGVAFTWVMALACAAP
PLAGWSRYIPEGLQCSCGIDYYTLKPEVNNESFVIYMFVVHFTIPMIIIFFCYGQLVFT
VKEAAAQQQESATTQKAEKEVTRMVIIMVIAFLICWVPYASVAFYIFTHQGSNFGPIF
MTIPAFFAKSAAIYNPVIYIMMNKQFRNCMLTTICCGKNPLGDDEASATVSKTETSQ
VAPA
```

SEQ ID NO: 7
```
ACGGGTGTGGTACGCAGCCACT
```

SEQ ID NO: 8
```
TGCCCACACCATGCGTCGGTGA
```

SEQ ID NO: 9
```
ACGGGTGTGGTACGCAGCCCCT
```

SEQ ID NO: 10
```
TGCCCACACCATGCGTCGGGGA
```

SEQ ID NO: 11
```
MNTKYNKEFLLYLAGFVDGDGSIFARIFKGQHWKFKHYIRLTFSVRQKTQRRWFLD
KLVDEIGVGYVVDSGSVSEYYLSEIKPLHNFLTQLQPFLKLKQKQANLVLKIIEQLPS
AKESPDKFLEVCTWVDQIAALNDSKTRKTTSETVRAVLDSLPGSVGGLSPSQASSAA
SSASSSPGSGISEALRAGAGSGTGYNKEFLLYLAGFVDGDGSIWASIIPEQRLKFKHRL
RLSFTVAQKTQRRWFLDKLVDEIGVGYVVDQGSVSEYRLSEIKPLHNFLTQLQPFLK
LKQKQANLVLKIIEQLPSAKESPDKFLEVCTWVDQIAALNDSKTRKTTSETVRAVLD
SLSEKKKSSP
```

SEQ ID NO: 12
```
MNTKYNKEFLLYLAGFVDGDGSIFARIFKGQHWKFKHYIRLTFSVRQKTQRRWFLD
KLVDEIGVGYVCDSGSVSEYYLSEIKPLHNFLTQLQPFLKLKQKQANLVLKIIEQLPS
AKESPDKFLEVCTWVDQIAALNDSKTRKTTSETVRAVLDSLPGSVGGLSPSQASSAA
SSASSSPGSGISEALRAGAGSGTGYNKEFLLYLAGFVDGDGSIWASIIPEQNGKFKHR
LRLSFTVAQKTQRRWFLDKLVDEIGVGYVVDQGSVSEYRLSEIKPLHNFLTQLQPFL
KLKQKQANLVLKIIEQLPSAKESPDKFLEVCTWVDQIAALNDSKTRKTTSETVRAVL
DSLSEKKKSSP
```

SEQ ID NO: 13
```
MNTKYNKEFLLYLAGFVDGDGSIYARIFKGQHWKFKHYIRLTFSVRQKTQRRWFLD
KLVDEIGVGYVQDSGSVSEYYLSEIKPLHNFLTQLQPFLKLKQKQANLVLKIIEQLPS
AKESPDKFLEVCTWVDQIAALNDSKTRKTTSETVRAVLDSLPGSVGGLSPSQASSAA
```

Sequence Listing

SSASSSPGSGISEALRAGAGSGTGYNKEFLLYLAGFVDGDGSIWASIIPEQAYKFKHR
LRLSFTVAQKTQRRWFLDKLVDEIGVGYVVDQGSVSEYRLSEIKPLHNFLTQLQPFL
KLKQKQANLVLKIIEQLPSAKESPDKFLEVCTWVDQIAALNDSKTRKTTSETVRAVL
DSLSEKKKSSP

SEQ ID NO: 14
MNTKYNKEFLLYLAGFVDGDGSIFARIFKGQHWKFKHYIRLTFSVRQKTQRRWFLD
KLVDEIGVGYVYDSGSVSEYYLSEIKPLHNFLTQLQPFLKLKQKQANLVLKIIEQLPS
AKESPDKFLEVCTWVDQIAALNDSKTRKTTSETVRAVLDSLPGSVGGLSPSQASSA
SSSASSSPGSGISEALRAGAGSGTGYNKEFLLYLAGFVDGDGSIWASIIPEQKSKFKHRL
RLSFTVAQKTQRRWFLDKLVDEIGVGYVVDQGSVSEYRLSEIKPLHNFLTQLQPFLK
LKQKQANLVLKIIEQLPSAKESPDKFLEVCTWVDQIAALNDSKTRKTTSETVRAVLD
SLSEKKKSSP

SEQ ID NO: 15
KEFLLYLAGFVDGDGSIWASIIPEQRLKFKHRLRLSFTVAQKTQRRWFLDKLVDEIGV
GYVVDQGSVSEYRLSEIKPLHNFLTQLQPFLKLKQKQANLVLKIIEQLPSAKESPDKF
LEVCTWVDQIAALNDSKTRKTTSETVRAVLD

SEQ ID NO: 16
KEFLLYLAGFVDGDGSIWASIIPEQNGKFKHRLRLSFTVAQKTQRRWFLDKLVDEIG
VGYVVDQGSVSEYRLSEIKPLHNFLTQLQPFLKLKQKQANLVLKIIEQLPSAKESPDK
FLEVCTWVDQIAALNDSKTRKTTSETVRAVLD

SEQ ID NO: 17
KEFLLYLAGFVDGDGSIWASIIPEQAYKFKHRLRLSFTVAQKTQRRWFLDKLVDEIG
VGYVVDQGSVSEYRLSEIKPLHNFLTQLQPFLKLKQKQANLVLKIIEQLPSAKESPDK
FLEVCTWVDQIAALNDSKTRKTTSETVRAVLD

SEQ ID NO: 18
KEFLLYLAGFVDGDGSIWASIIPEQKSKFKHRLRLSFTVAQKTQRRWFLDKLVDEIGV
GYVVDQGSVSEYRLSEIKPLHNFLTQLQPFLKLKQKQANLVLKIIEQLPSAKESPDKF
LEVCTWVDQIAALNDSKTRKTTSETVRAVLD

SEQ ID NO: 19
KEFLLYLAGFVDGDGSIFARIFKGQHWKFKHYIRLTFSVRQKTQRRWFLDKLVDEIG
VGYVVDSGSVSEYYLSEIKPLHNFLTQLQPFLKLKQKQANLVLKIIEQLPSAKESPDK
FLEVCTWVDQIAALNDSKTRKTTSETVRAVLD

SEQ ID NO: 20
KEFLLYLAGFVDGDGSIFARIFKGQHWKFKHYIRLTFSVRQKTQRRWFLDKLVDEIG
VGYVCDSGSVSEYYLSEIKPLHNFLTQLQPFLKLKQKQANLVLKIIEQLPSAKESPDK
FLEVCTWVDQIAALNDSKTRKTTSETVRAVLD

SEQ ID NO: 21
KEFLLYLAGFVDGDGSIYARIFKGQHWKFKHYIRLTFSVRQKTQRRWFLDKLVDEIG
VGYVQDSGSVSEYYLSEIKPLHNFLTQLQPFLKLKQKQANLVLKIIEQLPSAKESPDK
FLEVCTWVDQIAALNDSKTRKTTSETVRAVLD

SEQ ID NO: 22
KEFLLYLAGFVDGDGSIFARIFKGQHWKFKHYIRLTFSVRQKTQRRWFLDKLVDEIG
VGYVYDSGSVSEYYLSEIKPLHNFLTQLQPFLKLKQKQANLVLKIIEQLPSAKESPDK
FLEVCTWVDQIAALNDSKTRKTTSETVRAVLD

SEQ ID NO: 23
CCGGGCGAAGGGTGTGGTGAGTGGCCACTTG

SEQ ID NO: 24
GGCCCGCTTCCCACACCACTCACCGGTGAAC

SEQ ID NO: 25
ATGAATACAAAATATAATAAAGAGTTCTTACTCTACTTAGCAGGGTTTGTAGACG
GTGACGGTTCCATCTTTGCCCGTATCTTTAAGGGTCAACATTGGAAGTTCAAGCA
CTATATTCGTTTGACCTTCTCGGTGCGGCAGAAGACACAGCGCCGTTGGTTCCTC
GACAAGCTGGTGGACGAGATCGGTGTGGGTTACGTGGTTGACTCTGGCAGCGTTT
CCGAGTACTACCTGTCCGAGATTAAACCATTACATAATTTTTTAACACAACTACA
ACCTTTTCTAAAACTAAAACAAAAACAAGCAAATTTAGTTTTAAAAATTATTGAA
CAACTTCCGTCAGCAAAAGAATCCCCGGACAAATTCTTAGAAGTTTGTACATGGG
TGGATCAAATTGCAGCTCTGAATGATTCGAAGACGCGTAAAACAACTTCTGAAA
CCGTTCGTGCTGTGCTAGACAGTTTACCAGGATCCGTGGGAGGTCTATCGCCATC
TCAGGCATCCAGCGCCGCATCCTCGGCTTCCTCAAGCCCGGGTTCAGGGATCTCC
GAAGCACTCAGAGCTGGAGCAGGTTCCGGCACTGGATACAACAAGGAATTCCTG
CTCTACCTGGCGGGCTTCGTCGACGGGGACGGCTCCATCTGGGCCTCGATCATTC
CTGAGCAACGGCTTAAATTCAAGCATAGGCTGCGCCTCTCTTTCACTGTCGCTCA
GAAGACACAGCGCCGTTGGTTCCTCGACAAGCTGGTGGACGAGATCGGTGTGGG
TTACGTGGTTGACCAGGGCAGCGTCTCCGAGTATAGGCTGTCCGAGATCAAGCCT
CTGCACAACTTCCTGACCCAGCTCCAGCCCTTCCTGAAGCTCAAGCAGAAGCAGG

-continued

Sequence Listing

```
CCAACCTCGTGCTGAAGATCATCGAGCAGCTGCCCTCCGCCAAGGAATCCCCGG
ACAAGTTCCTGGAGGTGTGCACCTGGGTGGACCAGATCGCCGCTCTGAACGACTC
CAAGACCCGCAAGACCACTTCCGAAACCGTCCGCGCCGTTCTAGACAGTCTCTCC
GAGAAGAAGAAGTCGTCCCCC

SEQ ID NO: 26
ATGAATACAAAATATAATAAAGAGTTCTTACTCTACTTAGCAGGGTTTGTAGACG
GTGACGGTTCCATCTTTGCCCGTATCTTTAAGGGTCAACATTGGAAGTTCAAGCA
CTATATTCGTTTGACCTTCAGTGTGCGGCAGAAGACACAGCGCCGTTGGTTCCTC
GACAAGCTGGTGGACGAGATCGGTGTGGGTTACGTGTGTGACTCTGGCAGCGTTT
CCGAGTACTACCTGTCCGAGATTAAACCATTACATAATTTTTTAACACAACTACA
ACCTTTTCTAAAACTAAAACAAAAACAAGCAAATTTAGTTTTAAAAATTATTGAA
CAACTTCCGTCAGCAAAAGAATCCCCGGACAAATTCTTAGAAGTTTGTACATGGG
TGGATCAAATTGCAGCTCTGAATGATTCGAAGACGCGTAAAACAACTTCTGAAA
CCGTTCGTGCTGTGCTAGACAGTTTACCAGGATCCGTGGGAGGTCTATCGCCATC
TCAGGCATCCAGCGCCGCATCCTCGGCTTCCTCAAGCCCGGGTTCAGGGATCTCC
GAAGCACTCAGAGCTGGAGCAGGTTCCGGCACTGGATACAACAAGGAATTCCTG
CTCTACCTGGCGGGCTTCGTCGACGGGGACGGCTCCATCTGGGCCTCGATCATTC
CTGAGCAAAATGGTAAATTCAAGCATAGGCTGCGCCTCTCTTTCACTGTCGCTCA
GAAGACACAGCGCCGTTGGTTCCTCGACAAGCTGGTGGACGAGATCGGTGTGGG
TTACGTGGTTGACCAGGGCAGCGTCTCCGAGTATAGGCTGTCCGAGATCAAGCCT
CTGCACAACTTCCTGACCCAGCTCCAGCCCTTCCTGAAGCTCAAGCAGAAGCAGG
CCAACCTCGTGCTGAAGATCATCGAGCAGCTGCCCTCCGCCAAGGAATCCCCGG
ACAAGTTCCTGGAGGTGTGCACCTGGGTGGACCAGATCGCCGCTCTGAACGACTC
CAAGACCCGCAAGACCACTTCCGAAACCGTCCGCGCCGTTCTAGACAGTCTCTCC
GAGAAGAAGAAGTCGTCCCCC

SEQ ID NO: 27
ATGAATACAAAATATAATAAAGAGTTCTTACTCTACTTAGCAGGGTTTGTAGACG
GTGACGGTTCCATCTATGCCCGTATCTTTAAGGGTCAACATTGGAAGTTCAAGCA
CTATATTCGTTTGACCTTCAGTGTGCGGCAGAAGACACAGCGCCGTTGGTTCCTC
GACAAGCTGGTGGACGAGATCGGTGTGGGTTACGTGCAGGACTCTGGCAGCGTT
TCCGAGTACTACCTGTCCGAGATTAAACCATTACATAATTTTTTAACACAACTAC
AACCTTTTCTAAAACTAAAACAAAAACAAGCAAATTTAGTTTTAAAAATTATTGA
ACAACTTCCGTCAGCAAAAGAATCCCCGGACAAATTCTTAGAAGTTTGTACATGG
GTGGATCAAATTGCAGCTCTGAATGATTCGAAGACGCGTAAAACAACTTCTGAA
ACCGTTCGTGCTGTGCTAGACAGTTTACCAGGATCCGTGGGAGGTCTATCGCCAT
CTCAGGCATCCAGCGCCGCATCCTCGGCTTCCTCAAGCCCGGGTTCAGGGATCTC
CGAAGCACTCAGAGCTGGAGCAGGTTCCGGCACTGGATACAACAAGGAATTCCT
GCTCTACCTGGCGGGCTTCGTCGACGGGGACGGCTCCATCTGGGCCTCGATCATT
CCTGAGCAAGCGTATAAATTCAAGCATAGGCTGCGCCTCTCTTTCACTGTCGCTC
AGAAGACACAGCGCCGTTGGTTCCTCGACAAGCTGGTGGACGAGATCGGTGTGG
GTTACGTGGTTGACCAGGGCAGCGTCTCCGAGTATAGGCTGTCCGAGATCAAGCC
TCTGCACAACTTCCTGACCCAGCTCCAGCCCTTCCTGAAGCTCAAGCAGAAGCAG
GCCAACCTCGTGCTGAAGATCATCGAGCAGCTGCCCTCCGCCAAGGAATCCCCG
GACAAGTTCCTGGAGGTGTGCACCTGGGTGGACCAGATCGCCGCTCTGAACGAC
TCCAAGACCCGCAAGACCACTTCCGAAACCGTCCGCGCCGTTCTAGACAGTCTCT
CCGAGAAGAAGAAGTCGTCCCCC

SEQ ID NO: 28
ATGAATACAAAATATAATAAAGAGTTCTTACTCTACTTAGCAGGGTTTGTAGACG
GTGACGGTTCCATCTTTGCCCGTATCTTTAAGGGTCAACATTGGAAGTTCAAGCA
CTATATTCGTTTGACCTTCTCGGTGCGGCAGAAGACACAGCGCCGTTGGTTCCTC
GACAAGCTGGTGGACGAGATCGGTGTGGGTTACGTGTATGACTCTGGCAGCGTTT
CCGAGTACTACCTGTCCGAGATTAAACCATTACATAATTTTTTAACACAACTACA
ACCTTTTCTAAAACTAAAACAAAAACAAGCAAATTTAGTTTTAAAAATTATTGAA
CAACTTCCGTCAGCAAAAGAATCCCCGGACAAATTCTTAGAAGTTTGTACATGGG
TGGATCAAATTGCAGCTCTGAATGATTCGAAGACGCGTAAAACAACTTCTGAAA
CCGTTCGTGCTGTGCTAGACAGTTTACCAGGATCCGTGGGAGGTCTATCGCCATC
TCAGGCATCCAGCGCCGCATCCTCGGCTTCCTCAAGCCCGGGTTCAGGGATCTCC
GAAGCACTCAGAGCTGGAGCAGGTTCCGGCACTGGATACAACAAGGAATTCCTG
CTCTACCTGGCGGGCTTCGTCGACGGGGACGGCTCCATCTGGGCCTCGATCATTC
CTGAGCAAAGTCGAAATTCAAGCATAGGCTGCGCCTCTCTTTCACTGTCGCTCA
GAAGACACAGCGCCGTTGGTTCCTCGACAAGCTGGTGGACGAGATCGGTGTGGG
TTACGTGGTTGACCAGGGCAGCGTCTCCGAGTATAGGCTGTCCGAGATCAAGCCT
CTGCACAACTTCCTGACCCAGCTCCAGCCCTTCCTGAAGCTCAAGCAGAAGCAGG
CCAACCTCGTGCTGAAGATCATCGAGCAGCTGCCCTCCGCCAAGGAATCCCCGG
ACAAGTTCCTGGAGGTGTGCACCTGGGTGGACCAGATCGCCGCTCTGAACGACTC
CAAGACCCGCAAGACCACTTCCGAAACCGTCCGCGCCGTTCTAGACAGTCTCTCC
GAGAAGAAGAAGTCGTCCCCC

SEQ ID NO: 29
MAPKKKRKVH
```

What is claimed is:

1. An engineered meganuclease that binds and cleaves a recognition sequence consisting of SEQ ID NO: 7 in a rhodopsin gene, wherein said engineered meganuclease comprises a first subunit and a second subunit, wherein said first subunit binds to a first recognition half-site of said recognition sequence and comprises a first hypervariable (HVR1) region, wherein said second subunit binds to a second recognition half-site of said recognition sequence and comprises a second hypervariable (HVR2) region, and wherein said engineered meganuclease comprises the amino acid sequence of SEQ ID NO: 11.

2. A polynucleotide comprising a nucleic acid sequence encoding said engineered meganuclease of claim 1.

3. A recombinant DNA construct comprising a polynucleotide comprising a nucleic acid sequence encoding said engineered meganuclease of claim 1.

4. The recombinant DNA construct of claim 3, wherein said recombinant DNA construct encodes a recombinant virus comprising said polynucleotide.

5. The recombinant DNA construct of claim 4, wherein said recombinant virus is a recombinant adeno-associated virus (AAV).

6. The recombinant DNA construct of claim 5, wherein said recombinant AAV has an AAV5 or AAV2 serotype.

7. The recombinant DNA construct of claim 3, wherein said nucleic acid sequence comprises an eye-specific promoter sequence operably linked to said nucleic acid sequence encoding said engineered meganuclease.

8. The recombinant DNA construct of claim 7, wherein said promoter is a human G-protein-coupled receptor protein kinase 1 (GRK1) promoter.

9. A recombinant virus comprising a polynucleotide comprising a nucleic acid sequence encoding said engineered meganuclease of claim 1.

10. The recombinant virus of claim 9, wherein said recombinant virus is a recombinant adenovirus or a recombinant AAV.

11. The recombinant virus of claim 10, wherein said recombinant AAV has an AAV5 or AAV2 serotype.

12. The recombinant virus of claim 9, wherein said nucleic acid sequence comprises an eye-specific promoter sequence operably linked to said nucleic acid sequence encoding said engineered meganuclease.

13. The recombinant virus of claim 12, wherein said promoter is a human G-protein-coupled receptor protein kinase 1 (GRK1) promoter.

14. A lipid nanoparticle composition comprising lipid nanoparticles comprising a polynucleotide, wherein said polynucleotide comprises a nucleic acid sequence encoding said engineered meganuclease of claim 1.

* * * * *

SEQUENCE LISTING

<160> NUMBER OF SEQ ID NOS: 29

<210> SEQ ID NO 1
<211> LENGTH: 163
<212> TYPE: PRT
<213> ORGANISM: Chlamydomonas reinhardtii

<400> SEQUENCE: 1

Met Asn Thr Lys Tyr Asn Lys Glu Phe Leu Leu Tyr Leu Ala Gly Phe
1               5                   10                  15

Val Asp Gly Asp Gly Ser Ile Ile Ala Gln Ile Lys Pro Asn Gln Ser
            20                  25                  30

Tyr Lys Phe Lys His Gln Leu Ser Leu Ala Phe Gln Val Thr Gln Lys
        35                  40                  45

Thr Gln Arg Arg Trp Phe Leu Asp Lys Leu Val Asp Glu Ile Gly Val
    50                  55                  60

Gly Tyr Val Arg Asp Arg Gly Ser Val Ser Asp Tyr Ile Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Trp Arg Leu
            100                 105                 110

Pro Ser Ala Lys Glu Ser Pro Asp Lys Phe Leu Glu Val Cys Thr Trp
            115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Ser Glu Lys Lys Lys
145                 150                 155                 160

Ser Ser Pro

<210> SEQ ID NO 2
<211> LENGTH: 9
<212> TYPE: PRT
<213> ORGANISM: Chlamydomonas reinhardtii

<400> SEQUENCE: 2

Leu Ala Gly Leu Ile Asp Ala Asp Gly
1               5

<210> SEQ ID NO 3
<211> LENGTH: 13706
<212> TYPE: DNA
<213> ORGANISM: Homo sapiens

<400> SEQUENCE: 3
gtgggggacc aggagaaaga aagccaagga agaggaggag gaggaggaga aggaggagaa        60
ggatgctgac ctagcagctc ctctcacagc agctcctctc ttgcagaggc tgaagagcga       120
tttgtgccct gcaagctaag cccctaatcc accgaggcaa aggcaaagcc cctagccggg       180
ctcccgaggg ctgggactcg ggtgccccaa gatggctgca tccagccatc ttggcttaga       240
aagcccccca catgccagct tggccaacac ccacaccatg ggtttctctg gactgcccga       300
cacaaggtgt gggtgctggc caggcctgtg ttcaaatccc agctctgcag aggaactttg       360
accctgcata ccccagattc ctcagtggtc agtggggagt tagaccctct tcatagggggg      420 caggaggagt tgttcattca ttcaacaaat gtttattgaa cacctcctat gggttgtgag       480
ctcagaggca gcgatgaaca ggccaggctg gtcctgcatt ctagaaatag atgggaagtc       540

-continued

```
agtcaataag tagacaaatg aggccaggtg tggtggcatg cctgtagacc cagttactcg      600
ggatgctgag gtaggaggat cacttgagcc taggacagga attcaaggct gcagtaagct      660
atgattgcgc cactgcactc cagcctgggc aacagagcaa gactcatctc taaaaaacat      720
ttaaaaattg ttttaagaag acaaatgaga tagtcgctga tggtaatgac tgtgtaaaaa      780
ctgaacatgg ctgggtgtgg ttgctcacac ctataatctc agcactttgg gaggctgaga      840
ttacagcctc ccaagtggct cccaaggcag gaggatcact tgagcctggg agttagagaa      900
cagcttggac aatataggga gagcccaact ctacaaaaat gaaaataaat tagccaggca      960
tggtggcaca caccaatggt cccagctact caggggttga ggtggtggac cgcttgagcc     1020
caggaggttg aggctgcagt gagccatgat catgccgctg cactccaacc tgagtcacag     1080
agtgataccc tgtctcaaaa aacaataggc caggtgtggt ggctcacgcc tgtaacccca     1140
gcactttggg aggccgaggc ggatggatca cttgagatca ggagttagag accagcctgg     1200
ctaacatggc aaaatcctgt ctgtactaaa aatataaaaa ttagccaggc atggcagtac     1260
atgcctgtag tcctggttac ttgggaggct aaggcaggag aatcgcttga acccaggaag     1320
aggaggttgc agtgagccaa gatcacacca ctgcactcca gcttgggtga cagagtgaga     1380
ccctgtctca aaacagctaa acctggtggg ggtgcctggt gtgtaggatg gtcaggggtg     1440
gtctctccaa ggacatgagt gtgagcggag acctgaagga gactcaggaa gagattaata     1500
ctgtcagcaa caaatatatt gatcacttac aagcactccc aataatccta ttaggtaggc     1560
actattatca ttcccatttt acagagtgga gaaccgaagc acactctcgg gagggcgggg     1620
tagctggctg cacccaggct gtgtagcctc agtccagatg taagggtggg tggaaaagag     1680
ccttgcccaa tgagggagaa cagtgaaacc aaggccatag ggtctaaaga ttcacgaacc     1740
aggctctcat ggagaaagca ggtgaggttt actgtataga tgggtgtgcc cctacccac      1800 actgaggctt cctcgtctga gcaaactgag gcccagagag gggaaggaag caggactacc     1860
atggtgactc aaagaccagc tagaatccag cctcctctcc tcgaggcttc cactgcccca     1920
cgccaggcct gtgtgactca gtctagggcc tttccattac cccagctaaa cctttcttta     1980
gtcatttata ccatggtgtg aatggctggc tggtctttcc tgagagctat ctttgatgag     2040
gggagggagg catagccagg tttgggaagc tgataccca ggaagcccag ttgactgtgt      2100
gggttatagc ccaggctgtc actgatttgt aacgggacct gagcaactct gcagagctag     2160
gcctcagtct tttcatctgc aaaatggata tagcagagat ggtcagagta ggtgacttcg     2220
aatgaccctt ccagctcact atgagtctgt tttcctgaac aaagagcatt ttttgtttaa     2280
aaaaaaattt cttgggccgg acacggtggt tcactcctat aatcctggca ctttgggagg     2340
ccgaggaggg tggatcgctt gagccaggag ttcaggacca gcctgggcaa catagcgaga     2400 ctccaccct acaaaaaata caaaaactag tggtgtgcac ttgtggtccc agctactcag      2460
gaggctgagg tgagaggatc gcttgagccc aggaggcaga ggctacagtg agctatgatt     2520
gtggcactgc actccagcct gggcgacaga gaccttgtct caaaacttt ttttcttcg       2580 tcaagcttta cagaataaag agcactgtca cctcagtgat ggctgttagt tccccatcac     2640
cagggctcca tgaggttgca attgtgaaac tcacaaagga ggaacctgag acagagaggg     2700
gaagtactga gatcatctag gtccattccc ccactcactc gttcattcaa caaatattca     2760
ggagcacctt ctaggtgcca ggccctggag acacatcagt gaacaaaaca gacatcatcc     2820
cacctctttc cactacaggc caagcaccat gctggtctct gggaaccctg ttgtgagcaa     2880
gacagaccca ggcttacccct tgtggactca tgttacaggc agggagacgg gcacaaaaca     2940
```

```
caaataaaaa gcttccatgc tgtcagaagc actatgcaaa aagcaagatg ctgaggtact    3000
gctaagctgt gtgggatggg ggctcagccc ggccagggag gggccagttg tgggtcagtc    3060
ttgacccaag gcatccagga caccctcctt ctggccatga gggtccacgt cagaatcaaa    3120
ccctcacctt aacctcatta gcgttgggca taatcaccag gccaagcgcc ttaaactacg    3180
agaggcccca tcccacccgc cctgccttag ccctgccacg tgtgccaaac gctgttagac    3240
ccaacaccac ccaggccagg taggggggctg gagcccaggt gggctgcagg gaaggggggca    3300 ctcttctgag cagacagatc tgggaatcct gggtgggaag agagacagtg agagagagat    3360
taagggatat ttcccaggca tcagggcttt gcactctcag gggtccttcc gcctggatgt    3420
ccttcccctg aagcttcctc ctgttgttcc gttctcagct caagctccag cttctcagag    3480
aagcctcctg tgttgggagt ggctgcgact gaactgtccc tactgttatt cgctcttcta    3540
tttgtttgtg gtccctgtgc ccctcaccc cacaaaaaca ctggcttctt gtgagcagga    3600
gcttgctctt tcgtgtaccc tgtgtgtccc caaggaccaa gcaccttgtc tgggccacag    3660
taggtgctca atacacatgt tggctggaca gtggtcactg agcggccgca cgtcgggcac    3720
tctcagcact tgcacaggcc gccccagaca ccccacttca ttcctgggag gtgtcatcat    3780
gttgcttgga cgacggggag aggggggacct gccagtgttg gcctccattt tcccccagtc    3840
atctgccccc aaggctctga ctactttctt tctcacggta catcctgcta ttctggaatc    3900
ggccctcgtg gggccacctg gtacatggca tttgaggccc tcgtggctga ttaggcctcc    3960
cccaacagtg ccctgtctgc tgcctccagg gccagcctcc ccttcagact ggagtcccct    4020
gaagggttct gccccctcccc tgctctggta gccccctcca tcctccctcc ctccactcca    4080
tctttggggg catttgagtc accttttctac accagtgatc tgcccaagcc actgctcact    4140
ttcctctgga taaagccagg ttccccggcc tagcgttcaa gacccattac aactgccccc    4200
agcccagatc ttccccacct agccacctgg caaactgctc cttctctcaa aggcccaaac    4260
atggcctccc agactgcaac ccccaggcag tcaggccctg tctccacaac ctcacagcca    4320
ccctggacgg aatctgcttc ttcccacatt tgagtcctcc tcagcccctg agctcctctg    4380
ggcagggctg tttctttcca tctttgtatt cccaggggcc tgcaaataaa tgtttaatga    4440
acgaacaaga gagtgaattc caattccatg caacaaggat tgggctcctg ggccctaggc    4500
tatgtgtctg gcaccagaaa cggaagctgc aggttgcagc ccctgccctc atggagctcc    4560
tcctgtcaga ggagtgtggg gactggatga ctccagaggt aacttgtggg ggaacgaaca    4620
ggtaaggggc tgtgtgacga gatgagagac tgggagaata aaccagaaag tctctagctg    4680
tccagaggac atagcacaga ggcccatggt ccctatttca aacccaggcc accagactga    4740
gctgggacct tgggacagac aagtcatgca gaagttaggg gaccttctcc tcccttttcc    4800
tggatcctga gtacctctcc tccctgacct caggcttcct cctagtgtca ccttggcccc    4860
tcttagaagc caattaggcc ctcagtttct gcagcgggga ttaatatgat tatgaacacc    4920
cccaatctcc cagatgctga ttcagccagg agcttaggag ggggaggtca ctttataagg    4980 gtctggggggg gtcagaaccc agagtcatcc agctggagcc ctgagtggct gagctcaggc    5040
cttcgcagca ttcttgggtg ggagcagcca cgggtcagcc acaagggcca cagccatgaa    5100
tggcacagaa ggccctaact tctacgtgcc cttctccaat gcgacgggtg tggtacgcag    5160
ccccttcgag tacccacagt actacctggc tgagccatgg cagttctcca tgctggccgc    5220
ctacatgttt ctgctgatcg tgctgggctt ccccatcaac ttcctcacgc tctacgtcac    5280
```

```
cgtccagcac aagaagctgc gcacgcctct caactacatc ctgctcaacc tagccgtggc    5340
tgacctcttc atggtcctag gtggcttcac cagcaccctc tacacctctc tgcatggata    5400
cttcgtcttc gggcccacag gatgcaattt ggagggcttc tttgccaccc tgggcggtat    5460
gagccgggtg tgggtggggt gtgcaggagc ccgggagcat ggaggggtct gggagagtcc    5520
cgggcttggc ggtggtggct gagaggcctt ctcccttctc ctgtcctgtc aatgttatcc    5580
aaagccctca tatattcagt caacaaacac cattcatggt gatagccggg ctgctgtttg    5640
tgcagggctg gcactgaaca ctgccttgat cttatttgga gcaatatgcg cttgtctaat    5700
ttcacagcaa gaaaactgag ctgaggctca aagaagtcaa gcgccctgct ggggcgtcac    5760
acagggacgg gtgcagagtt gagttggaag cccgcatcta tctcgggcca tgtttgcagc    5820
accaagcctc tgtttccctt ggagcagctg tgctgagtca gacccaggct gggcactgag    5880
ggagagctgg gcaagccaga cccctcctct ctgggggccc aagctcaggg tgggaagtgg    5940
attttccatt ctccagtcat tgggtcttcc ctgtgctggg caatgggctc ggtcccctct    6000
ggcatcctct gcctcccctc tcagcccctg tcctcaggtg cccctccagc ctccctgccg    6060
cgttccaagt ctcctggtgt tgagaaccgc aagcagccgc tctgaagcag ttcctttttg    6120
ctttagaata atgtcttgca tttaacagga aaacagatgg ggtgctgcag ggataacaga    6180
tcccacttaa cagagaggaa aactgaggca gggagagggg aagagactca tttagggatg    6240
tggccaggca gcaacaagag cctaggtctc ctggctgtga tccaggaata tctctgctga    6300
gatgcaggag gagacgctag aagcagccat tgcaaagctg ggtgacgggg agagcttacc    6360
gccagccaca agcgtctctc tgccagcctt gccctgtctc ccccatgtcc aggctgctgc    6420
ctcggtccca ttctcaggga atctctggcc attgttgggt gtttgttgca ttcaataatc    6480
acagatcact cagttctggc cagaaggtgg gtgtgccact tacgggtggt tgttctctgc    6540
agggtcagtc ccagtttaca aatattgtcc cttttcactgt taggaatgtc ccagtttggt    6600
tgattaacta tatggccact ctccctatgg aacttcatgg ggtggtgagc aggacagatg    6660
tctgaattcc atcatttcct tcttcttcct ctgggcaaaa cattgcacat tgcttcatgg    6720
ctcctaggag aggcccccac atgtccgggt tatttcattt cccgagaagg gagagggagg    6780
aaggactgcc aattctgggt ttccaccacc tctgcattcc ttcccaacaa ggaactctgc    6840
cccacattag gatgcattct tctgctaaac acacacacac acacacacac acacaacaca    6900
cacacacaca cacacacaca cacacacaca aaactcccta ccgggttccc agttcaatcc    6960
tgaccccctg atctgattcg tgtcccttat gggcccagag cgctaagcaa ataacttccc    7020
ccattccctg gaatttcttt gcccagctct cctcagcgtg tggtccctct gccccttccc    7080
cctcctccca gcaccaagct ctctccttcc ccaaggcctc ctcaaatccc tctcccactc    7140
ctggttgcct tcctagctac cctctccctg tctaggggg agtgcaccct ccttaggcag    7200
tggggtctgt gctgaccgcc tgctgactgc cttgcaggtg aaattgccct gtggtccttg    7260
gtggtcctgg ccatcgagcg gtacgtggtg gtgtgtaagc ccatgagcaa cttccgcttc    7320
ggggagaacc atgccatcat gggcgttgcc ttcacctggg tcatggcgct ggcctgcgcc    7380 gcaccccac tcgccggctg gtccaggtaa tggcactgag cagaagggaa gaagctccgg    7440
gggctctttg tagggtcctc cagtcaggac tcaaacccag tagtgtctgg ttccaggcac    7500
tgaccttgta tgtctcctgg cccaaatgcc cactcagggt aggggtgtag ggcagaagaa    7560
gaaacagact ctaatgttgc tacaagggct ggtcccatct cctgagcccc atgtcaaaca    7620
gaatccaaga catcccaacc cttcaccttg gctgtgcccc taatcctcaa ctaagctagg    7680
```

```
cgcaaattcc aatcctcttt ggtctagtac cccgggggca gcccctcta accttgggcc   7740 tcagcagcag gggaggccac accttcctag tgcaggtggc catattgtgg ccccttggaa   7800
ctgggtccca ctcagcctct aggcgattgt ctcctaatgg ggctgagatg agacacagtg   7860
gggacagtgg tttggacaat aggactggtg actctggtcc ccagaggcct catgtccctc   7920
tgtctccaga aaattcccac tctcacttcc ctttcctcct cagtcttgct agggtccatt   7980
tcttacccct tgctgaattt gagcccaccc cctggacttt ttccccatct tctccaatct   8040
ggcctagttc tatcctctgg aagcagagcc gctggacgct ctgggtttcc tgaggcccgt   8100
ccactgtcac caatatcagg aaccattgcc acgtcctaat gacgtgcgct ggaagcctct   8160
agtttccaga agctgcacaa agatccctta gatactctgt gtgtccatct ttggcctgga   8220
aaatactctc accctggggc taggaagacc tcggtttgta caaacttcct caaatgcaga   8280
gcctgagggc tctccccacc tcctcaccaa ccctctgcgt ggcatagccc tagcctcagc   8340
gggcagtgga tgctggggct gggcatgcag ggagaggctg ggtggtgtca tctggtaacg   8400
cagccaccaa acaatgaagc gacactgatt ccacaaggtg catctgcatc cccatctgat   8460
ccattccatc ctgtcaccca gccatgcaga cgtttatgat ccccttttcc agggagggaa   8520
tgtgaagccc cagaaagggc cagcgctcgg cagccacctt ggctgttccc aagtccctca   8580
caggcagggt ctccctacct gcctgtcctc aggtacatcc ccgagggcct gcagtgctcg   8640
tgtggaatcg actactacac gctcaagccg gaggtcaaca acgagtcttt tgtcatctac   8700
atgttcgtgg tccacttcac catccccatg attatcatct ttttctgcta tgggcagctc   8760
gtcttcaccg tcaaggaggt acgggccggg gggtgggcgg cctcacggct ctgagggtcc   8820
agcccccagc atgcatctgc ggctcctgct ccctggagga gccatggtct ggacccgggt   8880
cccgtgtcct gcaggccgct gcccagcagc aggagtcagc caccacacag aaggcagaga   8940
aggaggtcac ccgcatggtc atcatcatgg tcatcgcttt cctgatctgc tgggtgccct   9000
acgccagcgt ggcattctac atcttcaccc accagggctc caacttcggt cccatcttca   9060
tgaccatccc agcgttcttt gccaagagcg ccgccatcta caaccctgtc atctatatca   9120
tgatgaacaa gcaggtgcct actgcgggtg ggagggcccc agtgcccag gccacaggcg   9180 ctgcctgcca aggacaagct acttcccagg gcaggggagg gggctccatc agggttactg   9240
gcagcagtct tgggtcagca gtcccaatgg gggagtgtgtg agaaatgcag attcctggcc   9300
ccactcagaa ctgctgaatc tcagggtggg cccaggaacc tgcatttcca gcaagccctc   9360
cacaggtggc tcagatgctc actcaggtgg gagaagctcc agtcagctag ttctggaagc   9420
ccaatgtcaa agtcagaagg acccaagtcg ggaatgggat gggccagtct ccataaagct   9480
gaataaggag ctaaaaagtc ttattctgag gggtaaaggg gtaaagggtt cctcggagag   9540
gtacctccga ggggtaaaca gttgggtaaa cagtctctga agtcagctct gccattttct   9600
agctgtatgg ccctgggcaa gtcaatttcc ttctctgtgc tttggtttcc tcatccatag   9660
aaaggtagaa agggcaaaac accaaactct tggattacaa gagataattt acagaacacc   9720
cttggcacac agagggcacc atgaaatgtc acgggtgaca cagcccccctt gtgctcagtc   9780 cctggcatct ctaggggtga ggagcgtctg cctagcaggt tccctccagg aagctggatt   9840
tgagtggatg gggcgctgga atcgtgaggg gcagaagcag gcaaagggtc ggggcgaacc   9900
tcactaacgt gccagttcca agcacactgt gggcagccct ggccctgact caagcctctt   9960
gccttccagt tccggaactg catgctcacc accatctgct gcggcaagaa cccactgggt  10020
```

-continued

```
gacgatgagg cctctgctac cgtgtccaag acggagacga gccaggtggc cccggcctaa  10080
gacctgccta ggactctgtg gccgactata ggcgtctccc atccccctaca ccttcccccca  10140 gccacagcca tcccaccagg agcagcgcct gtgcagaatg aacgaagtca cataggctcc  10200
ttaatttttt tttttttttt aagaaataat taatgaggct cctcactcac ctgggacagc  10260
ctgagaaggg acatccacca agacctactg atctggagtc ccacgttccc caaggccagc  10320
gggatgtgtg cccctcctcc tcccaactca tctttcagga acacgaggat tcttgctttc  10380
tggaaaagtg tcccagctta gggataagtg tctagcacag aatggggcac acagtaggtg  10440
cttaataaat gctggatgga tgcaggaagg aatggaggaa tgaatgggaa gggagaacat  10500
atctatcctc tcagaccctc gcagcagcag caactcatac ttggctaatg atatggagca  10560
gttgtttttc cctccctggg cctcactttc ttctcctata aaatggaaat cccagatccc  10620
tggtcctgcc gacacgcagc tactgagaag accaaaagag gtgtgtgtgt gtctatgtgt  10680
gtgtttcagc actttgtaaa tagcaagaag ctgtacagat tctagttaat gttgtgaata  10740
acatcaatta atgtaactag ttaattacta tgattatcac ctcctgatag tgaacatttt  10800
gagattgggc attcagatga tggggtttca cccaaccttg gggcaggttt ttaaaaatta  10860
gctaggcatc aaggccagac cagggctggg ggttgggctg taggcaggga cagtcacagg  10920
aatgcagaat gcagtcatca gacctgaaaa aacaacactg ggggaggggg acggtgaagg  10980
ccaagttccc aatgagggtg agattgggcc tggggtctca cccctagtgt ggggcccccag  11040 gtcccgtgcc tcccccttccc aatgtggcct atggagagac aggccctttct ctcagcctct  11100 ggaagccacc tgctcttttg ctctagcacc tgggtcccag catctagagc atggagcctc  11160
tagaagccat gctcacccgc ccacatttaa ttaacagctg agtccctgat gtcatcctta  11220
tctcgaagag cttagaaaca aagagtggga aattccactg ggcctacctt ccttgggggat  11280 gttcatgggc cccagtttcc agtttccctt gccagacaag cccatcttca gcagttgcta  11340
gtccattctc cattctggag aatctgctcc aaaaagctgg ccacatctct gaggtgtcag  11400
aattaagctg cctcagtaac tgctcccccct tctccatata agcaaagcca gaagctctag  11460
ctttacccag ctctgcctgg agactaaggc aaattgggcc attaaaagct cagctcctat  11520
gttggtatta acggtggtgg gttttgttgc tttcacactc tatccacagg atagattgaa  11580
actgccagct tccacctgat ccctgaccct gggatggctg gattgagcaa tgagcagagc  11640
caagcagcac agagtcccct ggggctagag gtggaggagg cagtcctggg aatgggaaaa  11700
accccaactt tggggtcata gaggcacagg taacccataa aactgcaaac aagctttgtc  11760
acctctcaga gcttccttat ctgcaaaaaa gaatcttaaa actgaccttg gctgggcaca  11820
gtggctcaca cctctaatcc cagcactttg ggaggccaag gtgggcagat cacgaggtca  11880
ggagtttgag accagcctga ccaacacggt gaaacctgt ctctactaaa aatacaaaaa  11940
tcagctgggc atggtggcgc gtgcctgtaa tcccagctat tcagtgggct gaggcaggag  12000
aatcgcttga acctgggagg tggaggttgc agtgagccga gattgcgcca ctgcactcca  12060
gcctgagcaa cagagggaca gtctgtctcc aaacaaaaca aaacaaacaa acaaacaaac  12120
aaacaaacaa aaaacaacaa caaaaaaacc acttgatcct aaggggatta gatgcgactg  12180
tggactttaa gtggccagcc tactgcctgg catgcagcag atgagactat ggcaatactg  12240
ggcttcagct cagagctggc cttactagag accctgtccc aaaggggaaa aggatggagc  12300
taaagctccc gagagtcacc ccctcctccg aggtgagaaa ggaggcagg agcatgagat  12360 agccgatcct cggtgccttg gtgaggctgg ggcaaatcat gctgggatct ctatcattgt  12420
```

```
ccctctttac tgtgactcac tagataatat cagtcaggat acttttggtc acaagtgata   12480
ggaaatccaa ctcatttggg ctgaagcaaa agggacacat tgttggctca catgaacaaa   12540
aagcccgggg cttcaggcac agggtatcac catgactgag atggggatta attctgtgat   12600
tggccaagtc taggtcacct gatcatacgt aactcattta tgcctgaggt tgcaattttt   12660
tggatttttg caatcagacc ttggcgatga ccttgagcag taggatataa ataactccca   12720
catgcttagc gttccaataa tggaatacta ggcatacgca ggtctaactg catcaccatg   12780
gctggaatgg ggattcatcc tctgattggt cagacctagg tcacatgctc accctgcagc   12840
ccaagcaggc tgaatgggga gaggtaggtt tcacaaagga aagcccaggt gctgttacct   12900
gaagtaggag ggcaggaggc agggtgagca gagccaacat caacccagag ggaatggaat   12960
ctaagttggt gttttctggg cacgtggctg gaccaggcct ccctccctca tcatctcagg   13020
gacatgaggg agaagattcc tatgggtggt cccgaaggtc tcacccttttg ttttggatgc   13080 tgtgttgggc cagggtggca gtgggtggga cagtggcatc ttagctgccc tgacttgcag   13140
gcagcccatt ccagctcccc gccccaaccc caacccagcc cacttttttct gagaaatggt   13200 acatttgccc cagcctcatg tccagaggaa aattttactc taacaccaga acattctctg   13260
gtttgtcctg atagacaaga aagcctccac ctccttaatt tacaaatgac ttgacagctg   13320
cttcgtgggc acttgcatac ataaagagaa ggagctgctg ccttaagttg cagcaagttt   13380
ggccccacct catctccagg cagccagcag atgtacagag tgcctcttgg gtacaatggc   13440
agctccattc aaccaaacct gagcaagctg accccatgcc agaatgcact ggggactcgg   13500
agatgaattg gagcctagag accaagtctc taggctatga cctgggctgc ctcacggcca   13560
cagagctctg tcacgccaag ggagagatgc acccctgaaa gcctgaggtg ccccataagg   13620
agagagtggg tgcccttccc aactatgtag cttcagggca agttctcttt ctttctttt   13680 ctttctttct ctttctttct ttcttt                                       13706
```

<210> SEQ ID NO 4
<211> LENGTH: 13706
<212> TYPE: DNA
<213> ORGANISM: Homo sapiens

<400> SEQUENCE: 4

```
gtgggggacc aggagaaaga aagccaagga agaggaggag gaggaggaga aggaggagaa     60
ggatgctgac ctagcagctc ctctcacagc agctcctctc ttgcagaggc tgaagagcga    120
tttgtgccct gcaagctaag cccctaatcc accgaggcaa aggcaaagcc cctagccggg    180
ctcccgaggg ctgggactcg ggtgccccaa gatggctgca tccagccatc ttggcttaga    240
aagcccccca catgccagct tggccaacac ccacaccatg ggtttctctg gactgcccga    300
cacaaggtgt gggtgctggc caggcctgtg ttcaaatccc agctctgcag aggaactttg    360
accctgcata ccccagattc ctcagtggtc agtggggagt tagaccctct tcataggggg    420
caggaggagt tgttcattca ttcaacaaat gtttattgaa cacctcctat gggttgtgag    480
ctcagaggca gcgatgaaca ggccaggctg gtcctgcatt ctagaaatag atgggaagtc    540
agtcaataag tagacaaatg aggccaggtg tggtggcatg cctgtagacc cagttactcg    600
ggatgctgag gtaggaggat cacttgagcc taggacagga attcaaggct gcagtaagct    660
atgattgcgc cactgcactc cagcctgggc aacagagcaa gactcatctc taaaaaacat    720
ttaaaaattg tttttaagaag acaaatgaga tagtcgctga tggtaatgac tgtgtaaaaa    780
```

-continued

```
ctgaacatgg ctgggtgtgg ttgctcacac ctataatctc agcactttgg gaggctgaga     840
ttacagcctc ccaagtggct cccaaggcag gaggatcact tgagcctggg agttagagaa     900
cagcttggac aatatagggo gagcccaact ctacaaaaat gaaaataaat tagccaggca     960
tggtggcaca caccaatggt cccagctact caggggttga ggtggtggac cgcttgagcc    1020
caggaggttg aggctgcagt gagccatgat catgccgctg cactccaacc tgagtcacag    1080
agtgataccc tgtctcaaaa aacaataggc caggtgtggt ggctcacgcc tgtaaccCca    1140
gcactttggg aggccgaggc ggatggatca cttgagatca ggagttagag accagcctgg    1200
ctaacatggc aaaatcctgt ctgtactaaa aatataaaaa ttagccaggc atggcagtac    1260
atgcctgtag tcctggttac ttgggaggct aaggcaggag aatcgcttga acccaggaag    1320
aggaggttgc agtgagccaa gatcacacca ctgcactcca gcttgggtga cagagtgaga    1380
ccctgtctca aaacagctaa acctggtggg ggtgcctggt gtgtaggatg gtcaggggtg    1440
gtctctccaa ggacatgagt gtgagcggag acctgaagga gactcaggaa gagattaata    1500
ctgtcagcaa caaatatatt gatcacttac aagcactccc aataatccta ttaggtaggc    1560
actattatca ttcccatttt acagagtgga gaaccgaagc acactctcgg gagggcgggg    1620
tagctggctg cacccaggct gtgtagcctc agtccagatg taagggtggg tggaaaagag    1680
ccttgcccaa tgagggagaa cagtgaaacc aaggccatag ggtctaaaga ttcacgaacc    1740
aggctctcat ggagaaagca ggtgaggttt actgtataga tgggtgtgcc cctaccccac    1800
actgaggctt cctcgtctga gcaaactgag gcccagagag gggaaggaag caggactacc    1860
atggtgactc aaagaccagc tagaatccag cctcctctcc tcgaggcttc cactgcccca    1920
cgccaggcct gtgtgactca gtctagggcc tttccattac cccagctaaa cctttcttta    1980
gtcatttata ccatggtgtg aatggctggc tggtctttcc tgagagctat ctttgatgag    2040
gggagggagg catagccagg tttgggaagc tgataccCca ggaagcccag ttgactgtgt    2100
gggttatagc ccaggctgtc actgatttgt aacgggacct gagcaactct gcagagctag    2160
gcctcagtct tttcatctgc aaaatggata tagcagagat ggtcagagta ggtgacttcg    2220
aatgacccTt ccagctcact atgagtctgt tttcctgaac aaagagcatt ttttgtttaa    2280 aaaaaattt cttgggccgg acacggtggt tcactcctat aatcctggca ctttgggagg    2340
ccgaggaggg tggatcgctt gagccaggag ttcaggacca gcctgggcaa catagcgaga    2400
ctccacccct acaaaaaata caaaaactag tggtgtgcac ttgtggtccc agctactcag    2460
gaggctgagg tgagaggatc gcttgagccc aggaggcaga ggctacagtg agctatgatt    2520
gtggcactgc actccagcct gggcgacaga gaccttgtct caaaactttt tttttcttcg    2580
tcaagcttta cagaataaag agcactgtca cctcagtgat ggctgttagt tccccatcac    2640
cagggctcca tgaggttgca attgtgaaac tcacaaagga ggaacctgag acagagaggg    2700
gaagtactga gatcatctag gtccattccc ccactcactc gttcattcaa caaatattca    2760
ggagcacctt ctaggtgcca ggccctggag acacatcagt gaacaaaaca gacatcatcc    2820
cacctctttc cactacaggc caagcaccat gctggtctct gggaaccctg ttgtgagcaa    2880
gacagaccca ggcttaccct tgtggactca tgttacaggc agggagacgg gcacaaaaca    2940
caaataaaaa gcttccatgc tgtcagaagc actatgcaaa aagcaagatg ctgaggtact    3000
gctaagctgt gtgggatggg ggctcagccc ggccagggag gggccagttg tgggtcagtc    3060
ttgacccaag gcatccagga caccctcctt ctggccatga gggtccacgt cagaatcaaa    3120
ccctcacctt aacctcatta gcgttgggca taatcaccag gccaagcgcc ttaaactacg    3180
```

```
agaggccccca tcccacccgc cctgccttag ccctgccacg tgtgccaaac gctgttagac      3240
ccaacaccac ccaggccagg tagggggctg gagcccaggt gggctgcagg gaaggggca        3300 ctcttctgag cagacagatc tgggaatcct gggtgggaag agagacagtg agagagagat       3360
taagggatat ttcccaggca tcagggcttt gcactctcag gggtccttcc gcctggatgt       3420
ccttcccctg aagcttcctc ctgttgttcc gttctcagct caagctccag cttctcagag       3480
aagcctcctg tgttgggagt ggctgcgact gaactgtccc tactgttatt cgctcttcta       3540
tttgtttgtg gtccctgtgc cccctcaccc cacaaaaaca ctggcttctt gtgagcagga       3600
gcttgctctt tcgtgtaccc tgtgtgtccc caaggaccaa gcaccttgtc tgggccacag       3660
taggtgctca atacacatgt tggctggaca gtggtcactg agcggccgca cgtcgggcac       3720
tctcagcact tgcacaggcc gccccagaca ccccacttca ttcctgggag gtgtcatcat       3780
gttgcttgga cgacggggag aggggggacct gccagtgttg gcctccattt tcccccagtc      3840
atctgccccc aaggctctga ctactttctt tctcacggta catcctgcta ttctggaatc       3900
ggccctcgtg gggccacctg gtacatggca tttgaggccc tcgtggctga ttaggcctcc       3960
cccaacagtg ccctgtctgc tgcctccagg gccagcctcc ccttcagact ggagtccccct      4020 gaagggttct gcccctcccc tgctctggta gccccctcca tcctccctcc ctccactcca       4080 tctttgggg catttgagtc accttttctac accagtgatc tgcccaagcc actgctcact      4140
ttcctctgga taaagccagg ttccccggcc tagcgttcaa gacccattac aactgccccc       4200
agcccagatc ttccccacct agccacctgg caaactgctc cttctctcaa aggcccaaac       4260
atggcctccc agactgcaac ccccaggcag tcaggccctg tctccacaac ctcacagcca       4320
ccctggacgg aatctgcttc ttcccacatt tgagtcctcc tcagcccctg agctcctctg       4380
ggcagggctg tttctttcca tctttgtatt cccaggggcc tgcaaataaa tgtttaatga       4440
acgaacaaga gagtgaattc caattccatg caacaaggat tgggctcctg ggccctaggc       4500
tatgtgtctg gcaccagaaa cggaagctgc aggttgcagc ccctgccctc atggagctcc       4560
tcctgtcaga ggagtgtggg gactggatga ctccagaggt aacttgtggg ggaacgaaca       4620
ggtaaggggc tgtgtgacga gatgagagac tgggagaata aaccagaaag tctctagctg       4680
tccagaggac atagcacaga ggcccatggt ccctatttca aacccaggcc accagactga       4740
gctgggacct tgggacagac aagtcatgca gaagttaggg gaccttctcc tcccttttcc       4800
tggatcctga gtacctctcc tccctgacct caggcttcct cctagtgtca ccttggcccc       4860
tcttagaagc caattaggcc ctcagtttct gcagcgggga ttaatatgat tatgaacacc       4920
cccaatctcc cagatgctga ttcagccagg agcttaggag ggggaggtca ctttataagg       4980 gtctggggg gtcagaaccc agagtcatcc agctggagcc ctgagtggct gagctcaggc       5040
cttcgcagca ttcttgggtg ggagcagcca cgggtcagcc acaagggcca cagccatgaa      5100
tggcacagaa ggccctaact tctacgtgcc cttctccaat gcgacgggtg tggtacgcag      5160
ccacttcgag tacccacagt actacctggc tgagccatgg cagttctcca tgctggccgc      5220
ctacatgttt ctgctgatcg tgctgggctt cccatcaac ttcctcacgc tctacgtcac      5280
cgtccagcac aagaagctgc gcacgcctct caactacatc ctgctcaacc tagccgtggc      5340
tgacctcttc atggtcctag gtggcttcac cagcacccct cacacctctc tgcatggata      5400
cttcgtcttc gggcccacag gatgcaattt ggagggcttc tttgccaccc tgggcggtat      5460
gagccgggtg tgggtggggt gtgcaggagc ccgggagcat ggaggggtct gggagagtcc      5520
```

-continued

```
cgggcttggc ggtggtggct gagaggcctt ctcccttctc ctgtcctgtc aatgttatcc      5580
aaagccctca tatattcagt caacaaacac cattcatggt gatagccggg ctgctgtttg      5640
tgcagggctg gcactgaaca ctgccttgat cttatttgga gcaatatgcg cttgtctaat      5700
ttcacagcaa gaaaactgag ctgaggctca aagaagtcaa gcgccctgct ggggcgtcac      5760
acagggacgg gtgcagagtt gagttggaag cccgcatcta tctcgggcca tgtttgcagc      5820
accaagcctc tgtttccctt ggagcagctg tgctgagtca gacccaggct gggcactgag      5880
ggagagctgg gcaagccaga cccctcctct ctggggccc aagctcaggg tgggaagtgg       5940
attttccatt ctccagtcat tgggtcttcc ctgtgctggg caatgggctc ggtcccctct      6000
ggcatcctct gcctcccctc tcagccctg tcctcaggtg cccctccagc ctccctgccg       6060
cgttccaagt ctcctggtgt tgagaaccgc aagcagccgc tctgaagcag ttccttttg       6120 ctttagaata atgtcttgca tttaacagga aaacagatgg ggtgctgcag ggataacaga      6180
tcccacttaa cagagaggaa aactgaggca gggagagggg aagagactca tttagggatg      6240
tggccaggca gcaacaagag cctaggtctc ctggctgtga tccaggaata tctctgctga      6300
gatgcaggag gagacgctag aagcagccat tgcaaagctg ggtgacgggg agagcttacc      6360
gccagccaca agcgtctctc tgccagcctt gccctgtctc ccccatgtcc aggctgctgc      6420
ctcggtccca ttctcaggga atctctggcc attgttgggt gtttgttgca ttcaataatc      6480
acagatcact cagttctggc cagaaggtgg gtgtgccact tacgggtggt tgttctctgc      6540
agggtcagtc ccagtttaca aatattgtcc cttcactgt taggaatgtc ccagtttggt       6600
tgattaacta tatggccact ctccctatgg aacttcatgg ggtggtgagc aggacagatg      6660
tctgaattcc atcatttcct tcttcttcct ctgggcaaaa cattgcacat tgcttcatgg      6720
ctcctaggag aggcccccac atgtccgggt tatttcattt cccgagaagg gagagggagg      6780
aaggactgcc aattctgggt ttccaccacc tctgcattcc ttcccaacaa ggaactctgc      6840
cccacattag gatgcattct tctgctaaac acacacacac acacacac acacaacaca        6900 cacacacaca cacacacaca cacacaca aaactcccta ccgggttccc agttcaatcc        6960
tgaccccctg atctgattcg tgtcccttat gggcccagag cgctaagcaa ataacttccc      7020
ccattccctg gaatttcttt gcccagctct cctcagcgtg tggtccctct gccccttccc      7080
cctcctccca gcaccaagct ctctccttcc ccaaggcctc ctcaaatccc tctcccactc      7140
ctggttgcct tcctagctac cctctccctg tctaggggg agtgcaccct ccttaggcag       7200
tggggtctgt gctgaccgcc tgctgactgc cttgcaggtg aaattgccct gtggtccttg      7260
gtggtcctgg ccatcgagcg gtacgtggtg gtgtgtaagc ccatgagcaa cttccgcttc      7320
ggggagaacc atgccatcat gggcgttgcc ttcacctggg tcatggcgct ggcctgcgcc      7380 gcaccccac tcgccggctg gtccaggtaa tggcactgag cagaagggaa gaagctccgg       7440
gggctctttg tagggtcctc cagtcaggac tcaaacccag tagtgtctgg ttccaggcac      7500
tgaccttgta tgtctcctgg cccaaatgcc cactcagggt aggggtgtag ggcagaagaa      7560
gaaacagact ctaatgttgc tacaagggct ggtcccatct cctgagcccc atgtcaaaca      7620
gaatccaaga catcccaacc cttcaccttg gctgtgcccc taatcctcaa ctaagctagg      7680
cgcaaattcc aatcctcttt ggtctagtac cccgggggca gcccctcta accttgggcc       7740 tcagcagcag gggaggccac accttcctag tgcaggtggc catattgtgg cccttggaa       7800 ctgggtccca ctcagcctct aggcgattgt ctcctaatgg ggctgagatg agacacagtg      7860
gggacagtgg tttggacaat aggactggtg actctggtcc ccagaggcct catgtccctc      7920
```

-continued

```
tgtctccaga aaattcccac tctcacttcc ctttcctcct cagtcttgct agggtccatt    7980
tcttacccct tgctgaattt gagcccaccc cctggacttt ttccccatct tctccaatct    8040
ggcctagttc tatcctctgg aagcagagcc gctggacgct ctgggtttcc tgaggcccgt    8100
ccactgtcac caatatcagg aaccattgcc acgtcctaat gacgtgcgct ggaagcctct    8160
agtttccaga agctgcacaa agatcccta gatactctgt gtgtccatct ttggcctgga    8220
aaatactctc accctggggc taggaagacc tcggtttgta caaacttcct caaatgcaga    8280
gcctgagggc tctccccacc tcctcaccaa ccctctgcgt ggcatagccc tagcctcagc    8340
gggcagtgga tgctggggct gggcatgcag ggagaggctg ggtggtgtca tctggtaacg    8400
cagccaccaa acaatgaagc gacactgatt ccacaaggtg catctgcatc cccatctgat    8460
ccattccatc ctgtcaccca gccatgcaga cgtttatgat cccctttttcc agggagggaa    8520 tgtgaagccc cagaaagggc cagcgctcgg cagccacctt ggctgttccc aagtccctca    8580
caggcagggt ctccctacct gcctgtcctc aggtacatcc ccgagggcct gcagtgctcg    8640
tgtggaatcg actactacac gctcaagccg gaggtcaaca acgagtcttt tgtcatctac    8700
atgttcgtgg tccacttcac catccccatg attatcatct ttttctgcta tgggcagctc    8760
gtcttcaccg tcaaggaggt acgggccggg gggtgggcgg cctcacggct ctgagggtcc    8820
agcccccagc atgcatctgc ggctcctgct ccctggagga gccatggtct ggacccgggt    8880
cccgtgtcct gcaggccgct gcccagcagc aggagtcagc caccacacag aaggcagaga    8940
aggaggtcac ccgcatggtc atcatcatgg tcatcgcttt cctgatctgc tgggtgccct    9000
acgccagcgt ggcattctac atcttcaccc accagggctc caacttcggt cccatcttca    9060
tgaccatccc agcgttcttt gccaagagcg ccgccatcta caaccctgtc atctatatca    9120
tgatgaacaa gcaggtgcct actgcgggtg ggagggcccc agtgcccag gccacaggcg    9180 ctgcctgcca aggacaagct acttcccagg gcaggggagg gggctccatc agggttactg    9240
gcagcagtct tgggtcagca gtcccaatgg ggagtgtgtg agaaatgcag attcctggcc    9300
ccactcagaa ctgctgaatc tcagggtggg cccaggaacc tgcatttcca gcaagccctc    9360
cacaggtggc tcagatgctc actcaggtgg gagaagctcc agtcagctag ttctggaagc    9420
ccaatgtcaa agtcagaagg acccaagtcg ggaatgggat gggccagtct ccataaagct    9480
gaataaggag ctaaaaagtc ttattctgag gggtaaaggg gtaaagggtt cctcggagag    9540
gtacctccga ggggtaaaca gttgggtaaa cagtctctga agtcagctct gccattttct    9600
agctgtatgg ccctgggcaa gtcaatttcc ttctctgtgc tttggtttcc tcatccatag    9660
aaaggtagaa agggcaaaac accaaactct tggattacaa gagataattt acagaacacc    9720
cttggcacac agagggcacc atgaaatgtc acgggtgaca cagcccccctt gtgctcagtc    9780 cctggcatct ctaggggtga ggagcgtctg cctagcaggt tccctccagg aagctggatt    9840
tgagtggatg gggcgctgga atcgtgaggg cagaagcag gcaaagggtc ggggcgaacc    9900
tcactaacgt gccagttcca agcacactgt gggcagccct ggccctgact caagcctctt    9960
gccttccagt tccggaactg catgctcacc accatctgct gcggcaagaa cccactgggt   10020
gacgatgagg cctctgctac cgtgtccaag acggagacga gccaggtggc cccggcctaa   10080
gacctgccta ggactctgtg gccgactata ggcgtctccc atccctaca ccttcccca    10140 gccacagcca tccaccagg agcagcgcct gtgcagaatg aacgaagtca cataggctcc   10200 ttaattttttt tttttttttt aagaaataat taatgaggct cctcactcac ctgggacagc   10260
```

-continued

```
ctgagaaggg acatccacca agacctactg atctggagtc ccacgttccc caaggccagc   10320
gggatgtgtg cccctcctcc tcccaactca tctttcagga acacgaggat tcttgctttc   10380
tggaaaagtg tcccagctta gggataagtg tctagcacag aatggggcac acagtaggtg   10440
cttaataaat gctggatgga tgcaggaagg aatggaggaa tgaatgggaa gggagaacat   10500
atctatcctc tcagaccctc gcagcagcag caactcatac ttggctaatg atatggagca   10560
gttgtttttc cctccctggg cctcactttc ttctcctata aaatggaaat cccagatccc   10620
tggtcctgcc gacacgcagc tactgagaag accaaaagag gtgtgtgtgt gtctatgtgt   10680
gtgtttcagc actttgtaaa tagcaagaag ctgtacagat tctagttaat gttgtgaata   10740
acatcaatta atgtaactag ttaattacta tgattatcac ctcctgatag tgaacatttt   10800
gagattgggc attcagatga tggggtttca cccaaccttg gggcaggttt ttaaaaatta   10860
gctaggcatc aaggccagac cagggctggg ggttgggctg taggcaggga cagtcacagg   10920
aatgcagaat gcagtcatca gacctgaaaa aacaacactg ggggagggg acggtgaagg   10980 ccaagttccc aatgagggtg agattgggcc tggggtctca cccctagtgt ggggcccag   11040 gtcccgtgcc tcccttccc aatgtggcct atggagagac aggcctttct ctcagcctct   11100
ggaagccacc tgctcttttg ctctagcacc tgggtcccag catctagagc atggagcctc   11160
tagaagccat gctcacccgc ccacatttaa ttaacagctg agtccctgat gtcatcctta   11220
tctcgaagag cttagaaaca aagagtggga aattccactg ggcctacctt ccttgggggat   11280 gttcatgggc cccagtttcc agtttccctt gccagacaag cccatcttca gcagttgcta   11340
gtccattctc cattctggag aatctgctcc aaaaagctgg ccacatctct gaggtgtcag   11400
aattaagctg cctcagtaac tgctccccct tctccatata agcaaagcca gaagctctag   11460
ctttacccag ctctgcctgg agactaaggc aaattgggcc attaaaagct cagctcctat   11520
gttggtatta acggtggtgg gttttgttgc tttcacactc tatccacagg atagattgaa   11580
actgccagct tccacctgat ccctgaccct gggatggctg gattgagcaa tgagcagagc   11640
caagcagcac agagtccct ggggctagag gtggaggagg cagtcctggg aatgggaaaa   11700
accccaactt tggggtcata gaggcacagg taacccataa aactgcaaac aagctttgtc   11760
acctctcaga gcttccttat ctgcaaaaaa gaatcttaaa actgaccttg gctgggcaca   11820
gtggctcaca cctctaatcc cagcactttg ggaggccaag gtgggcagat cacgaggtca   11880
ggagtttgag accagcctga ccaacacggt gaaaccctgt ctctactaaa aatacaaaaa   11940
tcagctgggc atggtggcgc gtgcctgtaa tcccagctat tcagtgggct gaggcaggag   12000
aatcgcttga acctgggagg tggaggttgc agtgagccga gattgcgcca ctgcactcca   12060
gcctgagcaa cagagggaca gtctgtctcc aaacaaaaca aaacaaacaa acaaacaaac   12120
aaacaaacaa aaacaacaa caaaaaaacc acttgatcct aagggggatta gatgcgactg   12180 tggactttaa gtggccagcc tactgcctgg catgcagcag atgagactat ggcaatactg   12240
ggcttcagct cagagctggc cttactagag accctgtccc aaagggggaaa aggatggagc   12300 taaagctccc gagagtcacc ccctcctccg aggtgagaaa ggagggcagg agcatgagat   12360
agccgatcct cggtgccttg gtgaggctgg ggcaaatcat gctgggatct ctatcattgt   12420
ccctctttac tgtgactcac tagataatat cagtcaggat acttttggtc acaagtgata   12480
ggaaatccaa ctcatttggg ctgaagcaaa agggacacat tgttggctca catgaacaaa   12540
aagcccgggg cttcaggcac agggtatcac catgactgag atgggggatta attctgtgat   12600 tggccaagtc taggtcacct gatcatacgt aactcattta tgcctgaggt tgcaattttt   12660
```

```
tggattttttg caatcagacc ttggcgatga ccttgagcag taggatataa ataactccca   12720
catgcttagc gttccaataa tggaatacta ggcatacgca ggtctaactg catcaccatg   12780
gctggaatgg ggattcatcc tctgattggt cagacctagg tcacatgctc accctgcagc   12840
ccaagcaggc tgaatgggga gaggtaggtt tcacaaagga aagcccaggt gctgttacct   12900
gaagtaggag ggcaggaggc agggtgagca gagccaacat caacccagag ggaatggaat   12960
ctaagttggt gttttctggg cacgtggctg accaggcct ccctccctca tcatctcagg   13020
gacatgaggg agaagattcc tatgggtggt cccgaaggtc tcacccttg ttttggatgc   13080 tgtgttgggc cagggtggca gtgggtggga cagtggcatc ttagctgccc tgacttgcag   13140
gcagcccatt ccagctcccc gccccaaccc caacccagcc cacttttct gagaaatggt   13200 acatttgccc cagcctcatg tccagaggaa aattttactc taacaccaga acattctctg   13260
gtttgtcctg atagacaaga aagcctccac ctccttaatt tacaaatgac ttgacagctg   13320
cttcgtgggc acttgcatac ataaagagaa ggagctgctg ccttaagttg cagcaagttt   13380
ggccccacct catctccagg cagccagcag atgtacagag tgcctcttgg gtacaatggc   13440
agctccattc aaccaaacct gagcaagctg accccatgcc agaatgcact ggggactcgg   13500
agatgaattg gagcctagag accaagtctc taggctatga cctgggctgc ctcacggcca   13560
cagagctctg tcacgccaag ggagagatgc acccctgaaa gcctgaggtg ccccataagg   13620
agagagtggg tgcccttccc aactatgtag cttcagggca agttctcttt ctttcttttt   13680
ctttctttct ctttctttct ttcttt                                          13706
```

<210> SEQ ID NO 5
<211> LENGTH: 348
<212> TYPE: PRT
<213> ORGANISM: Homo sapiens

<400> SEQUENCE: 5

```
Met Asn Gly Thr Glu Gly Pro Asn Phe Tyr Val Pro Phe Ser Asn Ala
1               5                   10                  15

Thr Gly Val Val Arg Ser Pro Phe Glu Tyr Pro Gln Tyr Tyr Leu Ala
            20                  25                  30

Glu Pro Trp Gln Phe Ser Met Leu Ala Ala Tyr Met Phe Leu Leu Ile
        35                  40                  45

Val Leu Gly Phe Pro Ile Asn Phe Leu Thr Leu Tyr Val Thr Val Gln
    50                  55                  60

His Lys Lys Leu Arg Thr Pro Leu Asn Tyr Ile Leu Leu Asn Leu Ala
65                  70                  75                  80

Val Ala Asp Leu Phe Met Val Leu Gly Gly Phe Thr Ser Thr Leu Tyr
                85                  90                  95

Thr Ser Leu His Gly Tyr Phe Val Phe Gly Pro Thr Gly Cys Asn Leu
            100                 105                 110

Glu Gly Phe Phe Ala Thr Leu Gly Gly Glu Ile Ala Leu Trp Ser Leu
        115                 120                 125

Val Val Leu Ala Ile Glu Arg Tyr Val Val Val Cys Lys Pro Met Ser
    130                 135                 140

Asn Phe Arg Phe Gly Glu Asn His Ala Ile Met Gly Val Ala Phe Thr
145                 150                 155                 160

Trp Val Met Ala Leu Ala Cys Ala Ala Pro Pro Leu Ala Gly Trp Ser
                165                 170                 175

Arg Tyr Ile Pro Glu Gly Leu Gln Cys Ser Cys Gly Ile Asp Tyr Tyr
```

-continued

```
                  180               185               190
Thr Leu Lys Pro Glu Val Asn Asn Glu Ser Phe Val Ile Tyr Met Phe
            195               200               205

Val Val His Phe Thr Ile Pro Met Ile Ile Ile Phe Phe Cys Tyr Gly
            210               215               220

Gln Leu Val Phe Thr Val Lys Glu Ala Ala Ala Gln Gln Gln Glu Ser
225               230               235               240

Ala Thr Thr Gln Lys Ala Glu Lys Glu Val Thr Arg Met Val Ile Ile
            245               250               255

Met Val Ile Ala Phe Leu Ile Cys Trp Val Pro Tyr Ala Ser Val Ala
            260               265               270

Phe Tyr Ile Phe Thr His Gln Gly Ser Asn Phe Gly Pro Ile Phe Met
            275               280               285

Thr Ile Pro Ala Phe Phe Ala Lys Ser Ala Ala Ile Tyr Asn Pro Val
            290               295               300

Ile Tyr Ile Met Met Asn Lys Gln Phe Arg Asn Cys Met Leu Thr Thr
305               310               315               320

Ile Cys Cys Gly Lys Asn Pro Leu Gly Asp Asp Glu Ala Ser Ala Thr
                  325               330               335

Val Ser Lys Thr Glu Thr Ser Gln Val Ala Pro Ala
            340               345

<210> SEQ ID NO 6
<211> LENGTH: 348
<212> TYPE: PRT
<213> ORGANISM: Homo sapiens

<400> SEQUENCE: 6

Met Asn Gly Thr Glu Gly Pro Asn Phe Tyr Val Pro Phe Ser Asn Ala
1               5               10               15

Thr Gly Val Val Arg Ser His Phe Glu Tyr Pro Gln Tyr Tyr Leu Ala
            20               25               30

Glu Pro Trp Gln Phe Ser Met Leu Ala Ala Tyr Met Phe Leu Leu Ile
            35               40               45

Val Leu Gly Phe Pro Ile Asn Phe Leu Thr Leu Tyr Val Thr Val Gln
            50               55               60

His Lys Lys Leu Arg Thr Pro Leu Asn Tyr Ile Leu Leu Asn Leu Ala
65               70               75               80

Val Ala Asp Leu Phe Met Val Leu Gly Gly Phe Thr Ser Thr Leu Tyr
            85               90               95

Thr Ser Leu His Gly Tyr Phe Val Phe Gly Pro Thr Gly Cys Asn Leu
            100               105               110

Glu Gly Phe Phe Ala Thr Leu Gly Gly Glu Ile Ala Leu Trp Ser Leu
            115               120               125

Val Val Leu Ala Ile Glu Arg Tyr Val Val Val Cys Lys Pro Met Ser
            130               135               140

Asn Phe Arg Phe Gly Glu Asn His Ala Ile Met Gly Val Ala Phe Thr
145               150               155               160

Trp Val Met Ala Leu Ala Cys Ala Ala Pro Pro Leu Ala Gly Trp Ser
            165               170               175

Arg Tyr Ile Pro Glu Gly Leu Gln Cys Ser Cys Gly Ile Asp Tyr Tyr
            180               185               190

Thr Leu Lys Pro Glu Val Asn Asn Glu Ser Phe Val Ile Tyr Met Phe
            195               200               205
```

-continued

```
Val Val His Phe Thr Ile Pro Met Ile Ile Ile Phe Phe Cys Tyr Gly
    210             215             220

Gln Leu Val Phe Thr Val Lys Glu Ala Ala Ala Gln Gln Gln Glu Ser
225             230             235             240

Ala Thr Thr Gln Lys Ala Glu Lys Glu Val Thr Arg Met Val Ile Ile
            245             250             255

Met Val Ile Ala Phe Leu Ile Cys Trp Val Pro Tyr Ala Ser Val Ala
            260             265             270

Phe Tyr Ile Phe Thr His Gln Gly Ser Asn Phe Gly Pro Ile Phe Met
        275             280             285

Thr Ile Pro Ala Phe Phe Ala Lys Ser Ala Ala Ile Tyr Asn Pro Val
    290             295             300

Ile Tyr Ile Met Met Asn Lys Gln Phe Arg Asn Cys Met Leu Thr Thr
305             310             315             320

Ile Cys Cys Gly Lys Asn Pro Leu Gly Asp Asp Glu Ala Ser Ala Thr
            325             330             335

Val Ser Lys Thr Glu Thr Ser Gln Val Ala Pro Ala
            340             345
```

```
<210> SEQ ID NO 7
<211> LENGTH: 22
<212> TYPE: DNA
<213> ORGANISM: Homo sapiens

<400> SEQUENCE: 7
acgggtgtgg tacgcagcca ct                                      22

<210> SEQ ID NO 8
<211> LENGTH: 22
<212> TYPE: DNA
<213> ORGANISM: Homo sapiens

<400> SEQUENCE: 8
tgcccacacc atgcgtcggt ga                                      22

<210> SEQ ID NO 9
<211> LENGTH: 22
<212> TYPE: DNA
<213> ORGANISM: Homo sapiens

<400> SEQUENCE: 9
acgggtgtgg tacgcagccc ct                                      22

<210> SEQ ID NO 10
<211> LENGTH: 22
<212> TYPE: DNA
<213> ORGANISM: Homo sapiens

<400> SEQUENCE: 10
tgcccacacc atgcgtcggg ga                                      22

<210> SEQ ID NO 11
<211> LENGTH: 354
<212> TYPE: PRT
<213> ORGANISM: Artificial Sequence
<220> FEATURE:
<223> OTHER INFORMATION: Synthesized

<400> SEQUENCE: 11

Met Asn Thr Lys Tyr Asn Lys Glu Phe Leu Leu Tyr Leu Ala Gly Phe
1               5                   10                  15
```

-continued

```
Val Asp Gly Asp Gly Ser Ile Phe Ala Arg Ile Phe Lys Gly Gln His
            20                  25                  30

Trp Lys Phe Lys His Tyr Ile Arg Leu Thr Phe Ser Val Arg Gln Lys
            35                  40                  45

Thr Gln Arg Arg Trp Phe Leu Asp Lys Leu Val Asp Glu Ile Gly Val
            50                  55                  60

Gly Tyr Val Val Asp Ser Gly Ser Val Ser Glu Tyr Tyr Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
            115                 120                 125

Val Asp Gln Ile Ala Ala Leu Asn Asp Ser Lys Thr Arg Lys Thr Thr
            130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
            165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
            195                 200                 205

Asp Gly Asp Gly Ser Ile Trp Ala Ser Ile Ile Pro Glu Gln Arg Leu
            210                 215                 220

Lys Phe Lys His Arg Leu Arg Leu Ser Phe Thr Val Ala Gln Lys Thr
225                 230                 235                 240

Gln Arg Arg Trp Phe Leu Asp Lys Leu Val Asp Glu Ile Gly Val Gly
            245                 250                 255

Tyr Val Val Asp Gln Gly Ser Val Ser Glu Tyr Arg Leu Ser Glu Ile
            260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
            290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
            325                 330                 335

Glu Thr Val Arg Ala Val Leu Asp Ser Leu Ser Glu Lys Lys Lys Ser
            340                 345                 350

Ser Pro
```

```
<210> SEQ ID NO 12
<211> LENGTH: 354
<212> TYPE: PRT
<213> ORGANISM: Artificial Sequence
<220> FEATURE:
<223> OTHER INFORMATION: Synthesized

<400> SEQUENCE: 12

Met Asn Thr Lys Tyr Asn Lys Glu Phe Leu Leu Tyr Leu Ala Gly Phe
1               5                   10                  15
```

-continued

Val Asp Gly Asp Gly Ser Ile Phe Ala Arg Ile Phe Lys Gly Gln His
           20              25                  30

Trp Lys Phe Lys His Tyr Ile Arg Leu Thr Phe Ser Val Arg Gln Lys
       35              40                  45

Thr Gln Arg Arg Trp Phe Leu Asp Lys Leu Val Asp Glu Ile Gly Val
       50              55                  60

Gly Tyr Val Cys Asp Ser Gly Ser Val Ser Glu Tyr Tyr Leu Ser Glu
65               70                  75                  80

Ile Lys Pro Leu His Asn Phe Leu Thr Gln Leu Gln Pro Phe Leu Lys
               85                  90                  95

Leu Lys Gln Lys Gln Ala Asn Leu Val Leu Lys Ile Ile Glu Gln Leu
           100                 105                 110

Pro Ser Ala Lys Glu Ser Pro Asp Lys Phe Leu Glu Val Cys Thr Trp
           115                 120                 125

Val Asp Gln Ile Ala Ala Leu Asn Asp Ser Lys Thr Arg Lys Thr Thr
       130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
           165                 170                 175

Ser Pro Gly Ser Gly Ile Ser Glu Ala Leu Arg Ala Gly Ala Gly Ser
           180                 185                 190

Gly Thr Gly Tyr Asn Lys Glu Phe Leu Leu Tyr Leu Ala Gly Phe Val
           195                 200                 205

Asp Gly Asp Gly Ser Ile Trp Ala Ser Ile Ile Pro Glu Gln Asn Gly
       210                 215                 220

Lys Phe Lys His Arg Leu Arg Leu Ser Phe Thr Val Ala Gln Lys Thr
225                 230                 235                 240

Gln Arg Arg Trp Phe Leu Asp Lys Leu Val Asp Glu Ile Gly Val Gly
               245                 250                 255

Tyr Val Val Asp Gln Gly Ser Val Ser Glu Tyr Arg Leu Ser Glu Ile
           260                 265                 270

Lys Pro Leu His Asn Phe Leu Thr Gln Leu Gln Pro Phe Leu Lys Leu
           275                 280                 285

Lys Gln Lys Gln Ala Asn Leu Val Leu Lys Ile Ile Glu Gln Leu Pro
       290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
           325                 330                 335

Glu Thr Val Arg Ala Val Leu Asp Ser Leu Ser Glu Lys Lys Lys Ser
           340                 345                 350

Ser Pro

<210> SEQ ID NO 13
<211> LENGTH: 354
<212> TYPE: PRT
<213> ORGANISM: Artificial Sequence
<220> FEATURE:
<223> OTHER INFORMATION: Synthesized

<400> SEQUENCE: 13

Met Asn Thr Lys Tyr Asn Lys Glu Phe Leu Leu Tyr Leu Ala Gly Phe
1               5                   10                  15

Val Asp Gly Asp Gly Ser Ile Tyr Ala Arg Ile Phe Lys Gly Gln His

-continued

```
                  20                  25                  30

Trp Lys Phe Lys His Tyr Ile Arg Leu Thr Phe Ser Val Arg Gln Lys
            35                  40                  45

Thr Gln Arg Arg Trp Phe Leu Asp Lys Leu Val Asp Glu Ile Gly Val
        50                  55                  60

Gly Tyr Val Gln Asp Ser Gly Ser Val Ser Glu Tyr Tyr Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
        130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
            165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
            195                 200                 205

Asp Gly Asp Gly Ser Ile Trp Ala Ser Ile Ile Pro Glu Gln Ala Tyr
        210                 215                 220

Lys Phe Lys His Arg Leu Arg Leu Ser Phe Thr Val Ala Gln Lys Thr
225                 230                 235                 240

Gln Arg Arg Trp Phe Leu Asp Lys Leu Val Asp Glu Ile Gly Val Gly
            245                 250                 255

Tyr Val Val Asp Gln Gly Ser Val Ser Glu Tyr Arg Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
            325                 330                 335

Glu Thr Val Arg Ala Val Leu Asp Ser Leu Ser Glu Lys Lys Lys Ser
            340                 345                 350

Ser Pro
```

<210> SEQ ID NO 14
<211> LENGTH: 354
<212> TYPE: PRT
<213> ORGANISM: Artificial Sequence
<220> FEATURE:
<223> OTHER INFORMATION: Synthesized

<400> SEQUENCE: 14

```
Met Asn Thr Lys Tyr Asn Lys Glu Phe Leu Leu Tyr Leu Ala Gly Phe
1               5                   10                  15

Val Asp Gly Asp Gly Ser Ile Phe Ala Arg Ile Phe Lys Gly Gln His
            20                  25                  30
```

-continued

```
Trp Lys Phe Lys His Tyr Ile Arg Leu Thr Phe Ser Val Arg Gln Lys
        35                  40                  45

Thr Gln Arg Arg Trp Phe Leu Asp Lys Leu Val Asp Glu Ile Gly Val
    50                  55                  60

Gly Tyr Val Tyr Asp Ser Gly Ser Val Ser Glu Tyr Tyr Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
            115                 120                 125

Val Asp Gln Ile Ala Ala Leu Asn Asp Ser Lys Thr Arg Lys Thr Thr
        130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
                180                 185                 190

Gly Thr Gly Tyr Asn Lys Glu Phe Leu Leu Tyr Leu Ala Gly Phe Val
            195                 200                 205

Asp Gly Asp Gly Ser Ile Trp Ala Ser Ile Ile Pro Glu Gln Lys Ser
        210                 215                 220

Lys Phe Lys His Arg Leu Arg Leu Ser Phe Thr Val Ala Gln Lys Thr
225                 230                 235                 240

Gln Arg Arg Trp Phe Leu Asp Lys Leu Val Asp Glu Ile Gly Val Gly
                245                 250                 255

Tyr Val Val Asp Gln Gly Ser Val Ser Glu Tyr Arg Leu Ser Glu Ile
                260                 265                 270

Lys Pro Leu His Asn Phe Leu Thr Gln Leu Gln Pro Phe Leu Lys Leu
            275                 280                 285

Lys Gln Lys Gln Ala Asn Leu Val Leu Lys Ile Ile Glu Gln Leu Pro
        290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro
```

```
<210> SEQ ID NO 15
<211> LENGTH: 147
<212> TYPE: PRT
<213> ORGANISM: Artificial Sequence
<220> FEATURE:
<223> OTHER INFORMATION: Synthesized

<400> SEQUENCE: 15

Lys Glu Phe Leu Leu Tyr Leu Ala Gly Phe Val Asp Gly Asp Gly Ser
1               5                   10                  15

Ile Trp Ala Ser Ile Ile Pro Glu Gln Arg Leu Lys Phe Lys His Arg
            20                  25                  30
```

-continued

```
Leu Arg Leu Ser Phe Thr Val Ala Gln Lys Thr Gln Arg Arg Trp Phe
        35                  40                  45

Leu Asp Lys Leu Val Asp Glu Ile Gly Val Gly Tyr Val Val Asp Gln
        50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
                100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
        130                 135                 140

Val Leu Asp
145

<210> SEQ ID NO 16
<211> LENGTH: 147
<212> TYPE: PRT
<213> ORGANISM: Artificial Sequence
<220> FEATURE:
<223> OTHER INFORMATION: Synthesized

<400> SEQUENCE: 16

Lys Glu Phe Leu Leu Tyr Leu Ala Gly Phe Val Asp Gly Asp Gly Ser
1               5                   10                  15

Ile Trp Ala Ser Ile Ile Pro Glu Gln Asn Gly Lys Phe Lys His Arg
                20                  25                  30

Leu Arg Leu Ser Phe Thr Val Ala Gln Lys Thr Gln Arg Arg Trp Phe
        35                  40                  45

Leu Asp Lys Leu Val Asp Glu Ile Gly Val Gly Tyr Val Val Asp Gln
        50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
                100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
        130                 135                 140

Val Leu Asp
145

<210> SEQ ID NO 17
<211> LENGTH: 147
<212> TYPE: PRT
<213> ORGANISM: Artificial Sequence
<220> FEATURE:
<223> OTHER INFORMATION: Synthesized

<400> SEQUENCE: 17

Lys Glu Phe Leu Leu Tyr Leu Ala Gly Phe Val Asp Gly Asp Gly Ser
1               5                   10                  15

Ile Trp Ala Ser Ile Ile Pro Glu Gln Ala Tyr Lys Phe Lys His Arg
                20                  25                  30
```

-continued

```
Leu Arg Leu Ser Phe Thr Val Ala Gln Lys Thr Gln Arg Arg Trp Phe
        35                  40                  45

Leu Asp Lys Leu Val Asp Glu Ile Gly Val Gly Tyr Val Val Asp Gln
        50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
                100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
        130                 135                 140

Val Leu Asp
145

<210> SEQ ID NO 18
<211> LENGTH: 147
<212> TYPE: PRT
<213> ORGANISM: Artificial Sequence
<220> FEATURE:
<223> OTHER INFORMATION: Synthesized

<400> SEQUENCE: 18

Lys Glu Phe Leu Leu Tyr Leu Ala Gly Phe Val Asp Gly Asp Gly Ser
1               5                   10                  15

Ile Trp Ala Ser Ile Ile Pro Glu Gln Lys Ser Lys Phe Lys His Arg
                20                  25                  30

Leu Arg Leu Ser Phe Thr Val Ala Gln Lys Thr Gln Arg Arg Trp Phe
        35                  40                  45

Leu Asp Lys Leu Val Asp Glu Ile Gly Val Gly Tyr Val Val Asp Gln
        50                  55                  60

Gly Ser Val Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
                100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
        130                 135                 140

Val Leu Asp
145

<210> SEQ ID NO 19
<211> LENGTH: 147
<212> TYPE: PRT
<213> ORGANISM: Artificial Sequence
<220> FEATURE:
<223> OTHER INFORMATION: Synthesized

<400> SEQUENCE: 19

Lys Glu Phe Leu Leu Tyr Leu Ala Gly Phe Val Asp Gly Asp Gly Ser
1               5                   10                  15

Ile Phe Ala Arg Ile Phe Lys Gly Gln His Trp Lys Phe Lys His Tyr
```

-continued

```
                20                  25                  30
Ile Arg Leu Thr Phe Ser Val Arg Gln Lys Thr Gln Arg Arg Trp Phe
            35                  40                  45

Leu Asp Lys Leu Val Asp Glu Ile Gly Val Gly Tyr Val Val Asp Ser
        50                  55                  60

Gly Ser Val Ser Glu Tyr Tyr Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
                100                 105                 110

Pro Asp Lys Phe Leu Glu Val Cys Thr Trp Val Asp Gln Ile Ala Ala
            115                 120                 125

Leu Asn Asp Ser Lys Thr Arg Lys Thr Thr Ser Glu Thr Val Arg Ala
        130                 135                 140

Val Leu Asp
145

<210> SEQ ID NO 20
<211> LENGTH: 147
<212> TYPE: PRT
<213> ORGANISM: Artificial Sequence
<220> FEATURE:
<223> OTHER INFORMATION: Synthesized

<400> SEQUENCE: 20

Lys Glu Phe Leu Leu Tyr Leu Ala Gly Phe Val Asp Gly Asp Gly Ser
1               5                   10                  15

Ile Phe Ala Arg Ile Phe Lys Gly Gln His Trp Lys Phe Lys His Tyr
                20                  25                  30

Ile Arg Leu Thr Phe Ser Val Arg Gln Lys Thr Gln Arg Arg Trp Phe
            35                  40                  45

Leu Asp Lys Leu Val Asp Glu Ile Gly Val Gly Tyr Val Cys Asp Ser
        50                  55                  60

Gly Ser Val Ser Glu Tyr Tyr Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
                100                 105                 110

Pro Asp Lys Phe Leu Glu Val Cys Thr Trp Val Asp Gln Ile Ala Ala
            115                 120                 125

Leu Asn Asp Ser Lys Thr Arg Lys Thr Thr Ser Glu Thr Val Arg Ala
        130                 135                 140

Val Leu Asp
145

<210> SEQ ID NO 21
<211> LENGTH: 147
<212> TYPE: PRT
<213> ORGANISM: Artificial Sequence
<220> FEATURE:
<223> OTHER INFORMATION: Synthesized

<400> SEQUENCE: 21

Lys Glu Phe Leu Leu Tyr Leu Ala Gly Phe Val Asp Gly Asp Gly Ser
1               5                   10                  15
```

-continued

```
Ile Tyr Ala Arg Ile Phe Lys Gly Gln His Trp Lys Phe Lys His Tyr
            20                  25                  30

Ile Arg Leu Thr Phe Ser Val Arg Gln Lys Thr Gln Arg Arg Trp Phe
            35                  40                  45

Leu Asp Lys Leu Val Asp Glu Ile Gly Val Gly Tyr Val Gln Asp Ser
            50                  55                  60

Gly Ser Val Ser Glu Tyr Tyr Leu Ser Glu Ile Lys Pro Leu His Asn
65                  70                  75                  80

Phe Leu Thr Gln Leu Gln Pro Phe Leu Lys Leu Lys Gln Lys Gln Ala
                    85                  90                  95

Asn Leu Val Leu Lys Ile Ile Glu Gln Leu Pro Ser Ala Lys Glu Ser
                100                 105                 110

Pro Asp Lys Phe Leu Glu Val Cys Thr Trp Val Asp Gln Ile Ala Ala
            115                 120                 125

Leu Asn Asp Ser Lys Thr Arg Lys Thr Thr Ser Glu Thr Val Arg Ala
            130                 135                 140

Val Leu Asp
145

<210> SEQ ID NO 22
<211> LENGTH: 147
<212> TYPE: PRT
<213> ORGANISM: Artificial Sequence
<220> FEATURE:
<223> OTHER INFORMATION: Synthesized

<400> SEQUENCE: 22

Lys Glu Phe Leu Leu Tyr Leu Ala Gly Phe Val Asp Gly Asp Gly Ser
1               5                   10                  15

Ile Phe Ala Arg Ile Phe Lys Gly Gln His Trp Lys Phe Lys His Tyr
            20                  25                  30

Ile Arg Leu Thr Phe Ser Val Arg Gln Lys Thr Gln Arg Arg Trp Phe
            35                  40                  45

Leu Asp Lys Leu Val Asp Glu Ile Gly Val Gly Tyr Val Tyr Asp Ser
            50                  55                  60

Gly Ser Val Ser Glu Tyr Tyr Leu Ser Glu Ile Lys Pro Leu His Asn
65                  70                  75                  80

Phe Leu Thr Gln Leu Gln Pro Phe Leu Lys Leu Lys Gln Lys Gln Ala
                    85                  90                  95

Asn Leu Val Leu Lys Ile Ile Glu Gln Leu Pro Ser Ala Lys Glu Ser
                100                 105                 110

Pro Asp Lys Phe Leu Glu Val Cys Thr Trp Val Asp Gln Ile Ala Ala
            115                 120                 125

Leu Asn Asp Ser Lys Thr Arg Lys Thr Thr Ser Glu Thr Val Arg Ala
            130                 135                 140

Val Leu Asp
145

<210> SEQ ID NO 23
<211> LENGTH: 31
<212> TYPE: DNA
<213> ORGANISM: Artificial Sequence
<220> FEATURE:
<223> OTHER INFORMATION: Synthesized

<400> SEQUENCE: 23
ccgggcgaag ggtgtggtga gtggccactt g                              31
```

```
<210> SEQ ID NO 24
<211> LENGTH: 31
<212> TYPE: DNA
<213> ORGANISM: Artificial Sequence
<220> FEATURE:
<223> OTHER INFORMATION: Synthesized

<400> SEQUENCE: 24
ggcccgcttc ccacaccact caccggtgaa c                                      31

<210> SEQ ID NO 25
<211> LENGTH: 1062
<212> TYPE: DNA
<213> ORGANISM: Artificial Sequence
<220> FEATURE:
<223> OTHER INFORMATION: Synthesized

<400> SEQUENCE: 25
atgaatacaa aatataataa agagttctta ctctacttag cagggtttgt agacggtgac        60
ggttccatct ttgcccgtat ctttaagggt caacattgga agttcaagca ctatattcgt       120
ttgaccttct cggtgcggca gaagacacag cgccgttggt tcctcgacaa gctggtggac       180
gagatcggtg tgggttacgt ggttgactct ggcagcgttt ccgagtacta cctgtccgag       240
attaaaccat tacataattt tttaacacaa ctacaacctt ttctaaaact aaaacaaaaa       300
caagcaaatt tagtttttaaa aattattgaa caacttccgt cagcaaaaga atccccggac      360
aaattcttag aagtttgtac atgggtggat caaattgcag ctctgaatga ttcgaagacg       420
cgtaaaacaa cttctgaaac cgttcgtgct gtgctagaca gtttaccagg atccgtggga       480
ggtctatcgc catctcaggc atccagcgcc gcatcctcgg cttcctcaag cccgggttca       540 gggatcccg aagcactcag agctggagca ggttccggca ctggatacaa caaggaattc       600
ctgctctacc tggcgggctt cgtcgacggg gacggctcca tctgggcctc gatcattcct       660
gagcaacggc ttaaattcaa gcataggctg cgcctctctt tcactgtcgc tcagaagaca       720
cagcgccgtt ggttcctcga caagctggtg gacgagatcg gtgtgggtta cgtggttgac       780
cagggcagcg tctccgagta taggctgtcc gagatcaagc tctgcacaa cttcctgacc       840 cagctccagc ccttcctgaa gctcaagcag aagcaggcca acctcgtgct gaagatcatc       900
gagcagctgc cctccgccaa ggaatccccg gacaagttcc tggaggtgtg cacctgggtg       960
gaccagatcg ccgctctgaa cgactccaag acccgcaaga ccacttccga aaccgtccgc      1020
gccgttctag acagtctctc cgagaagaag aagtcgtccc cc                        1062

<210> SEQ ID NO 26
<211> LENGTH: 1062
<212> TYPE: DNA
<213> ORGANISM: Artificial Sequence
<220> FEATURE:
<223> OTHER INFORMATION: Synthesized

<400> SEQUENCE: 26
atgaatacaa aatataataa agagttctta ctctacttag cagggtttgt agacggtgac        60
ggttccatct ttgcccgtat ctttaagggt caacattgga agttcaagca ctatattcgt       120
ttgaccttca gtgtgcggca gaagacacag cgccgttggt tcctcgacaa gctggtggac       180
gagatcggtg tgggttacgt gtgtgactct ggcagcgttt ccgagtacta cctgtccgag       240
attaaaccat tacataattt tttaacacaa ctacaacctt ttctaaaact aaaacaaaaa       300
caagcaaatt tagtttttaaa aattattgaa caacttccgt cagcaaaaga atccccggac      360
```

```
aaattcttag aagtttgtac atgggtggat caaattgcag ctctgaatga ttcgaagacg        420
cgtaaaacaa cttctgaaac cgttcgtgct gtgctagaca gtttaccagg atccgtggga        480
ggtctatcgc catctcaggc atccagcgcc gcatcctcgg cttcctcaag cccgggttca        540
gggatctccg aagcactcag agctggagca ggttccggca ctggatacaa caaggaattc        600
ctgctctacc tggcgggctt cgtcgacggg gacggctcca tctgggcctc gatcattcct        660
gagcaaaatg gtaaattcaa gcataggctg cgcctctctt tcactgtcgc tcagaagaca        720
cagcgccgtt ggttcctcga caagctggtg gacgagatcg gtgtgggtta cgtggttgac        780
cagggcagcg tctccgagta taggctgtcc gagatcaagc ctctgcacaa cttcctgacc        840
cagctccagc ccttcctgaa gctcaagcag aagcaggcca acctcgtgct gaagatcatc        900
gagcagctgc cctccgccaa ggaatccccg gacaagttcc tggaggtgtg cacctgggtg        960
gaccagatcg ccgctctgaa cgactccaag acccgcaaga ccacttccga aaccgtccgc       1020
gccgttctag acagtctctc cgagaagaag aagtcgtccc cc                          1062
```

<210> SEQ ID NO 27
<211> LENGTH: 1062
<212> TYPE: DNA
<213> ORGANISM: Artificial Sequence
<220> FEATURE:
<223> OTHER INFORMATION: Synthesized

<400> SEQUENCE: 27

```
atgaatacaa aatataataa agagttctta ctctacttag cagggtttgt agacggtgac         60
ggttccatct atgcccgtat ctttaagggt caacattgga agttcaagca ctatattcgt        120
ttgaccttca gtgtgcggca gaagacacag cgccgttggt tcctcgacaa gctggtggac        180
gagatcggtg tgggttacgt gcaggactct ggcagcgttt ccgagtacta cctgtccgag        240
attaaaccat tacataattt tttaacacaa ctacaacctt ttctaaaact aaaacaaaaa        300
caagcaaatt tagtttttaaa aattattgaa caacttccgt cagcaaaaga atccccggac       360
aaattcttag aagtttgtac atgggtggat caaattgcag ctctgaatga ttcgaagacg        420
cgtaaaacaa cttctgaaac cgttcgtgct gtgctagaca gtttaccagg atccgtggga        480
ggtctatcgc catctcaggc atccagcgcc gcatcctcgg cttcctcaag cccgggttca        540
gggatctccg aagcactcag agctggagca ggttccggca ctggatacaa caaggaattc        600
ctgctctacc tggcgggctt cgtcgacggg gacggctcca tctgggcctc gatcattcct        660
gagcaagcgt ataaattcaa gcataggctg cgcctctctt tcactgtcgc tcagaagaca        720
cagcgccgtt ggttcctcga caagctggtg gacgagatcg gtgtgggtta cgtggttgac        780
cagggcagcg tctccgagta taggctgtcc gagatcaagc ctctgcacaa cttcctgacc        840
cagctccagc ccttcctgaa gctcaagcag aagcaggcca acctcgtgct gaagatcatc        900
gagcagctgc cctccgccaa ggaatccccg gacaagttcc tggaggtgtg cacctgggtg        960
gaccagatcg ccgctctgaa cgactccaag acccgcaaga ccacttccga aaccgtccgc       1020
gccgttctag acagtctctc cgagaagaag aagtcgtccc cc                          1062
```

<210> SEQ ID NO 28
<211> LENGTH: 1062
<212> TYPE: DNA
<213> ORGANISM: Artificial Sequence
<220> FEATURE:
<223> OTHER INFORMATION: Synthesized

```
<400> SEQUENCE: 28
atgaatacaa aatataataa agagttctta ctctacttag cagggtttgt agacggtgac      60
ggttccatct ttgcccgtat ctttaagggt caacattgga agttcaagca ctatattcgt     120
ttgaccttct cggtgcggca gaagacacag cgccgttggt tcctcgacaa gctggtggac     180
gagatcggtg tgggttacgt gtatgactct ggcagcgttt ccgagtacta cctgtccgag     240
attaaaccat tacataattt tttaacacaa ctacaacctt ttctaaaact aaaacaaaaa     300
caagcaaatt tagttttaaa aattattgaa caacttccgt cagcaaaaga atccccggac     360
aaattcttag aagtttgtac atgggtggat caaattgcag ctctgaatga ttcgaagacg     420
cgtaaaacaa cttctgaaac cgttcgtgct gtgctagaca gtttaccagg atccgtggga     480
ggtctatcgc catctcaggc atccagcgcc gcatcctcgg cttcctcaag cccgggttca     540
gggatctccg aagcactcag agctggagca ggttccggca ctggatacaa caaggaattc     600
ctgctctacc tggcgggctt cgtcgacggg gacggctcca tctgggcctc gatcattcct     660
gagcaaaagt cgaaattcaa gcataggctg cgcctctctt tcactgtcgc tcagaagaca     720
cagcgccgtt ggttcctcga caagctggtg gacgagatcg gtgtgggtta cgtggttgac     780
cagggcagcg tctccgagta taggctgtcc gagatcaagc ctctgcacaa cttcctgacc     840
cagctccagc ccttcctgaa gctcaagcag aagcaggcca acctcgtgct gaagatcatc     900
gagcagctgc cctccgccaa ggaatccccg gacaagttcc tggaggtgtg cacctgggtg     960
gaccagatcg ccgctctgaa cgactccaag acccgcaaga ccacttccga aaccgtccgc    1020
gccgttctag acagtctctc cgagaagaag aagtcgtccc cc                       1062

<210> SEQ ID NO 29
<211> LENGTH: 10
<212> TYPE: PRT
<213> ORGANISM: Artificial Sequence
<220> FEATURE:
<223> OTHER INFORMATION: Synthesized

<400> SEQUENCE: 29

Met Ala Pro Lys Lys Lys Arg Lys Val His
1               5                   10
```